US009561244B2

(12) United States Patent
Einbond

(10) Patent No.: US 9,561,244 B2
(45) Date of Patent: *Feb. 7, 2017

(54) ANTI-NEOPLASTIC COMPOSITIONS COMPRISING EXTRACTS OF BLACK COHOSH

(75) Inventor: Linda Saxe Einbond, Crestwood, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 1079 days.

This patent is subject to a terminal disclaimer.

(21) Appl. No.: 13/374,496

(22) Filed: Dec. 30, 2011

(65) Prior Publication Data

US 2012/0269800 A1    Oct. 25, 2012

Related U.S. Application Data

(60) Continuation of application No. 13/208,962, filed on Aug. 12, 2011, which is a continuation of application No. 12/221,478, filed on Aug. 4, 2008, now abandoned, which is a division of application No. 10/746,960, filed on Dec. 23, 2003, now Pat. No. 7,407,675.

(60) Provisional application No. 60/437,159, filed on Dec. 27, 2002.

(51) Int. Cl.
*A61K 36/71* (2006.01)
*A61K 31/7048* (2006.01)
*A61K 45/06* (2006.01)

(52) U.S. Cl.
CPC ........... *A61K 31/7048* (2013.01); *A61K 36/71* (2013.01); *A61K 45/06* (2013.01)

(58) Field of Classification Search
CPC ..................................................... A61K 36/71
USPC ................................................. 424/773, 778
See application file for complete search history.

(56) References Cited

U.S. PATENT DOCUMENTS

| | | | |
|---|---|---|---|
| 5,296,506 A | 3/1994 | Kingston |
| 5,440,057 A | 8/1995 | Nicolaou |
| 5,475,120 A | 12/1995 | Rao |
| 5,484,809 A | 1/1996 | Hostetler |
| 5,527,924 A | 6/1996 | Danishefsky |
| 5,530,020 A | 6/1996 | Gunawardana |
| 5,565,478 A | 10/1996 | Kohn |
| 5,569,729 A | 10/1996 | Leclerc |
| 5,972,986 A | 10/1999 | Seibert et al. |
| 6,267,994 B1 | 7/2001 | Nusselhut |
| 6,436,991 B1 * | 8/2002 | Majeed et al. |
| 6,444,233 B1 | 9/2002 | Arntzen |
| 2006/0210659 A1 | 9/2006 | Nadaoka |

FOREIGN PATENT DOCUMENTS

JP    09030977 A    2/1997

OTHER PUBLICATIONS

Watanabe et al. "Cycloartane ?glycosides from the Rhizomes of Cimicifuga racemosa and Their Cytotoxic Activities", Chem. Pharm. Bull. 50(1) Jan. 2002; 121-125.*
Kaplan, J., Biochemistry of Na,K-ATPase. Annu Rev Biochem. 71:511-35 (2002).
Katz, Therapy Insight: potential of statins for cancer chemoprevention and therapy, Nature Clin. Pract. Oncology, 2:82-89 (2005).
Kesiry, R. et al., GRP78/BIP is involved in ouabain-induced endocytosis of the Na/K-ATPase in LLC-PK1 cells., Front Biosci., 10:2045-55 (2005).
Kometiani, P. et al., Digitalis-induced signaling by Na+/K+-ATPase in human breast cancer cells, Mol Pharmacol, 67 (3):929-36 (2005).
Kotzka, J. et al. Sterol regulatory element binding proteins (SREBP)-1a and SREBP-2 are linked to the MAP-kinase cascade, Journal of Lipid Research, 41:99-108 (2000).
Lavoie, J.N. et al., Cyclin D1 expression is regulated positively by the p42/p44MAPK and negatively by the p38/HOGMAPK pathway, J Bioi Chem. 271:20608-16 (1996).
Li, Z. et al., The Na/K-ATPase/Src complex and cardiotonic steroid-activated protein kinase cascades., Pflugers Arch.—Eur. J. Physiol., 457:635-644 (2009).
Lingrel, J. et al., Na+,K(+)-ATPase. J Bioi Chem 269(31 ):19659-62 (1994).
Liu, J. et al., Ouabain-induced endocytosis of the plasmalemma I Na/K-ATPase in LLC-PK1 cells requires caveolin-1, Kidney Int., 67:1844-54 (2005).
Lopez-Lazaro, M. et al.., Digitoxin inhibits the growth of cancer cell lines at concentrations commonly found in cardiac patients, J Nat Prod., 68(11)1642-5, (2005).
Lopez-Lazaro, M. et al., Anti-tumour activity of *Digitalis purpurea* L. subsp. heywoodii, Planta Med., 69(8):701-4 (2003).
Lude, S. et al., Hepatic effects of Cimicifuga racemosa extract in vivo and in vitro, Cell Mol Life ScL, 64(21):2848-2857 (2007).
Mallory, J.C. et al., A novel group of genes regulates susceptibility to antineoplastic drugs in highly tumorigenic breast cancer cells, Mol Pharmacol, 68:1747-56 (2005).

(Continued)

*Primary Examiner* — Chris R Tate
*Assistant Examiner* — Deborah Davis
(74) *Attorney, Agent, or Firm* — Hoffmann & Baron, LLP

(57) ABSTRACT

A method for treating, preventing or ameliorating breast cancer is provided by administering a synergistic amount of digitoxin and either actein or an extract of black cohosh comprising triterpene glycosides, and optionally another chemopreventive agent which may be paclitaxel. Methods for treating or preventing a neoplasia using a synergistic combination, and compositions of a synergistic combination of a cardiac glycoside and either actein or an extract of black cohosh comprising triterpene glycosides, and optionally another chemopreventive agent which may be a taxane are also provided. The compositions may also be used in a method for modulating $Na^+K^+ATPase$ activity. In addition, a method for inhibiting the progression or development of breast cancer in vivo by administering either actein or an extract of black cohosh comprising triterpene glycosides and optionally at least one other chemoprotective agent is provided.

5 Claims, 57 Drawing Sheets

(56) References Cited

OTHER PUBLICATIONS

McConkey, D. et al., Cardiac glycosides stimulate Ca2+ increases and apoptosis in androgen-independent . . . , Cancer Res., 60(14):3807-12 (2000).

Mo, H. et al., Studies of the Isoprenoid-Mediated Inhibition of Mevalonate Synthesis Applied to . . . , Society for Experimental Biology and Medicine, 229, 567-85 (2004).

Natsoulis et al., Classification of a large microarray data set: algorithm comparison and analysis of drug signatures, Genome Res, 15(5):724-36 (2005).

Pocas, E.S. et al., Synergistic interaction between ouabain and 8-methoxy-3,9-dihydroxy coumestan . . . , Life Sci, Sep. 22,81 (15):1199-1204 (2007).

Raus et al., First-time proof of endometrial safety of the special black cohosh extract (Actaea or Cimicifuga racemosa extract) CR BNO 1055, Menopause, 13:678-91 (2006).

Rebbeck et al., A retrospective case-control study of the use of hormone-related supplements and association with breast cancer, Int. J. Cancer, 120(7):1523-1528 (2007).

Rivas, M.A. et al., TNF alpha acting on TNFR1 promotes breast cancer growth via p42/P44 MAPK, JNK, Akt and NF-kappa B-dependent pathways., Exp Cell Res. 314:509-29 (2008).

Rizvi, S.1. et al., Impairment of sodium pump and Na/H exchanger in erythrocytes from non-insulin . . . , Clin. Chim. Acta., 354(1-2):59-67 (2005).

Sakurai et al., Cancer preventive agents. Part 1: chemopreventive potential of cimigenol, cimigenol-3,15-dione, and related compounds, Bioorg Med Chem, 13(4):1403-8 (2005).

Sanguino, E. et al., Sexual dimorphism in lipid metabolic phenotype associated with old age in Sprague-Dawley rats, Exp Gerontol, 39(9):1295-306 (2004).

Seidlova-Wuttke et ai, Inhibitory Effects of a Black Cohosh (Cimicifuga racemosa) Extract on Prostate Cancer, Planta Med, 72(6):521-26 (2006).

Seidman, R. et al., The role of ERK 1/2 and p38 MAP-kinase pathways in taxol-induced apoptosis in human ovarian carcinoma cells., Exp Cell Res. 268:84-92 (2001).

Shahidi et al., Champaign, ILL: AOCS Press, pp. 360-370 (2000).

Shao, Y. et al., "Triterpene Glycosides from Cimicifuga racemosa," J. Nat. Prod., 63(7):905-910 (2000).

Shibata, F. et al., Fibroblast growth-stimulating activity of S100A9 (MRP-14), Eur J Biochem. 271, 2137-43 (2004).

Shtil, A.A. et al., Differential regulation of mitogen-actibated protein kinases by microtubule-binding agents in human breast cancer cells, Oncogene, 18:377-84 (1999).

Skou, J., The Na,K-pump, Methods Enzymol. 156:1-25 (1988).

Smyth, G.K. et al., Use of within-array replicate spots for assessing differential expression in microarray experiments, Bioinformatics, 21 (9):2067-75 (2005).

Spangler et al., The effects of black cohosh therapies on lipids, fibrinogen, glucose and insulin, Maturitas, 57:195-204 (2007).

Srivastava, M. et al. Digitoxin mimics gene therapy with CFTR and suppresses hypersecretion . . . , Proc Natl Acad Sci USA 101:7693-8 (2004).

Steiner, S. et al., Proteomics to display lovastatin-induced protein and pathway regulation in rat liver, Electrophoresis, 21, 2129-37 (2000).

Swezey, R.R. et al., Absorption,•tissue distribution and elimination of 4-[(3) h]-epigallocatechin gallate in beagle dogs, Int J Toxicol., 22, 187-93 (2003).

Tian, Z. et al., Anti-cancer activity and mechanisms of 25-anhydrocimigenol-3-O-beta-d-xylopyranoside isolated . . . , Anticancer Drugs, 17(5):545-51 (2006).

Tian, Z. et al., Antitumor activity and mechanisms of action of total glycosides from aerial part of Cimicifuga dahurica targeted against hepatoma, BMC Cancer, 7:237 (2007).

Tian, Z. et al., Binding of Src to Na+/K+-ATPase forms a functional signaling complex., Mol Bioi Cell, 17:317-26 (2006).

Tian, Z. et al., Cimicifuga foetida extract inhibits proliferation ofhepatocelluar cells via induction . . ., J. Ethnopharmacol., Nov. 1; 114(2):227-33 (2007).

Tian, Z. et al., Cytoxicity of cycloartane triterpenoids from aerial part of Cimicifuga foetida, Fitoterapia, 77(1):39-42 (2006).

Tian, Z. et al., Cytoxicity of three cycloartane triterpenoids from Cimicifuga dahurica, Cancer Lett., 226(1):65-75 (2005).

Tsukamoto et al., Isolation of CYP3A4 Inhibitors from the Black Cohosh (Cimicifuga racemosa), eCAM, 2(2):223-6 (2005).

Tsutsumi, S. et al., Celecoxib upregulates endoplasmic reticulum chaperones that inhibit celecoxib-induced apoptosis in human gastric cells, Oncogene. 25:1018-29 (2006).

Winnicka. K. et al. Cardiac glycosides in cancer research and cancer therapy, Acta Pol Pharm. 63(2):109-15 (2006).

Wu, Y. et at., Endoplasmic reticulum stress signal mediators are targets of selenium action, Cancer Res. 65(19):9073-9 (2005).

Wuttke et al., Effects of black cohosh (Cimicifuga racemosa) on bone turnover, vaginal mucosa, and various blood parameters . . . , Menopause, 13(2):185-196 (2006).

Xu, C. et al., Endoplasmic reticulum stress: cell life and death ,decisions, J. Clin Invest, 115:2656-64 (2005).

Yan, C. et al., Gene expression profiling identifies activating transcription factor 3 as a novel contributor . . . , Mol Cancer Ther, 4:233-41 (2005).

Yang. Q. et al. Cardiac glycosides inhibit TNF-alpha/NF-kappaB signaling by blocking recruitment of TNF . . . , Proc Natl Acad Sci USA 102(27):9631-6 (2005).

Zhang, K. et al., The unfolded protein response: a stress signaling pathway critical for health and disease, Neurology, 66(2 Suppl 1):S102-9 (2006).

Chow et al., Pharmacokinetics and Safety of Green Tea Polyphenols After Multiple-dose Administration of Epigallocatechin Galate and Polyphenon E in Healthy Individuals, Clin Cancer Res., 9:3312-9 (2003).

Bedir, E. et al., Chem. Pharm. Bull. (2000), 48(3):425-427. Cimiracemoside A: A new cycloanostanol xyloside from the rhizome of Cimicifuga racemosa.

Corsano, S. Corsi e Seminari di Chimica, Consiglio Nazionale delle Ricerche e Fondazione F. Giordani (1968), 11, 61-4. Structure of the glucoside acetin.

http://www.holistic-online.com/Herbal-Med/.sub.--Herbs/h32.htm.

Gura, T. Science, 1997, 278:1041-1042. Systems for identifying new drugs are often faulty.

Jain, R. K. Sci. Am., 1994, 271:58-65. Barriers to drug delivery in solid tumors.

Curti, B. D. Crit. Rev. In Oncology/Hematology, 1993, 14:29-39. Physical barriers to drug delivery in tumors.

Beers and Berkow, eds., The Merck Manual of Diagnosis and Therapy, 17th ed. (Whitehouse Station, N. J. : Merck Research Laboratories, 1999). 973-974, 976, 986, 988, 991.

Bodinet and Freudenstein, Influence of Cimicifuga racemosa on the proliferation of estrogen receptor-positive human breast cancer cells. Breast Cancer Research and Treatment, 76:1-10, 2002.

Burdette, et al., Black cohosh (Cimicifuga racemosa L.) protects against menadione-induced DNA damage through scavenging of reactive oxygen species: bioassay-directed isolation and characterization of active principles. J. Agric. Food Chem., 50:7022-7028, 2002.

Chen et al., Isolation, structure elucidation, and absolute configuration of 26-deoxyactein from Cimicifuga racemosa and clarification of nomenclature associated with 27-deoxyactein. J. Nat. Prod., 65:601-605, 2002.

Chou and Talalay, Quantitative analysis of dose-effect relationships: the combined effects of multiple drugs or enzyme inhibitors. Adv. Enzyme Regul., 22:27-55, 1984.

Dixon-Shanies and Shaikh, Growth inhibition of human breast cancer cells by herbs and phytoestrogens. Oncol. Rep., 6:1383-1387, 1999.

Foster, S., Black cohosh: Cimicifuga racemosa. A literature review. HerbalGram, 45:35-49, 1999.

Fulda and Debatin, Betulinic acid induces apoptosis through a direct effect on mitochondria in neuroectodermal tumors. Med. Pediatr. Oncol., 35:616-618, 2000.

(56) References Cited

OTHER PUBLICATIONS

Hall et al., The fractional inhibitory concentration (FIC) index as a measure of synergy. J. Antimicrob. Chemother., 11 (5):427-433, 1983.

Han et al., Stable overexpression of cyclin D1 in a human mammary epithelial cell line prolongs the S-phase and inhibits growth. Oncogene, 10:953-961, 1995.

Han et al., Effects of sulindac and its metabolites on growth and apoptosis in human mammary epithelial and breast carcinoma cell lines. Breast Cancer Res. Treat., 48:195-203, 1998.

Haridas et al., Avicins: triterpenoid saponins from Acacia victoriae (Bentham) induce apoptosis by mitochondrial perturbation. Proc. Natl. Acad. Sci. USA, 98:5821-5826, 2001.

Ito et al., The novel triterpenoid CDDO induces apoptosis and differentiation of human osterosarcoma cells by a caspase-8 dependent mechanism. Mol. Pharmacol., 5:1094-1099, 2001.

Joe et al., Cyclin D1 overexpression is more prevalent in non-Caucasian breast cancer. Anticancer Res., 21:3535-3539, 2001.

Joe et al., Resveratrol induces growth inhibition, S-phase arrest, apoptosis, and changes in biomarker expression in several human cancer cell lines. Clin. Cancer Res., 8:893-903, 2002.

Kruse et al., Fukic and piscidic acid esters from the rhizome of Cimicifuga racemosa and the in vitro estrogenic activity of fukinolic acid. Planta. med., 65:763-764, 1999.

Lehmann-Willenbrock and Riedel, Clinical and endocrinologic studies of the treatment of ovarian insufficiency manifestations following hysterectomy with intact adnexa. Zent. Bl Gynakol., 110:611-618, 1988.

Lim et al., Sulindac derivatives inhibit growth and induce apoptosis in human prostate cancer cell lines. Biochem. Pharmacol., 58:1097-1107, 1999.

Loser et al., Inhibition of neutrophil elastase activity by cinnamic acid derivatives from Cimicifuga racemosa. Planta. Med., 66:751-753, 2000.

Luo et al., PM-3, a benzo-g-pyran derivative isolated from propolis, inhibits growth of MCF-7 human breast cancer cells. Anticancer Res. 21:1665-1672, 2001.

Masuda et al., Effects of epigallocatechin-3-gallafate on growth, epidermal growth factor receptor signaling pathways, gene expression, and chemosensitivity in human head and neck squamous cell carcinoma cell lines. Clinical Cancer Research, 7:4220-4229, 2001.

Masuda et al., Epigallocatechin-3-gallate inhibits activation of HER-2/neu and downstream signaling pathways in human head and neck and breast carcinoma cells. Clin. Cancer Res., 9:3486-3491, 2003.

Meiers et al., The anthocyanidins cyaniding and delphindin are potent inhibitors of the epidermal growth-factor receptor. J. Agric. Food Chem., 49:958-962, 2001.

Nesselhut et al., Studies on mammary carcinoma cells regarding the proliferation potential of herbal medication with estrogen-like effects. Archives of Gynecology and Obstetrics, 254:817-818, 1993.

Pedersen et al., The triterpenoid CDDO induces apoptosis in refractory CLL B cells. Blood, 8:2965-2972, 2002.

Pisha et al., Discovery of betulinic acid as a selective inhibitor of human melanoma that functions by induction of apoptosis. Nat. Med., 1:1046-1051, 1995.

Sakurai et al., Antitumor agents 220. Antitumor-promoting effects of cimigenol and related compounds on Epstein-Barr virus activation and two-stage mouse skin carcinogenesis. Bioorg. Med. Chem. 11:1137-1140, 2003.

Sgambato et al., Overexpression of p27 (Kip1) inhibits the growth of both normal and transformed human mammary epithelial cells. Cancer Research, 58:3448-3454, 1998.

Soh et al., Novel roles of specific isoforms of protein kinase C in activation of the c-fos serum response element. Molecular and Cellular Biology, 19:1313-1324, 1999.

Soh et al., Cyclic GMP mediates apoptosis induced by sulindac derivatives via activation of c-Jun NH2-terminal kinase 1. Clin. Cancer Res., 10:4136-4141, 2000.

Soriano et al., Synergistic effects of new chemoprotective agents and conventional cytotoxic agents against human lung cancer cell lines. Cancer Res., 59:61, 78-84, 1999.

Sporn and Suh, Chemoprevention of Cancer. Carcinogenesis, 21:525-530, 2000.

Stadheim et al., The novel triterpenoid 2-cyano-3,12-dioxooleana-1,9-dien-28-oic acid (CDDO) potently enhances apoptosis induced by tumor necrosis factor in human leukemia cells. J. Biol. Chem., 19:16448-16455, 2002.

Stoll, W., Phytotherapy influences atrophic vaginal epithelium: double-blind study—cimicifuga vs. estrogenic substances. Therapeuticum, 1:23-31, 1987.

Suh et al., Novel triterpenoids suppress inducible nitric oxide synthase (iNOS) and inducible cyclooxygenase (COX-2) in mouse macrophages. Cancer Res., 58:717-723, 1998.

Suh et al., A novel synthetic oleanane triterpenoid, 2-cyano-3,12-dioxoolean-1,9-dien-28-oic acid, with potent differentiating, antiproliferative, and anti-inflammatory activity. Cancer Res., 59:336-341, 1999.

Suzui et al., Growth inhibition of human hepatoma cells by acyclic retinoid is associated with induction of p21 (CIP1) and inhibition of expression of cyclin D1. Cancer Research, 62:3997-4006, 2002.

Tsutsui et al., Prognostic value of c-erbB2 expression in breast cancer. J. Surg. Oncol., 79:216-233, 2002.

Wang et al., A synthetic triterpenoid, 2-cyano-2,12-dioxooleana-1,9-dien-28-oic acid (CDDO), is a ligand for the peroxisome proliferators-activated receptor gamma. Mol. Endocrinol., 14:1550-1556, 2000.

Watanabe et al., Cycloartane glycosides from the rhizomes of Cimicifuga racemosa and their cytotoxic activities. Chem. Pham. Bull., 50:121-125, 2002, Sep. 19, 2016.

Weinstein, I. B., Disorders in cell circuitry during multistage carcinogenesis: the role of homeostasis. Carcinogenesis, 5:857-864, 2000.

Zheng et al., Cimipure (Cimicifuga racemosa): a standardized black cohosh extract with novel triterpene glycoside for menopausal women. In Phytochem. Phytopharm., Shahidi and Ho, eds. (Champaign, IL: AOCS Press, 2000) pp. 360-370.

Boik J., Natural Compounds in Cancer Therapy. Oregon Medical Press: Princeton, 2001.

Baselga J., et al., Recombinant humanized anti-HER2 antibody (Herceptin) enhances the antitumor activity of paclitaxel and doxorubicin against HER2/neu overexpressing human breast cancer xenografts. Cancer Res. 58:2825-2831, 1998.

Davis V., et al., Effects of black cohosh on mammary tumor development and progression in MMTV-neu transgenic mice. American Association for Cancer Research, vol. 44, 2nd ed., Jul. 2003 (Abstract No. R910).

Dog, TL: Black Cohosh. 2000 In: 7th Annual Course Botanical Medicine in Modern Clinical Practice, New York, May 20-24, 2002, p. 556.

Goluboff ET, et al., Exisulind (sulindac sulfone) suppresses growth of human prostate cancer in a nude mouse xenograft model by increasing apoptosis. Urology, 53:440-445, 1999.

Hsu H-Y, et al., Oriental Materia Medica: A concise Guide. Keats Publishing, Inc., New Canaan, 1986.

Kellof GJ, et al., Cancer chemoprevention: progress and promise. Eur. J. Cancer, 14:2031-2038, 1999.

Kennelly EJ, et al., Introduction of quinine reductase by withanolides isolated from Physalis philadelphia (tomatillos). J. Agric. Food Chem., 45:3771-3777, 1997.

Liske E. Therapeutic efficacy and safety of Cimicifuga racemosa for gynecologic disorders. Adv. Nat. Ther., 15:45-52, 1998.

Nesselhut T., Antitumor use of an extract from Cimicifuga racemosa. Patent Assignee: Schaper und Bruemmer G. m. b. H. un Co. K.-G., Germany, 1996.

Rockwell S., The herbal medicine black cohosh alters the response of breast cancer cells to some agents used in cancer therapy. American Association for Cancer Research, vol. 44, 2nd ed., Jul. 2003 (Abstract No. 2721).

Shirin H., et al., Antiproliferative effects of S-allylmercaptocysteine on colon cancer cells, when tested alone or in combination with sulindac sulfide. Cancer Res., 61:725-731, 2001.

(56) References Cited

OTHER PUBLICATIONS

Upton R: Black Cohosh Rhizome. In: American Herbal Pharamacoeia and Therapeutic Compendium. American Herbal Pharmacopoeia, Santa Cruz, 2002.
Yoon JT., et al., CP 248, a derivative of exisulind, caused growth inhibition, mitotic arrest, and abnormalities in microtubule polymerization in glioma cells. Mol. Cancer Ther., 6:393-404, 2002.
Zhang QW, et al., A new cycloartane saponin from Cimicifuga acerina. J. Asian Nat. Prod. Res., 2:45-49, 1999.
He, K. et al., "Direct Analysis and Identification of Triterpene Glycosides by LC/MS in Black Cohosh, Cimicifuga racemosa, and in Several Commercially Available Black Cohosh Products", Planta Medica, 66(7):635-640 (2000).
Arispe, N. et al., Heart failure drug digitoxin induces calcium uptake into cells by forming transmembrane calcium channels., Proc Natl Acad Sci USA, 105:2610-5 (2008).
Benjamin, I.J. et al., Viewing a stressful episode of ER: is ATF6 the triage nurse?, Circ Res, 98(9):1120-2 (2006).
Borowski, P. et al., Biochemical properties of a minimal functional domain . . . , Eur J. Biochem. 266(3):715-23 (1999).
Bottone, F.G., Jr. et al., Transcriptional regulation of activating transcription factor . . . , J. Pharmacol Exp Ther. 315(2):668-77 (2005).
Brinkman, K. et al., Mitochondrial toxicity induced by nucleoside-analogue . . . , Lancet, 354(9184):1112-5 (1999).
Campbell, M.J. et al., Breast Cancer Growth Prevention by Statins, Cancer Research, 66:8707-14 (2006).
Cohen, S. et al., Autoimmune hepatitis associated with the use of black cohosh: a case study, Menopause, 11(5):575-7 (2004).
Davis, V. et al., Breast Cancer . . . , Workshop on the Safety of Black Cohash in Clinical Studies, Bethesda, MD: National Institutes of Health, pp. 18-20 (2004).
de Hoon, M.J. et al., Open source clustering software, Bioinformatics, 20 (9):1453-4 (2004).
Deane, N. et al., Hepatocellular Carcinoma Results from Chronic Cyclin D1 Overexpression in Transgenic Mice, Cancer Research, 61:5389-95 (2001).
Einbond, L.S. et al., Actein and a fraction of black cohosh potentiate antiproliferative effects . . . , Planta Med., 72:1200-6 (2006).
Einbond, L.S. et al., Gene expression analysis of the mechanisms whereby black cohosh inhibits human breast cancer cell growth, Anticancer Res., 27(2):697-712 (2007).
Einbond, L.S. et al., Growth inhibitory activity of extracts and purified components of black cohosh on human breast cancer cells, Breast Cancer Res Treat, 83(3):221-31 (2004).
Einbond, L.S. et al., Growth inhibitory activity of extracts and compounds from Cimicifuga species on human breast cancer cells, Phytomedicine, 15:504-511 (2008).
Einbond, L.S. et al., The growth inhibitory effect of actein on human breast cancer cells . . . , Int J Cancer, 121(9):2073-83 (2007).
Einbond, L.S. et al., Actein inhibits the Na+-K+-ATPase and enhances the growth inhibitory effect . . . , Biochem. Biophys. Res. Commun., 375:608-613 (2008).

Esserman, L. et al., Breast cancer inhibition by statins, 2004 ASCO Annual Meeting Proceedings (Post-Meeting Ed.), Journal of Clinical Oncology, 22(Jul. 15 Suppl.):1003 (2004).
Fan, F. et al., ATF3 induction following DNA damage is regulated by distinct signaling pathways and over-expression . . . , Oncogene, 21:7488-96 (2002).
Fielden, M.R. et al., Preclinical drug safety analysis by chemogenomic profiling in the liver, Am J Pharmacogenomics, 5:161-71 (2005).
Ganter et al., Development of a large-scale chemogenomics database to improve . . . , J Biotechnol, 119(3):219-44 (2005).
Gaube, F. et al., Gene expression profiling reveals effects of Cimicifuga racemosa . . ., CBMC Pharmacol., 7:11 (2007).
Gorshkova, I.A. et al., Two different modes of inhibition of the rat brain Na+, K+-ATPase by . . . , Comp Biochem Physiol C Pharmacol Toxicol Endocrinol., 122:101-8 (1999).
Gorshkova, I.A. et al., Inhibition of rat brain Na+-K+-ATPase by triterpene glycosides from holothurians., Toxicon, 27(8):927-36 (1989).
Gurley et al., In vivo effects of goldenseal, kava kava, black cohosh, and valerian . . . , Clin. Pharmacol. Ther., 77:415-26 (2005).
Haas, M. et al., Involvement of Src and Epidermal Growth Factor Receptor in the Signal-transducing Function of Na+/ K+-ATPase, J. Biol. Chem, 275(36):27832-27837 (2000).
Zepelin et al. Isopropanolic black cohosh extract and recurrence-free survival after breast cancer, Int. J. Clin Pharmacol Ther, 45(3):143-54 (2007).
Harding, H.P. et al., An integrated stress response regulates amino acid metabolism and resistance to oxidative stress, Mol. Cell., 11(3):619-33 (2003).
Harding, H.P. et al., Bioactive small molecules reveal antagonism between the integrated stress response and sterol-regulated gene expression, Cell Metab 2:361-71 (2005).
Hartman, M.G. et al., Role for activating transcription factor 3 in stress-induced beta-cell apoptosis, Mol Cell Biol., 24(13):5721-32 (2004).
Hemmi et al., Inhibition of thymidine transport into phytohemagglutinin-stimulated lymphocytes by triterpenoids from Cimicifuga species, J. Pharma.-Dyn, 2:339-349 (1979).
Lavarone, A. et al., 10 proteins as targets in cancer and tools in neurobiology, Trends Mol Med., 12:588-94 (2006).
Inada, A et al. Anti-tumor promoting activities of natural products. II. Inhibitory effects of digitoxin on two-stage carcinogenesis . . . , Bioi Pharm Bull., 16(9):930-1 (1993).
Irizarry, R.A. et al., Summaries of Affymetrix GeneChip probe level data, Nucleic Acids Res., 31(4):e15 (2003).
Jiang, B. et al., Evaluation of the botanical authenticity and phytochemical profile of black cohosh products . . . , J. Agric. Food Chem., 54:3242-53 (2006).
Johnson et al., In vitro formation of quinoid metabolites of the dietary supplement Cimicifuga racemosa (black cohosh), Chem Res Toxicol, 16:838-46 (2003).
Kadowaki, K. et al., Sex differences in PPARgamma expressions in rat adipose tissues, Bioi Pharm Bull, 30(4):818-20 (2007).

* cited by examiner

| 26 hrs | ug/ml | viable |
|---|---|---|
| DMSO | | 1.00 |
| ac20 | 20 | 0.89 |
| ac40 | 40 | 0.30 |
| butanol 20 | 20 | 0.21 |
| 96 hrs | | viable |
| DMSO | | 1.00 |
| ETOAc | 12.5 | 0.64 |
| H2OMeOH | 12.5 | 0.91 |
| MHP20 | 12.5 | 0.86 |
| AM HP20 | 12.5 | 0.94 |
| Ac | 12.5 | 0.80 |
| ac | 6.25 | 1.15 |

Fibroadenoma, control, age detected 93 weeks, age at death 95 weeks

Gland: blue; connective: pink
White, Undefined, empty space or filled with secretory material or blood vessels Fibroadenoma, black cohosh 7.14 mg/kg, age detected: 89 weeks, age at death: 101 weeks Fibroadenoma, black cohosh 35.7 mg/kg, age detected: 89 weeks, age at death: 96 weeks

Localization of Lipid Accumulation

186254 - TREATED

40x
Periportal Localization

186293 - CONTROL

40x

Combination index (CI) values for MDA-MD-453 cells treated with Digitoxin plus paclitaxel (TAX).

Digitoxen (ug?ml)

| A | 0.001 | 0.01 | 0.05 | 0.1 |
|---|---|---|---|---|
| 0.25 | 4.18 (--) | 2.79 (--) | 2.23 (--) | 2.23 (--) |
| 0.5 | 2.42 (--) | 1.04 (+-) | 0.47 (+++) | 0.47 (+++) |
| 1 | 2.15 (--) | 0.76 (++) | 0.20 (+++) | 0.20 (+++) |
| 4 | 1.95 (--) | 0.57 (+++) | 0 (+++) | 0 (+++) |

TAX(nM)

| Symbols: | CI | |
|---|---|---|
| -- | >1.3 | Antagonism |
| - | 1.1-1.3 | moderate antagonism |
| +/- | 0.9-1.1 | additive effect |
| + | 0.8-0.9 | slight synergism |
| ++ | 0.6-0.8 | moderate synergism |
| +++ | <0.6 | synergism |

$IC_{50}$ values determined from the graphs in Fig. 4 were used to obtain combination index values:
CI = {$IC_{50}$(digitoxen + paclitaxe) / $IC_{50}$(digitoxin alone)}
+ {$IC_{50}$(paclitaxel + digitoxin) / $IC_{50}$(paclitaxel alone)}.

*FIG. 33B*

ANTI-NEOPLASTIC COMPOSITIONS COMPRISING EXTRACTS OF BLACK COHOSH

RELATED APPLICATIONS

This application is a continuation-in-part of U.S. Patent Application deposited under Express Mail label No. EQ 523728379 US, on Aug. 4, 2008 (informally designated U.S. Ser. No. 12/221,478), which is a divisional of U.S. patent application Ser. No. 10/746,960, filed on Dec. 23, 2003, which claims the benefit of U.S. Provisional Application Ser. No. 60/437,159, filed on Dec. 27, 2002, and entitled "ANTI-CANCER COMPOSITIONS OF EXTRACTS OF BLACK COHOSH". The contents of these prior applications are incorporated herein by reference in their entireties.

STATEMENT OF GOVERNMENT INTEREST

This invention was made with government support under NIH Grant Nos. 3P50 AT 00090-02S02 and NIH NCCAM 5K01AT001692-03. As such, the United States Government has certain rights in this invention.

BACKGROUND OF THE INVENTION

Black cohosh, *Actaea racemosa* L. (*Cimicifuga racemosa*), a perennial in the buttercup family (Ranunculaceae), is frequently used to treat gynecological and other conditions. In particular, the roots and rhizomes of black cohosh have been used to treat a variety of disorders, including inflammatory conditions, diarrhea, dysmenorrhea, and rheumatism; they have also been used to stimulate menstrual flow and to suppress coughs (Foster, S., Black cohosh: *Cimicifuga racemosa*. A literature review. *Herbal-Gram*, 45:35-49, 1999).

Additionally, black cohosh has been used as a natural alternative to hormone-replacement therapy. In fact, American women are increasingly turning to black cohosh as a "more natural" alternative to estrogen, in the belief that it has the benefits, without the risks, of estrogen-replacement therapy. To date, a standardized black cohosh extract (Remifemin), developed in Germany, has been studied, both in animals and in short-term clinical trials of menopausal women. These studies suggest that the extract alleviates a variety of menopausal symptoms, particularly hot flashes (Lehmann-Willenbrock and Riedel, Clinical and endocrinological examinations concerning therapy of climacteric symptoms following hysterectomy with remaining ovaries. *Zent. Bl. Gynakol.*, 110:611-18, 1988; Stoll, W., Phytotherapy influences atrophic vaginal epithelium: double-blind study—*cimicifuga* vs. estrogenic substances. *Therapeuticum*, 1:23-31, 1987). Although most studies report that black cohosh is free of significant side-effects, these studies have not been carried out for a length of time sufficient to ensure the safety of black cohosh with respect to uterine function and/or the induction or stimulation of breast cancer growth. Since the population using black cohosh (i.e., middle-aged females in developed countries) is at a higher risk for breast cancer, research is needed to clarify whether black cohosh extracts stimulate or inhibit breast cancer cells. Such studies could also identify new approaches to breast cancer prevention and treatment.

The components of the black-cohosh rhizome have been examined in several studies. It is known that the rhizome contains triterpene glycosides, aromatic acids, cinnaminic acid esters, sugars, tannins, and long-chain fatty acids (Zheng et al., CimiPure (*Cimicifuga racemosa*): a standardized black cohosh extract with novel triterpene glycoside for menopausal women. In *Phytochem. Phytopharm.*, Shahidi and Ho, eds. (Champaign, Ill.: AOCS Press, 2000) pp. 360-70). However, little is known about the mechanisms by which these compounds are metabolized in vivo.

Crude extracts of black cohosh, and several components present in black cohosh, have been shown to exhibit biological activity. Fukinolic acid (2-E-caffeoylfukiic acid) exhibited weak estrogenic activity on MCF7 cells (Kruse et al., Fukic and piscidic acid esters from the rhizome of *Cimicifuga racemosa* and the in vitro estrogenic activity of fukinolic acid. *Planta. Med.*, 65:763-64, 1999); it also inhibited the activity of neutrophil elastase, which is involved on the inflammatory process (Loser et al., Inhibition of neutrophil elastase activity by cinnamic acid derivatives from *Cimicifuga racemosa*. *Planta. Med.*, 66:751-53, 2000). Bioactivity-guided fractionation of the methanolic extract resulted in the isolation of nine antioxidant compounds. Of these, methyl caffeate was the most active in reducing menadione-induced DNA damage in cultured S30 breast cancer cells (Burdette et al., Black cohosh (*Cimicifuga racemosa* L.) protects against menadione-induced DNA damage through scavenging of reactive oxygen species: bioassay-directed isolation and characterization of active principles. *J. Agric. Food Chem.*, 50:7022-28, 2002). None of the compounds was cytotoxic to S30 cells (Burdette et al., Black cohosh (*Cimicifuga racemosa* L.) protects against menadione-induced DNA damage through scavenging of reactive oxygen species: bioassay-directed isolation and characterization of active principles. *J. Agric. Food Chem.*, 50:7022-28, 2002).

Extracts and components purified from black cohosh have also been shown to exhibit anti-cancer activity, in vitro and in vivo. Extracts of black cohosh (ethanol extract, 0.1% v/v) inhibited the growth of serum-stimulated T-47D breast cancer cells (Dixon-Shanies and Shaikh, Growth inhibition of human breast cancer cells by herbs and phytoestrogens. *Oncol. Rep.*, 6:1383-87, 1999), and, at doses starting at 2.5 µg/ml, inhibited the proliferation of the mammary carcinoma cell line, 435 (Nesselhut et al., Studies on mammary carcinoma cells regarding the proliferation potential of herbal medication with estrogen-like effects. *Archives of Gynecology and Obstetrics*, 254:817-18, 1993). Furthermore, isopropanolic extracts of black cohosh inhibited estrogen-induced proliferation of MCF7 cells, and enhanced the inhibitory effect of tamoxifen (Bodinet and Freudenstein, Influence of *Cimicifuga racemosa* on the proliferation of estrogen receptor-positive human breast cancer cells. *Breast Cancer Research and Treatment*, 76:1-10, 2002).

More recently, it has been shown that cycloartane glycosides isolated from black cohosh inhibit the growth of human oral squamous cell carcinoma cells (Watanabe et al., Cycloartane glycosides from the rhizomes of *Cimicifuga racemosa* and their cytotoxic activities. *Chem. Pharm. Bull.*, 50:121-25, 2002). Additionally, recent studies by Sakurai et al. have indicated that triterpene glycosides and aglycones— the most active of which is cimigenol—inhibit Epstein-Barr virus early antigen activation (induced by 12-O-tetradecanoylphorbol-13-acetate) in Raji cells (Sakurai et al., Antitumor agents 220. Antitumor-promoting effects of cimigenol and related compounds on Epstein-Barr virus activation and two-stage mouse skin carcinogenesis. *Bioorg. Med. Chem.* 11:1137-40, 2003). Cimigenol has also been shown to inhibit mouse skin tumor promotion using DMBA as an initiator and TPA as a promoter.

All of the foregoing studies, however, have been limited in scope, and have not addressed issues of specificity and mechanism of action.

SUMMARY OF THE INVENTION

The invention disclosed herein generally relates to the effects of extracts of black cohosh on the growth and progression of the cell cycle, and on the expression of proteins involved in cell-cycle control in cancer-cell lines. More particularly, the present invention relates to the effects of actein and triterpene-glycoside extracts of black cohosh on neoplastic cells—when used alone or in combination with a chemopreventive or chemotherapeutic agent.

Accordingly, in one aspect, the present invention provides a composition for use in treating or preventing neoplasia, comprising an effective anti-neoplastic amount of an ethyl acetate extract of black cohosh.

In another aspect, the present invention provides a combination of anti-neoplastic agents, comprising an effective anti-neoplastic amount of an ethyl acetate extract of black cohosh and an effective anti-neoplastic amount of at least one additional chemopreventive or chemotherapeutic agent. In one embodiment of the invention, the combination is a synergistic combination.

In a further aspect, the present invention provides a composition for use in treating or preventing neoplasia, comprising an effective anti-neoplastic amount of actein. In one embodiment, the composition further comprises an effective anti-neoplastic amount of at least one additional chemopreventive or chemotherapeutic agent.

In yet another aspect, the present invention provides a method for treating or preventing neoplasia in a subject, by administering to the subject an amount of an ethyl acetate extract of black cohosh effective to treat or prevent the neoplasia.

In still another aspect, the present invention provides a method for treating or preventing neoplasia in a subject, by administering to the subject an amount of an ethyl acetate extract of black cohosh effective to treat or prevent the neoplasia, in combination with an amount of at least one additional chemopreventive or chemotherapeutic agent effective to treat or prevent the neoplasia. In one embodiment of the invention, a synergistic anti-neoplastic effect results.

Furthermore, the present invention provides a method for treating or preventing neoplasia in a subject, comprising administering to the subject an amount of actein effective to treat or prevent the neoplasia. In one embodiment, the method further comprises administering to the subject an amount of at least one additional chemopreventive or chemotherapeutic agent effective to treat or prevent the neoplasia.

Additional aspects of the present invention will be apparent in view of the description that follows.

BRIEF DESCRIPTION OF THE FIGURES

FIG. 2A shows the effect of the ethyl acetate extract when MCF7 cells were treated with the indicated concentrations of the ethyl acetate fraction for increasing times. FIG. 2B shows the effect of actein when MCF7 cells were treated with the indicated concentrations of actein for increasing times. In each case, the number of viable cells was determined using a Coulter Counter, and the control contained 0.08% DMSO. Bars=SD

FIG. 11 shows the effects of butanol fractions from black cohosh on cell proliferation in MCF7 cells. MCF7 cells were exposed to increasing concentrations of the indicated purified components, for 26 or 96 h, and the number of viable cells was determined using a Coulter Counter.

DETAILED DESCRIPTION OF THE INVENTION

Figure 1:
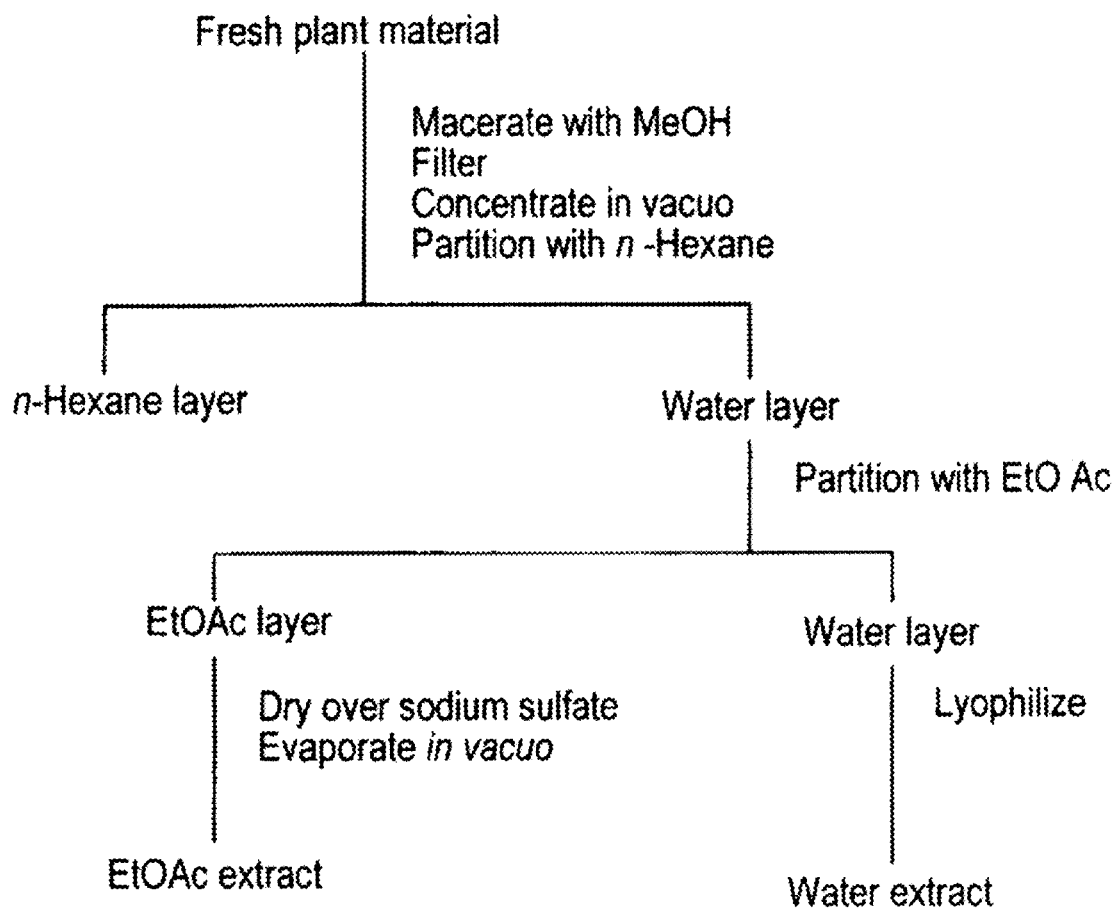
FIG. 1 is an illustration of the methods of the invention which were used to fractionate black cohosh.

The Examples below provide the first detailed examination of the effects on human breast cancer cells of extracts and purified compounds present in black cohosh. In these studies, the roots and rhizomes of black cohosh were extracted with MeOH/H$_2$O, and fractionated by solvent-solvent partitioning to yield three fractions: hexane, ethyl acetate (EtOAc), and H$_2$O. The EtOAc fraction exhibited the greatest growth-inhibitory activity. This fraction inhibited growth of both the ER+ MCF7 and ER−/Her2+MDA-MB-453 human breast cancer cell lines, with IC$_{50}$ values of about 18 µg/ml and 10 µg/ml, respectively. The normal human mammary epithelial cell line, MCF10F, was much less sensitive to growth inhibition by this extract (with an IC$_{50}$ value of 46 µg/ml). It is possible that the greater sensitivity of the malignant cells may reflect, in part, the difference in growth rates of the malignant and non-malignant cells.

The inventors tested the effects of crude extracts, methanol and ethanol, as well as ethanol extracts provided by Pure World, native and plus expedient: the IC$_{50}$ values for these extracts after 96 hours of treatment were: methanol: 100 µg/ml; ethanol: >200 µg/ml; Pure World native: 175 µg/ml; and Pure World plus expedient: 195 µg/ml. To partition the phytochemicals according to polarity, the water portion was also partitioned sequentially with hexane and n-butanol (n-BuOH). The n-BuOH fraction was tested for its effect on the growth of MDA-MB-453 breast cancer cells. The IC50 value after 96 hours of treatment was: 40 µg/ml.

The inventors also examined the effects of the EtOAc fraction of black cohosh on SW480 human colon cancer cells. The IC50 values after 48 hours of incubation using the MTT assay were: SW480: 42 µg/ml; MCF7: 38 µg/ml (Luo et al., PM-3, a benzo-g-pyran derivative isolated from propolis, inhibits growth of MCF-7 human breast cancer cells. Anticancer Res 21: 1665-1672, 2001).

The inventors further demonstrated that the EtOAc fraction of black cohosh induced cell-cycle arrest in MCF7 human breast cancer cells at G1 at 30 µg/ml, and at G2/M at 60 µg/ml. The triterpene glycoside fraction that was obtained by polyamide column chromatography, and the specific triterpene glycosides (actein, 23-epi-26-deoxy-actein, and cimiracemoside A), inhibited growth of MCF7 human breast cancer cells and induced cell-cycle arrest at G1. At 60 µg/ml, actein induced a less-pronounced G1 arrest. Therefore, it is likely that, at high concentrations, actein and related compounds affect proteins that regulate later phases in the cell cycle.

Because the triterpene glycosides induced cell-cycle arrest at G1, the inventors decided to ascertain the effect of the most potent compound, actein, on cell-cycle proteins that control G1 cell-cycle progression. As discussed below, actein decreased the level of cyclin D1, cdk4, and the hyperphosphorylated form of pRb, and increased the level of the cdk inhibitory protein, p21$^{cip1}$, in MCF7 cells—changes that may contribute to the arrest in G1. The inventors also found that actein reduced the level of cyclin D1 mRNA within 3 h of treatment, and significantly reduced the level at 24 h, suggesting an effect at the level of transcription. The level of the EGFR was not altered after treatment with actein; nor was there a consistent effect on the level of the phosphorylated form of the EGFR (p-EGFR), which reflects its state of activation. Thus, the EGFR did not appear to be a direct target for actein. This result is in contrast to the effect of another plant-derived compound—a flavonol, epigallocatechin-gallate—which is the active component in green tea (Masuda et al., Effects of epigallocatechin-β-gall-ate on growth, epidermal growth factor receptor signaling pathways, gene expression, and chemosensitivity in human head and neck squamous cell carcinoma cell lines. *Clinical Cancer Research*, 7:4220-29, 2001). Previous studies have also indicated that micromolar concentrations of the aglycone compounds, cyanidin and delphinidin, inhibited activation of the EGFR and cell proliferation in the human vulva carcinoma cell line, A431, whereas the corresponding glycosides had a minimal effect (Meiers et al., The anthocyanidins cyanidin and delphinidin are potent inhibitors of the epidermal growth-factor receptor. J. Agric. Food Chem., 49:958-62, 2001). The inventors tested the effects of the aglycone cimigenol on the growth of human breast cancer cells. Cimigenol was less active than cimigenol glycoside.

Triterpene molecules are structurally related to steroids, and have been present in the plant kingdom for millions of years. Some may have evolved to become ligands for receptors on animal cells (Sporn and Suh, Chemoprevention of cancer. *Carcinogenesis*, 21:525-30, 2000). However, the mode of action triterpene glycosides is not well understood. Studies by Haridas et al. (Avicins: triterpenoid saponins from *Acacia victoriae* (Bentham) induce apoptosis by mitochondrial perturbation. *Proc. Natl. Acad. Sci. USA*, 98:5821-26, 2001) indicate that avicins—triterpenoid saponins from the plant *Acacia victoriae* (Bentham)—are potent inhibitors of the transcription factor, nuclear factor kappa B (NF-κB), and act by inhibiting its translocation to the nucleus and its capacity to bind DNA-perhaps by altering sulfhydryl groups critical for NF-κB activation. Betulinic acid, a pentacyclic triterpene present in the bark of white birch trees, is a selective inhibitor of human melanoma (Pisha et al., Discovery of betulinic acid as a selective inhibitor of human melanoma that functions by induction of apoptosis. *Nat. Med.*, 1:1046-51, 1995). It induces apoptosis in neuroectodermal tumors by a direct effect on mitochondria (Fulda and Debatin, Betulinic acid induces apoptosis through a direct effect on mitochondria in neuroectodermal tumors. *Med. Pediatr. Oncol.*, 35:616-18, 2000).

Suh et al. (Novel triterpenoids suppress inducible nitric oxide synthase (iNOS) and inducible cyclooxygenase (COX-2) in mouse macrophages. *Cancer Res.*, 58:717-23, 1998) have generated a series of derivatives of the triterpenes, oleanic and ursolic acids, that are highly potent in suppressing the expression of inducible nitric oxide synthase and cyclooxygenase-2 in primary mouse macrophages. Indeed, the derivative, 2-cyano-3,12-dioxooleana-1,9-dien-28-oic acid (CDDO), is 1000 times more potent than oleanic acid in this cell system (Sporn and Suh, Chemoprevention of cancer. *Carcinogenesis*, 21:525-30, 2000). Suh et al. also found that CDDO displays potent differentiating, anti-proliferative, and anti-inflammatory activities (Suh et al., A novel synthetic oleanane triterpenoid, 2-cyano-3,12-dioxoolean-1,9-dien-28-oic acid, with potent differentiating, antiproliferative, and anti-inflammatory activity. *Cancer Res.*, 59:336-41, 1999).

CDDO further induces apoptosis by a caspase-8-dependent mechanism (Ito et al., The novel triterpenoid CDDO induces apoptosis and differentiation of human osteosarcoma cells by a caspase-8 dependent mechanism. *Mol. Pharmacol.*, 5:1094-99, 2001; Pedersen et al., The triterpenoid CDDO induces apoptosis in refractory CLL B cells. *Blood*, 8:2965-72, 2002), and inhibits NF-κB-mediated gene expression, following translocation of the activated form to the nucleus (Stadheim et al., The novel triterpenoid 2-cyano-3,12-dioxooleana-1,9-dien-28-oic acid (CDDO) potently enhances apoptosis induced by tumor necrosis factor in human leukemia cells. *J. Biol. Chem.*, 19:16448-55, 2002). It is a ligand for the peroxisome proliferator activated receptor-γ (PPAR-γ) (Wang et al., A synthetic triterpenoid, 2-cyano-2,12-dioxooleana-1,9-dien-1-28-oic acid (CDDO), is a ligand for the peroxisome proliferator-activated receptor gamma. *Mol. Endocrinol.*, 14:1550-56, 2000), but the specific cellular target of CDDO and related compounds, for mediating the above biologic effects, is not known.

The triterpene glycoside, actein, and the fraction of black cohosh enriched for triterpene glycosides (which are selective for human breast cancer versus normal mammary epithelial cells), synergize with several classes of chemotherapy agents. For example, the inventors have demonstrated that actein has synergy with the taxane, paclitaxel; the antimetabolite, 5-fluorouracil (5-FU); the Her2 antibody, herceptin; the anthracycline antibiotic, doxorubicin; and the platinum analog, cisplatin. Additionally, the inventors have shown that black cohosh extracts have synergy with paclitaxel and doxorubicin. Because it is easier to prepare enriched extracts, the extracts of black cohosh might represent the preferred sources to be used in combination with such chemotherapeutic agents.

In view of the foregoing, the present invention provides methods for treating and preventing neoplasia in a subject. The subject is preferably a mammal (e.g., humans, domestic animals, and commercial animals, including cows, dogs, monkeys, mice, pigs, and rats). More preferably, the subject is a human.

As used herein, "neoplasia" refers to the uncontrolled and progressive multiplication of cells under conditions that would not elicit, or would otherwise cause cessation of, the multiplication of normal or non-neoplastic cells. Neoplasia results in the formation of a neoplasm, which is any new and abnormal growth, particularly a new growth of tissue, in which the growth is uncontrolled and progressive. Malignant neoplasms are distinguished from benign in that the former show a greater degree of anaplasia, or loss of differentiation and orientation of cells, and have the properties of invasion and metastasis. Thus, neoplasia includes "cancer", which refers herein to a proliferation of cells having the unique trait of loss of normal controls, resulting in unregulated growth, lack of differentiation, local tissue invasion, and metastasis (Beers and Berkow, eds., *The Merck Manual of Diagnosis and Therapy*, 17th ed. (Whitehouse Station, N.J.: Merck Research Laboratories, 1999) 973-74, 976, 986, 988, 991).

Neoplasias which may be treated and/or prevented by the methods of the present invention include, without limitation, carcinomas, particularly those of the bladder, breast, cervix, colon, head, kidney, lung, neck, ovary, prostate, and stomach; lymphocytic leukemias, particularly acute lymphoblastic leukemia and chronic lymphocytic leukemia; myeloid leukemias, particularly acute monocytic leukemia, acute promyelocytic leukemia, and chronic myelocytic leukemia; malignant lymphomas, particularly Burkitt's lymphoma and Non-Hodgkin's lymphoma; malignant melanomas; myeloproliferative diseases; sarcomas, particularly Ewing's sarcoma, hemangiosarcoma, Kaposi's sarcoma, liposarcoma, peripheral neuroepithelioma, and synovial sarcoma; and mixed types of neoplasias, particularly carcinosarcoma and Hodgkin's disease. Preferably, the methods of the present invention are used to treat or prevent breast cancer, colon cancer, leukemia, lung cancer, malignant melanoma, ovarian cancer, or prostate cancer. More preferably, the cancer is breast cancer. Liver cancer can also be treated and/or prevented by the methods of the invention.

The method of the present invention comprises administering to the subject an ethyl acetate extract of black cohosh or a composition comprising actein. It is well known that black cohosh is a medicinal plant from the genus *Cimicifuga* (or *Actea*) and the species *racemosa*. The ethyl acetate extract of black cohosh is a partially-purified extract, enriched for triterpene glycosides. It is a safe and effective extract, with few side effects. The ethyl acetate extract of black cohosh may be prepared in any suitable manner that maintains or enriches the triterpene glycosides component in the extract. By way of example, the method of extraction may comprise a first extraction of the rhizome of black cohosh, with an aqueous solution of a lower alkyl alcohol, followed by partitioning of the aqueous alcohol layer with a lower alkyl acetate. A preferred lower alkyl alcohol is methanol, and a preferred lower alkyl acetate is ethyl acetate. The resultant extract comprises triterpene glycoside compounds and cinnamic acid esters. Of interest to the invention are the triterpene glycosides, which can be separated from the cinnamic acid esters by purification of the ethyl acetate extract. Such triterpene glycosides include, without limitation, actein, cimifugoside, cimigenol glycoside, cimiracemoside A, 23-epi-26-deoxyactein and the aglycone cimigenol. Preferably, the triterpene glycoside compound is actein.

The individual triterpenoid components in the ethyl acetate extract of black cohosh can be individually separated by purification. The ethyl acetate extract may be maintained in any form, provided that the activity of the triterpene glycosides, and of each component therein, is maintained. Activity of the triterpene glycosides may be assayed by reference to the Examples presented below. Furthermore, actein and related triterprene glycosides may be modified to increase their activity, while retaining their selectivity for neoplastic cells.

In accordance with the method of the present invention, the ethyl acetate extract of black cohosh may be administered to the subject in an anti-neoplastic amount, which is an amount that is effective to treat or prevent neoplasia in the subject. As used herein, "anti-neoplastic" includes the ability to inhibit or prevent the development or spread of a neoplasm, and the ability to limit, suspend, terminate, or otherwise control the development, maturation, and proliferation of cells in a neoplasm. As further used herein, an amount of the ethyl acetate extract of black cohosh that is "effective to treat or prevent the neoplasia" is an amount that is effective to ameliorate or minimize the clinical impairment or symptoms of the neoplasia, or to inhibit their development. For example, the clinical impairment or symptoms of the neoplasia may be ameliorated or minimized by diminishing any pain or discomfort suffered by the subject; by extending the survival of the subject beyond that which would otherwise be expected in the absence of such treatment; by inhibiting or preventing the development or spread of the neoplasm; or by limiting, suspending, terminating, or otherwise controlling the development, maturation, and proliferation of cells in the neoplasm.

Exemplary doses of actein, administered intraperitoneally, may be between about 0.5 µg/ml and about 40.0 µg/ml, and preferably, between about 1 µg/ml and about 3.0 µg/ml. However, the amount of actein effective to treat or prevent neoplasia or other disorders in a subject will vary depending on the particular factors of each case, including the target molecule, the type of neoplasia, the stage of neoplasia, the subject's weight, the severity of the subject's condition, and the method of administration. These amounts can be readily determined by the skilled artisan, based upon known procedures, including analysis of titration curves established in vivo, dose-response experiments analogous to those provided in the Examples, and methods and assays disclosed herein.

The ethyl acetate extract of black cohosh or the actein composition may be administered to a human or animal subject by known procedures, including, without limitation, oral administration, parenteral administration, transdermal administration, and by way of catheter. Preferably, the ethyl acetate extract of black cohosh or the actein composition is administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual injection.

For oral administration, a formulation comprising the ethyl acetate extract of black cohosh or the actein composition may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, *acacia*, corn starch, and gelatins. Additionally, the formulation may be presented with disintegrators, such as corn starch, potato starch, and sodium carboxymethylcellulose. The formulation also may be presented with dibasic calcium phosphate anhydrous or sodium starch glycolate. Finally, the formulation may be presented with lubricants, such as talc and magnesium stearate.

For parenteral administration (i.e., administration by injection through a route other than the alimentary canal), the ethyl acetate extract of black cohosh or the actein composition may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, and sublingual.

For transdermal administration, the ethyl acetate extract of black cohosh or the actein composition may be combined with skin penetration enhancers, such as propylene glycol, polyethylene glycol, isopropanol, ethanol, oleic acid, N-methylpyrrolidone, and the like, which increase the permeability of the skin to the ethyl acetate extract of black cohosh, and permit the ethyl acetate extract of black cohosh to penetrate through the skin and into the bloodstream. The ethyl acetate extract of black cohosh, or the actein composition, /enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in a solvent, such as methylene chloride, evaporated to the desired viscosity, and then applied to backing material to provide a patch.

In accordance with the method of the present invention, the ethyl acetate extract of black cohosh or the actein composition also may be administered to a subject by way of a pharmaceutical composition for use in treating or preventing neoplasia. The pharmaceutical composition of the present invention comprises an effective anti-neoplastic amount of the ethyl acetate extract of black cohosh or an effective amount of the actein composition and a pharmaceutically-acceptable carrier. The pharmaceutically-acceptable carrier must be "acceptable" in the sense of being compatible with the other ingredients of the composition, and not deleterious to the recipient thereof. The pharmaceutically-acceptable carrier employed herein is selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

In the pharmaceutical composition of the present invention, the ethyl acetate extract of black cohosh is provided in an effective anti-neoplastic amount. For example, where the ethyl acetate extract comprises actein, the actein may be present in an amount between about 0.5 µg/ml and about 40.0 µg/ml. Preferably, the actein is present in an amount between about 1.0 µg/ml and about 3.0 µg/ml.

The pharmaceutical composition of the present invention may be prepared by methods well-known in the pharmaceutical arts. Actein may be obtained from plant extracts or by chemical synthesis. For example, the ethyl acetate extract of black cohosh may be brought into association with a carrier or diluent, as a suspension or solution. Optionally, one or more accessory ingredients (e.g., buffers, flavoring agents, surface active agents, and the like) also may be added. The choice of carrier will depend upon the route of administration.

Since multiple genetic and epigenetic targets are altered in the process of carcinogenesis, combination chemoprevention and chemotherapy are generally optimal. Accordingly, the present invention further provides a method for treating or preventing neoplasia in a subject, by administering to the subject an amount of an ethyl acetate extract of black cohosh or the actein composition, as described above, in combination with an amount of at least one additional chemopreventive or chemotherapeutic agent effective to treat or prevent the neoplasia. As used herein, the term "effective" also covers the dosages at which the chemopreventive or chemotherapeutic agent by itself does not have any significant effect on neoplasia but may significantly promote or enhance the anti-neoplastic effects of the ethyl acetate extract of black cohosh, and vice-versa.

Examples of additional chemopreventive or chemotherapeutic agents for use in the method of the present invention include, without limitation cisplatin, docetaxel, doxorubicin, 5-fluorouracil (5-FU), herceptin, paclitaxel, tamoxifen, and vinblastine, and any fragments, analogues, and derivatives thereof. In a preferred embodiment, the chemopreventive or chemotherapeutic agent is paclitaxel. Ethyl acetate extracts of black cohosh, and additional chemopreventive or chemotherapeutic agents, are referred to herein as "anti-neoplastic agents."

By way of example, the term "paclitaxel" includes a natural or synthetic functional variant of paclitaxel which has paclitaxel biological activity, as well as a fragment of paclitaxel having paclitaxel biological activity.

As used herein, the term "paclitaxel biological activity" refers to paclitaxel activity which interferes with cellular mitosis by affecting microtubule formation and/or action, thereby producing antimitotic and anti-neoplastic effects. Methods of preparing paclitaxel and its analogues and derivatives are well-known in the art, and are described, for example, in U.S. Pat. Nos. 5,569,729; 5,565,478; 5,530,020; 5,527,924; 5,484,809; 5,475,120; 5,440,057; and 5,296,506.

Paclitaxel and its analogues and derivatives are also available commercially. For example, synthetic paclitaxel can be obtained from Bristol-Myers Squibb Company, Oncology Division (Princeton, N.J.), under the registered trademark Taxol™. Moreover, paclitaxel may be synthesized in accordance with known organic chemistry procedures that are readily understood by one skilled in the art. Taxol for injection may be obtained in a single-dose vial, having a concentration of 30 mg/5 ml (6 mg/ml per 5 ml) (Physicians' Desk Reference, 54$^{th}$ ed. (Montvale, N.J.: Medical Economics Company, Inc., 2000) 307, 682).

Paclitaxel and its analogues and derivatives have been used successfully to treat leukemias and tumors. In particular, paclitaxel is useful in the treatment of breast, lung, and ovarian cancers. Since paclitaxel is frequently utilized in the treatment of human cancers, a strategy to enhance its utility in the clinical setting, by combining its administration with that of an ethyl acetate extract of black cohosh, may be of great benefit to many subjects suffering from malignant neoplasias, particularly advanced cancers.

In the method of the present invention, administration of an ethyl acetate extract of black cohosh "in combination with" one or more additional chemopreventive or chemotherapeutic agents refers to co-administration of the anti-neoplastic agents. Co-administration may occur concurrently, sequentially, or alternately. Concurrent co-administration refers to administration of the anti-neoplastic agents at essentially the same time. For concurrent co-administration, the courses of treatment with the ethyl acetate extract of black cohosh, and with the one or more additional chemopreventive or chemotherapeutic agents, may be run simultaneously. For example, a single, combined formulation, containing both an amount of the ethyl acetate extract of black cohosh and an amount of the additional chemopreventive or chemotherapeutic agent, in physical association with one another, may be administered to a subject. By way of example, the single, combined formulation may consist of a liquid mixture, containing amounts of both anti-neoplastic agents, which may be injected into a subject, or an oral formulation, containing amounts of both anti-neoplastic agents, which may be orally administered to a subject.

It is also within the confines of the present invention that an amount of the ethyl acetate extract of black cohosh, and an amount of the one or more additional chemopreventive or chemotherapeutic agents, may be administered concurrently to a subject, in separate, individual formulations. Accordingly, the method of the present invention is not limited to concurrent co-administration of the anti-neoplastic agents in physical association with one another.

In the method of the present invention, the ethyl acetate extract of black cohosh, and the one or more additional chemopreventive or chemotherapeutic agents, also may be co-administered to a subject in separate, individual formulations that are spaced out over a period of time, so as to obtain the maximum efficacy of the combination. Administration of each drug may range in duration from a brief, rapid administration to a continuous perfusion. When spaced out over a period of time, co-administration of the anti-neoplastic agents may be alternate or sequential. For alternate co-administration, partial courses of treatment with the ethyl acetate extract of black cohosh may be alternated with partial courses of treatment with the one or more additional chemopreventive or chemotherapeutic agents, until a full treatment of each drug has been administered. For sequential co-administration, one of the anti-neoplastic agents is separately administered, followed by the other. For example, a full course of treatment with the ethyl acetate extract of black cohosh may be completed, and then may be followed by a full course of treatment with the one or more additional chemopreventive or chemotherapeutic agents. Alternatively, for sequential co-administration, a full course of treatment with the one or more additional chemopreventive or chemotherapeutic agents may be completed, then followed by a full course of treatment with the ethyl acetate extract of black cohosh.

The anti-neoplastic agents of the present invention (i.e., the ethyl acetate extract of black cohosh or the actein composition and the one or more additional chemopreventive or chemotherapeutic agents, either in a single, combined formulation, or in separate, individual formulations) may be administered to a human or animal subject by known procedures, including, but not limited to, oral administration, parenteral administration, and transdermal administration, as described above. Preferably, the anti-neoplastic agents of the present invention are administered orally or intravenously. For oral administration, the formulations of the ethyl acetate extract of black cohosh or the actein composition and the one or more additional chemopreventive or chemotherapeutic agents (whether individual or combined) may be presented as capsules, tablets, powders, granules, as a suspension, or in any other form described herein. For parenteral administration, the formulations of the ethyl acetate extract of black cohosh or the actein composition and the one or more additional chemopreventive or chemotherapeutic agents (whether individual or combined) may be combined with a sterile aqueous solution which is preferably isotonic with the blood of the subject. Such formulations may be prepared in accordance with methods described herein. For transdermal administration, the formulations of the ethyl acetate extract of black cohosh or the actein composition and the one or more additional chemopreventive or chemotherapeutic agents (whether individual or combined) may be combined with skin penetration enhancers, such as propylene glycol, polyethylene glycol, isopropanol, ethanol, oleic acid, N-methylpyrrolidone, and the like, and prepared in accordance with methods described herein.

Additionally, in accordance with the method of the present invention, the ethyl acetate extract of black cohosh or the actein composition and the one or more additional chemopreventive or chemotherapeutic agents are administered to a subject in amounts effective to treat or prevent neoplasia and other disorders in the subject. As discussed above, exemplary doses of actein may range from about 0.5 μg/ml to about 40.0 μg/ml; exemplary doses of paclitaxel, for example, may range from 0.5 nM to about 5.0 nM. However, the amounts of the ethyl acetate extract of black cohosh, or the actein composition, and the one or more additional chemopreventive or chemotherapeutic agents, that are effective to treat or prevent neoplasia in a subject will vary depending on the particular factors of each case, including the type and stage of disorders (e.g. neoplasia), the subject's weight, the severity of the subject's condition, and the method of administration. These amounts can be readily determined by the skilled artisan, based upon known procedures, including analysis of titration curves established in vivo, dose-response experiments analogous to those provided in the Examples, and methods and assays disclosed herein.

In one embodiment of the present invention, an ethyl acetate extract of black cohosh or the actein composition is administered to a subject in combination with at least one additional chemopreventive or chemotherapeutic agent, such that a synergistic anti-neoplastic effect is produced. As used herein, a "synergistic anti-neoplastic effect" refers to a greater-than-additive anti-neoplastic effect which is produced by a combination of two drugs, and which exceeds that which would otherwise result from individual administration of either drug alone.

In the method of the present invention, combination therapy using an ethyl acetate extract of black cohosh or the actein composition and at least one additional anti-neoplastic agent preferably results in an anti-neoplastic effect that is greater than additive, as determined by any of the measures of synergy known in the art. One measure of synergy between two drugs is the fractional inhibitory concentration (FIC) (Hall et al., The fractional inhibitory concentration (FIC) index as a measure of synergy. *J. Antimicrob. Chemother.*, 11(5):427-33, 1983). This fractional value is determined by expressing the $IC_{50}$ of a drug acting in combination, as a function of the $IC_{50}$ of the drug acting alone. For two interacting drugs, the sum of the FIC value for each drug represents the measure of synergistic interaction. Where the FIC is less than 1, there is synergy between the two drugs. An FIC value of 1 indicates an additive effect. The smaller the FIC value, the greater the synergistic interaction.

Another measurement of synergy is the combination index (CI) method of Chou and Talalay (Quantitative analysis of dose-effect relationships: the combined effects of multiple drugs or enzyme inhibitors. *Adv. Enzyme Regul.*, 22:27-55, 1984), which is based on the median-effect principle. This method calculates the degree of synergy, additivity, or antagonism between two drugs at various levels of cytotoxicity. Where the CI value is less than 1, there is synergy between the two drugs. Where the CI value is 1, there is an additive effect, but no synergistic effect. CI values greater than 1 indicate antagonism. The smaller the CI value, the greater the synergistic effect.

As the inventors have demonstrated herein, administration of an ethyl acetate extract of black cohosh, in combination with at least one additional chemopreventive or chemotherapeutic agent, frequently results (unexpectedly) in a synergistic anti-neoplastic effect, by providing greater efficacy than would result from use of either of the anti-neoplastic agents alone. In these cases, the ethyl acetate extract of black cohosh enhances the effects of the additional chemopreventive or chemotherapeutic agent; therefore, lower doses of one or both of the anti-neoplastic agents may be used in treating and preventing neoplasias, resulting in increased chemotherapeutic/chemopreventive efficacy, and decreased side-effects.

By way of example, the ethyl acetate fraction of black cohosh (2 μg/ml) may be combined with doxorubicin (0.2 μg/ml; 0.34 μM) or paclitaxel (4 nM) for a synergistic effect. Furthermore, actein (2 μg/ml; 3.0 μM) may be combined with 5-FU (0.002 μg/ml, 0.015 μM) for a synergistic effect; actein (0.2 or 2 μg/ml) may be combined with herceptin (8 μg/ml; 54 nM) for a synergistic effect; actein (1 μg/ml) may be combined with paclitaxel (1 nM) for a synergistic effect; actein (2 μg/ml; 3.0 μM) may be combined with doxorubicin (0.2 μg/ml; 0.34 μM) for a synergistic effect; actein (2 μg/ml; 2.8 μM) may be combined with tamoxifen (2 μg/ml; 5.4 μM) for a synergistic effect; actein (2 μg/ml; 3.0 μM) may be combined with cisplatin (2 μg/ml; 6.7 μM) for a synergistic effect; and actein (2 μg/ml; 3.0 μM) may be combined with vinblastine (4 μg/ml; 4.4 μM) for an additive effect. In a preferred embodiment of the present invention, actein (e.g., about 0.5 µg/ml to about 5.0 µg/ml) is administered to a subject in combination with paclitaxel (e.g., about 0.5 nM to about 5.0 nM).

As shown herein, administration of the ethyl acetate extract of black cohosh (particularly the extract containing one or more triterpene glycosides, such as actein, cimifugoside, cimigenol glycoside, cimiracemoside A, and 23-epi-26-deoxyactein), or the actein composition, in combination with one or more additional chemopreventive or chemotherapeutic agents (particularly the anti-neoplastic agents, cisplatin, docetaxel, doxorubicin, 5-fluorouracil, herceptin, paclitaxel, tamoxifen, and vinblastine), may unexpectedly result in a synergistic anti-neoplastic effect by providing greater efficacy than would result from use of either of the anti-neoplastic agents alone. Accordingly, it is also within the confines of the present invention that a formulation of the ethyl acetate extract of black cohosh or the actein composition and a formulation of the one or more additional chemopreventive or chemotherapeutic agents (whether individual or combined) may be further associated with a pharmaceutically-acceptable carrier, thereby comprising a combination of anti-neoplastic agents. In one embodiment of the invention, the combination of anti-neoplastic agents is a synergistic combination. As used herein, a "synergistic combination" of anti-neoplastic agents refers to a combination of anti-neoplastic agents that achieves a greater anti-neoplastic effect than would otherwise result if the anti-neoplastic agents were administered individually.

The formulations of the combination of the present invention may be prepared by methods well-known in the pharmaceutical arts and described herein. Exemplary acceptable pharmaceutical carriers have been discussed above. An additional carrier, Cremophor™, may be useful, as it is a common vehicle for Taxol.

In the combination of the present invention, the relative proportions of the ethyl acetate extract of black cohosh (including the triterpene glycoside compounds) or the actein composition and the one or more chemopreventive or chemotherapeutic agents will depend on the specific application of the combination. Thus, while certain proportions may be beneficial in treating one type of tumor, entirely different proportions may be beneficial in treating other tumors. Such a determination can be made by a person skilled in the art, in accordance with methods known in the art and described in the Examples provided below. Some preferred combinations, containing at least one triterpene glycoside compound in the ethyl acetate extract of black cohosh, and at least one additional chemopreventive or chemotherapeutic agent, may be formulated such that the amount of the triterpene glycoside is selected synergistically to enhance the effect of the chemopreventive or chemotherapeutic agents, while alleviating unwanted side effects attributable to such agents. Exemplary combinations comprising the ethyl acetate extract of black cohosh, and at least one additional chemopreventive or chemotherapeutic agent, are described above. In a preferred embodiment of the present invention, the combination comprises actein (e.g., about 0.5 µg/ml to about 5.0 µg/ml) and paclitaxel (e.g., about 0.5 nM to about 5.0 nM).

In the combination of anti-neoplastic agents of the present invention, the ethyl acetate extract of black cohosh, or the actein composition, and the one or more additional chemopreventive or chemotherapeutic agents, may be combined in a single formulation, such that the extract is in physical association with the agent. This single, combined formulation may consist of a liquid mixture, containing amounts of both the extract and the agent, which may be injected into a subject, or an oral formulation, containing amounts of both the extract and the agent, which may be orally administered to a subject.

Alternatively, in the combination of the present invention, a separate, individual formulation of the extract may be combined with a separate, individual formulation of the agent. For example, an amount of the extract may be packaged in a vial or unit dose, and an amount of the agent may be packaged in a separate vial or unit dose. A combination of the extract and the agent then may be produced by mixing the contents of the separate vials or unit doses in vitro. Additionally, a synergistic combination of the extract and the agent may be produced in vivo by co-administering to a subject the contents of the separate vials or unit doses, according to the methods described above. Accordingly, the combination of the present invention is not limited to a combination in which amounts of the extract and the agent are in physical association with one another in a single formulation.

It is also within the confines of the present invention for the ethyl acetate extract of black cohosh, or the actein composition, and the one or more additional chemopreventive or chemotherapeutic agents, to be co-administered in combination with radiation therapy or an anti-angiogenic compound (either natural or synthetic). Examples of anti-angiogenic compounds with which the anti-neoplastic agents may be combined include, without limitation, angiostatin, thalidomide, and thrombospondin.

The combination of anti-neoplastic agents of the present invention comprises an effective anti-neoplastic amount of the ethyl acetate extract of black cohosh and an effective anti-neoplastic amount of the one or more additional chemopreventive or chemotherapeutic agents. As used herein, an "effective anti-neoplastic amount" of the extract or the agent is an amount of the extract or the agent that is effective to ameliorate or minimize the clinical impairment or symptoms of neoplasia in a subject, in either a single or multiple dose.

The present invention is described in the following Examples, which are set forth to aid in the understanding of the invention, and should not be construed to limit in any way the scope of the invention as defined in the claims which follow thereafter.

EXAMPLES

Example 1

Chemicals and Reagents

Polyamide resin SC6<0.07 mm was purchased from Alltech Associates, Inc. (Deerfield, Ill.). $RP_{18}CC$ silica gel (40 µM) was obtained from J. T. Baker (Phillipsburg, N.J.), and the $RP_{18}F_{254}$ plate (1-mm layer thickness) was obtained from EM Science (Darmstadt, Germany). Actein, 27-deoxyactein (23-epi-26-deoxyactein) (Zheng et al., CimiPure (*Cimicifuga racemosa*): a standardized black cohosh extract with novel triterpene glycoside for menopausal women. In *Phytochem. Phytopharm.*, Shahidi and Ho, eds. (Champaign, Ill.: AOCS Press, 2000) pp. 360-70), cimifugoside, and cimiracemoside A were obtained from ChromaDex (Laguna Hills, Calif.), and 27-deoxyactein was also obtained from Herbstandard (Chesterfield, Mo.). Tamoxifen, 5-fluorouracil (5-FU), doxorubicin, cisplatin, and paclitaxel were purchased from Sigma (St. Louis, Mo.). Herceptin was obtained from Genentech (CA). Cimigenol and cimigenol glycoside were obtained from Dr. W C Ye (Department of Phytochemistry, China Pharmaceutical University, Nanjing 210009, China).

Black cohosh extracts and purified components were dissolved in dimethylsulfoxide (DMSO) (Sigma Chemical Co.). Water ($H_2O$) was distilled and deionized. All solvents and reagents were reagent grade.

Example 2

Plant Material

Black cohosh roots and rhizomes (GFP) were obtained from PureWorld Botanicals (South Hackensack, N.J.; lot number 9-2677).

Example 3

Separation of the Ethyl Acetate Extract

As shown in FIG. 1, black cohosh roots and rhizomes were extracted with 80% methanol (MeOH)/$H_2O$, and partitioned with n-hexane. Two layers were obtained: a water layer and an n-hexane layer. N-hexane was used to extract the non-polar phytochemicals, respectively, with yields of 0.05% hexane, 0.73% ethyl acetate, and 1.69% water. The water layer was partitioned with ethyl acetate, and two fractions were obtained: a water layer and an ethyl acetate layer. Ethyl acetate was used to extract the mid-polar and polar phytochemicals. The ethyl acetate layer was dried and evaporated to yield an ethyl acetate extract. The triterpene glycosides and cinnamic acid esters were separated from the ethyl acetate extract by polyamide chromatography (Kruse et al., Fukic and piscidic acid esters from the rhizome of *Cimicifuga racemosa* and the in vitro estrogenic activity of fukinolic acid. *Planta. Med.*, 65:763-64, 1999).

Example 4

Cell Cultures

MDA-MB-453 human breast cancer cells (HER2 overexpressing, ER negative), MCF7 cells (ER positive, HER2 low), MDA-MB-231 cells (ER negative, HER2 low), MCF10F cells (normal mammary epithelial cells), and SW480 colon cancer cells were obtained from ATCC (Manassas, Va.). BT474 clone Sc-1 cells (ER positive, Her2 overexpressing) were the kind gift of Dr. S. Friedman (Incyte Pharmaceuticals). Cells were grown in Dulbecco's Modified Eagle medium (DMEM) (Gibco BRL Life Technologies, Inc., Rockville, Md.) containing 10% (v/v) fetal bovine serum (FBS) (Gibco BRL), at 37° C. and 5% $CO_2$. The medium was supplemented with bovine insulin (0.01 mg/ml) for the growth of BT474 cells.

Example 5

Cell-Growth Assays

Cell cultures were treated with increasing concentrations of extracts and/or purified compounds for increasing times and cytotoxicity (for SW480 cells) measured using the MTT {3-(4,5-dimethyl-2-thiazol)-2,5-diphenyl-2H tetrazolilum bromide} (Dojindo, Tokyo, Japan) method (Luo et al., PM-3, a benzo-g-pyran derivative isolated from propolis, inhibits growth of MCF-7 human breast cancer cells. Anticancer Res 21: 1665-1672, 2001) and inhibition of cell proliferation by performing cell counts using a Coulter Counter (Lim et al., 1999, supra). For the cell count assay, breast cancer cells were seeded, in triplicate, at $2 \times 10^4$ cells per well, in 24- or 96-well plates. Two or 3 days later, the medium was replaced with fresh medium—with or without black cohosh extracts or purified compounds—and the number of attached viable cells was counted at increasing times (or, to determine $IC_{50}$ values, at 48 or 96 h), using a Coulter Counter, model $Z_F$ (Coulter Electronics Inc., Hialeah, Fla.) (Lim et al., Sulindac derivatives inhibit growth and induce apoptosis in human prostate cancer cell lines. *Biochem. Pharmacol.*, 58:1097-107, 1999).

For the MTT assay, cells were seeded at $3 \times 10^3$ cells per well in 96-well plates; 24 hours later the medium was replaced with fresh medium containing black cohosh extracts or components and assayed with MTT reagents at 48 hours.

To determine the combination index (CI) for potential combination therapies, the inventors treated the breast cancer cells with all combinations of 3 concentrations of the black cohosh component and 3 concentrations of the chemotherapy agent, using a solvent control. Surviving cells were counted using the Coulter Counter (Masuda et al., Effects of epigallocatechin-3-gallate on growth, epidermal growth factor receptor signaling pathways, gene expression, and chemosensitivity in human head and neck squamous cell carcinoma cell lines. *Clinical Cancer Research*, 7:4220-29, 2001). Data that were obtained were analyzed for possible synergistic effects using previously-described methods (e.g., the median-effect plot method of Chou and Talalay (Quantitative analysis of dose-effect relationships: the combined effects of multiple drugs or enzyme inhibitors. *Adv. Enzyme Regul.*, 22:27-55, 1984)). The CIs were calculated using the index-isobologram method (Soriano et al., Synergistic effects of new chemopreventive agents and conventional cytotoxic agents against human lung cancer cell lines. *Cancer Res.*, 59:61, 78-84, 1999) based on the median-effect principle of Chou and Talalay, 1984, supra.

Example 6

Statistical Analysis

The inventors were interested in determining the effects of combinations of actein and paclitaxel concentrations on MDA-MB-453 cells. In calculating statistical significance, a Two-Way Analysis of Variance (ANOVA) was performed to test whether the effects of paclitaxel and actein concentrations were independent, or were related, or "interacted" with each other (alpha=0.05; significant difference=$p<0.05$; very significant difference=$p<0.01$). If the F-test showed that the interaction was significant, the Least Significant Difference method (LSD) was then used for multiple comparisons, to clarify the significance between the different combinations of paclitaxel and actein concentrations.

Example 7

Cell-Cycle Analysis

To obtain exponential cultures of breast cancer cells, $3 \times 10^5$ cells were plated onto 10-cm dishes, and grown for 2-3 days; the medium was then replaced with fresh medium containing black cohosh extracts or purified components alone and in combination with chemotherapy agents. Synchrony: To synchronize the cells, $3 \times 10^5$ cells were plated onto 10 cm dishes and grown for 2 days in DMEM supplemented with 10% fetal bovine serum. The medium was then replaced with DMEM containing 0.25% FBS (Imoto et al., 1997) and black cohosh extracts or purified components.

After incubation for 1-3 days, the supernatant was collected, and the cells were trypsinized, collected, and washed with phosphate buffered saline (PBS) containing 5% FBS. Cell pellets were re-suspended in 1 ml of PBS plus 5% FBS. Thereafter, 5 ml of 70% ethanol were added drop-wise, while vortexing the tube, and the mixture was stored at 4° C. Cells were centrifuged, washed with PBS plus 5% FBS, and re-suspended in 400 µl of propidium iodide (0.1 mg/ml) (Sigma Chemical Co.). 400 µl (2 mg/ml) of RNase (Sigma Chemical Co.) were added, and the cells were incubated in the dark at room temperature for 30 min. The suspension was filtered through a 41-µM spectra/mesh filter (Spectrum Medical Industries, CA), and analyzed with a FACScalibur instrument (Becton Dickinson, Franklin Lakes, N.J.) equipped with Cell Quest software (Becton Dickinson). The percentage of cells in different cell-cycle phases was then calculated (Lim et al., Sulindac derivatives inhibit growth and induce apoptosis in human prostate cancer cell lines. *Biochem. Pharmacol.*, 58:1097-107, 1999; Luo et al., PM-3, a benzo-g-pyran derivative isolated from propolis, inhibits growth of MCF7 human breast cancer cells. *Anticancer Research*, 21:1665-72, 2001; Soh et al., Cyclic GMP mediates apoptosis induced by sulindac derivatives via activation of c-Jun NH2-terminal kinase 1. *Clin. Cancer Res.*, 10:4136-41, 2000).

Example 8

Western-Blot Analysis

Cells were treated for increasing times with approximately the $IC_{50}$ concentration, or twice the $IC_{50}$ concentration, of actein. The cells were harvested, washed with PBS, and sonicated in extraction buffer according to the procedure of Han et al. (Han et al., Stable overexpression of cyclin D1 in a human mammary epithelial cell line prolongs the S-phase and inhibits growth. *Oncogene*, 10:953-61, 1995). The lysates were subjected to electrophoresis on a 10% or 12.5% SDS-polyacrylamide gel, and then transferred to a polyvinylidene difluoride (PVDF) membrane. The membrane was blocked with milk protein, and incubated with a solution containing the primary antibody against the following: cyclin D1 (Upstate Biotechnology, Lake Placid, N.Y.), $p21^{cip1}$ (Oncogene Research Products, Darmstadt, Germany), ppRb (ser 780, Medical and Biological Laboratories, Nagoya, Japan), cdk4 (Upstate Biotechnology, Lake Placid, N.Y.), EGFR (clone-74, Transduction Laboratories, Lexington, Ky.), p-EGFR (phospho (Y1173)-EGFR) (Cell Signaling, Beverly, Mass.), actin (Sigma, St. Louis, Mo.), Her-2/neu (Cell Signaling, Beverly, Mass.), or phospho-(Y1248)-Her-2/neu (Cell Signaling, Beverly, Mass.)), IκB (Sant Cruz Biotechnolgy, Santa Cruz, Calif.), IκκB (Sigma, St. Louis, Mo.) and PPARγ (Santa Cruz biotechnology, Santa Cruz, Calif.) (Masuda et al., Epigallocatechin-3-gallate inhibits activation of HER-2/neu and downstream signaling pathways in human head and neck and breast carcinoma cells. *Clin. Cancer Res.*, 9: 3486-91, 2003). The membrane was washed, and incubated with horseradish peroxidase conjugated secondary antibody.

Protein bands were visualized with the ECL-enhanced chemiluminescence system, according to the manufacturer's directions (Amersham Pharmacia Biotech) (Sgambato et al., Overexpression of p27 (Kip1) inhibits the growth of both normal and transformed human mammary epithelial cells. *Cancer Research*, 58:3448-54, 1998). The staining intensities of the visualized blots were quantified using NIH image software. For each protein, the relative band intensities were determined by comparing treated samples with untreated controls. These values were then normalized, using β-actin as an internal control.

Example 9

Thin-Layer Chromatography Analysis

Extracts were tested for triterpene glycosides and cinnamic acid esters using silica gel 60 $F_{254}$ plates (0.25-mm layer thickness) and $RP_{18}F_{254}$ plates (1-mm layer thickness) from EM Science (Darmstadt, Germany). The solvent system for the silica gel thin-layer chromatography (TLC) was chloroform-MeOH (9:1); the solvent system for the $RP_{18}$ plates was MeOH—$H_2O$ (9:1). After development, the compounds were visualized under UV, and visualized by spraying with vanillin in 10% (v/v) $H_2SO_4$ in ethanol (EtOH).

Example 10

Polyamide Chromatography

Polyamide SC6 resin (1.5 gm), pre-conditioned with MeOH (15 min) and $H_2O$ (10 min), was packed under pressure in a 12-ml syringe (approximately 3.3 cm in height, with a column volume of 4.5 ml); the syringe was then rinsed with water. The black cohosh ethyl acetate extract (100 mg) was dissolved in 1 ml of $H_2O$/MeOH (1:1), and adsorbed to the polyamide column for 20 min before elution. The column was then eluted sequentially, twice, with 6 ml of $H_2O$/MeOH (50:50), $H_2O$/MeOH (75:25), MeOH, EtOH, and EtOH+0.1% TFA, to yield 10 fractions (Kruse et al., Fukic and piscidic acid esters from the rhizome of *Cimicifuga racemosa* and the in vitro estrogenic activity of fukinolic acid. *Planta. Med.*, 65:763-64, 1999).

Example 11

Cyclin D1 Reporter Assay

The cyclin D1 promoter luciferase reporter plasmid, 1745CD1LUC, was prepared by Dr. R. Pestell (Albert Einstein Cancer Center, New York, N.Y.). The method used for transient transfection reporter assays was previously described (Soh et al., Novel roles of specific isoforms of protein kinase C in activation of the c-fos serum response element. Molecular and Cellular Biology, 19:1313-24, 1999). Using lipofectin, triplicate samples of MDA-MB-453 breast cancer cells ($1 \times 10^5$ cells in 35-mm plates) were co-transfected using DNA of the indicated reporter plasmid (1 µg) and the β-gal plasmid as an internal control (10 µg of the pCMV-b-gal plasmid) in opti-MEM 1 medium (Life Technologies, Inc.). After 24 h, the medium was replaced with serum-free medium containing the indicated concentrations of actein. After 24 h, cells were harvested, and luciferase activity was determined with the luciferase assay system (Promega Corp. Madison, Wis.); β-gal activities were determined with the β-gal enzyme assay system (Promega). Luciferase activities were normalized to β-gal activities, to correct for differences in transfection efficiency.

Example 12

Bioactivity-Guided Fractionation

Open chromatography techniques were used to fractionate the extracts further. The stationary phases used included Diaion HP-20, Sephadex, normal and reversed-phase silica, and polyamide.

1. Alcoholic black cohosh powder extract was redissolved in MeOH/H$_2$O, and evaporated to dryness, leaving the water portion.

2. To partition the phytochemicals according to polarity, the water portion was partitioned sequentially with hexane and n-butanol (n-BuOH). The three resulting fractions—hexane, n-BuOH, and water—were evaporated to dryness, and tested for their effects on the growth of MCF7 breast cancer cells. The n-BuOH extract showed high activity (FIG. 11).

3. The n-BuOH extract was further separated using Diaion HP-20 as a stationary phase, and eluting sequentially with MeOH/H$_2$O (1:1), MeOH, and acetone. By thin-layer chromatography, the MeOH/H$_2$O (1:1) contained mostly UV-absorbing compounds (aromatic acid derivatives), while the MeOH contained mostly triterpenoids (FIG. 11).

Figure 12:
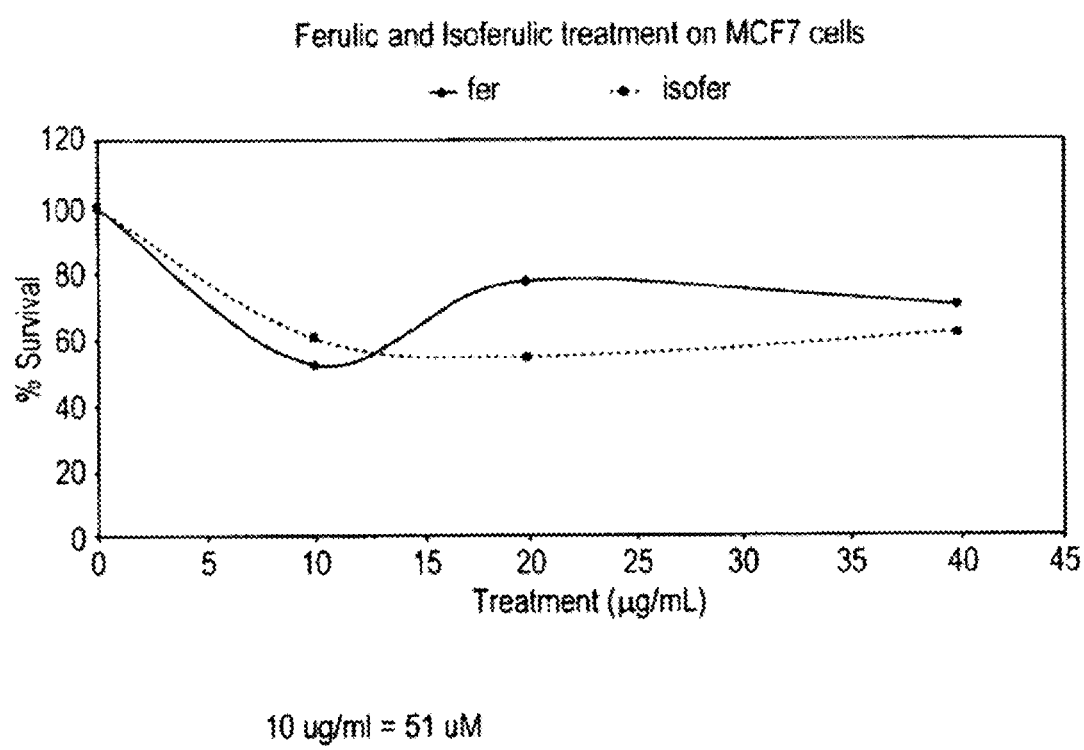
FIG. 12 demonstrates the effects of the components ferulic and isoferulic acid, purified from black cohosh, on cell proliferation in MCF7 cells. MCF7 cells were exposed to increasing concentrations of the indicated purified components for 96 hrs, and the number of viable cells was determined using a Coulter Counter.

4. Further separation of the MeOH/H$_2$O fraction, over silica gel, RP$_{18}$, and polyamide columns, yielded isoferulic acid, ferulic acid, and caffeic acid. Preliminary experiments indicated that isoferulic, the more potent, and ferulic acids were active in suppressing the growth of MCF7 human breast cancer cells (FIG. 12).

Summarized below are results obtained by the inventors in connection with the experiments described in Examples 1-12:

Effects of Extracts of Black Cohosh on the Growth of Human Breast Cancer Cells Black cohosh roots and rhizomes were extracted with MeOH/H$_2$O, and fractionated by solvent-solvent partitioning to yield three fractions: hexane, ethyl acetate (EtOAc), and H$_2$O (FIG. 1). These fractions were assayed for growth inhibition on human breast cancer cell lines. By TLC, it was determined that triterpene glycosides are present at the highest level in the EtOAc extract; low levels were detected in the hexane and water extracts.

The effects of increasing amounts of the three black cohosh fractions on the growth of the (ER+) human breast cancer cell line, MCF7, were determined after exposure of the cells for 96 h. The results, expressed as IC$_{50}$ values (i.e., the concentration that causes approximately 50% inhibition of growth), are set forth in Table 1. The results indicate that the EtOAc extract was the most active fraction.

The inventors tested the effects of crude extracts, methanol and ethanol, as well as ethanol extracts provided by Pure World, native and plus expedient: the IC$_{50}$ values for these extracts after 96 hours of treatment of MDA-MB-453 cells were: methanol: 100 µg/ml; ethanol: >200 µg/ml; PW native 175 µg/ml: and PW expedient: 195 µg/ml.

To partition the phytochemicals according to polarity, the water portion was also partitioned sequentially with hexane and n-butanol (n-BuOH). The n-BuOH fraction was tested for its effect on the growth of MDA-MB-453 breast cancer cells. The IC50 value after 96 hours of treatment was: 40 µg/ml.

The inventors also examined the effects of the EtOAc fraction of black cohosh on SW480 human colon cancer cells. The IC50 values after 48 hours of incubation using the MTT assay were: SW480: 42 µg/ml; MCF7: 38 µg/ml (Luo et al., PM-3, a benzo-g-pyran derivative isolated from propolis, inhibits growth of MCF-7 human breast cancer cells. *Anticancer. Res.* 21: 1665-1672, 2001).

TABLE 1

Effects of black cohosh extracts on MCF7 cells.

| Black Cohosh Extracts | IC$_{50}$ Values (µg/ml) |
|---|---|
| H$_2$O extract | 150 |
| ethyl acetate extract | 18 |
| hexane extract | 28 |
| Purified Components | |
| Actein | 14 (21 µM) |
| 23-cpi-26-deoxyactein | 21 (32 µM) |
| Cimifugoside | 22 (36 µM) |
| cimiracemoside A | 41 (61 µM) |

Figure 2A:
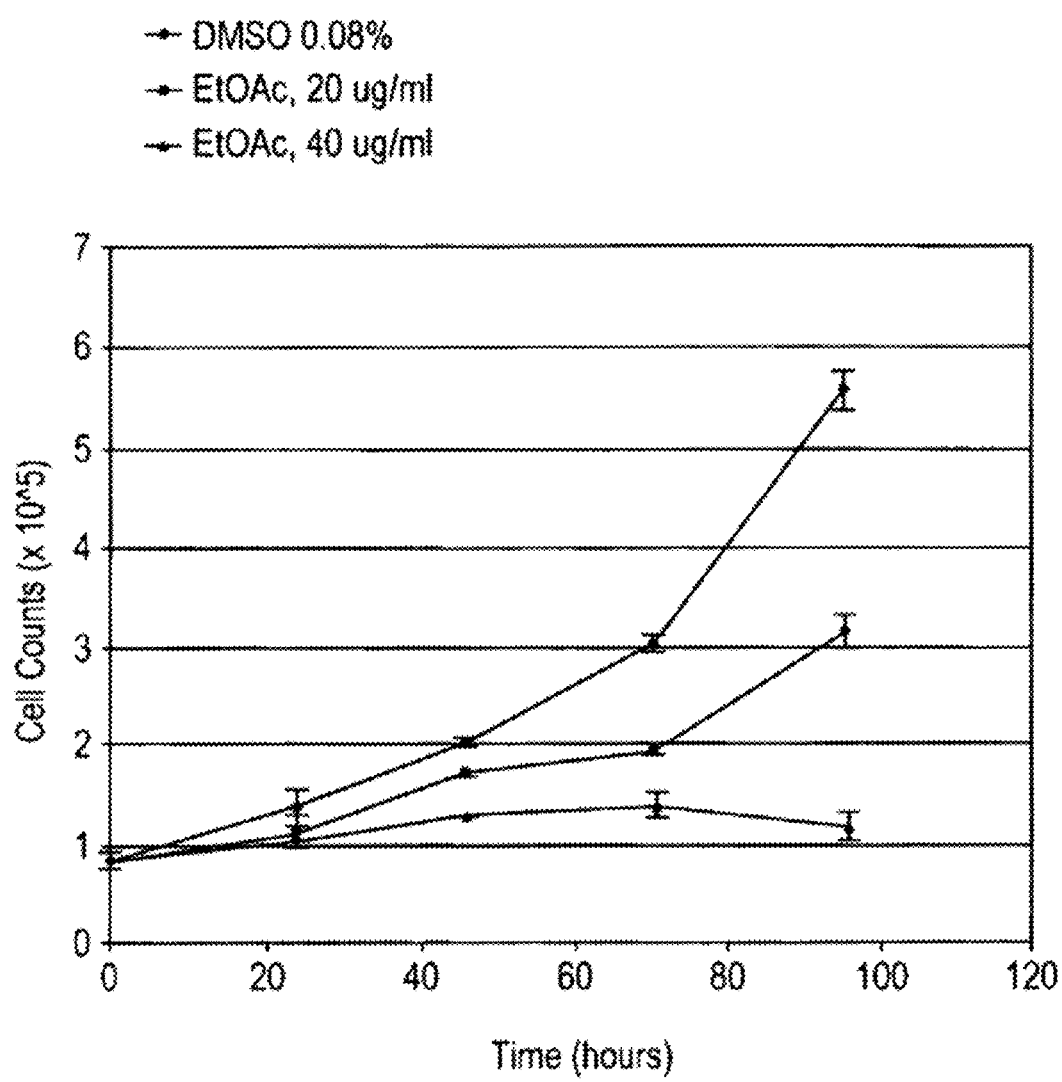
FIGS. 2A and 2B illustrate the effect of black cohosh extracts on the growth of MCF7 cells.

The effects of two concentrations of the EtOAc fraction on the growth of MCF7 cells were examined at increasing times. Exposure to 20 µg/ml of the EtOAc fraction led to partial inhibition of cell proliferation as early as 24 h after addition; 40 µg/ml resulted in complete inhibition and cell death after 72 h (FIG. 2A), while 60 µg/ml resulted in cell death at 24 h.

Two major signaling pathways in breast cancer cells are the ER-mediated signaling pathway (exemplified in the estrogen-dependent human breast cancer cell line, MCF7) and the HER2-mediated signaling pathway (exemplified in the estrogen-independent human breast cancer cell line, MDA-MB-453, which overexpresses HER2 (erb2, c-neu), a membrane-associated tyrosine kinase receptor (p185 HER2)). Clinical studies indicate that a reciprocal relationship often occurs in the expression of the two pathways in primary human breast cancers (Tsutsui et al., Prognostic value of c-erbB2 expression in breast cancer. *J. Surg. Oncol.*, 79:216-33, 2002). It was important, therefore, for the inventors to determine if black cohosh extracts have different effects on the two cell types. Accordingly, the following three breast cancer cell lines were tested: MCF7 (ER positive, HER2 low), MDA-MB-231 (ER negative, HER2 low), and MDA-MB-453 (HER2 overexpressing, ER negative).

Treatment with the EtOAc fraction for 48 h inhibited the growth of all three cell lines, with IC$_{50}$ values in the range of 20-40 µg/ml (Table 2). The Her2 overexpressing cells were the most sensitive. It is of interest that the normal human mammary epithelial cell line, MCF10F, was considerably less sensitive, with an IC$_{50}$ value of 85 µg/ml.

TABLE 2

Effects of black cohosh extracts on breast cancer cells.

| Cells | Receptors Expressed | IC$_{50}$ (µg/ml) |
|---|---|---|
| MDA-MB-453 | ER−/HER2+ | 18 |
| MCF7 | ER+/HER2− | 35 |
| MDA-MB-231 | ER+/HER2− | 39 |
| MCF10F | Normal Mammary Epithelial Cells (ER−) | 85 |

Observed over a 48-h period, the approximate doubling times for the malignant cells were 36 h for MDA-MB-453, 32 h for MCF7, and 30 h for MDA-MB-231; the approximate doubling time for the non-malignant MCF10F cells was 48 h. It is possible that the greater sensitivity of the malignant cells may reflect, in part, the difference in growth rates. The $IC_{50}$ values were less when the cells were treated for 96 h: 18 µg/ml for MCF7 cells, 10 µg/ml for MDA-MB-453 cells, and 46 µg/ml for MCF10F cells. Based upon these results, it can be concluded that the EtOAc fraction of black cohosh does not act specifically through the ER or the Her2 receptors.

Characterization of the Active Components in the Ethyl Acetate Extract

As the ethyl acetate extract of black cohosh contains many components, it was important for the inventors to identify the specific active compounds and their modes of action.

To separate the triterpene glycosides from the aromatic acids and esters, the ethyl acetate extract was fractionated on a polyamide SC6 column (Kruse et al., Fukic and piscidic acid esters from the rhizome of Cimicifuga racemosa and the in vitro estrogenic activity of fukinolic acid. Planta. Med., 65:763-64, 1999). The first four fractions (water/methanol-50:50; 75:25), which are enriched for triterpene glycosides, suppressed the growth of MCF7 cells. Incubation with fraction 1 (5.7 µg/ml) resulted in 25% cell death; incubation with fraction 2 (23 µg/ml) resulted in 67% cell death; and incubation with fraction 3 (30 µg/ml) resulted in 73% cell death. In view of these results, it appears that the triterpene glycosides are among the active components in the ethyl acetate extract.

Figure 2B:
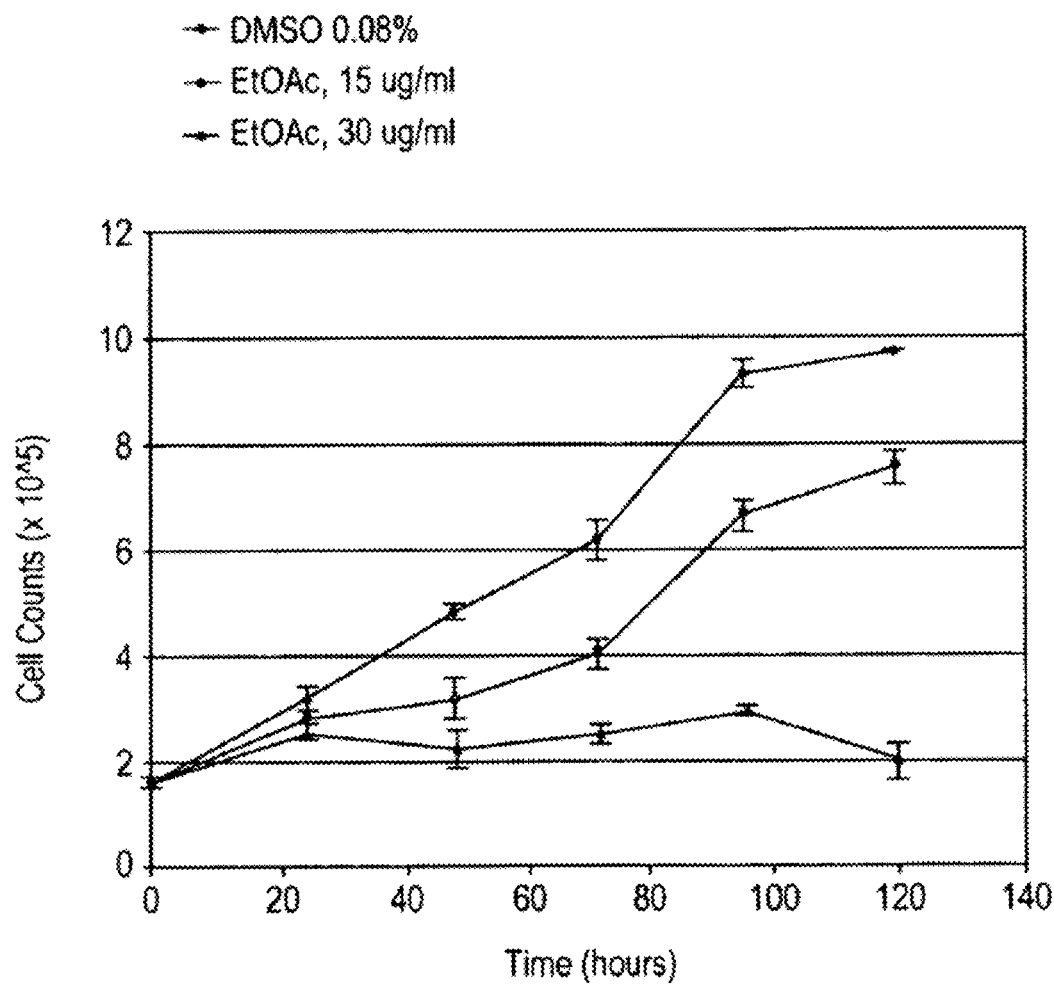
Figure 3:
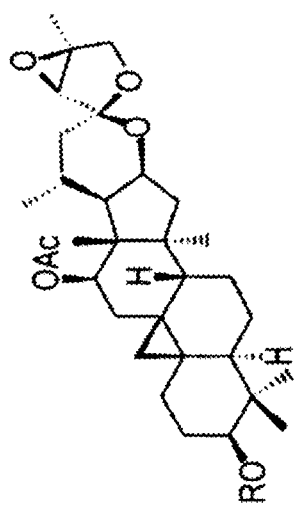
FIG. 3 shows the structures of the triterpene glycoside compounds of the invention.
Figure 3:
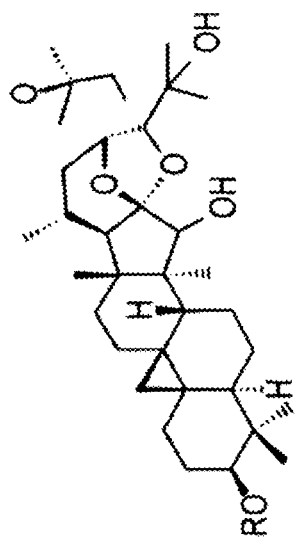
Figure 3:
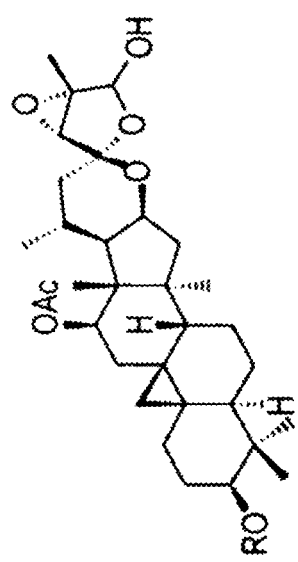
Figure 3:
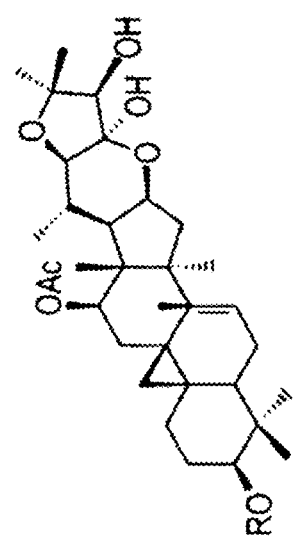

Effects of Triterpene Glycoside Fraction and Pure Components on Cell Proliferation To ascertain the nature of the triterpene glycosides of black cohosh, the purified triterpene glycosides (set forth in FIG. 3) were tested for growth inhibition on MCF7 cells (FIG. 2B and Table 1). Actein, which has an hydroxyl group on the C-26 position of 23-epi-26-deoxyactein (Chen et al., Isolation, structure elucidation, and absolute configuration of 26-deoxyactein from Cimicifuga racemosa and clarification of nomenclature associated with 27-deoxyactein. J. Nat. Prod., 65:601-05, 2000)), had an $IC_{50}$ of 21 µM; it was approximately 1.5-fold more potent than 23-epi-26-deoxyactein or cimifugoside, and approximately 3 times more potent than cimiracemoside A, in inhibiting the growth of MCF7 cells (Table 1). The substitution of an hydroxyl on the aglycone moiety can significantly alter this inhibitory activity.

The effects of two concentrations of actein on the proliferation of MCF7 cells were examined at increasing times. Treatment with actein (15 µg/ml) resulted in partial inhibition of growth, within 24 h after addition of the compound, while treatment with actein at 30 µg/ml resulted in complete inhibition of growth (FIG. 2B). In additional studies, it was found that MCF7 cells were approximately three times more sensitive to growth inhibition by actein than the MCF10F normal mammary epithelial cells; the respective $IC_{50}$ values were 14µ/ml vs. 42 µg/ml, when measured at 96 h of exposure. The mean of the MCF7 cells that were alive (38.0%±3.0) after 96 h of treatment with actein (20 µg/ml) was significantly less than the mean of the MCF10F cells that were alive (63.8%±1.4) after 96 h of treatment with actein (20 µg/ml) (p<0.01). As was the case for the EtOAc fraction, the MDA-MB-453 cells were the most sensitive to treatment with actein—with an $IC_{50}$ value of approximately 8 µg/ml at 96 h.

Figure 4:
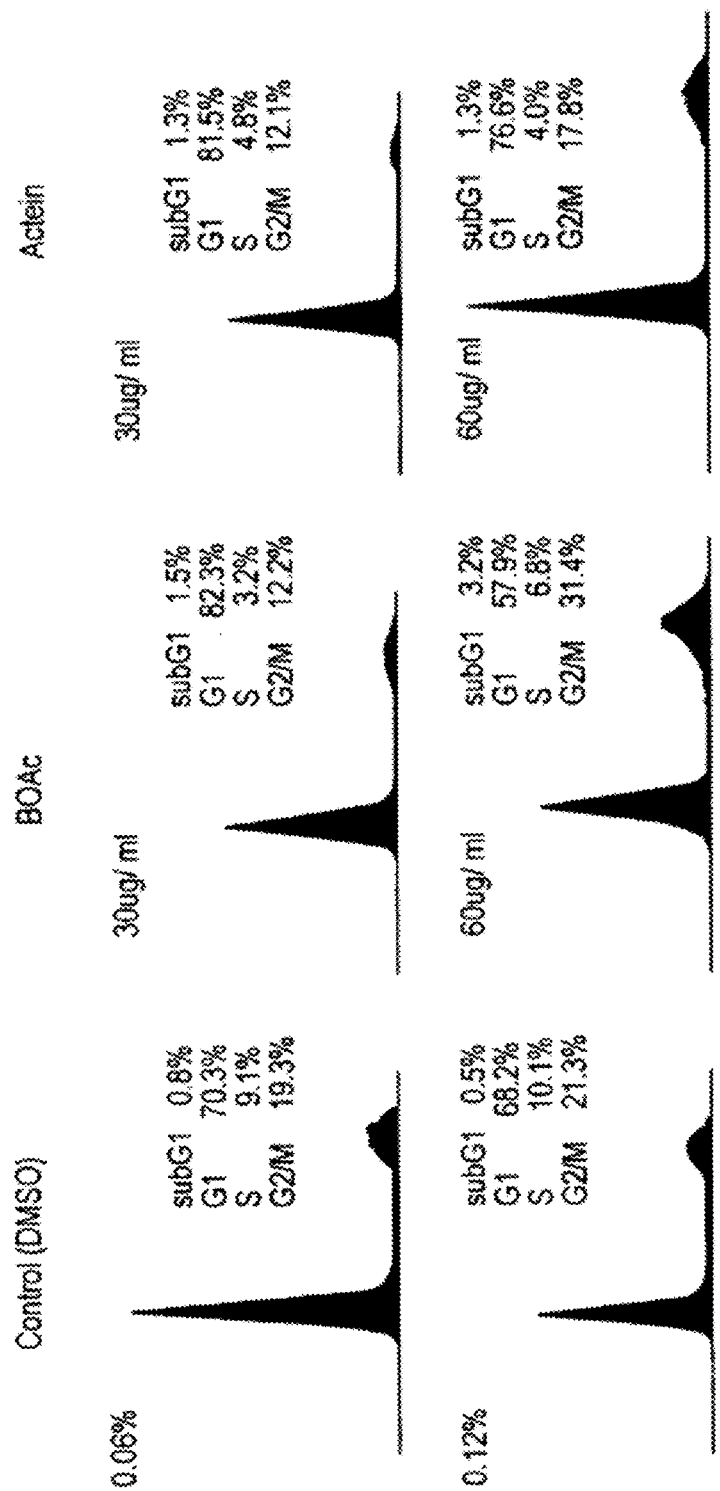
FIG. 4 depicts the effect of actein and the effect of the ethyl acetate fraction of black cohosh on MCF7 cell-cycle distribution at 48 h. MCF7 cells were treated with 0, 30, and 60 μg/ml of the ethyl acetate extract, or actein, and then analyzed at 48 h by DNA flow cytometry. The values indicate the percentage of cells in the indicated phases of the cell cycle.

Effects of the EtOAc Extract and Purified Components of Black Cohosh on Cell-Cycle Kinetics The ability of an extract or purified compound to affect specific phases of the cell cycle may provide clues to its mechanism of action (Weinstein, I. B., Disorders of cell circuitry during multistage carcinogenesis: the role of homeostasis. Carcinogenesis, 5:857-64, 2000). To determine the effects of black cohosh on the cell cycle, MCF7 cells were treated with 30 and 60 µg/ml of the EtOAc fraction of black cohosh, or 30 and 60 µg/ml of actein, for 48 h. The cells were then stained with propidium iodide, and analyzed by DNA flow cytometry (FIG. 4). After exposure to 30 µg/ml of the EtOAc fraction, there was an increase of cells in G1 (from 70% to 82%) when compared to the DMSO solvent control, and a concomitant decrease of cells in S (9% to 3%) and G2/M (19% to 12%). After treatment with 60 µg/ml of the EtOAc fraction, there was a decrease of cells in G1 (68% to 58%) and an increase of cells in G2/M (21% to 31%).

The above results indicate that the extract contains more than one component, with the more active or abundant component inducing G1 arrest, and the less active component inducing G2/M arrest, and/or that individual components in the extract exert different effects at different concentrations. To distinguish between these possibilities, cells were treated with the purified compound, actein, at 30 and 60 µg/ml. Exposure to actein at 30 µg/ml also resulted in an increase of cells in G1 (70% to 82%) and a decrease of cells in G2/M (19% to 12%). After exposure to 60 µg/ml of actein, there was also an increase of cells in G1 (68% to 77%), and a decrease of cells in G2/M (21% to 18%). Thus, with 60 µg/ml of actein, the inventors did not observe the increase in G2/M cells that was seen with 60 µg/ml of the EtOAc extract (FIG. 4).

Figure 5:
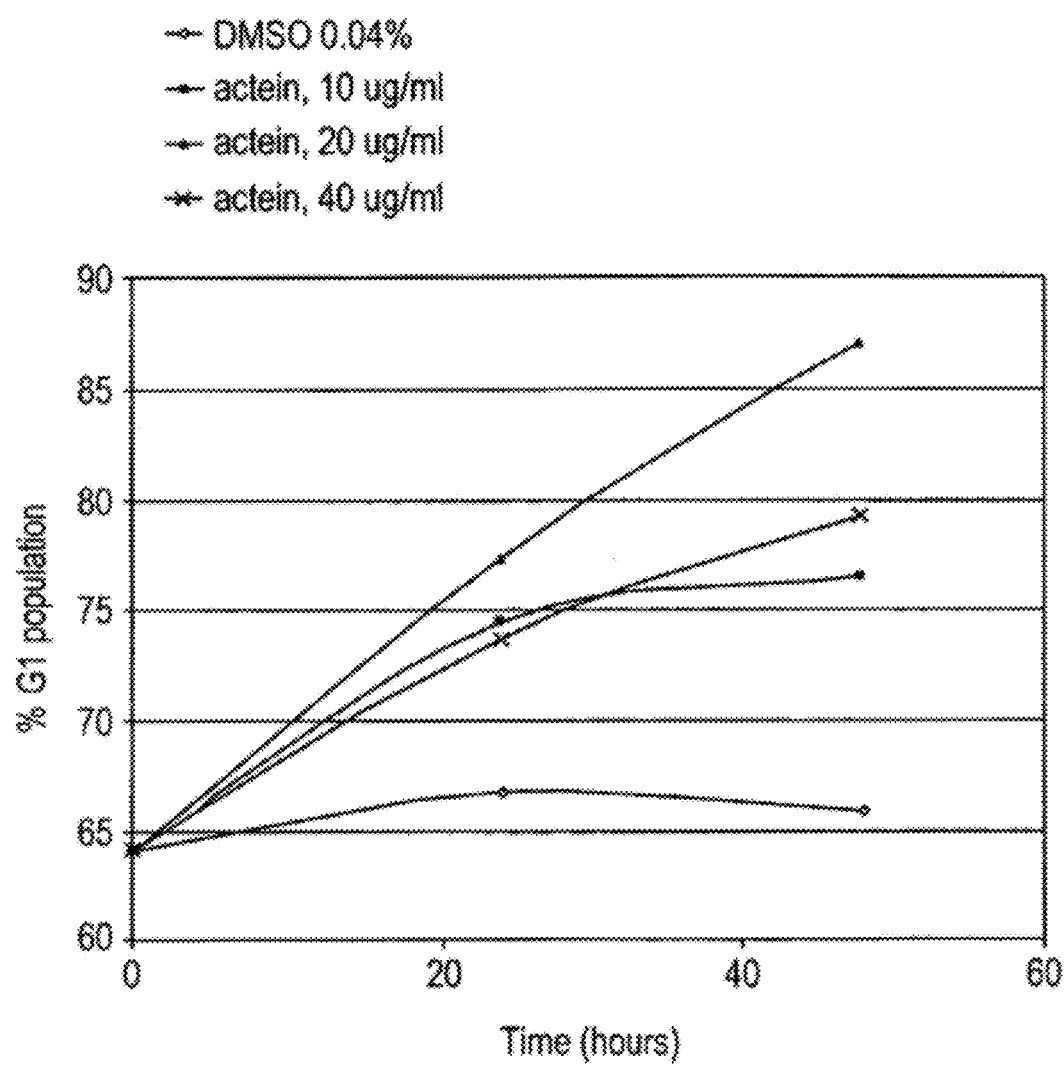
FIG. 5 illustrates the effect of actein on the G1 phase of the cell cycle in MCF7 cells. MCF7 cells were treated with 10 (14.8 μM), 20, or 40 μg/ml actein, and then analyzed at 24 and 48 h by DNA flow cytometry. The values indicate the percentage of cells in the G1 phase of the cell cycle.

To examine in greater detail the effects of actein on cell-cycle progression, MCF7 cells were treated with 0, 10, 20, or 40 µg/ml of actein, and analyzed at 0, 24, and 48 h by DNA flow cytometry. FIG. 5 summarizes the results obtained with respect to the percent of cells in G1. When cells were treated with 10 µg/ml of actein, the percentage of cells in G1 increased from 64% at time zero to 75% at 24 h, and to 77% at 48 h. With 20 µg/ml of actein, the respective values were 64%, 77%, and 87%; with µg/ml of actein, the respective values were 64%, 74%, and 79%. These increases in the G1 population were associated with decreases in both the S and G2/M populations of cells. Indeed, the maximal increase in the G1 population occurred at about 20 µg/ml actein. Therefore, it is possible that, at high concentrations, actein and related compounds affect proteins that regulate later phases in the cell cycle. The triterpene glycoside fraction of black cohosh (polyamide eluate, fraction 3), 23-epi-26-deoxyactein, and cimiracemoside A also induced cell-cycle arrest at G1, when tested at about 40 µg/ml.

Treatment with the EtOAc fraction at 30 µg/ml induced a small amount of apoptosis for 48 h (1.3%); at 60 µg/ml, there was a further increase in apoptosis (3.2%), as determined by the sub G1 fraction (FIG. 4). When the cells were exposed to 20 µg/ml actein for 48 h, approximately 1.4% of the population displayed apoptosis; at 72 h, this value was 3.6%, when assessed by the size of the sub G1 peak.

Effects of Actein on the Expression of Specific Proteins Involved in Cell-Cycle Control and Apoptosis Since actein induces cell-cycle arrest at G1, the inventors examined the effect of actein on proteins which control the progression of the cell cycle. Cyclin D1 was of particular interest, since it plays a critical role in mediating the transition from G1 to S, is overexpressed in approximately 50-60% of primary human breast carcinomas (Joe et al., Cyclin D1 overexpression is more prevalent in non-Caucasian breast cancer. *Anticancer Res.*, 21:3535-39, 2001), and is overexpressed in several human breast cancer cell lines (Han et al., Effects of sulindac and its metabolites on growth and apoptosis in human mammary epithelial and breast carcinoma cell lines. *Breast Cancer Res. Treat.*, 48:195-203, 1998). Therefore, the inventors monitored possible changes in cellular levels of cyclin D1 by Western-blot analysis of extracts obtained from control and actein-treated cells.

Figure 6A:
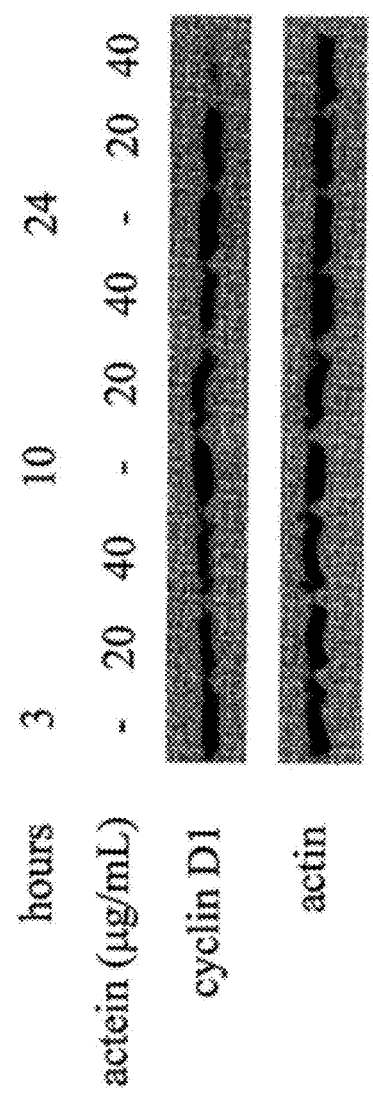
FIGS. 6A-6F show Western-blot analyses of MCF7 cells treated with actein. The cells were treated with 0, 20, or 40 μg/ml actein. 20 μg/ml actein is equivalent to 29.6 μM actein. After 3, 10, and 24 h, extracts were analyzed by Western blotting with antibodies to: cyclin D1 (FIG. 6A); ppRb (FIG. 6B); cdk4 (FIG. 6C); $p21^{cip1}$ (FIG. 6D); EGFR (FIG. 6E); and phospho-EGFR (FIG. 6F). An antibody for β-actin was used as a loading control.

Treatment of MCF7 cells with 40 µg/ml of actein for 3 or 10 h resulted in a partial decrease, and treatment for 24 h caused a marked decrease, in the cellular level of cyclin D1, when compared to comparable time points in the control (untreated) cells. Indeed, after treatment with 40 µg/ml for 24 h, there was almost a complete loss of this protein (FIG. 6A). The MCF10F normal mammary epithelial cells did not express an appreciable level of cyclin D1. Thus, the inventors could not assess the effect of actein on cyclin D1 in these cells.

Figure 6B:
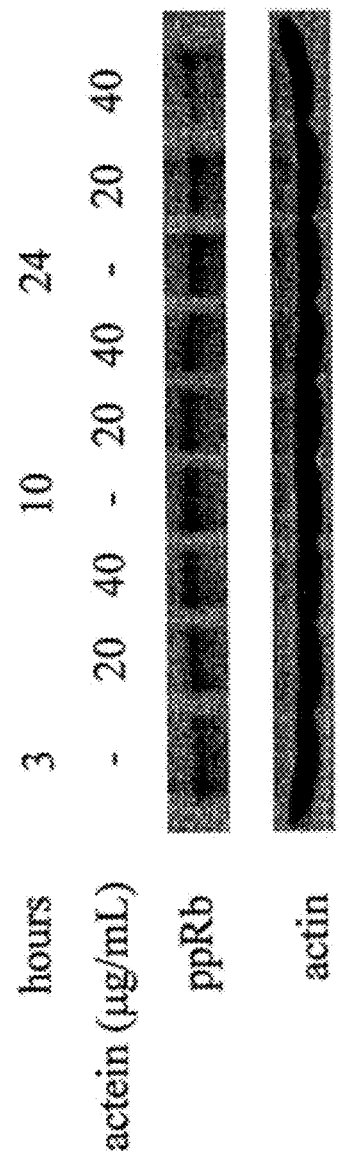
Figure 6C:
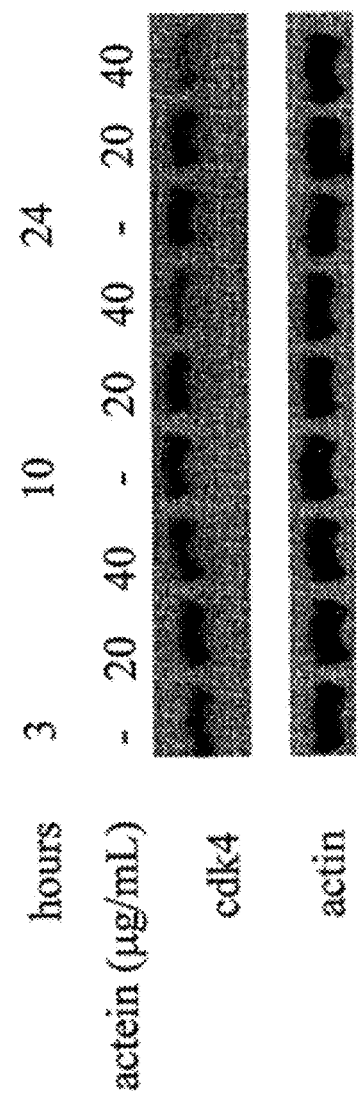

Cyclin D1 binds to and activates the cyclin dependent kinases, cdk4 and cdk6; the resulting complexes phosphorylate and inactivate pRb (retinoblastoma protein), thereby preventing pRb from inhibiting the transcription factor, E2F, and allowing the cells to progress from G1 to S (Weinstein, I. B., Disorders of cell circuitry during multistage carcinogenesis: the role of homeostasis. *Carcinogenesis*, 5:857-64, 2000). The inventors examined the effect of actein on the cellular level of the inactivated, hyperphosphorylated form of Rb (designated ppRb). After treatment with actein, the intensities of the ppRb bands relative to the pβ-actin bands were: 1.51 (3 h, 20 µg/ml), 1.59 (3 h, 40 µg/ml), 0.61 (10 h, 20 µg/ml), 0.64 (10 h, 40 µg/ml), 0.80 (24 h, 20 µg/ml), and 0.43 (24 h, 40 µg/ml). The inventors found that there was a increase in the level of ppRb at 3 hours and a decrease at 10 hours after treating MCF7 cells with 20 or 40 µg/ml actein; there was a marked decrease at 48 hours after exposure to 40 µg/ml actein (FIG. 6B). The inventors also observed a decrease in the level of cdk4 at 10 hours after treatment with 20 or 40 µg/ml actein and a pronounced decrease at 24 hours after exposure to 40 µg/ml actein (FIG. 6C).

Figure 6D:
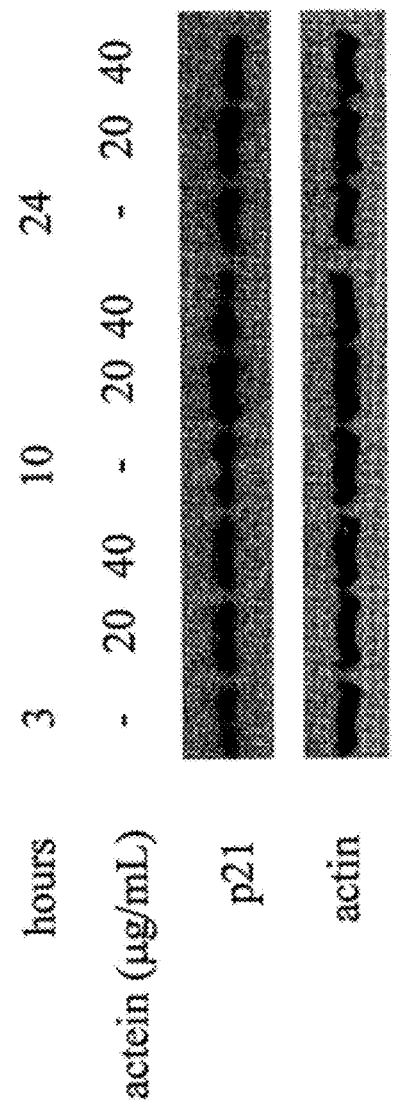

The cdk inhibitory protein $p21^{cip1}$ negatively regulates the activity of the cyclin D1/cdk4 complex. Therefore, the inventors examined the effect of actein on this protein. After exposure to actein, the intensities of the $p21^{cip1}$ bands relative to the β-actin bands were: 1.47 (3 h, 20 µg/ml), 1.17 (3 h, 40 µg/ml), 1.75 (10 h, 20 µg/ml), 1.37 (10 h, 40 µg/ml), 0.94 (24 h, 20 µg/ml), and 0.78 (24 h, 40 µg/ml). Thus treatment of MCF7 cells with 20 or 40 µg/ml of actein induced an increase in $p21^{cip1}$ within 3 hours and this increase persisted at 10 hours. The increase was more pronounced after treatment with 20 µg/ml. However, this increase was not seen with the 20 or 40 µg/ml dose at. 24 hours (FIG. 6D).

In view of the foregoing, the ability of actein to arrest cells in G1 (FIG. 5) may be due to the decreased expression of cyclin D1 and cdk4, and the increased expression of $p21^{cip1}$—both of which result in a decrease in the level of the hyperphosphorylated form of pRb.

Figure 6E:
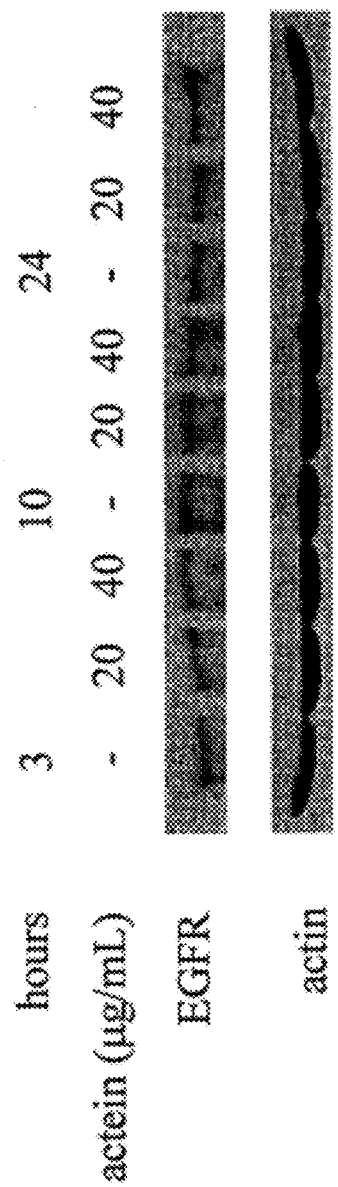
Figure 6F:
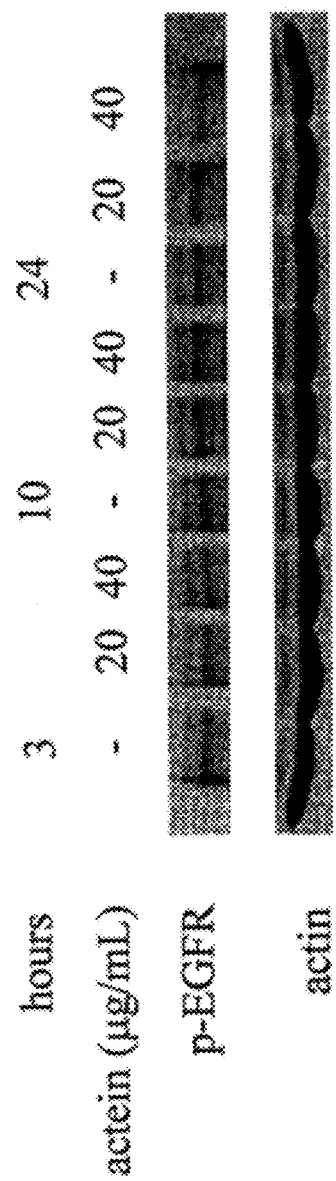

The level of the epidermal growth factor receptor (EGFR), which is overexpressed in various cancers (Masuda et al., Effects of epigallocatechin-3-gallate on growth, epidermal growth factor receptor signaling pathways, gene expression, and chemosensitivity in human head and neck squamous cell carcinoma cell lines. *Clinical Cancer Research*, 7:4220-29, 2001), was not significantly affected by treatment with actein (FIG. 6E). There was also not a consistent effect of actein on the phosphorylated and activated form of EGFR (p-EGFR). However, the inventors did observe a significant decrease with the 40 µg/ml dose at 24 h (FIG. 6F).

The Effects of Actein and the Ethyl Acetate Extract of Black Cohosh-Alone and in Combination with Chemotherapy Agents—on the Proliferation of Human Breast Cancer Cells It was essential for the inventors to explore the effects of actein (h e structure of which is set forth in FIG. 3) and extracts from black cohosh on Her2 overexpressing breast cancer cells, such as MDA-MB-453 cells, because these cells appeared to be more sensitive to inhibition by the black cohosh components, and because Her2 overexpressing breast cancers have a poorer clinical prognosis. To determine the interaction of black cohosh with chemotherapeutic drugs, actein was combined with several different classes of drugs. Among the chemotherapy drugs tested were the taxane, paclitaxel (Taxol); the selective estrogen receptor modulator (SERM), tamoxifen; the anthracycline antibiotic, doxorubicin; the anti-Her2 monoclonal antibody, herceptin (rhuMab Her2); the antimetabolite, 5-fluorouracil; the platinum analog, cisplatin; and the vinca alkaloid, vinblastine. The SERM, tamoxifen, was tested on ER+MCF7 cells; the Her2 antibody and the remainder of the agents were tested on MDA-MB-453 cells. The combinations of actein with herceptin and the EtOAc extract with doxorubicin were also tested on BT474 human breast cancer cells, which form xenografts in athymic mice.

Figure 7:
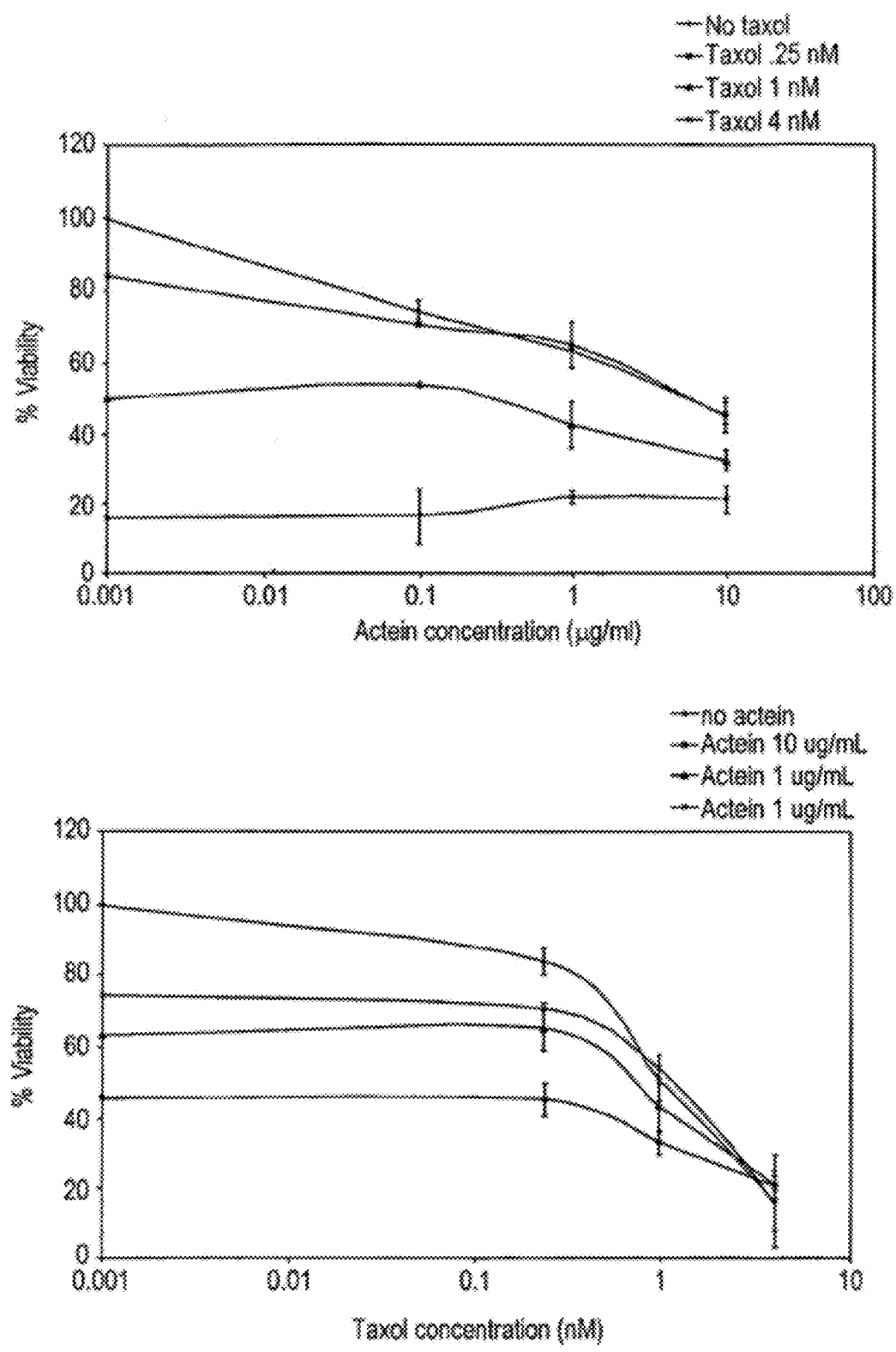
FIG. 7 shows the effects of actein alone, and in combination with paclitaxel, on cell proliferation in MDA-MB-453 (Her2 overexpressing) human breast cancer cells. MDA-MB-453 cells were treated with all combinations of 3 concentrations of actein and 3 concentrations of paclitaxel, and the solvent control, for 96 h. The number of viable cells was determined using a Coulter Counter. Similar results were obtained in two additional studies. The control contained 0.044% DMSO. bars=SD

The results for the combination of actein and Taxol are shown in FIG. 7. $IC_{50}$ values obtained from the graphs were used to calculate the combination index (CI) (Table 3). The inventors found that actein (2 µg/ml) potentiates the effect of Taxol at concentrations of 1 and 4 µM. These concentrations are reported to be attainable in the blood after treatment with Taxol.

TABLE 3

Combination index values for the combination of actein and paclitaxel on MDA-MB-453 cells.

| Taxol (nM) | Actein (µg/mL) | | | | | |
|---|---|---|---|---|---|---|
| | 0.1 | | 1 | | .10 | |
| 0.25 | 2.10 | -- | 3.70 | -- | 1.00 | +/- |
| 1 | 1.15 | – | 0.75 | ++ | 0.05 | +++ |
| 4 | 1.10 | +/- | 0.70 | ++ | 0.00 | +++ |

Symbols: CI -- >1.3 antagonism– 1.1-1.3 moderate antagonism +/– 0.9-1.1 additive effect+ 0.8-0.9 slight synergism ++ 0.6-0.8 moderate synergism +++ <0.6 synergisns[$C_{50}$ values determined from the graphs in FIG. 7 were used to obtain combination index values: CI = {$IC_{50}$ (actein + paclitaxel)/$IC_{50}$ (actein alone)} + {$IC_{50}$ (paclitaxel + actein)/$IC_{50}$ (actein alone)}.

Results of Statistical Analyses

In the two-way ANOVA analysis, the F-test showed very significant differences (p values approaching to zero) among the paclitaxel concentrations, among the actein concentrations, and among the combinations of actein and paclitaxel concentrations (i.e., there were very significant interactions between the actein and paclitaxel concentrations).

The LSD t-test indicated that, under the fixed paclitaxel concentrations, 0 and 0.25 nM, there were very significant differences (p<0.01) among the four different actein concentrations. Under the paclitaxel concentration, 1 nM, there were very significant differences between the actein concentrations, 0 and 1 μg/ml, and between the actein concentrations, 0.1 and 1 μg/ml. The addition of 0.1 μg/ml actein to 1 nM paclitaxel did not produce a significant effect; however, the addition of 1 μg/ml did.

same method was used to obtain the CI values for these classes of chemotherapy agents (Tables 5a and 5b).

Actein at concentrations achievable in vivo (0:2 or 2 μg/ml) potentiates the effects of several chemotherapy agents at clinically-relevant drug concentrations (Table 5a). Actein at 2 μg/ml (2.8 μM) enhances the effects of 5-FU (0.002-0.2 μg/ml; 1.54 μM), doxorubicin (0.2 μg/ml; 0.34

TABLE 4

2-way ANOVA.

|  | 1 | 2 | 3 | average |  |
|---|---|---|---|---|---|
| DMSO | 236742 | 255918 | 216444 | 236368 | 1 |
| actein .1 | 169636 | 175420 | 179339 | 174798.3 | 2 |
| actein 1 | 147900 | 148206 | 148502 | 148202.7 | 3 |
| actein 10 | 110402 | 105501 | 104339 | 106747.3 | 4 |
| tax .25 | 189954 | 205308 | 199987 | 198416.3 | 1 |
| actein .1 tax .25 | 165780 | 168440 | 164526 | 166248.7 | 2 |
| actein 1 tax .25 | 145603 | 159404 |  | 152503.5 | 3 |
| actein 1 tax .25 | 107455 | 98838 | 107202 | 104498.3 | 4 |
| tax 1 | 125602 | 119850 | 110420 | 118624 | 1 |
| actein .1 tax 1 | 126449 | 125399 |  | 125924 | 2 |
| actein 1 tax 1 | 105302 | 100944 | 92668 | 99638 | 3 |
| actein 10 tax 1 | 76402 | 72726 | 76398 | 75175.33 | 4 |
| tax 4 | 42388 | 35462 | 33332 | 37060.67 | 1 |
| actein .1 tax 4 | 40902 | 35448 | 35962 | 37437.33 | 2 |
| actein 1 tax 4 | 48694 | 50033 |  | 49363.5 | 3 |
| actein 10 tax 4 | 46204 | 50002 | 48033 | 48079.67 | 4 |

Two-way ANOVA

| V.R | DF | SS | MS | F | p-value |
|---|---|---|---|---|---|
| A | 3 | 1.09E+11 | 3.64E+10 | 753.6035 | 1.35E−27 |
| B | 3 | 2.55E+10 | 8.51E+09 | 176.1761 | 1.04E−18 |
| A × B | 9 | 1.92E+10 | 2.13E+09 | 44.18546 | 1.53E−14 |
| Error | 29 | 1.4E+09 | 48318909 |  |  |
| Total | 44 | 1.55E+11 |  |  |  |

Factor A is tax concentration;
Factor B is actein concentration;
A × B is combination t-test (Least Significant Difference Method; LSD)

| Combination | Average | t-value |  |  | p-value |  |  |
|---|---|---|---|---|---|---|---|
| DMSO | 236368 |  |  |  |  |  |  |
| actein .1 | 174798.3 | 10.8481 |  |  | 1.01E−11 |  |  |
| actein 1 | 148202.7 | 15.53406 | 4.685953 |  | 1.36E−15 | 6.0678E−05 |  |
| actein 10 | 106747.3 | 22.83817 | 11.99007 | 7.304113 | 4.37E−20 | 9.2448E−13 | 4.8E−08 |
| tax .25 | 198416.3 |  |  |  |  |  |  |
| actein .1 tax .25 | 166248.7 | 5.667697 |  |  | 3.98E−06 |  |  |
| actein 1 tax .25 | 152503.5 | 7.23546 | 2.166118 |  | 5.75E−08 | 0.03866239 |  |
| actein 1 tax .25 | 104498.3 | 16.54763 | 10.87994 | 7.565194 | 2.6E−16 | 9.4171E−12 | 2.44E−08 |
| tax 1 | 118624 |  |  |  |  |  |  |
| actein .1 tax 1 | 125924 | 1.150416 |  |  | 0.259371 |  |  |
| actein 1 tax 1 | 99638 | 3.345188 | 4.142443 |  | 0.002284 | 0.00027139 |  |
| actein 10 tax 1 | 75175.33 | 7.655323 | 7.997545 | 4.310135 | 1.93E−08 | 8.0625E−09 | 0.000171 |
| tax 4 | 37060.67 |  |  |  |  |  |  |
| actein .1 tax 4 | 37437.33 | 0.066366 | 0.947542 |  |  |  |  |
| actein 1 tax 4 | 49363.5 | 1.938819 | 1.879459 |  | 0.06231 | 0.07026431 |  |
| actein 10 tax 4 | 48079.67 | 1.941464 | 1.875098 | 0.202321 | 0.061975 | 0.07088192 | 0.841079 |

Bold numbers represent significant t-value and p-value.

$$t = \frac{x_1 - x_2}{\sqrt{MS(\text{error}) \times \left(\frac{1}{n_1} + \frac{1}{n_2}\right)}}$$

Similar experiments were performed on the combination of actein with herceptin, doxorubicin, cisplatin, 5-fluorouracil, and vinblastine on MD-MBA-453 cells, and on the combination of actein plus tamoxifen on MCF7 cells. The μM), cisplatin (2 μg/ml; 6.7 μM) and tamoxifen (2 μg/ml, 5.4 μM). Actein at 0.2 or 2 μg/ml enhances the effect of herceptin (8 μg/ml, 54 nM). At 2 μg/ml, actein has an additive effect on vinblastine (4 μg/ml).

When black cohosh was extracted with MeOH, and partitioned with EtOAc, hexane, and water, the triterpene glycosides were present primarily in the EtOAc extract. When the EtOAc extract was combined with doxorubicin or paclitaxel, synergy occurred with 2 μg/ml actein, and with 0.02-0.2 μg/ml (0.34 μM) doxorubicin or 4 nM paclitaxel (Table 5b).

TABLE 5

Combination index values for the combination of: (a) actein with various chemotherapy drugs: herceptin, tamoxifen, doxorubicin, cisplatin, 5-FU or vinblastine; and (b) EtOAc fraction with doxorubicin or paclitaxel.

(a)

| | Actein (µg/mL) | | | | | |
|---|---|---|---|---|---|---|
| | 0.2 | | 2 | | 20 | |
| 5-FU (µg/mL) | | | | | | |
| 0.002 | 1.75 | -- | 0.51 | +++ | 0.23 | +++ |
| 0.02 | 1.69 | -- | 0.45 | +++ | 0.17 | +++ |
| 0.2, 0.15 uM | 1.69 | -- | 0.45 | +++ | 0.17 | +++ |
| heroeptin (µg/mL) | | | | | | |
| 0.08 | 1.15 | - | 1.12 | - | 1.13 | - |
| 0.8 | 1.20 | - | 1.17 | - | 1.18 | - |
| 8, 54 nM | 0.35 | +++ | 0.32 | +++ | 0.33 | +++ |
| tamoxifen (µg/mL) | | | | | | |
| 0.5 | 1.47 | -- | 1.22 | - | 0.94 | +/- |
| 5 | 1.15 | -- | 0.90 | + | 0.61 | ++ |
| 50, 134 uM | 1.07 | +/- | 0.82 | + | 0.54 | +++ |
| cisplatin (µg/mL) | | | | | | |
| 0.2 | 3.33 | -- | 1.93 | -- | 1.44 | -- |
| 2 | 2.11 | -- | 0.71 | ++ | 0.22 | +++ |
| 20, 67 uM | 2.04 | -- | 0.64 | ++ | 0.15 | +++ |
| vinblastine (µg/mL) | | | | | | |
| 0.4 | 4.40 | -- | 4.45 | -- | 4.08 | -- |
| 4 | 0.95 | +/- | 1.00 | +/- | 0.63 | ++ |
| 40, 44 uM | 0.95 | +/- | 1.00 | +/- | 0.63 | ++ |

(b)

| | EtOAc (µg/mL) | | | | | |
|---|---|---|---|---|---|---|
| | 0.2 | | 2 | | 20 | |
| doxorubicin (µg/mL) | | | | | | |
| 0.002 | 1.13 | - | 1.21 | - | 0.75 | ++ |
| 0.02 | 0.43 | +++ | 0.51 | +++ | 0.05 | +++ |
| 0.2, 0.34 uM | 0.43 | +++ | 0.50 | +++ | 0.04 | +++ |
| taxol (nM) | | | | | | |
| 0.25 | 1.89 | -- | 1.86 | -- | 1.86 | -- |
| 1 | 1.08 | +/- | 1.05 | +/- | 1.05 | +/- |
| 4 | 0.79 | ++ | 0.76 | ++ | 0.76 | ++ |

Symbols:
CI
-- >1.3 antagonism
- 1.1-1.3 moderate antagonism
+/- 0.9-1.1 additive effect
+ 0.8-0.9 slight synergism
++ 0.6-0.8 moderate synergism
+++ <0.6 synergism
$IC_{50}$ values were determined from the combination of 3 concentrations of actein and 3 concentrations of the specific chemotherapy agent and the solvent control, as illustrated for the combination of actein and paclitaxel in Table 3.

TABLE 6

Combination index values for the combination of actein with the EtOAc fraction and cimigenol with paclitaxel.

| | EtOAc (µg/ml) | | | | | |
|---|---|---|---|---|---|---|
| actein (µg/ml) | EtOAc .2 | | EtOAc 2 | | EtOAc 20 | |
| actein .2 | 3.8166 | -- | 3.8166 | -- | 3.96666 | -- |
| actein 2 | 3.65 | -- | 3.65 | -- | 3.8 | -- |
| actein 20 | 0.15126 | +++ | 0.15126 | +++ | 0.30126 | +++ |

TABLE 6-continued

Combination index values for the combination of actein with the EtOAc fraction and cimigenol with paclitaxel.

| | Cimigenol (µg/ml) | | | | | |
|---|---|---|---|---|---|---|
| Taxol (µg/ml) | cimi .2 | | cimi 2 | | cimi 20 | |
| tax .25 | 1.5023 | -- | 1.5023 | -- | 1.4665 | -- |
| tax 1 | 1.85714 | -- | 1.85714 | -- | 1.82142 | -- |
| tax 4 | 0.85714 | + | 0.85714 | + | 0.82142 | + |

TABLE 7

Combination index values for the combination of actein with herceptin and the EtOAc fraction of black cohosh with doxorubicin on BT474 human breast cancer cells.

| | Actein (µg/mL) | | | | | |
|---|---|---|---|---|---|---|
| herceptin (µg/mL) | 0.2 | | 2 | | 20 | |
| 0.8, 5.4 nM | 3.14 | -- | 3.06 | -- | 3.06 | -- |
| 8 | 0.08 | +++ | 0 | +++ | 0 | +++ |
| 32 | 0.08 | +++ | 0 | +++ | 0 | +++ |

| | EtOAc (µg/mL) | | | | | |
|---|---|---|---|---|---|---|
| doxorubicin (µg/mL) | 0.2 | | 2 | | 20 | |
| 0.002 | 1.45 | -- | 1.79 | -- | 0.79 | ++ |
| 0.02 | 0.67 | ++ | 1 | +/- | 0 | +++ |
| 0.2, 0.34 uM | 0.67 | ++ | 1 | +/- | 0 | +++ |

Symbols:
CI
-- >1.3 antagonism
- 1.1-1.3 moderate antagonism
+/- 0.9-1.1 additive effect
+ 0.8-0.9 slight synergism
++ 0.6-0.8 moderate synergism
+++ <0.6 synergism
$IC_{50}$ values were determined from the combination of 3 concentrations of actein and 3 concentrations of the specific chemotherapy agent and the solvent control.

To further understand the effect of actein and the EtOAc fraction of black cohosh, the investigators tested the effects on BT474 human breast cancer cells (ER+, her2 overexpressing, 25-fold), which can form tumors in athymic mice. The investigators obtained strong synergy when actein (0.2 or 2 µg/ml) was combined with herceptin (0.8 or 8 µg/m) and additive effects when the EtOAc fraction (2 µg/ml) was combined with doxorubicin (0.02 µg/ml, 34 nM).

Actein, or the fraction enriched for triterpene glycosides, could be used in combination with agents, in single use (including paclitaxel, herceptin, and tamoxifen), to treat breast cancer. If actein or the triterpene glycoside fraction is free of significant side effects, they could be used in combination with herceptin for long-term treatment of patients with metastatic disease.

Effects of Actein, in Combination with Chemotherapy Agents on the Distribution of Cells in the Cell Cycle To understand the nature of the interaction of actein with the different classes of chemotherapy agents, we determined the effect of actein in combination with various chemotherapy agents on the distribution of cells in the cell cycle. When the cells were synchronized by serum starvation followed by serum stimulation, treatment with actein induced a dose dependent increase in the percent of cells in G1 at 48 hours (Table 8a). When actein (2 or 20 µg/ml) was combined with paclitaxel (1 nM), or when actein (20 µg/ml) was combined with doxorubicin (0.1 µg/ml, nM) or 5 FU (0.02 µg/ml, nM), there was a synergistic increase in the percent of cells in the subG$_1$ phase at 48 hours, an indicator of apoptosis (Table 8b, c).

In the case of doxorubicin and 5 FU, the addition of actein to the chemotherapy agent resulted in an increase in cells in the G1 phase of the cell cycle (Table 8). The inventors' results indicate that it may be better to give the chemotherapy agents before actein, in order to retain the block at S or G2/M that is induced by some chemotherapy agents.

TABLE 8

Effect of actein alone and in combination with chemotherapy agents on cell cycle distribution in MDA-MB-453 cells.

| | Sub G1 (%) | G1 (%) | S (%) | G2/M (%) |
|---|---|---|---|---|
| (a) The cells were grown in DMEM + 0.25% FBS for 48 hrs and then treated with actein at 20 µg/ml or 40 µg/ml and analyzed at 48 hrs by DNA flow cytometry. The values indicate the % of cells in the indicated phases of the cell cycle. The control contains 0.08% DMSO. | | | | |
| dmso, 0.08% | 2.1 | 74.3 | 10.5 | 13.6 |
| actein, 20 µg/ml | 1.8 | 79.6 | 8.5 | 10.0 |
| actein, 40 µg/ml | 2.2 | 83.8 | 4.9 | 9.0 |
| (b) The cells were treated with 0, 2 or 20 µg/ml (29.6 µM) actein alone and in combination with paclitaxel (1 nM) and analyzed at 48 hrs by DNA flow cytometry. The values indicate the % of cells in the indicated phases of the cell cycle. The control contains 0.044% DMSO. | | | | |
| Dmso | 1.0 | 70.6 | 11.8 | 17.0 |
| Actein 2 µg/mL | 0.9 | 69.8 | 11.0 | 18.6 |
| Actein 20 µg/mL | 1.6 | 70.8 | 9.7 | 18.2 |
| Taxol 1 nM | 1.0 | 71.0 | 10.8 | 17.0 |
| Taxol 1 nM + Actein 2 µg/mL | 1.8 | 69.2 | 10.6 | 18.5 |
| Taxol 1 nM + Actein 20 µg/mL | 2.8 | 70.1 | 8.6 | 18.9 |
| (c) The cells were treated with 0 or 20 µg/ml (29.6 µM) actein alone and in combination with doxorubicin (0.1 µg/ml, 0.17 µM), 5-FU (0.02 µg/ml, 0.15 µM) and analyzed at 48 hrs by DNA flow cytometry. The values indicate the % of cells in the indicated phases of the cell cycle. The control contains 0.08% DMSO. | | | | |
| dmso, 0.08% | 3.0 | 59.0 | 10.0 | 28.0 |
| Actein, 20 µg/mL | 2.7 | 59.2 | 8.6 | 29.5 |
| Doxorubicin, 0.1 µg/mL | 2.5 | 30.1 | 5.6 | 61.7 |
| Doxorubicin + Actein, 20 µg/mL | 5.3 | 39.2 | 9.6 | 46.0 |
| 5-FU, 0.02 µg/mL | 3. | 28.9 | 47.6 | 20.3 |
| 5-FU + Actein, 20 µg/mL | 6.8 | 38.0 | 34.1 | 21.2 |

Effects of Actein on Proteins Involved in Carcinogenesis

The inventors' previous results indicated that actein decreased the level of cyclin D1, cdk4, and the hyperphosphorylated form of the pRB protein, and increased the level of p21$^{cip1}$ in MCF7 cells-changes that may contribute to the arrest in G1. The level of the epidermal growth factor receptor (EGFR), which is overexpressed in various cancers (Suzui et al., Growth inhibition of human hepatoma cells by acyclic retinoid is associated with induction of p21 (CIP1) and inhibition of expression of cyclin D1. *Cancer Research*, 62:3997-4006, 2002), was not altered after treatment with actein. There also was no consistent effect of actein on the phosphorylated and activated form of EGFR (p-EGFR). However, the inventors did see a significant decrease of p-EGFR with the 40 µg/ml dose at 24 h. Thus, the EGFR did not appear to be a direct target for actein.

Figure 8:
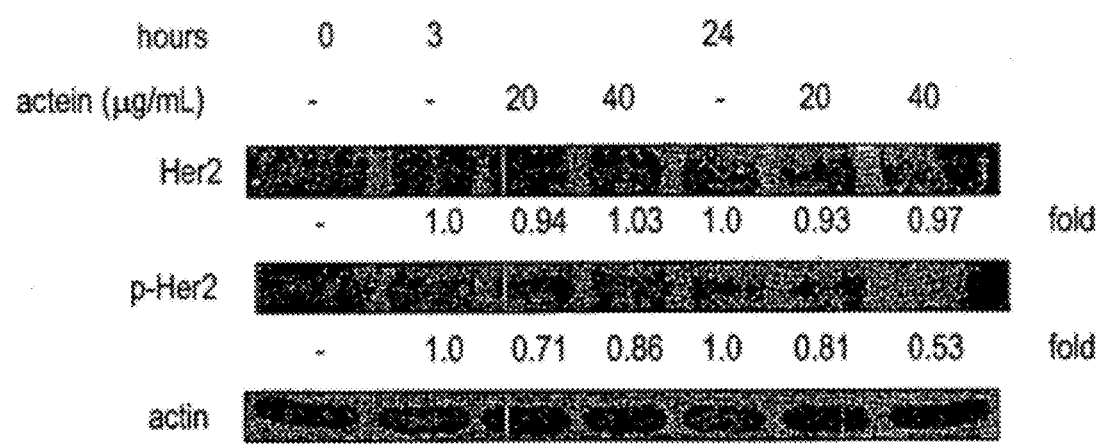
FIG. 8 illustrates a Western-blot analysis of extracts obtained from MDA-MB-453 cells treated with actein. The cells were treated with 0, 20, or 40 μg/ml of actein. After 3 and 24 h, extracts were prepared and analyzed by Western blotting with an antibody to Her2 or an antibody to phospho-Her2 (p-Her2). An antibody to β-actin was used as a loading control. The staining intensities of the visualized blots were quantified using NIH image software. For each protein, the relative band intensities were determined by comparing treated samples with untreated controls. These values were then normalized (fold), using β-actin as an internal control.

Since the Her2 overexpressing cells were the most sensitive to growth inhibition by black cohosh extracts and components, the inventors tested the effect of actein on the Her2 receptor and on the phosphorylation and activation of the Her2 receptor (p-Her2) (FIG. 8) in MDA-MB-453 human breast cancer cells (which express both Her2 and p-Her2 at high levels). Actein at 20 µg/ml caused a slight decrease in the level of the Her2 protein at 3 and 24 h. After exposure to actein at 20 or 40 µg/ml, there was a small effect on p-Her2 at 3 h. The inventors found that actein at 20 or 40 µg/ml induced a dose-dependent decrease in the level of the p-Her2 receptor at 24 h. It is not clear how actein inhibits phosphorylation. For example, it is not clear whether actein binds to and directly inhibits the kinase activity of the Her2 receptor, analogous to the action of Iressa (Masuda et al., Epigallocatechin-3-gall-ate inhibits activation of HER-2/neu and downstream signaling pathways in human head and neck and breast carcinoma cells. *Clin. Cancer Res.*, 9: 3486-91, 2003), or whether it inhibits activation of the other component of the heterodimeric complex.

Figure 18:
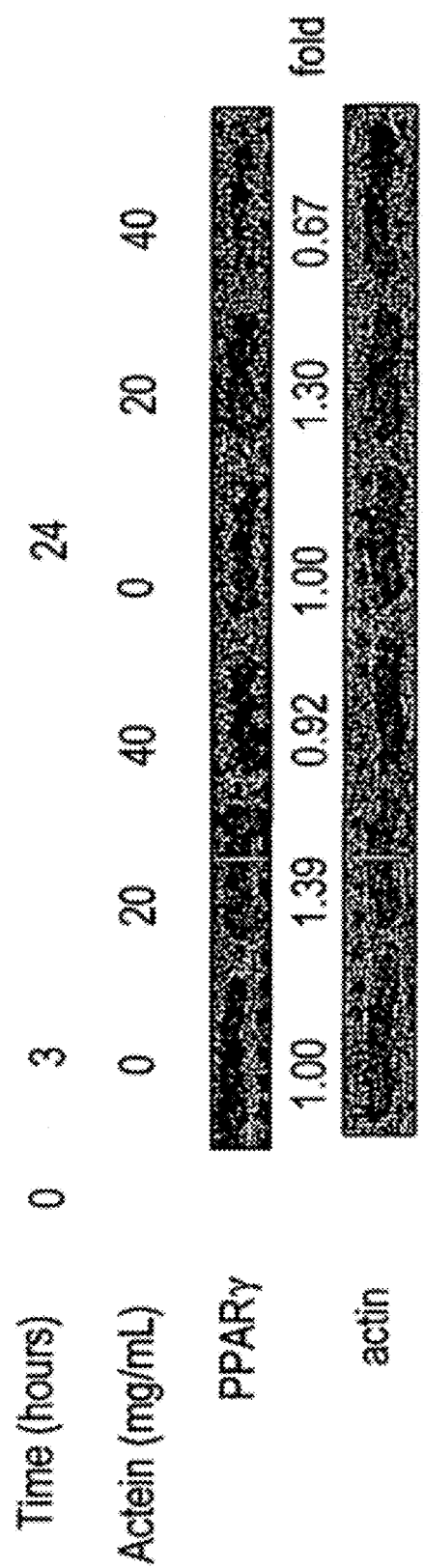
FIG. 18 illustrates MDA-MB-453 cells that were treated with 0, 20, or 40 μg/ml actein (20 μg/ml actein is equivalent to 29.6 μM). After 3 and 24 h, extracts were analyzed by Western blotting, with an antibody to PPARγ. An antibody for β-actin was used as a loading control.

As the synthetic triterpenoid 2-cyano-3,12-dioxooleana-1,9-dien-28-oic acid (CDDO) is a ligand for PPAR-γ (Wang et al., 2000; Lapillonne et al, 2003), the inventors next tested the effect of actein on PPAR-γ (FIG. 18). After treatment with actein, the intensities of the PPAR-γ bands relative to the β-actin bands were: 1.39 (3 h, 20 µg/ml), 0.93 (3 h, 40 µg/ml), 1.3 (24 h, 20 µg/ml), and 0.67 (24 h, 40 µg/ml). Thus actein 20 µg/ml increased the level of PPARγ at 3 and 24 hours. This anti-inflammatory protein is therefore among the targets of actein.

Effects of Actein on Transcriptional Control of Specific Genes

To further determine the nature of the target of actein, the inventors tested the effect of actein on molecules, such as cyclin D1, that function downstream of active Her2-containing heterodimers. Since the inventors found that actein induces cell-cycle arrest at G1, it was of interest to examine the effects of this compound on cellular levels of proteins that control cell-cycle progression. Cyclin D1 was of particular interest, because it plays a critical role in mediating the transition from G1 to S, is overexpressed in about 50-60% of primary human breast carcinomas (Joe et al., Resveratrol induces growth inhibition, S-phase arrest, apoptosis, and changes in biomarker expression in several human cancer cell lines. *Clin. Cancer Res.*, 8:893-903, 2002), and is overexpressed in several human breast cancer cell lines (Soh et al., Novel roles of specific isoforms of protein kinase C in activation of the c-fos serum response element. *Mol. Cel. Bio.*, 19:1313-24, 1999).

Figure 13:
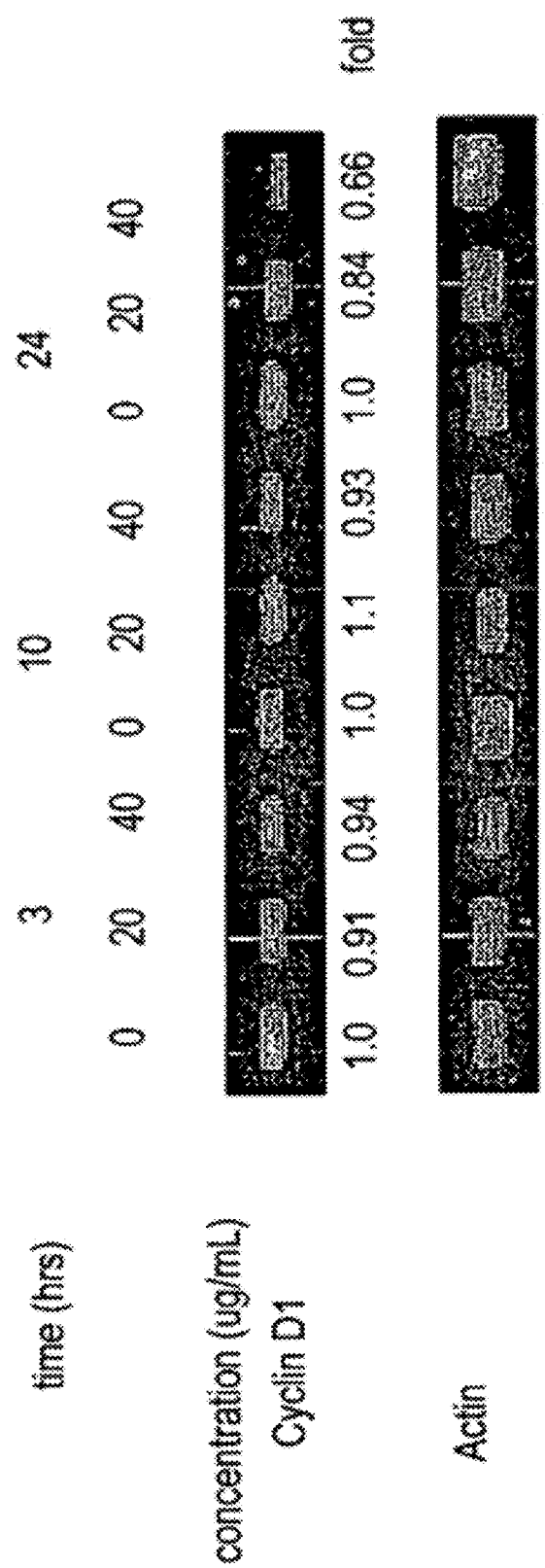
FIG. 13 illustrates the effects of actein on cyclin D1 mRNA in MCF7 cells (RT-PCR). MCF7 cells were treated with DMSO or actein for 3, 10, or 24 h. RNA was isolated and analyzed by RT-PCR, using primers for cyclin D1 and actin (control). The staining intensities of the visualized blots were quantified using NIH image software. The relative band intensities were determined by comparing treated samples with untreated controls. These values were then normalized (fold), using β-actin as an internal control.
Figure 14:
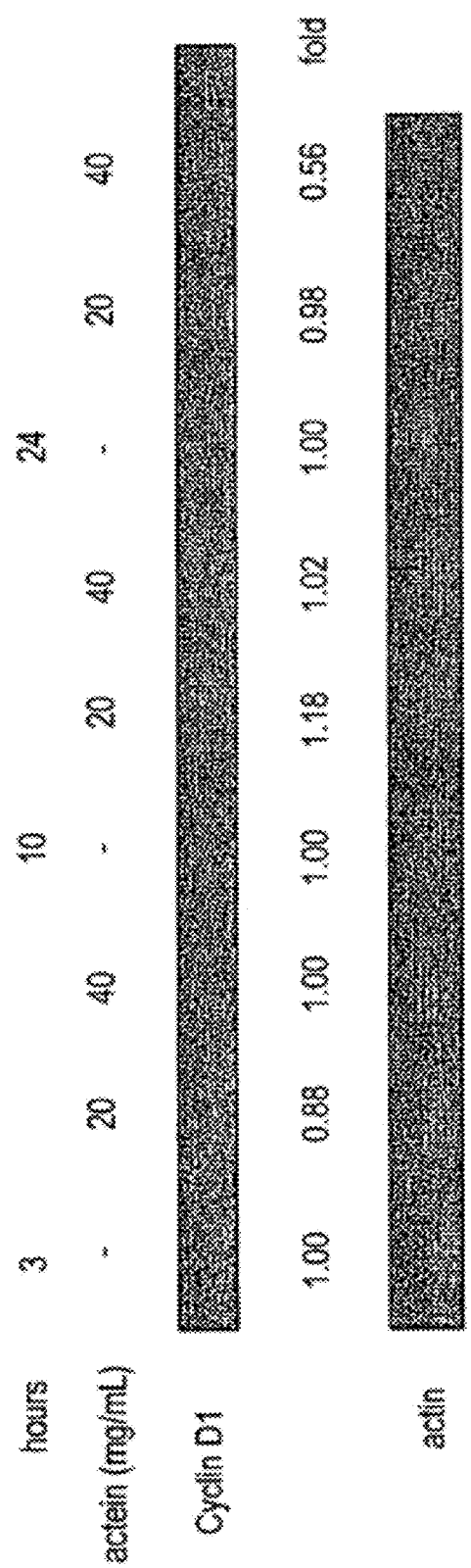
FIG. 14 demonstrates the effects of actein on cyclin D1 mRNA in MDA-MB-453 cells (RT-PCR). MDA-MB-453 cells were treated with DMSO or actein for 3, 10, or 24 h. RNA was isolated and analyzed by RT-PCR, using primers for cyclin D1 and actin (control). The staining intensities of the visualized blots were quantified using NIH image software. The relative band intensities were determined by comparing treated samples with untreated controls. These values were then normalized (fold), using β-actin as an internal control.
Figure 15:
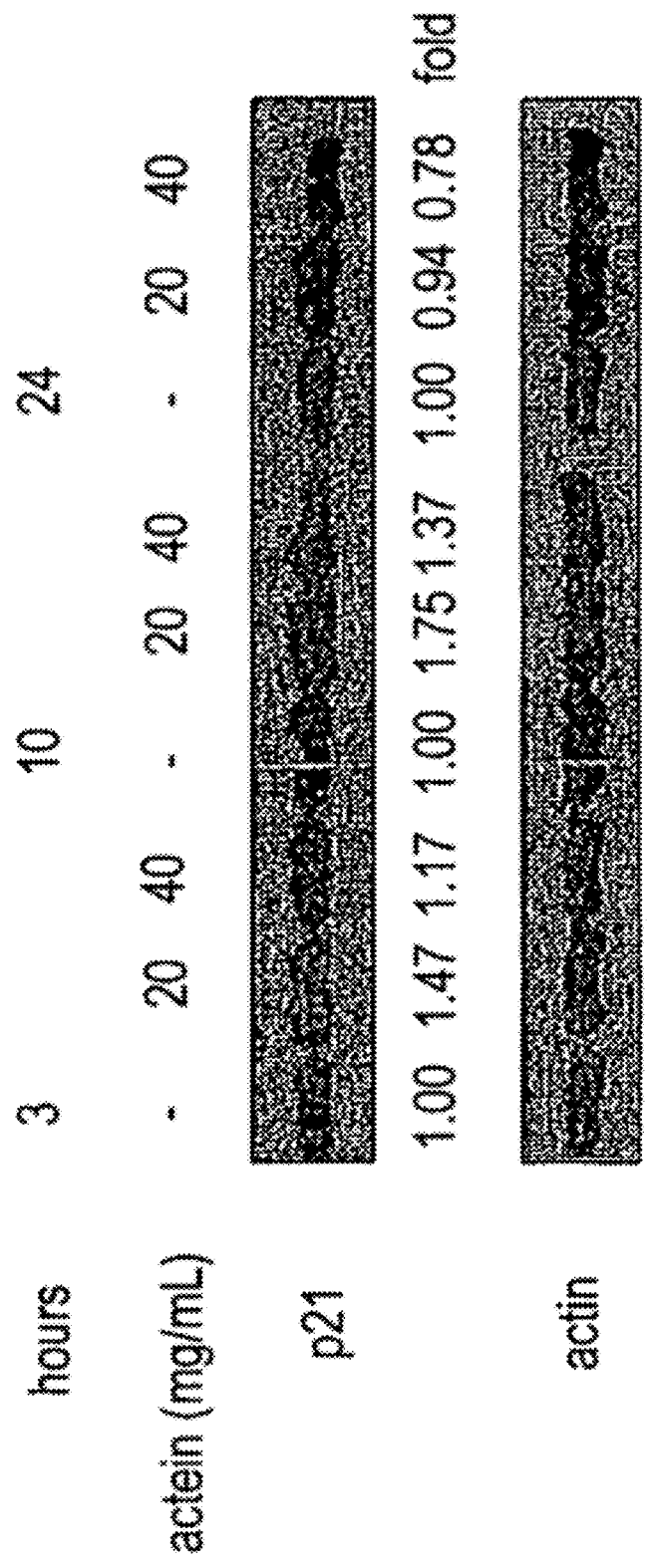
FIG. 15 illustrates MCF7 cells treated with 0, 20, or 40 μg/ml actein. 20 μg/ml actein is equivalent to 29.6 μM. After 3, 10, and 24 h, extracts were analyzed by Western blotting with an antibody to p21. An antibody for β-actin was used as a loading control.
Figure 16:
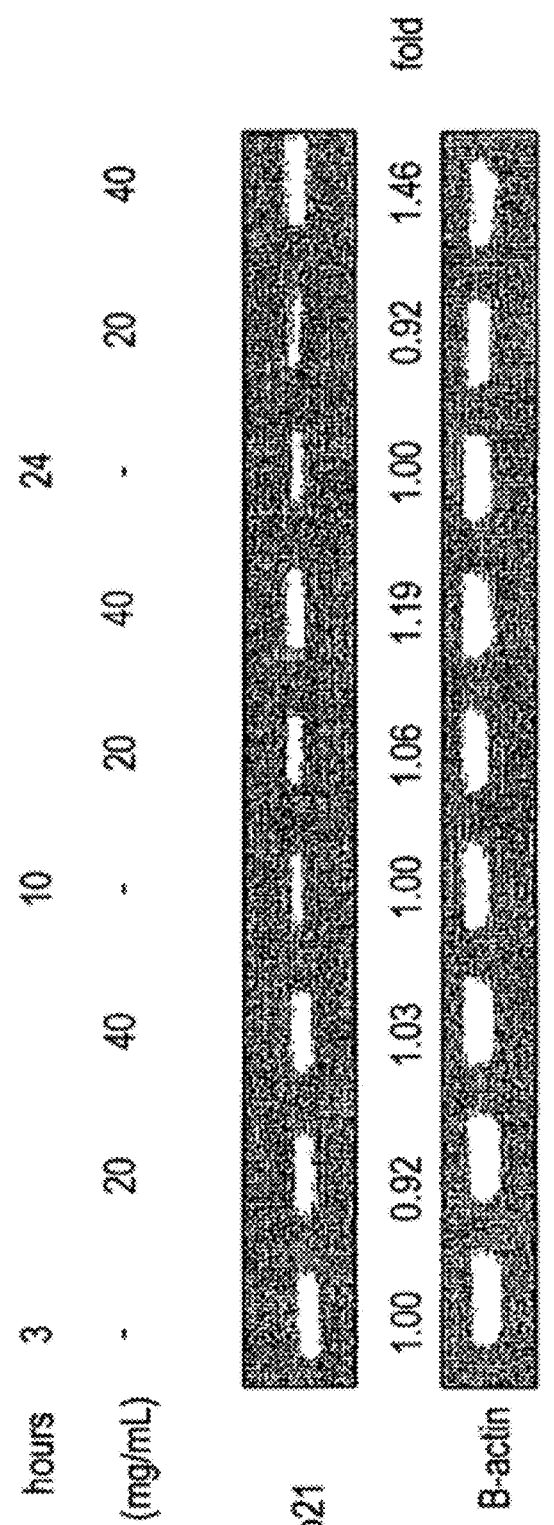
FIG. 16 shows the effects of actein on p21 mRNA in MDA-MB-453 cells (RT-PCR). MDA-MB-453 cells were treated with DMSO or actein for 3, 10, or 24 h. RNA was isolated and analyzed by RT-PCR, using primers for cyclin D1 and actin (control). The staining intensities of the visualized blots were quantified using NIH image software. The relative band intensities were determined by comparing treated samples with untreated controls. These values were then normalized (fold), using β-actin as an internal control.

Actein suppressed the level of cyclin D1 protein in MDA-MB-453 cells. After treatment with actein, the intensities of the cyclin D1 bands relative to the β-actin bands were: 3 hr, 40 µg/ml: 0.93; 24 hr, 20 µg/ml: 1.3; 40 µg/ml: 0.44. The inventors further show that actein at 40 µg/ml reduced the level of cyclin D1 mRNA at 24 hours, 0.66-fold in MCF7 cells (FIG. 13) and 0.56-fold in MDA-MB-453 cells (FIG. 14). The inventors next examined the effect of actein on cyclin D1 transcriptional promoter activity in MDA-MB-453 cells, using transient transfection reporter assays (Soh et al., Novel roles of specific isoforms of protein kinase C in activation of the c-fos serum response element. *Mol. Cell. Biol.*, 19:1313-24, 1999; Soh et al., Cyclic GMP mediates apoptosis induced by sulindac derivatives via activation of c-Jun NH2-terminal kinase 1. *Clin. Cancer Res.*, 10:4136-41, 2000; Masuda et al., Effects of epigallocatechin-3-gallate on growth, epidermal growth factor receptor signaling pathways, gene expression, and chemosensitivity in human head and neck squamous cell carcinoma cell lines. *Clin. Cancer Res.*, 7:4220-29, 2001). To accomplish this, the inventors used luciferase promoter activity at 24 h. It increases the level of p21 mRNA at 24 h. Its effects on the level of NF-κB promoter activity is complex: actein increase the level of NF-κB promoter activity at 20 µg/ml while decreases the level at 40 µg/ml at 24 h. Actein is capable of enhancing the effects of paclitaxel, herceptin, 5-FU, doxorubicin, and cisplatin.

TABLE 9

Summary.

Figure 9:
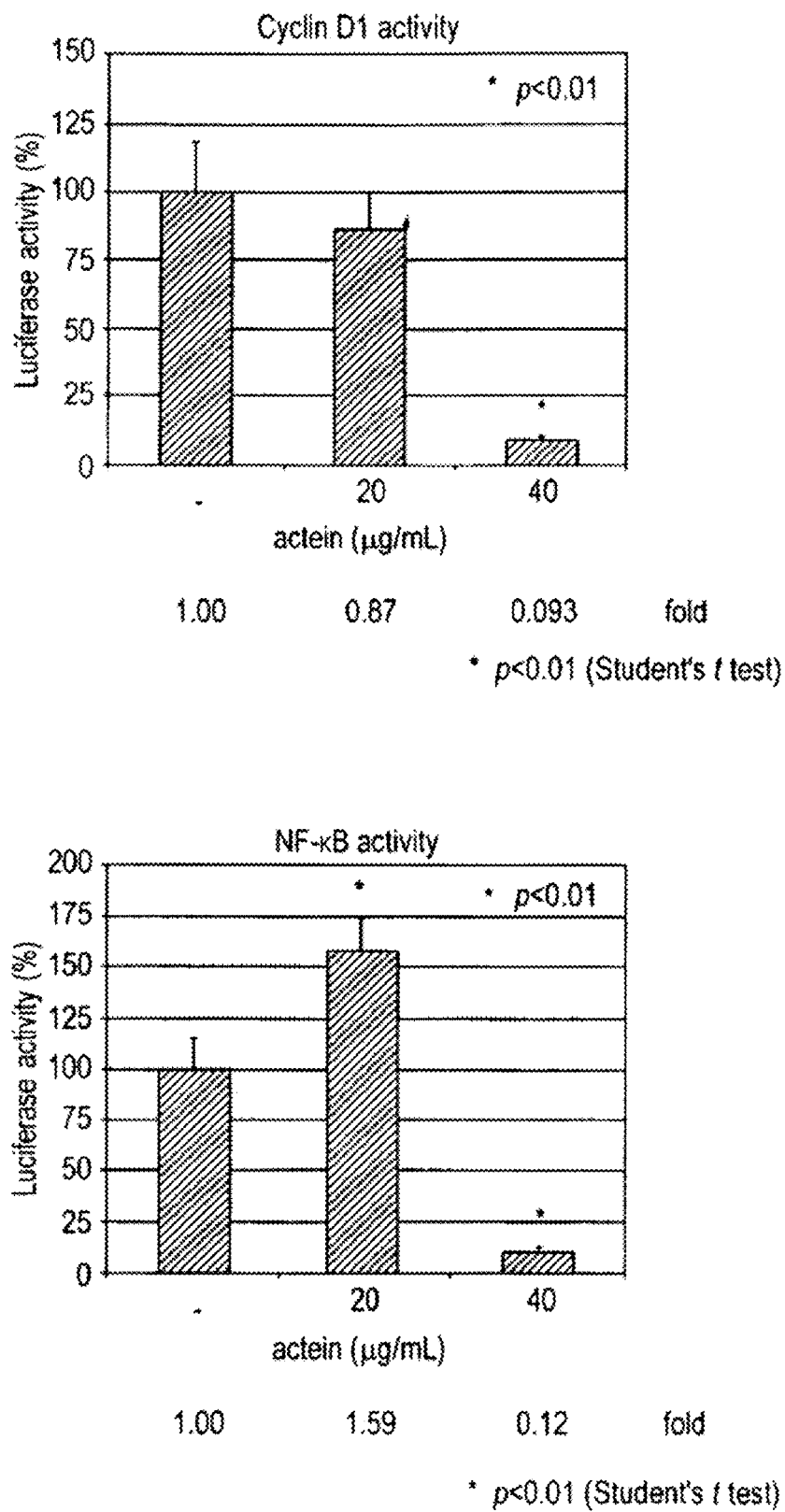
FIG. 9 presents a reporter promoter analysis of extracts obtained from MDA-MB-453 cells treated with actein. Using lipofectin, triplicate samples of MDA-MB-453 breast cancer cells were co-transfected with DNA of the indicated reporter plasmid, using β-gal DNA as an internal control. The cells were then treated with actein at 0, 20, and 40 μg/ml, in quadruplicate. Luciferase and β-gal activities were determined, as previously described (Masuda et al., Effects of epigallocatechin-3-gallate on growth, epidermal growth factor receptor signaling pathways, gene expression, and chemosensitivity in human head and neck squamous cell carcinoma cell lines. *Clinical Cancer Research*, 7:4220-29, 2001). Luciferase activities were normalized to β-gal activities. left panel=cyclin D1; right panel=nuclear factor kappa B (NF-κB); bars=SD FIG. 10 sets forth the effects of the aglycone cimigenol and the triterpene glycosides cimigenol glycoside, and actein, purified from black cohosh, on cell proliferation in MDA-MB-453 cells. MDA-MB-453 cells were exposed to increasing concentrations of the indicated purified components for 96 h, and the number of viable cells was determined using a Coulter Counter.
Figure 10:
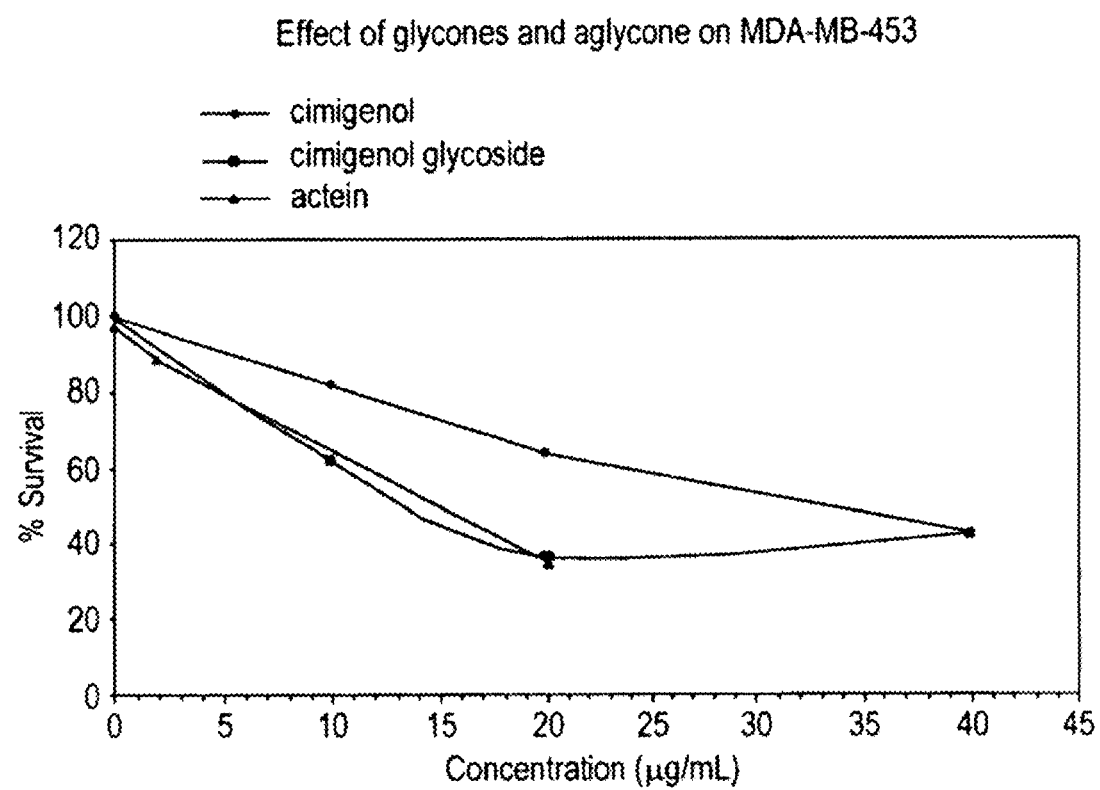

| molecule | assay | 0 | 3 hr, - | 20 ug/ml | 40 ug/ml | 10 hr, - | 20 ug/ml | 40 ug/ml | 24 hr,- | 20 ug/ml | 40 ug/ml |
|---|---|---|---|---|---|---|---|---|---|---|---|
| cyclin D1 | promoter | MDA-MB-453 | | | | | | | 1 | 0.87 | 0.093 |
| CD1 RNA | RT-PCR | MDA-MB-453 | 1 | 0.88 | 1 | 1 | 1.18 | 1.02 | 1 | 0.98 | 0.56 |
| CD1 RNA | RT-PCR | MCF7 | 1 | 0.91 | 0.94 | 1 | 1.1 | 0.93 | 1 | 0.84 | 0.66 |
| cyclin D1 | | MDA-MB-453 | 1 | | 0.93 | | | | 1 | 1.3 | 0.44 |
| p-Her2 | WB | MDA-MB-453 | 1 | 0.71 | 0.86 | | | | 1 | 0.81 | 0.53 |
| p21 | WB | MCF7 | 1 | 1.47 | 1 | 1 | 1.75 | 1.37 | 1 | 0.94 | 0.78 |
| | RT-PCR | MDA-MB-453 | 1 | 0.92 | 1.03 | | 1.06 | 1.19 | 1 | 0.92 | 1.46 |
| ppRB | WB | MCF7 | 1 | 1.51 | 1.59 | 1 | 0.61 | 0.64 | 1 | 0.8 | 0.43 |
| PPAR-g | | | 1 | 1.39 | 0.92 | | | | 1 | 1.3 | 0.67 |
| NF-kB | promoter | MDA-MB-453 | | | | | | | 1 | 1.59 | 0.12 |
| ikb | WB | MDA-MB-453 | 1 | 1.2 | 1.09 | | | | 1 | 0.81 | 0.53 |
| ikkb | WB | MDA-MB-453 | 1 | 1.79 | 1.78 | 1 | 0.48 | 0.59 | 1 | 1.06 | 0.95 | sequences that were 1745 bp upstream of the cyclin D1 gene. At 24 hours after exposure to actein at 20 (0.87 fold) or 40 µg/ml (0.093 fold), there was a dose dependent decrease in promoter activity, compared to R-gal as a control (FIG. 9). This result, in addition to the inventors' Western-blot data, suggests that actein inhibits the expression of cyclin D1 at the level of transcription.

Figure 17:
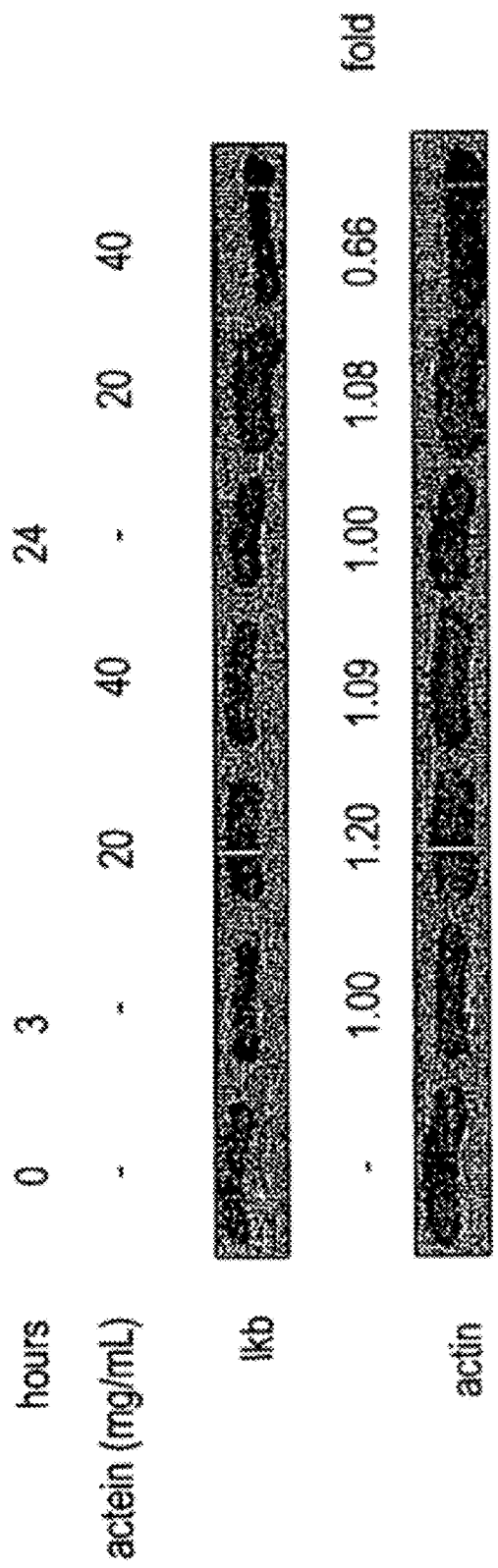
FIG. 17 illustrates MDA-MB-453 cells that were treated with 0, 20, or 40 μg/ml actein. 20 μg/ml actein is equivalent to 29.6 μM. After 3, 10, and 24 h, extracts were analyzed by Western blotting, with an antibody to ikβ. An antibody for β-actin was used as a loading control.

Since NF-κB is instrumental in controlling cell proliferation, the inventors then explored the effect of actein on NF-κB promoter activity. Actein at 20 µg/ml induced an increase (1.59 fold) and, at 40 µg/ml, a decrease (0.12 fold), in NF-κB promoter activity (FIG. 9). To understand the basis for this effect, the inventors checked the effect of actein on the level of the related proteins, IκB and IκκB. After treatment with actein, the intensities of the IκB bands relative to the β-actin bands were: 1.2 (3 h, 20 µg/ml), 1.09 (3 h, 40 µg/ml), 0.81 (24 h, 20 µg/ml), and 0.53 (24 h, 40 µg/ml) (FIG. 17). After treatment with actein, the intensities of the IκκB bands relative to the β-actin bands were: 1.79 (3 h, 20 µg/ml), 1.78 (3 h, 40 µg/ml), 0.48 (10 h, 20 µg/ml), 0.59 (10 h, 40 µg/ml), 1.06 (24 h, 20 µg/ml), and 0.95 (24 h, 40 µg/ml).

In summary, the EtOAc fraction of black cohosh: (1) inhibits cell proliferation at ~20 and 10 µg/ml, in ER+ and ER- human breast cancer cell lines, respectively; and (2) induces cell-cycle arrest at G1 at low concentrations (~$IC_{50}$), and at G2/M at high concentrations (~$3 \times IC_{50}$).

The triterpene glycoside fraction of black cohosh, and the triterpene glycosides-actein, 23-epi-26-deoxyactein, cimifugoside, and cimiracemoside A—inhibit the growth of human breast cancer cells, and induce cell cycle arrest at G1.

In MCF7 cells, actein decreases the level of cyclin D1, cdk4, and ppRb and increases the level of p21 and p27-changes which lead to G1 arrest. It reduces the level of cyclin D1 mRNA and promoter activity, thereby acting at the level of transcription. Actein does not affect the level of EGFR, and, therefore, does not specifically act through the estrogen receptor, the Her2 receptor, or the EGFR receptor. Actein is capable of enhancing the effects of tamoxifen on MCF7 breast cancer cells.

In MDA-MB-453 cells, actein decreases the level of p-Her2 and the level of cyclin D1 mRNA and promoter In an embodiment of the present invention, a composition is provided for use in treating or preventing neoplasia, comprising an effective anti-neoplastic amount of an ethyl acetate extract of black cohosh. In the composition, the ethyl acetate extract preferably comprises at least one triterpene glycoside compound. The triterpene glycoside compound is preferably selected from the group consisting of actein, cimifugoside, cimigenol glycoside, cimiracemoside A, and 23-epi-26-deoxyactein or mixtures thereof. The triterpene glycoside compound more preferably is actein or mixtures thereof.

In an embodiment, the effective anti-neoplastic amount of actein is between about 0.5 µg/ml and about 40.0 µg/ml. In a preferred embodiment, the effective anti-neoplastic amount of actein is between about 1.0 µg/ml and about 3.0 µg/ml.

In a further embodiment, the ethyl acetate extract of the composition comprises at least one aglycone. In a preferred embodiment, at least one aglycone is cimigenol.

In another embodiment of the present invention, a composition of anti-neoplastic agents is provided, comprising an effective anti-neoplastic amount of an ethyl acetate extract of black cohosh and an effective anti-neoplastic amount of at least one additional chemopreventive or chemotherapeutic agent. In a preferred embodiment, the composition is a synergistic combination.

In an embodiment of the composition of anti-neoplastic agents, the anti-neoplastic agents are combined in a single formulation. In an alternative embodiment, a separate, individual formulation of the ethyl acetate extract of black cohosh is combined with a separate, individual formulation of the at least one additional chemopreventive or chemotherapeutic agent.

In a preferred embodiment of the composition of anti-neoplastic agents, the ethyl acetate extract comprises a triterpene glycoside compound. The triterpene glycoside compound is preferably selected from the group consisting of actein, cimifugoside, cimigenol glycoside, cimiracemoside A, and 23-epi-26-deoxyactein, or mixtures thereof. The triterpene glycoside compound is more preferably actein or mixtures thereof.

In an embodiment of the composition of anti-neoplastic agents, the ethyl acetate extract comprises at least one aglycone. In a preferred embodiment, at least one aglycone is cimigenol.

In an embodiment of the composition of anti-neoplastic agents, the at least one additional chemopreventive or chemotherapeutic agent is selected from the group consisting of adriamycin, cisplatin, docetaxel, doxorubicin, 5-fluorouracil, herceptin, paclitaxel, tamoxifen, and vinblastine. In a preferred embodiment, the at least one additional chemopreventive or chemotherapeutic agent is paclitaxel.

In an embodiment of the composition of anti-neoplastic agents, the ethyl acetate extract of black cohosh comprises actein and the at least one additional chemopreventive or chemotherapeutic agent is paclitaxel. In a further embodiment, the effective anti-neoplastic amount of actein is between about 0.5 µg/ml and about 40.0 µg/ml, and the effective anti-neoplastic amount of paclitaxel is between about 0.5 nM and about 5.0 nM.

In a further embodiment of the present invention, a composition for use in treating or preventing neoplasia is provided, comprising an effective anti-neoplastic amount of actein. The neoplasia may be, but is not limited to, a carcinoma, a lymphocytic leukemia, a myeloid leukemia, a malignant lymphoma, a malignant melanoma, a myeloproliferative disease, a sarcoma, a brain tumor, a childhood tumor, or a mixed type of neoplasia.

In a further embodiment thereof, the composition comprises an effective anti-neoplastic amount of at least one additional chemopreventive or chemotherapeutic agent.

In another embodiment of the present invention, a composition is provided for use in treating or preventing disorders caused by or related to the abnormality of at least one factor selected from the group consisting of cyclin D1, cdk4, Her2, IκB, IκκB, NF-κB, p21, p27, PPARγ, and ppRb, wherein the composition comprises an effective amount of actein.

Pharmaceutical compositions of each of the compositions are provided, which have a pharmaceutically acceptable carrier.

In another aspect of the present invention, a method for treating or preventing neoplasia in a subject is provided, comprising administering to the subject an amount of an ethyl acetate extract of black cohosh effective to treat or prevent the neoplasia. The neoplasia may be, but is not limited to, a carcinoma, a lymphocytic leukemia, a myeloid leukemia, a malignant lymphoma, a malignant melanoma, a myeloproliferative disease, a sarcoma, a brain tumor, a childhood tumor, or a mixed type of neoplasia. The carcinoma may be, but is not limited to, breast cancer, colon cancer, lung cancer, ovarian cancer, prostate cancer, bladder cancer, uterine cancer, or skin cancer.

In an embodiment of a method for treating or preventing neoplasia, the ethyl acetate extract comprises at least one triterpene glycoside compound. In a preferred method, the triterpene glycoside compound is actein or mixtures thereof.

In another embodiment of a method for treating or preventing neoplasia, the effective amount of actein is between about 0.5 µg/ml and about 40.0 µg/ml.

In a further embodiment of a method for treating or preventing neoplasia, the ethyl acetate extract comprises at least one aglycone. In a preferred embodiment the at least one aglycone is cimigenol.

In an embodiment of the present invention, a method for treating or preventing neoplasia in a subject is provided, comprising administering to the subject an amount of an ethyl acetate extract of black cohosh effective to treat or prevent the neoplasia, in combination with an amount of at least one additional chemopreventive or chemotherapeutic agent effective to treat or prevent the neoplasia. In a preferred embodiment, the method results in a synergistic anti-neoplastic effect.

In an embodiment of the method, administration is concurrent. In an alternative embodiment, administration is sequential. In another embodiment, administration is alternate.

In a further embodiment of the method, the ethyl acetate extract comprises actein.

In a further embodiment of the method, the at least additional chemopreventive or chemotherapeutic agent is selected from the group consisting of cisplatin, docetaxel, doxorubicin, 5-fluorouracil, herceptin, paclitaxel, tamoxifen, and vinblastine. In a preferred embodiment, the at least one additional chemopreventive or chemotherapeutic agent is paclitaxel.

In an embodiment of a method for treating or preventing neoplasia, the ethyl acetate extract of black cohosh comprises actein and the at least one additional chemopreventive or chemotherapeutic agent is paclitaxel. Preferably, the effective amount of actein is between about 0.5 µg/ml and about 40.0 µg/ml, and the effective amount of paclitaxel is between about 0.5 nM and about 5.0 nM.

In an embodiment of the present invention, a method for treating or preventing neoplasia in a subject is provided, comprising administering to the subject an amount of actein effective to treat or prevent the neoplasia. The neoplasia may be, but is not limited to a carcinoma, a lymphocytic leukemia, a myeloid leukemia, a malignant lymphoma, a malignant melanoma, a myeloproliferative disease, a sarcoma, a brain tumor, a childhood tumor, or a mixed type of neoplasia. The carcinoma may be, but is not limited to, breast cancer, colon cancer, lung cancer, ovarian cancer, prostate cancer, bladder cancer, uterine cancer, or skin cancer.

In a further embodiment of a method for treating or preventing neoplasia, the method further comprises administering to the subject an amount of at least one additional chemopreventive or chemotherapeutic agent effective to treat or prevent the neoplasia. In a preferred embodiment, at least one additional chemopreventive or chemotherapeutic agent is selected from the group consisting of cisplatin, docetaxel, doxorubicin, 5-fluorouracil, herceptin, paclitaxel, tamoxifen, and vinblastine.

In a further embodiment of the present invention, a method for treating or preventing disorders in a subject caused by or related to the abnormality of at least one factor is provided, wherein the factor is selected from the group consisting of cyclin D1, cdk4, Her2, IκB, IκκB, NF-κB, p21, p27, PPARγ, and ppRb. The method comprising administering to the subject an amount of actein effective to treat or prevent the disorder.

It has been reported that extracts of black cohosh and isolated components inhibit the growth of human breast cancer cells (Einbond, et al., Gene expression analysis of the mechanisms whereby black cohosh inhibits human breast cancer cell growth, *Anticancer Res.*, 2007. 27(2): p. 697-712; Einbond, et al., The growth inhibitory effect of actein on human breast cancer cells is associated with activation of stress response pathways, *Int J Cancer*, 2007. 121(9): p. 2073-83; Einbond, et al., Growth inhibitory activity of extracts and purified components of black cohosh on human breast cancer cells, *Breast Cancer Res Treat*, 2004 83(3): p. 221-31), but the precise mechanism of action of this natural product is not known. Gene expression has been used to characterize the nature of the inhibition, in vitro. The results indicated that the growth inhibitory effect of actein (Einbond, et al., *Int J Cancer*, 2007. 121(9): p. 2073-83) or the MeOH extract (Einbond, et al., *Anticancer Res.*, 2007. 27(2): p. 697-712) on human breast cancer cells is associated with activation of stress response pathways (Benjamin, I. J., et al., Viewing a stressful episode of ER: is ATF6 the triage nurse? *Circ Res*, 2006. 98(9): p. 1120-2; Wu, Y. et al., Endoplasmic reticulum stress signal mediators are targets of selenium action, *Cancer Res*, 2005. 65(19): p. 9073-9). Both actein and the MeOH extract induced 2 phases of the integrated stress response, either the survival or the apoptotic phase, depending on the duration of treatment; for actein the results indicated that it also depends on the dose of treatment.

Recent case control and animal studies substantiate the in vitro findings of black cohosh's anticancer and chemopreventive potential. Rebbeck et al. (A retrospective case-control study of the use of hormone-related supplements and association with breast cancer, *Int. J. Cancer*, 2007. 120(7): p. 1523-1528) used a population-based case control study of women to show that black cohosh extracts and Remifemin appear to reduce the incidence of breast cancer, in particular PR positive tumors. The recent pharmacoepidemiologic observational retrospective cohort study of Zepelin et al. (Isopropanolic black cohosh extract and recurrence-free survival after breast cancer, *Clin Pharmacol Ther*, 2007. 45: p. 143-54) indicates that use of isoproanolic extracts, Remifemin and Remifemin plus were associated with prolonged recurrence-free survival after breast cancer. Studies of Sakurai et al. (2005) indicated that cimigenol and cimigenol-3,15-dione have antitumor initiating activity commensurate with EGCG (Sakurai, et al., Cancer preventive agents. Part 1: chemopreventive potential of cimigenol, cimigenol-3,15-dione, and related compounds, *Bioorg Med Chem*, 2005. 13(4): p. 1403-8), suggesting a chemopreventive role for these compounds. The studies of Seidlova-Wuttke et al, (Inhibitory Effects of a Black Cohosh (*Cimicifuga racemosa*) Extract on Prostate Cancer, *Planta Med*, 2006. 72(6): p. 521-26), indicated that the *Cimicifuga racemosa* extract BNO 1055 inhibited development, proliferation and malignancy of tumors induced by subcutaneous inoculation of LNCaP cells in immunodeficient mice.

To assess chemopreventive utility, considerations include whether, following oral administration, sufficient blood and tissue levels can be achieved, and whether this extract/compound exerts significant toxicity. The studies of Johnson, et al., (In vitro formation of quinoid metabolites of the dietary supplement *Cimicifuga racemosa* (black cohosh), *Chem Res Toxicol*, 2003. 16: p. 838-46) indicated that black cohosh catechols can be converted to (by metabolism or chemicals) to electrophilic quinones, in vitro, but these were not detected in the urine of women who ingested up to 256 mg of a standardized black cohosh extract (70% ethanol extract, prepared by Pure World Botanicals). The catechols do not appear to be absorbed across the intestinal epithelium, whereas the triterpenoids are absorbed.

It may be of concern that triterpene glycosides from black cohosh have been shown to inhibit thymidine transport into phytohemagglutinin-stimulated lymphocytes and cimifugoside appears to be immunosuppressive in PHA-stimulated lymphocytes in vitro. (Hemmi, et al., Inhibition of thymidine transport into phytohemagglutinin-stimulated lymphocytes by triterpenoids from *Cimicifuga* species, *J. Pharmacobio-Dyn*, 1979. 2: p. 339-349). Black cohosh may interact with CYP2D6 substrates (Gurley, et al., In vivo effects of goldenseal, kava kava, black cohosh, and valerian on human cytochrome P450 1A2, 2D6, 2E1, and 3A4/5 phenotypes, *Clin. Pharmacol. Ther.*, 2005. 77: p. 415-26). Studies indicate that commercially available black cohosh, whose active constituents were identified as triterpene glycosides, inhibited CYP3A4 in intestinal epithelium (Tsukamoto, et al. Isolation of CYP3A4 Inhibitors from the Black Cohosh (*Cimicifuga racemosa*). Evidence-based complementary and alternative medicine: *eCAM*, 2005. 2: p. 223-6). Black cohosh may thus increase the bioavailability of a variety of CYP3A4 substrates.

Animal studies indicate that extracts do not induce toxic, mutagenic or carcinogenic effects (Foster, et al., Black cohosh: *Cimicifuga racemosa*, A literature review. *HerbalGram*, 1999. 45: p. 35-49). Wistar rats given 5 g/kg of Remifemin granulate for 26 weeks did not show any organ or chemical toxicity (Liske, et al., Therapeutic efficacy and safety of *Cimicifuga racemosa* for gynecologic disorders, *Adv. Ther.*, 1998. 15: p. 45-53). Nor was toxicity, observed in dogs given 400 mg/kg/day for 26 weeks (Johnson, et al., *Chem Res Toxicol*, 2003. 16: p. 838-46). The results of the Ames test for a 40% 2-propanol extract were negative. The LD50 of a black cohosh preparation in mice was 7.7 mg/kg (intragastric) and 1.1 g/kg (intravenous).

Although black cohosh appears to be safe at doses higher than the human therapeutic dose, these results may or may not apply to the use of partially purified fractions of black cohosh or to purified components from black cohosh. It is also of concern that Davis et al. found (in an unpublished study) an increase in the incidence of lung metastases in a mouse MMTV neu model. (Davis et al. Black Cohosh, Breast Cancer, and Metastases to Lung: Data from the Mouse Model. Workshop on the Safety of Black Cohosh in Clinical Studies. 2004. Bethesda, Md.: National Institutes of Health).

Studies have yielded conflicting results on the effect of black cohosh on lipids. In a double blind study with placebo and CR extract BNO 1055 at 40 mg for three months, Wuttke et al. (Effects of black cohosh (*Cimicifuga racemosa*) on bone turnover, vaginal mucosa, and various blood parameters in postmenopausal women: a double-blind, placebo-controlled, and conjugated estrogens-controlled study, *Menopause*, 2006. 13(185-196)), induced a statistically significant increase in TTG, but no effects on total, LDL or HDL cholesterol. (Spangler et al., The effects of black cohosh therapies on lipids, fibrinogen, glucose and insulin, *Maturitas*, 2007. 57: p. 195-204), who conducted a randomized, placebo controlled trial using the same extract at a higher dose, 120 mg/kg, for twelve weeks; agreed in that they found no effect on cholesterol, but disagreed in that they did not find a difference in TTG. In another study, however, black cohosh (40 mg) for 52 weeks increased TTG and cholesterol (HDL-cholesterol) and lowered LDL-cholesterol (Raus et al., 2006; First-time proof of endometrial safety of the special black cohosh extract (*Actaea* or *Cimicifuga racemosa* extract) CR BNO 1055, *Menopause* 13, 678-91).

It is believed that there are no reports of gene expression profiles of the effects of black cohosh obtained in vivo.

There is evidence that the bioactive triterpene glycoside actein is selective for malignant cells and able to synergize at low concentrations with different classes of chemotherapy agents to inhibit breast cancer cell growth: (K. Watanabe, et al., Cycloartane glycosides from the rhizomes of *Cimicifuga racemosa* and their cytotoxic activities, *Chem Pharm Bull.* (*Tokyo*) 50 (2002) 121-5; L. S. Einbond, et al.), Growth inhibitory activity of extracts and purified components of black cohosh on human breast cancer cells, *Breast Cancer Res Treat.* 83 (2004) 221-31; and L. S. Einbond, et al., Actein and a fraction of black cohosh potentiate antiproliferative effects of chemotherapy agents on human breast cancer cells, *Planta Med.* 72 (2006) 1200-6). Actein's growth inhibitory effects may be related to the altered expression of genes involved in calcium homeostasis and stress response pathways, particularly the unfolded protein response and cell cycle control genes. (L. S. Einbond, et al. The growth inhibitory effect of actein on human breast cancer cells is associated with activation of stress response pathways, *Int J Cancer* 121 (2007) 2073-83). Actein's downregulation of cyclin D1, CDK4, pEGFR and the hyperphosphorylated form of pRb and upregulation of the CDK inhibitory protein p21$^{cip1}$ in MCF7 cells may contribute to its ability to arrest cells in G1. (L. S. Einbond, et al., Growth inhibitory activity of extracts and purified components of black cohosh on human breast cancer cells, *Breast Cancer Res Treat.* 83 (2004) 221-31).

Figure 26A:
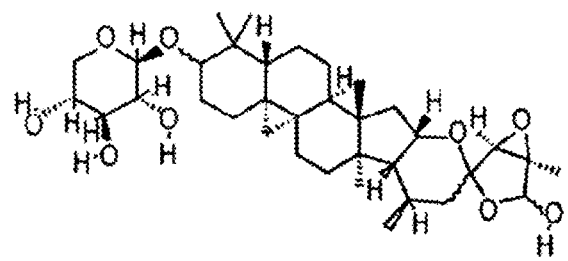
FIG. 26 Chemical structures of A) actein, and B) digitoxin. Shown in C) is a schematic diagram of pathways linking $Na^+$—$K^+$-ATPase with the ERK and Akt pathways (adapted from Haas et al., J. Biol. Chem. 275 (2000) 27832-27837, and Lavoie et al., J. Biol. Chem. 271 (1996) 20608-16).
Figure 26B:
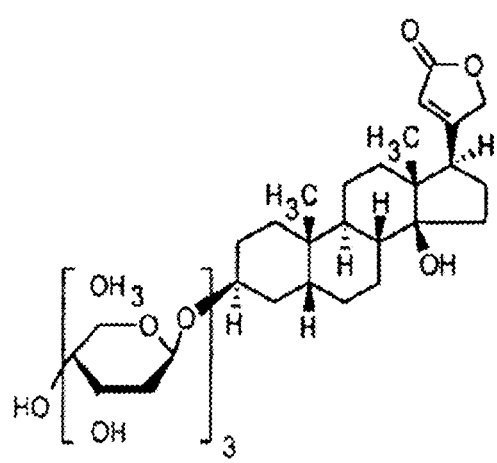

Actein is structurally related to the cardiac glycosides. (FIG. 26A, B). Both are members of the saponin group of glycosides, in which there are neutral steroidal saponins (such as the cardiac glycosides digitoxin and ouabain) and acid triterpenoid saponins (such as actein). As early as 1832, it was reported that the medical effects of black cohosh resembled, but were not as strong, as those of digitalis. (R. Upton, Black Cohosh Rhizome, American Herbal Pharamacopoeia and Therapeutic Compendium. *American Herbal Pharmacopoeia*. (2002)). Cardiac glycosides have been more highly studied than actein, and knowledge of their mode of action may provide insights to the mechanism of action of actein.

Figure 26C:
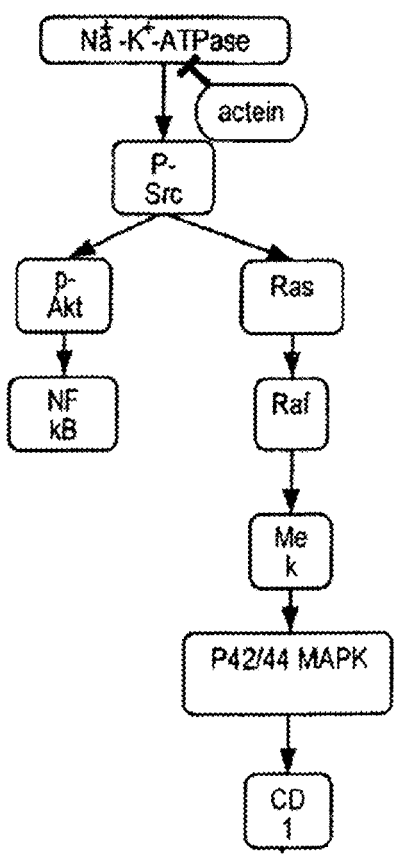

Cardiac glycosides bind to the alpha subunit of the Na$^+$—K$^+$-ATPase, an oligomeric complex with two non-covalently linked α (catalytic) and β subunits and a third subunit comprised of seven FXYD transmembrane proteins. The Na$^+$—K$^+$-ATPase and partners are present in caveolae (membrane microdomains) (J. Liu, et al., Ouabain-induced endocytosis of the plasmalemmal Na/K-ATPase in LLC-PK1 cells requires caveolin-1., *Kidney Int.* 67 (2005) 1844-54), and the Na$^+$—K$^+$-ATPase alpha subunit contains two conserved caveolin-1-binding motifs. Ouabain potently inhibits the enzyme's active transport of Na$^+$ and K$^+$ across cell membranes, leading to a small increase in intracellular Na$^+$ and a large increase in intacellular Ca$^{2+}$. In heart muscle, this enhances the force of contraction. (Kometiani P, et al. Digitalis-induced signaling by Na$^+$/K$^+$-ATPase in human breast cancer cells, *Mol Pharmacol* 67 (2005) 929-36). The binding of ouabain to this ATPase also converts the enzyme to a signal transducer (J. Tian, et al., Binding of Src to Na$^+$/K$^+$-ATPase forms a functional signaling complex, *Mol Biol Cell* 17 (2006) 317-26), by releasing and activating Src, which has been shown to subsequently phosphorylate effectors such as the epidermal growth factor receptor, leading to assembly and activation of multiple signaling cascades (FIG. 26c). Z. Li, et al., The Na/K-ATPase/Src complex and cardiotonic steroid-activated protein kinase cascades, *Pflugers Arch*. February 19; [Epub ahead of print] (2008)).

There is evidence that cardiac glycosides also have antitumor activity. Breast cancers from women on digitalis have more benign characteristics, and the rate of recurrence after 5 years following a mastectomy is 9.6% times less in patients on digitalis. (Lopez-Lazaro M, et al. Anti-tumour activity of *Digitalis purpurea* L. subsp. *heywoodii. Planta Med.* 69(8):701-4, 2003). In animal models, digitoxin has been shown to inhibit both two-stage carcinogenesis of mouse skin papillomas induced by 7,12-dimethylbenzanthracene (DMBA) and 12-O-tetradecanoylphorbol-13-acetate (TPA), and mouse pulmonary tumors induced by 4-nitroquinoline-N-oxide (4NQO) and glycerol. (Inada A et al. Anti-tumor promoting activities of natural products. II. Inhibitory effects of digitoxin on two-stage carcinogenesis of mouse skin tumors and mouse pulmonary tumors. *Biol Pharm Bull.* 16(9):930-1, 1993.)

The therapeutic range for digitoxin in the treatment of heart failure is narrow; it has a therapeutic plasma concentration greater than 10 ng/ml (13 nM), but is toxic at concentrations above 35 ng/ml (46 nM). Though it was initially thought that only toxic doses of digitoxin could be useful for anticancer activity, recent studies indicate that low doses of digitoxin induce apoptosis in malignant cell lines. (McConkey D et al. Cardiac glycosides stimulate Ca$^{2+}$ increases and apoptosis in androgen-independent, metastatic human prostate adenocarcinoma cells. *Cancer Res.* 60(14): 3807-12, 2000.) Crude extracts and several components present in foxglove appear to inhibit the growth of serum-stimulated breast cancer cells. Digitoxin is 7.2 fold more active than the aglycone on MCF7 human breast cancer cells. (Lopez-Lazaro M, et al. *Planta Med.* 69(8):701-4, 2003).

The growth inhibitory activity of cardiac glycosides may be related to their inhibition of the Na$^+$—K$^+$-ATPase, a member of evolutionarily conserved enzymes that couple ATP hydrolysis to ion translocation across cellular membranes. (Skou J., The Na,K-pump. *Methods Enzymol.* 156: 1-25, 1988; Kaplan J., Biochemistry of Na,K-ATPase. *Annu Rev Biochem.* 71:511-35, 2002; Lingrel J, Kuntzweiler T. Na$^+$, K(+)-ATPase. *J Biol Chem* 269(31):19659-62, 1994) When cardiac glycosides bind to the alpha subunit of the Na$^+$—K$^+$-ATPase, they potently inhibit the active transport of Na$^+$ and K$^+$ across cell membranes, (Goodman G, editor. Goodman and Gilman's The Pharmacological Basis of Therapeutics. 9 ed; 1996), leading to a small increase in intracellular Na$^+$ and resulting in a large increase in intacellular Ca$^{2+}$, which, as noted enhances the force of contraction in heart muscle. (Kometiani P, Liu L, A. A. *Mol Pharmacol* 67(3):929-36, 2005.) Inhibition of the enzyme also releases and activates. Src, which subsequently transactivates epidermal growth factor receptor, leading to assembly and activation of multiple signaling cascades such as Ras/Raf/ERK1/2 and phospholipase C-/protein kinase C pathways and mitochondrial ROS production. (Li Z, Xie Z. The Na/K-ATPase/Src complex and cardiotonic steroid-activated protein kinase cascades. *Pflugers Arch.* 2008. [Epub ahead of print]).

Cardiotonic steroids have been reported to exert growth regulatory effects at nano- and sub-nanomolar concentrations that do not inhibit cellular Na$^+$—K$^+$-ATPase pumping activity. (McConkey D et al., *Cancer Res.* 60(14):3807-12, 2000; Li Z, Xie Z. The Na/K-ATPase/Src complex and cardiotonic steroid-activated protein kinase cascades. *Pflugers Arch.* 2008. [Epub ahead of print]; Liu L, Askari A., *Cell Molec Biol* (Noisy-le-grand). 52(8):28-30, 2006.) Apoptosis may be induced by the cardiac glycosides' downstream Src-mediated effects involving NF-κB. (Winnicka K, et al. Cardiac glycosides in cancer research and cancer therapy. *Acta Pol Pharm.* 63(2):109-15, 2006.) Digitoxin has been shown to block phosphorylation of the NF-κB inhibitor IκBκ in cystic fibrosis lung epithelial cells (Srivastava M, et al. Digitoxin mimics gene therapy with CFTR and suppresses hypersecretion of IL-8 from cystic fibrosis lung epithelial cells. *Proc Natl Acad Sci USA* 101:7693-8, 2004), and inhibit TNF-α/NF-κB signaling by blocking recruitment of TNF receptor-associated death domain (TRADD) to the TNF receptor. (Yang Q, et al. Cardiac glycosides inhibit TNF-alpha/NF-kappaB signaling by blocking recruitment of TNF receptor-associated death domain to the TNF receptor. *Proc Nat Acad Sci USA* 102(27):9631-6, 2005.)

The risks of digitoxin administration in humans are well known.

In an embodiment of the present invention, a method for treating, preventing or ameliorating breast cancer is provided, comprising administering to a patient in need thereof a composition comprising a synergistic amount of digitoxin and an extract of black cohosh comprising a triterpene glycoside, and a pharmaceutically acceptable carrier, and optionally an effective amount of at least one additional chemopreventive or chemotherapeutic agent. In an alternative embodiment of the present invention, a method for treating, preventing or ameliorating breast cancer is provided comprising administering to a patient in need thereof a composition comprising a synergistic amount of digitoxin and actein, and a pharmaceutically acceptable carrier, and optionally an effective amount of at least one additional chemopreventive or chemotherapeutic agent.

In a further embodiment a method for treating or preventing neoplasia in a subject is provided, comprising administering to the subject an amount of an extract of black cohosh comprising a triterpene glycoside effective to treat or prevent neoplasia, in combination with an amount of an a cardiac glycoside which is effective to treat or prevent the neoplasia, and optionally an effective amount of at least one additional chemopreventive or chemotherapeutic agent. In a preferred embodiment, the extract comprises the triterpene glycoside actein. The extract optionally further comprises an aglycone which is preferably cimigenol.

In another preferred embodiment, the extract of black cohosh comprising a triterpene glycoside is selected from the group consisting of an ethyl acetate extract of black cohosh and an n-butanolic fraction of an EtOH/water extract of black cohosh. Preferred is the n-butanolic fraction of an EtOH/water extract of black cohosh. Black cohosh extract that is enriched for triterpene glycosides preferably has at least 15% triterpene glycosides. More preferably, the extract has at least 20% triterpene glycosides. Most preferred is an extract having about 27% triterpene glycosides.

In an alternative embodiment, a method for treating or preventing neoplasia in a subject is provided, comprising administering to the subject an amount of actein effective to treat or prevent neoplasia, in combination with an amount of a cardiac glycoside which is effective to treat or prevent the neoplasia, and optionally an effective amount of at least one additional chemopreventive or chemotherapeutic agent.

In any of the methods of treating or preventing neoplasia, the neoplasia is preferably a carcinoma. In a further preferred embodiment, the carcinoma is breast cancer.

Also, in any of the methods of treating or preventing neoplasia, the cardiac glycoside may be selected from the group consisting of digitoxin, ouabain, proscillaridin A, digoxin, lanatoside C, and combinations thereof. Preferably, the cardiac glycoside is digitoxin.

In any embodiment of the methods of the present invention in which actein and digitoxin are administered, actein and digitoxin are preferably in amounts that result in a synergistic anti-neoplastic effect.

In an embodiment of any of the methods, the effective anti-neoplastic amount of actein used is from about 0.2 µg/ml to about 40.0 µg/ml. In a further embodiment the effective anti-neoplastic amount of actein is from about 0.2 µg/ml to about 20.0 µg/ml.

In another embodiment of any of the methods, the amount of actein is from about 0.2 µg/ml to about 2 µg/ml and the digitoxin is in an amount of from about 0.01 µg/ml to about 0.8 µg/ml. Alternatively, the amount of actein is from about 2 µg/ml to about 20 µg/ml and the digitoxin is in an amount of from about 0.0004 µg/ml to about µg/ml.

In another embodiment, a method for modulating Na+—K+-ATPase activity is provided comprising contacting a cell that expresses Na+—K+-ATPase with an extract of black cohosh comprising a triterpene glycoside and a cardiac glycoside, and optionally at least one additional chemopreventive or chemotherapeutic agent. In an alternative embodiment, a method for modulating Na+—K+-ATPase activity is provided comprising contacting a cell that expresses Na+—K+-ATPase with actein and a cardiac glycoside, and optionally at least one additional chemopreventive or chemotherapeutic agent. In any of these methods, the cardiac glycoside is preferably digitoxin.

In another embodiment, a method for modulating a growth inhibitory effect of digitoxin on a carcinoma is provided which comprises contacting the carcinoma with digitoxin and an effective amount of an extract of black cohosh comprising a triterpene glycoside, which results in a synergistic effect of the digitoxin on the carcinoma, and optionally an effective amount of at least one additional chemopreventive or chemotherapeutic agent. In an alternative embodiment, a method for modulating a growth inhibitory effect of digitoxin on a carcinoma is provided which comprises contacting the carcinoma with digitoxin and an effective amount of actein, which results in a synergistic effect of the digitoxin on the carcinoma, and optionally an effective amount of at least one additional chemopreventive or chemotherapeutic agent. In a preferred embodiment of any of these methods, the cardiac glycoside is digitoxin. In another preferred embodiment, the carcinoma is breast cancer.

A further embodiment is a composition for use in treating or preventing neoplasia comprising an effective anti-neoplastic amount of an extract of black cohosh comprising a triterpene glycoside and an effective anti-neoplastic amount of a cardiac glycoside, and optionally an effective amount of at least one additional chemopreventive or chemotherapeutic agent. In a preferred embodiment, the extract comprises the triterpene glycoside actein. The extract optionally further comprises an aglycone which is preferably cimigenol. In another preferred embodiment, the extract is selected from the group consisting of an ethyl acetate extract of black cohosh and an n-butanolic fraction of an EtOH/water extract of black cohosh.

In an alternative embodiment a composition for use in treating or preventing neoplasia is provided comprising an effective anti-neoplastic amount of actein and an effective anti-neoplastic amount of a cardiac glycoside, and optionally an effective amount of at least one additional chemopreventive or chemotherapeutic agent. The cardiac glycoside is preferably selected from the group consisting of digitoxin, ouabain, proscillaridin A, digoxin, lanatoside C, and combinations thereof. More preferably, the cardiac glycoside is digitoxin.

In an embodiment of any composition of the present invention comprising actein and digitoxin, the actein and digitoxin are in amounts that result in a synergistic anti-neoplastic effect. More preferably, the composition is a pharmaceutical composition comprising a pharmaceutically acceptable carrier.

In an embodiment of compositions of the present invention, the effective anti-neoplastic amount of actein is from about 0.2 µg/ml to about 40.0 µg/ml. In a further embodiment, the effective anti-neoplastic amount of actein is from about 0.2 µg/ml to about 20.0 µg/ml.

In a further embodiment of a composition, the cardiac glycoside is digitoxin and the amount of actein is from about 0.2 µg/ml to about 2 µg/ml and the amount of digitoxin is from about 0.01 µg/ml to about 0.8 µg/ml. Alternatively, the amount of actein is from about 2 µg/ml to about 20 µg/ml, and the digitoxin is in an amount of from about 0.0004 µg/ml to about 5 µg/ml.

In an embodiment of each of the methods of the present invention that optionally provide an effective amount of at least one additional chemopreventive or chemotherapeutic agent, particularly in a method for treating, preventing or ameliorating breast cancer, the at least one additional chemopreventive or chemotherapeutic agent is paclitaxel.

In an embodiment of each of the methods of the present invention that optionally provide an effective amount of at least one additional chemopreventive or chemotherapeutic agent, the at least one additional chemopreventive or chemotherapeutic agent is a taxane. Preferably, the taxane is selected from the group consisting of paclitaxel, docetaxel, or mixtures thereof. More preferably, the taxane is paclitaxel.

In an embodiment of any of the methods of the present invention in which paclitaxel is used, the paclitaxel is in an amount that results in a synergistic effect with the digitoxin and one or more triterpene glycoside, preferably actein or mixtures with actein.

In preferred embodiments of compositions comprising paclitaxil and actein, the paclitaxel is in an amount that results in a synergistic effect with the digitoxin and one or more triterpene glycoside, preferably actein or mixtures with actein. Preferably, such a composition is a pharmaceutical composition which comprises the composition and a pharmaceutically acceptable carrier.

In a further embodiment, a method for modulating a growth inhibitory effect of paclitaxel on a carcinoma is provided which comprises contacting the carcinoma with paclitaxel and an effective amount of digitoxin, which results in a synergistic effect of the paclitaxel on the carcinoma, and optionally an additional chemopreventive or chemotherapeutic agent which is selected from the group consisting of an extract of black cohosh comprising a triterpene glycoside and actein. In an embodiment thereof, the amount of digitoxin and paclitaxel are at least 0.01 µg/ml digitoxin and 1 nM paclitaxel. In another embodiment thereof, the amount of digitoxin and paclitaxel are at least 0.05 µg/ml digitoxin and 0.025 nM paclitaxel.

In another aspect of the present invention, a method for inhibiting the progression or development of breast cancer in vivo is provided, comprising administering to a subject a composition comprising an extract of black cohosh comprising a triterpene glycoside, and optionally an effective amount of at least one additional chemopreventive or chemotherapeutic agent. In an alternative embodiment thereof, a method for inhibiting the progression or development of breast cancer in vivo is provided, comprising administering to a subject a composition comprising actein, and optionally an effective amount of at least one additional chemopreventive or chemotherapeutic agent.

The aglycone cimigenol is poorly soluble and tends to precipitate. Reporting an IC50 for such a compound with confidence in the value can be tenuous. A derivative of the aglycone cimigenol, 25-acetyl-7,8-didehydrocimigenol 3-O-β-D-xylopyranoside, however, has been found to be sufficiently soluble to obtain an IC50 with confidence to report. The IC50 of the derivative was determined in testing cell proliferation in MDA-MB-453 (Her2 overexpressing) human breast cancer cells. As provided in Einbond, et al., *Phytomedicine* 15 (2008) 504-511, the IC50 for the derivative is 3.2, which is more potent than actein. It is believed that the aglycone cimigenol is comparably potent to its derivative. It is contemplated that the present invention encompasses embodiments of methods and compositions as provided herein in which the aglycone cimigenol or the derivative, 25-acetyl-7,8-didehydrocimigenol 3-O-β-D-xylopyranoside, is used in place of actein.

Example 13

Chemopreventive Potential of Black Cohosh

Materials and Methods

Materials

All solvents and reagents were reagent grade; $H_2O$ was distilled and deionized. Naturex, Inc. (South Hackensack, N.J.) generously provided the black cohosh extract containing 27% triterpene glycosides. Black cohosh raw material was collected in the United States in 1998 from natural habitat, dried naturally by air and identified by Dr. Scott Mori from the New York Botanical Garden. Each lot of the raw material was compared with the authentic samples using HPLC. Black cohosh roots and rhizomes (Lot number 9-2677; South Hackensack, N.J.) were extracted with 75% EtOH/water as noted below. A voucher sample (9-2677) was deposited in Naturex's herbarium.

Black Cohosh Enriched for Triterpene Glycosides

The black cohosh fraction provided by Naturex was extracted and isolated from black cohosh as reported in Einbond et al. (*Phytomedicine* 15 (2008) 504-511), as follows. The black cohosh roots and rhizomes were extracted with 75% EtOH/water. The ethanol was removed at 45-55° C. under reduced pressure. The concentrated extract was partitioned between methylene chloride and water, which provided a fraction of 15% triterpene glycosides (TG) from methylene chloride and 1% TG from water. The methylene chloride was removed at 45-55° C. under reduced pressure. The concentrated fraction was further partitioned between n-butanol and water and a fraction was obtained from the n-butanol phase. The resulting n-butanolic extract of the EtOH/water extract of black cohosh was enriched for triterpene glycosides. The black cohosh enriched for triterpene glycosides had about 27% TG.

Animal Treatment and Data Collection

Experimental Animals:

The experimental animals were female Sprague-Dawley rats, 56 weeks old at the start of the experiment. This strain belongs to the colony used for over 30 years in the laboratory of the Cancer Research Centre (CRC) of the Ramazzini Foundation (RF); wide information dealing with normeoplastic and neoplastic pathologies is available on over 15,000 controls.

Treatment with Black Cohosh Extract:

Four groups of 99 females were treated with 35.7, 7.14, 0.714 or 0 mg/kg of body weight (b.w.) of the black cohosh enriched for triterpine glycosides (27%) by intragastric tube, from 56 to 96 weeks of age (the window of age for higher risk of mammary cancer in this strain of rats). A sample of each mammary tumor was collected, frozen in liquid nitrogen and kept at −70° C. Samples for studies of pharmacokinetics, pharmacodynamics and gene expression analysis of different organ and tissues were collected from two groups of 12 female rats treated with 35.7 or 0 mg/kg b.w. of black cohosh.

Necropsy:

During the necropsy, portions from the liver from the last 4 animals of both treated (with 35.7 mg/kg b.w.) and control groups (sacrificed 6 and 24 hours after the start of the experiment) were collected for analysis. Four portions of about 100 mg each were collected from the main lobe of the liver. Each portion was individually retained in a cryovial, frozen and stored at −70° C. until use. (Actein was used for pharmacokinetics and gene expression profile analysis.)

Analyses

Analysis by Microscopy:

Histopathological examination of H&E and H&E/Oil Red O stained sections of control and treated tissues obtained 6 or 24 hours after treatment were performed. Tissues were embedded in OCT (optimal cutting temperature compound to enable cryosectioning of the sample).

IHC Staining:

Mammary Tissue:

Cyclin D1 antibody concentration was 1:600, incubation 90 min, at room temperature, PBS Wash, secondary reagent: anti-mouse cytomation Envision+ system. labeled with HRP 30 min(DAKO). PBS wash, DAB 1 min. 2. Ki67 concentration was 1:200, 90 min incubation. Secondary antibody: Goat anti rabbit 1:200, (vector) 30 min incubation. PBS wash, ABC 30 min (vector), DAB 2 min.

Mammary tissue: ER; Liver Tissue: EGFR.

Lipid Analysis:

Hepatic lipids were extracted by homogenization of the liver followed by addition of choloroform:methanol (2:1). After vortex and centrifugation for min, the organic phase was collected and dried under nitrogen. The dried lipids were dissolved in 1% Triton X-100 in water and sonicated. Extracted hepatic lipids and plasma lipids were measured by cholesterol and triglyceride enzymatic assay kits from Infinity (Louisville, Colo.) according to the manufacturer's instruction. Free fatty acids were measured by Enzymatic assay using NEFA C kit from Wako Chemicals (Richmond, Va.). Tissue lipids were normalized by protein concentration.

Gene Expression Analysis:

Labeled cDNA was generated from liver tissue from each study animal and hybridized to Affymetrix RG230-2 rat whole genome arrays following standard Affymetrix protocols at Columbia University. Analyses were performed using 2 approaches: 1) Analysis was performed using the AffyLimmaGUI package in the open-source Bioconductor suite. All samples were normalized to remove chip-dependent regularities using the GCRMA method of Irizarry et al. (Speed, Summaries of Affymetrix GeneChip probe level data, Nucleic Acids Res, 2003. 31(4): p. e15). The statistical significance of differential expression was calculated using the empirical Bayesian LIMMA (LI Model for MicroArrays) method of Smyth et al. (Use of within-array replicate spots for assessing differential expression in microarray experiments, *Bioinformatics*, 2005. 21(9): p. 2067-75). A cut-off B>0 was used for the statistical significance of gene expression, as previously described (Einbond et al., 2007). 2) Array data was transmitted to Iconix Pharmaceuticals as CEL files and uploaded into the Iconix database (DrugMatrix®) for Drug Signature and pathway analysis, as previously described (Natsoulis, et al., Classification of a large microarray data set: algorithm comparison and analysis of drug signatures, *Genome Res*, 2005. 15(5): p. 724-36). Relative $\log_{10}$ expression ratios were generated for each probe set on the array by dividing the $\log_{10}$ of the average MAS5 normalized signal for the 3 black cohosh treated animals by the $\log_{10}$ of the average MAS5 normalized signal of 2 of the 3 control animals. Reproducibility of the data between replicate animals in the group was assessed, then the impact of the unknown compound on Iconix Drug Signatures was analyzed.

The database has been extensively mined for gene expression-based biomarkers called Drug Signatures® predictive of pharmacologic, toxicologic, and pathologic effects (Natsoulis, et al., *Genome Res*, 2005. 15(5): p. 724-36; Ganter, et al., Development of a large-scale chemogenomics database to improve drug candidate selection and to understand mechanisms of chemical toxicity and action, *J Biotechnol*, 2005. 119(3): p. 219-44). The approach employed to derive Drug Signatures is based on a Sparse Linear Programming (SPLP) classification algorithm that mathematically identifies specific gene expression markers for accurate sample classification.

$\log_{10}$ ratio data for the black cohosh array data set was compared to the Iconix collection Drug Signatures®. The version of DrugMatrix® used contains 29 Drug Signatures® derived on the RG230-2 array platform for liver. These signatures describe a variety of pharmacological and toxicological endpoints including steatosis, hepatic necrosis, glucocorticoid and mineralocorticoid receptor agonism and estrogen receptor agonism.

Pathway analysis using the curated pathways within the database was used to identify particular biological processes perturbed by exposure to the unknown compound. Gene expression changes were overlaid onto visual maps of up to 110 pathways, which illustrate semi-quantitatively which proteins in the pathway have mRNA levels altered by treatment. Gene lists generated from the perturbed pathways were then subjected to unsupervised hierarchical clustering and statistical analysis. Statistical evaluation was performed using a hypergeometric distribution calculation of the probability that the number of genes from a given pathway (DrugMatrix contains 135 curated pathways) that were perturbed in a given experiment could have happened by chance.

Real-Time RT-PCR Analysis:

Real-time quantitative RT-PCR methods were used to determine the nature of the RNA induced by treatment with black cohosh extract, as previously described (Einbond et al., 2007).

mRNA sequences were obtained from the public GeneBank database (www.ncbi.nlm.nih.gov), and primers were designed using Primer3 software from The Massachusetts Institute of Technology (frodo.wi.mit.edu/cgi-bin/primer3/primer3_www.cgi). All primers were synthesized by Invitrogen Company, and quality confirmed in pre-PCR by no primer dimer and only one peak in dissociation curve, and by only one band in agarose gel electrophoresis. All PCR products were in the 140-180 bp range.

Results

Chemoprevention Study: Tumor Incidence and Animal Wellness

Figure 19A:
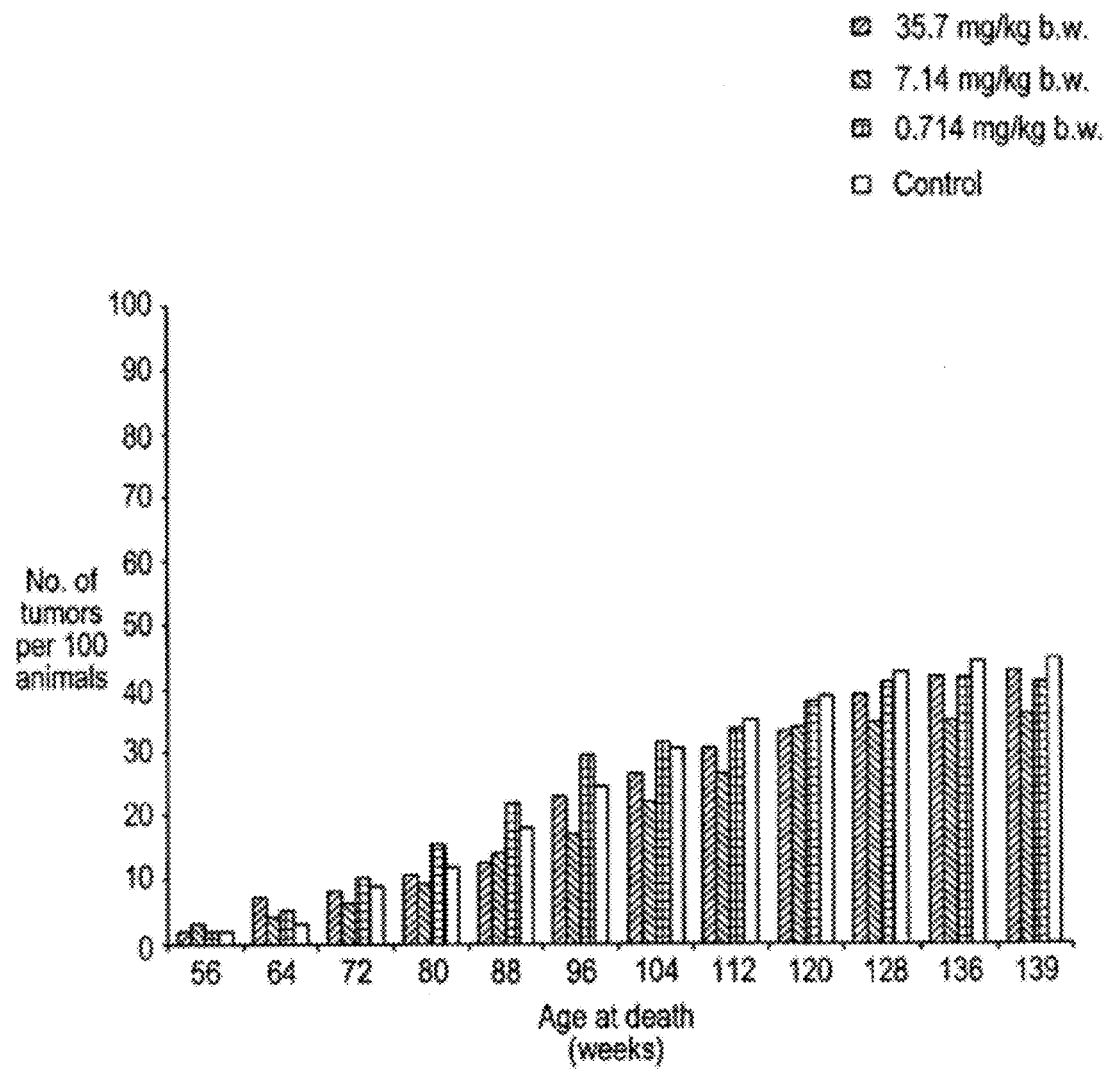
FIG. 19 Results of chemopreventive study: A) Cumulative number of mammary tumors (per 100 animals) by weeks of age (from 56 to 139 weeks of age at death), observed during clinical examination (for 35.7 mg/kg b.w, 7.14 mg·kg b.w., and 0.714 mg/kg b.w. of an extract of black cohosh enriched for triterpene glycosides, and control). B) Survival (as a percentage plotted against age at death (weeks)). C) Mean body weight (as a percentage plotted against age at death (weeks)).
Figure 19B:
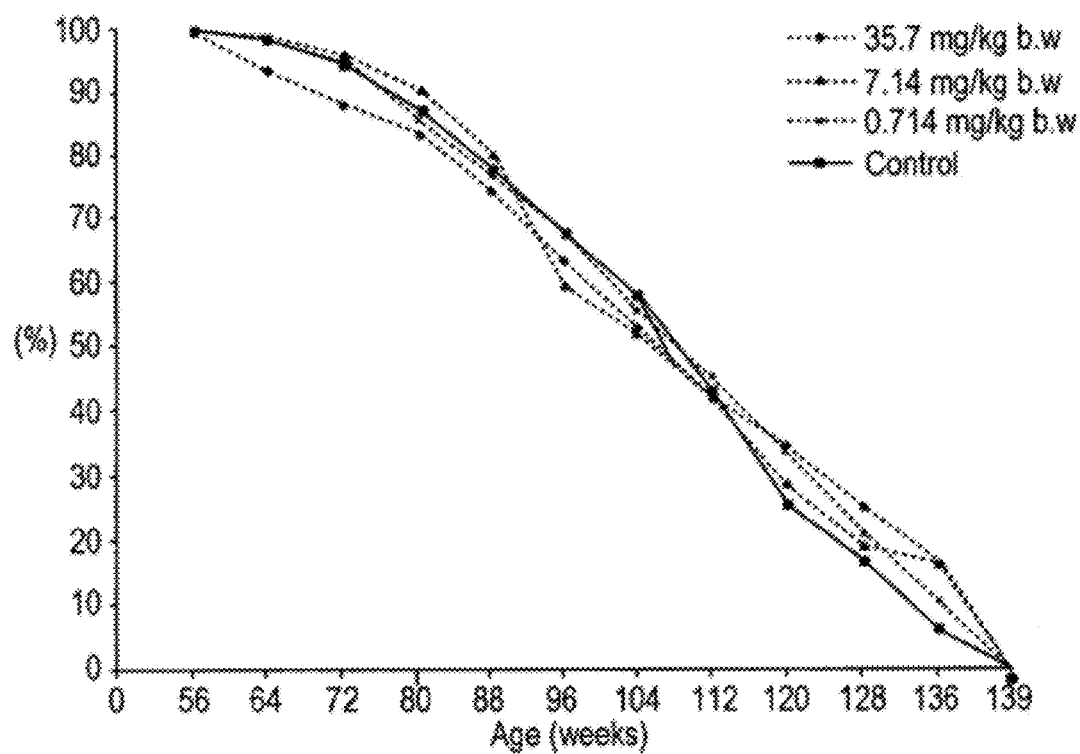
Figure 19C:
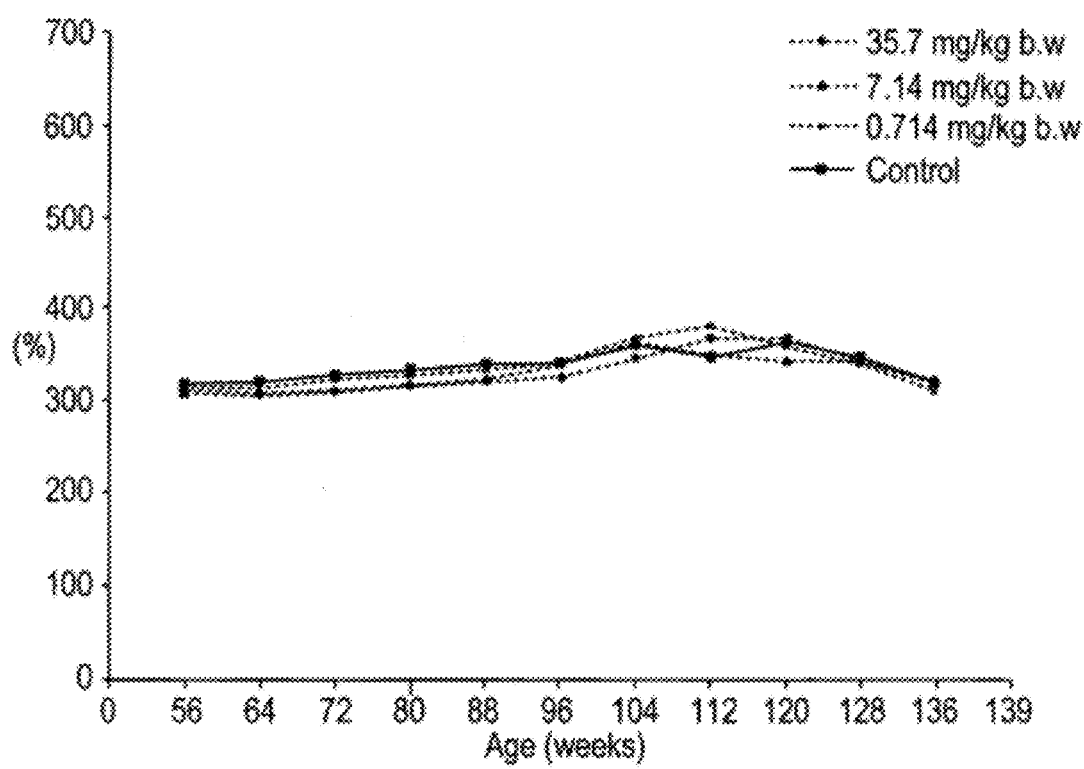

Black cohosh did not have any deleterious effects on the health of the Sprague-Dawley rats as assessed by weight gain, water consumption or survival (FIG. 19). Black cohosh reduced both the incidence of mammary tumors and the number of tumor-bearing animals. It was determined that 40 weeks of treatment with an extract of black cohosh (7.14 mg/kg) reduced breast cancer incidence in the rats with a protective index of 20.45%. (FIG. 19; Table 10).

TABLE 10

Protective effect of black cohosh on Sprague-Dawley rats.

| No | dose | tumor bearing no | % | Total tumors No | per 100 | protection index[a] |
|---|---|---|---|---|---|---|
| 99 | 35.7 mg/kg | 37 | 37.37 | 42 | 42.42 | 4.55 |
| 99 | 7.14 | 32 | 32.32 | 35 | 35.35 | 20.45 |
| 99 | 0.71 | 31 | 31.31 | 41 | 41.41 | 6.82 |
| 99 | control | 39 | 39.39 | 44 | 44.44 | |
| total | 396 | 139 | 35.1 | 162 | 40.91 | |

[a]protection index = {total tumors (control) − total tumors (treated)}/total tumors (control) × 100

Histopathological Examination of Mammary Tissues and Tumors

Figure 20A:
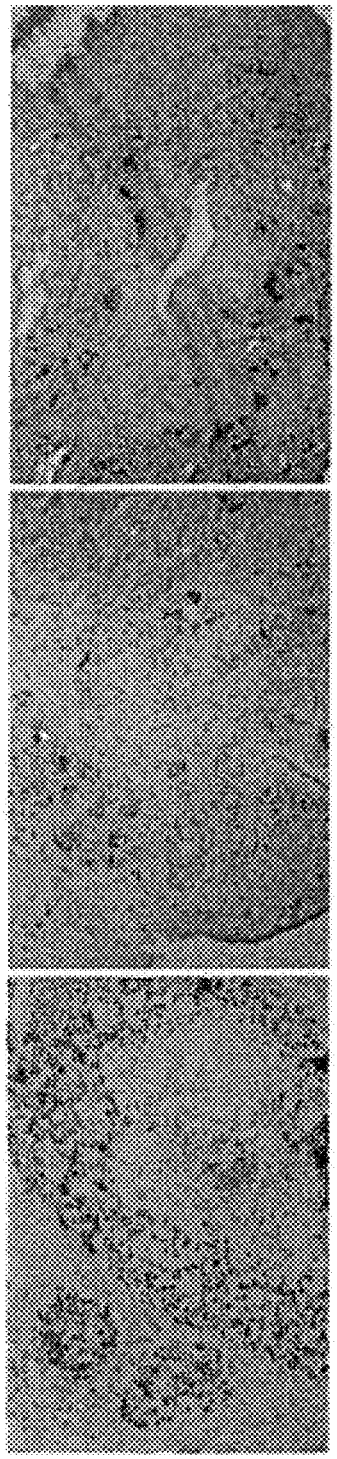
FIGS. 20 IHC staining of mammary gland tissue: A) ER; B) Her2; PC=positive control; MG=mammary gland (magnification: 100×). The mammary tissue was positive for ER in the nucleus as shown in panel A. The mammary tissue was negative for Her2 expression, as shown in panel B.
Figure 20B:
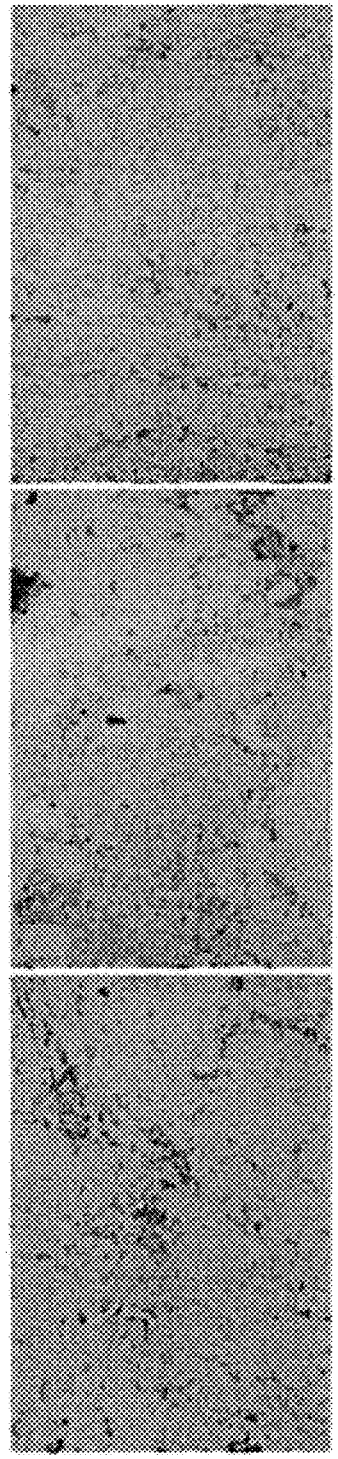

Histopathological examination of IHC stained sections of mammary tissues and fibroadenomas was performed. The mammary tissue was positive for ER in the nucleus (FIG. 20A) and negative for Her2 expression (FIG. 20B). These findings lend insight to the signaling pathways to explore in the gene expressed studies.

Figure 21A:
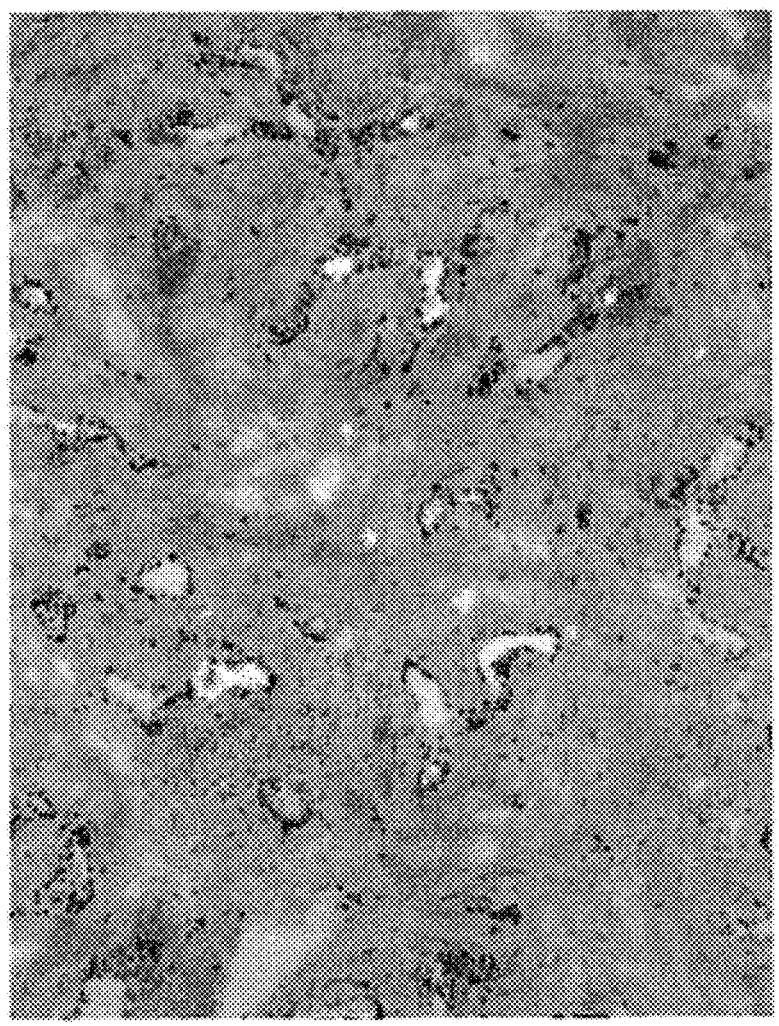
FIGS. 21 H&E staining of frozen sections of fibroadenomas: A) control; age detected: 93 weeks; age at death: 95 weeks; B) treated with black cohosh extract at 7.14 mg/kg; age detected: 89 weeks; age at death: 101 weeks; C) treated with black cohosh extract at 35.7 mg/kg; age detected: 89 weeks, age at death: 96 weeks. Treatment panels B and C show a decrease in the proportion of glandular tissue in treated versus control in panel C. (In color, glands are shown as blue; connective tissue as pink; white as undefined, empty space or filled with secretory material or blood vessels). Also shown is IHC of Fibroadenomas: D) IHC cyclin D1; Fibroadenoma, control, age detected 93 weeks, age at death 95 weeks; E) IHC cyclin D1: Fibroadenoma, 7.14 mg/kg, age detected: 89 weeks, age at death: 101 weeks; F) IHC cyclin Ki67; Fibroadenoma, control, age detected 93 weeks, age at death 95 weeks; G) IHC Ki67 Fibroadenoma, 7.14 mg/kg, age detected: 89 weeks, age at death: 101 weeks. A significant difference is seen comparing Ki67 (panels F and G) and cyclin D1 (panels D and E) staining for rats treated with 7.14 mg/kg black cohosh extract.
Figure 21B:
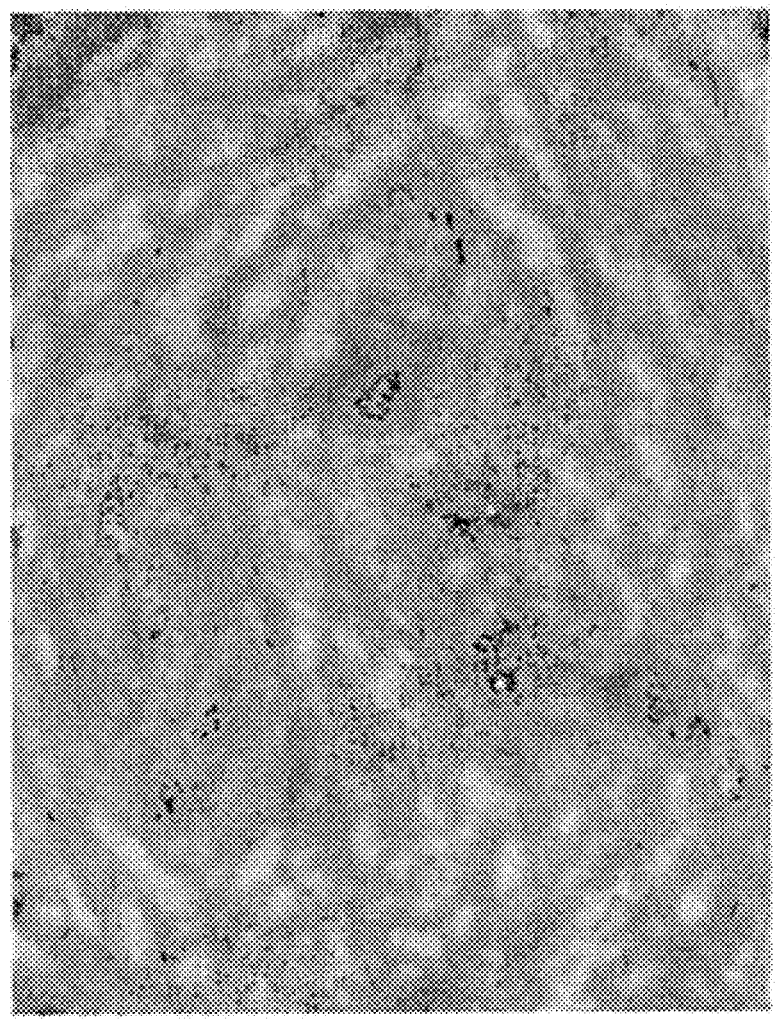
Figure 21C:
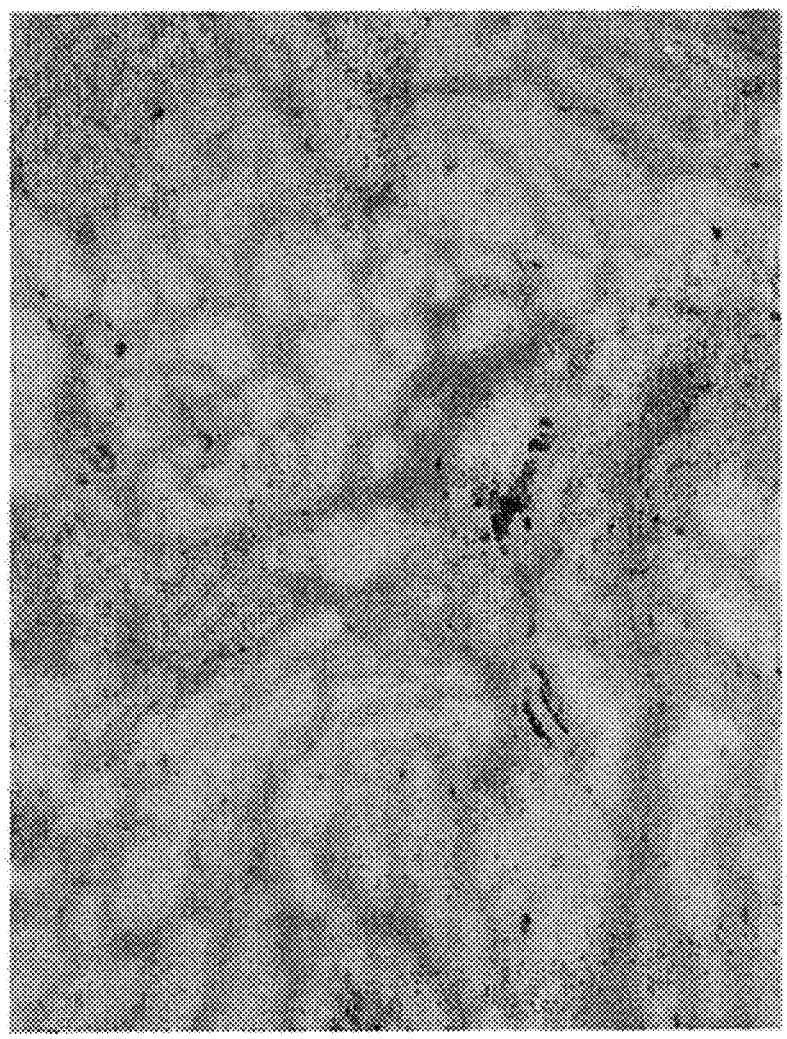

H and E Staining of Frozen and Paraffin Sections and IHC Staining of Paraffin Sections The fibroadenomas from rats treated with 7.14 mg/kg (FIG. 21B) or 35.7 mg/kg (FIG. 21C) black cohosh displayed a decrease in the proportion of glandular tissue and an increase in the proportion of connective tissue in treated versus control samples (FIG. 21A) (3 each); whereas one fibroadenoma from rats treated with the lowest dose (0.714 mg/kg) exhibited an increase in the proportion of glandular tissue (data not shown).

Figure 21D:
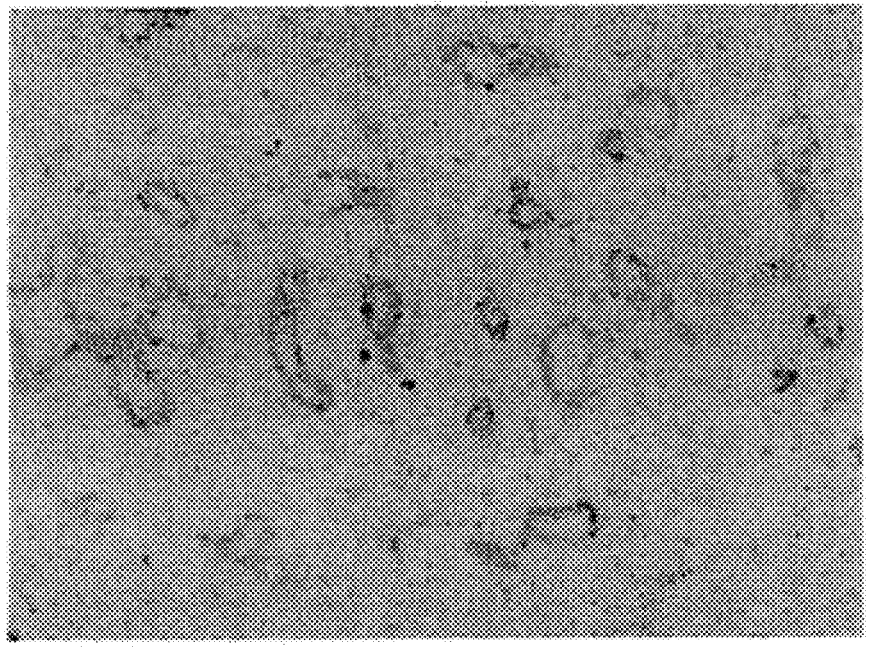
Figure 21E:
Figure 21F:
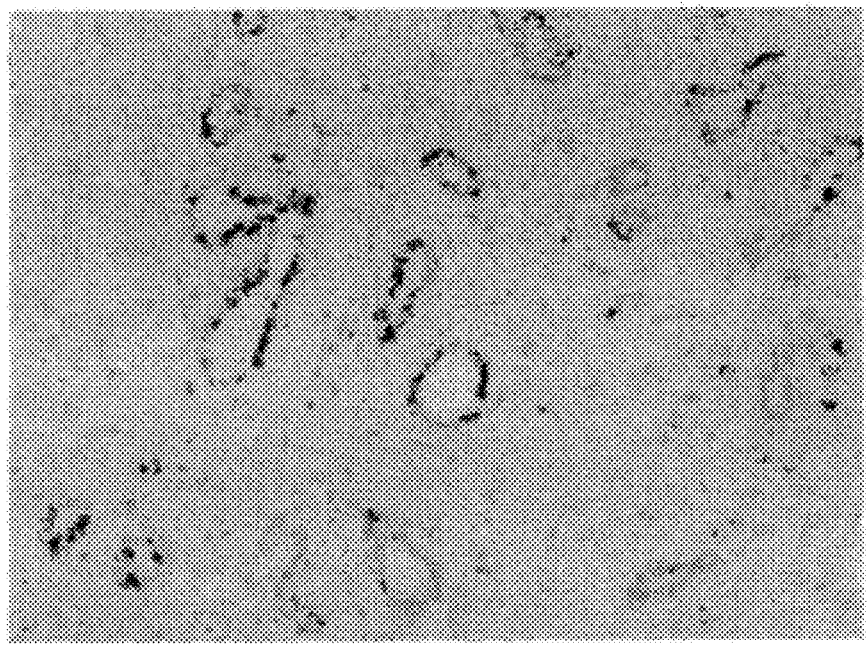
Figure 21G:
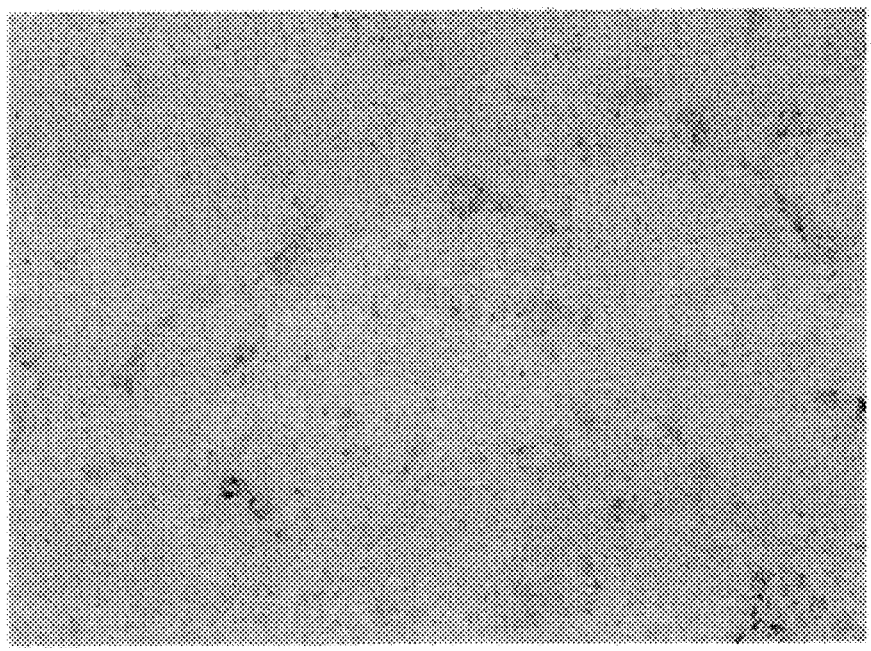

Immunohistochemical staining (IHC) was used to examine the fibroadenomas from Sprague-Dawley rats treated with black cohosh. Ten fields were counted on each slide and a significant difference was found in Ki67 and cyclin D1 staining for rats treated with the middle dose of black cohosh (7.14 mg/kg) versus water (control). For Ki67: the control was <5%. While treated with 7.14 mg/kg was ~1%. (FIG. 21B) For cyclin D1: the control was 20%; while treated with 7.14 mg/kg was 1% (FIGS. 21D, E, F and G).

Histopathological Examination

Figure 22A:
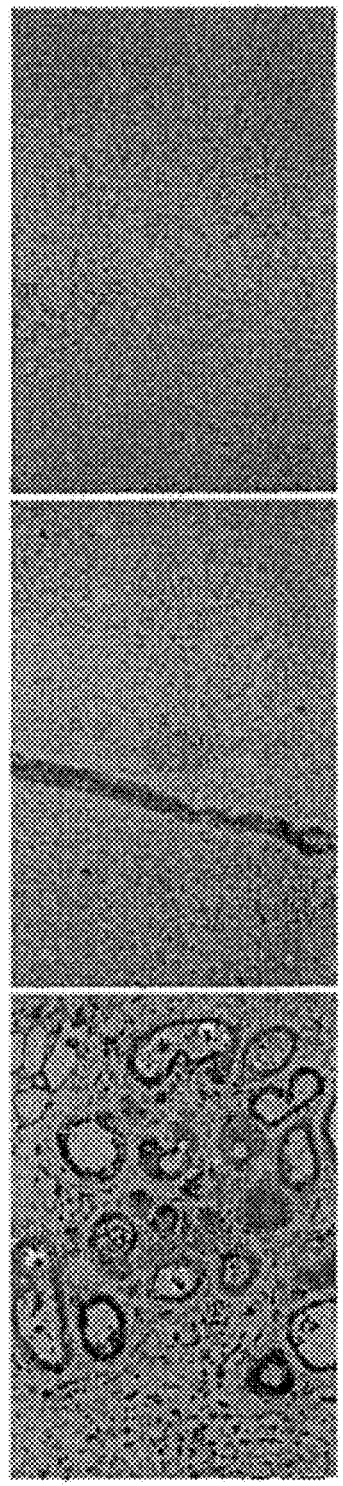
FIG. 22 A) IHC of rat liver tissue (24 hr): EGFR; PC=positive control. IHC staining indicated the presence of EGFR in the nucleus; B) H&E staining of frozen sections of rat liver with control (untreated) and treated with black cohosh 35.7 mg/kg. Mild toxicity was displayed; and C) H&E staining showing periportal localization of lipid accumulation in control and treated rat liver.
Figure 22B:
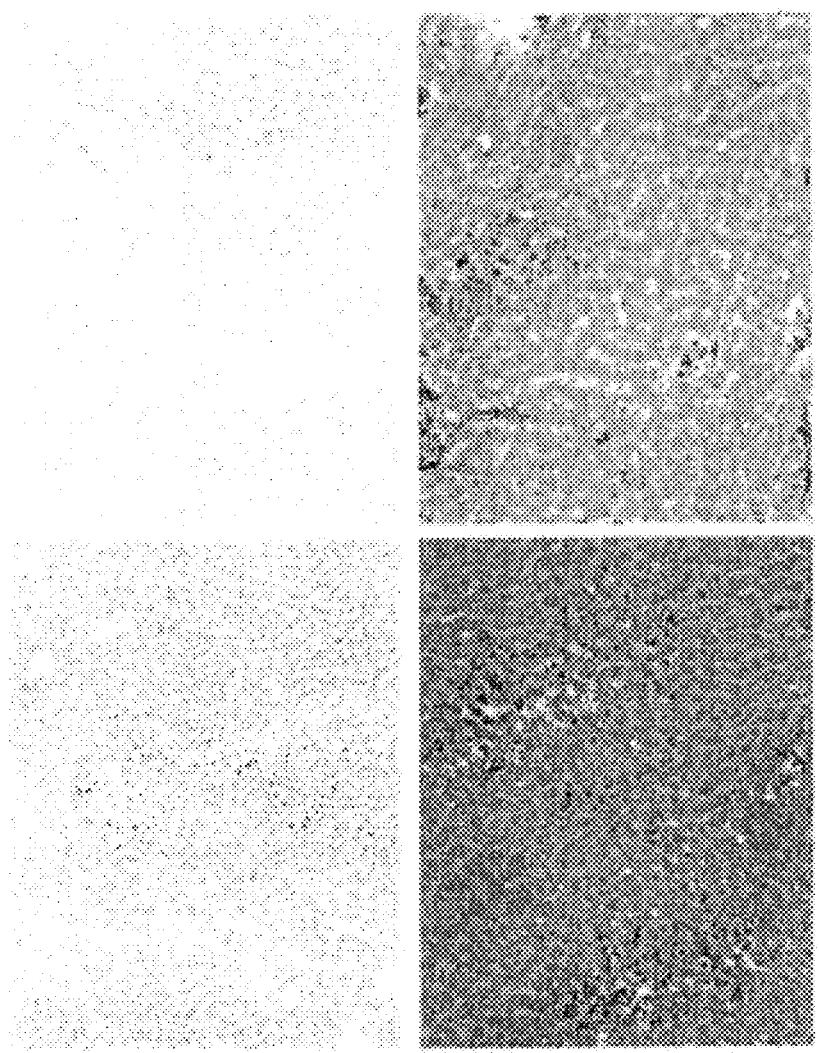
Figure 22C:
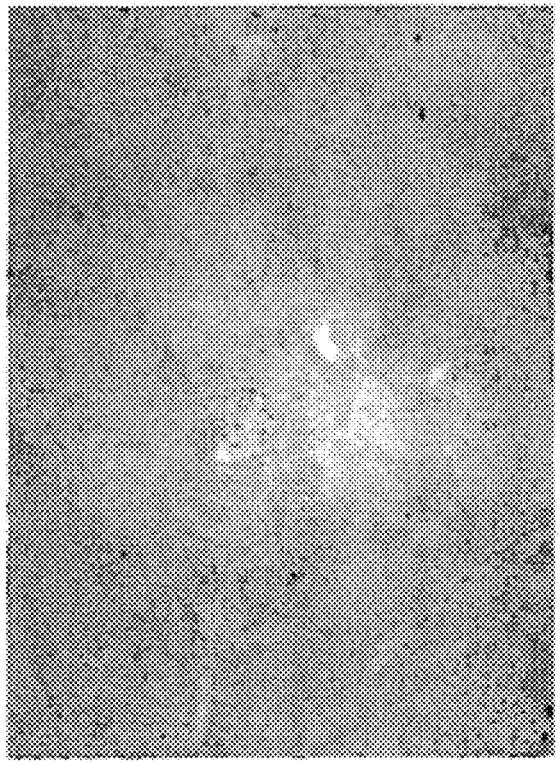
Figure 22C:

Rat liver treated with black cohosh samples were stained with Oil Red O for lipids and counterstained with H&E (Hematoxylin stains nucleus, Eosin stains cytoplasm). Lipid accumulation was not as obvious in control liver tissue as in the treated sample. The localization in the treated tissue occurred between the central veins (Periportal—closer to the portal triad area) and the droplets were small, diffuse, lobular, subendothelial, and perivenule. The samples displayed mild toxicity; the lipid droplets were microvesicular (FIG. 22B, C). IHC staining for EGFR indicated the presence of EGFR in the nucleus and cytoplasm (FIG. 22A).

Analysis of the lipid content of the livers revealed a 3.9 ($p=1.14\times E-5$) and 4.6-fold ($p=0.00131$) increase in the free fatty acid and triglyceride content, respectively, of the treated livers compared to the controls at 24 h.

For the rat kidney: in the treated sample there was the presence of a lymphoid, inflammatory infiltrate under the lining of the urinary tract that is not seen in the control. There was no tubular, no glomeruli damage, tissue inflammation or vascular damage; it was not a type of toxic injury since glomeruli were similar in both treated and control.

Chemogenomic Analysis of Black Cohosh Extract

A dataset derived from the livers of female rats treated with an extract of black cohosh (35.7 mg/kg) for 24 h was analyzed.

AFFY LIMMA Analysis

After exposure for 24 h, Affy-Limma analysis indicated that the extract altered the expression of 2 genes (B>0), the mitochondrial gene BZRP and the transcription factor F-box only protein 30.

Drug Matrix Analysis

Pathway Analysis

Considering both up and down-regulated genes in the analysis, the highest impact was observed on the Mitochondrial Oxidative Phosphorylation pathway (Table 11).

TABLE 11

Top 5 impacted pathways for black cohosh, 35.7 mg/kg, 24 h treatment. Both up and down-regulated genes (filtered for $p < 0.05$) were considered.

| PATHWAY | Impact Score |
|---|---|
| Mitochondrial Oxidative Phosphorylation | 4.01 |
| Urea & Aspartate Cycle | 1.93 |
| P450 Family | 1.77 |
| Apoptosis | 1.75 |
| Hemes from Protoporphyrin IX | 1.64 |

Figure 23:
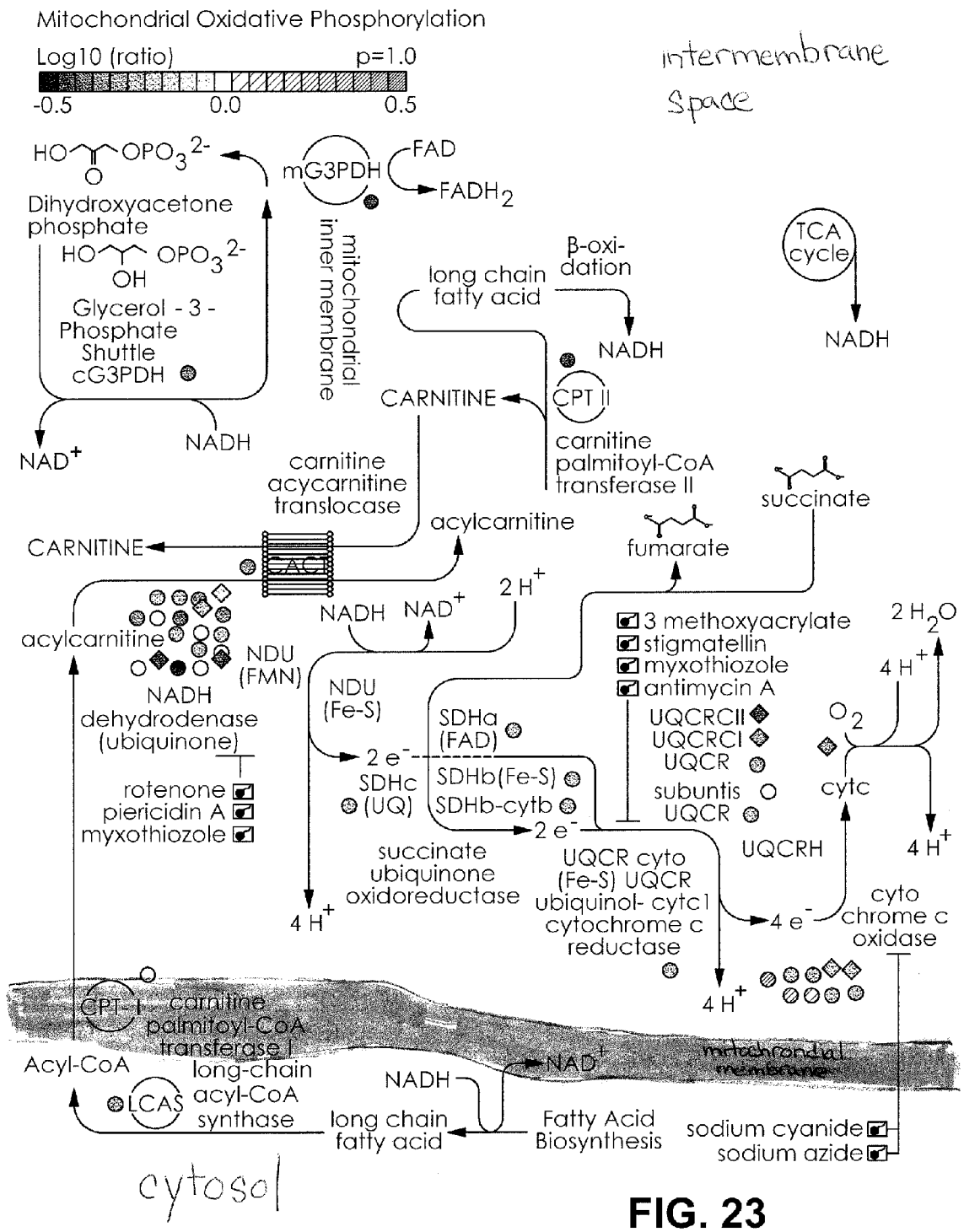
FIG. 23 Pathway map of the Mitochondrial Oxidative Phosphorylation pathway. Genes represented by probe sets on the array are shown as colored circles ($p>0.05$) or diamonds ($p<0.05$). Red indicates upregulation while green indicates downregulation of the gene.
Figure 23:
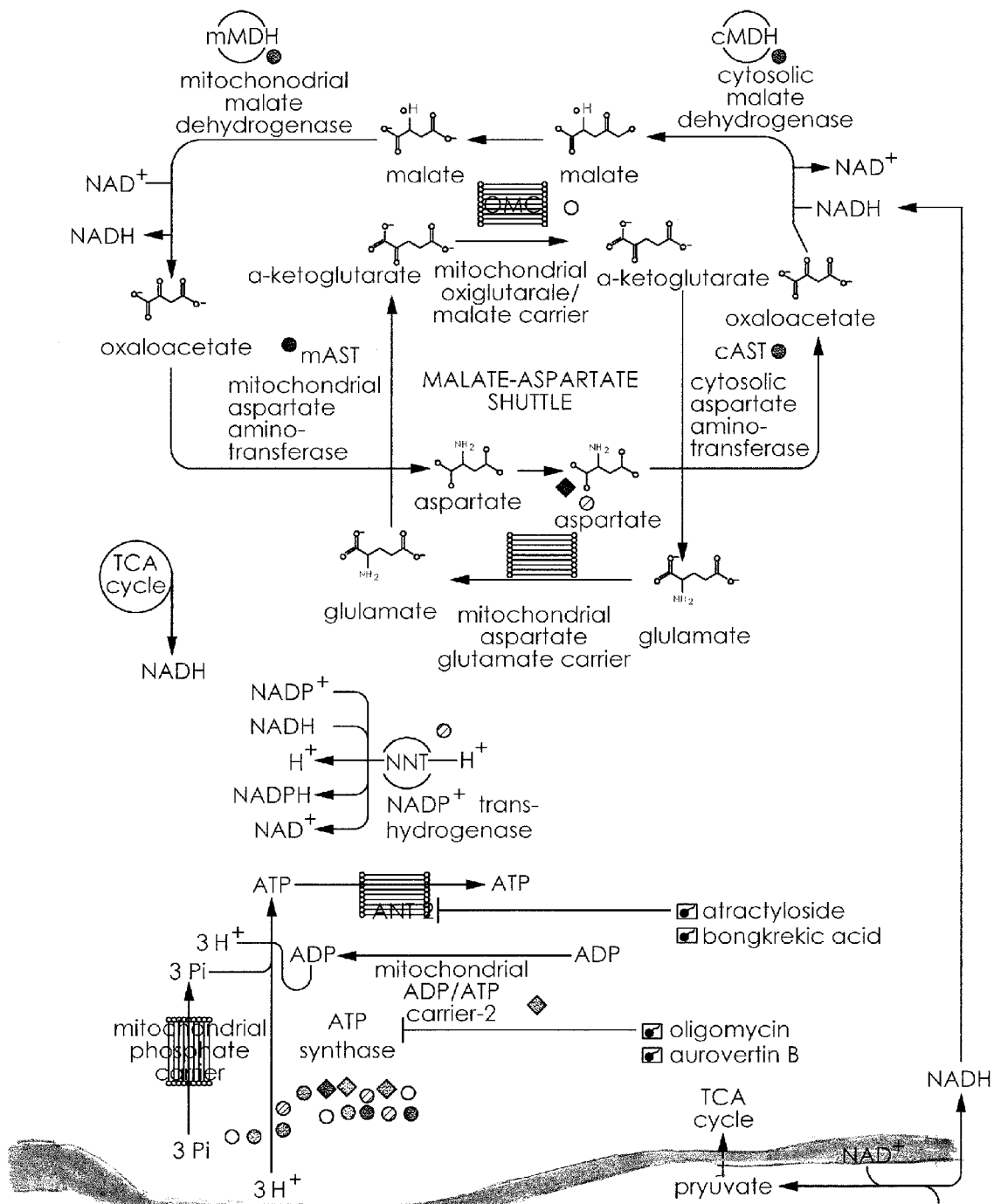

When the expression data for the genes in this pathway are overlaid on a map of the pathway (FIG. 23) it is clear that there is a profound downregulation of genes in this pathway in response to black cohosh exposure.

A general decrease in genes involved in urea and aspartate metabolism was also observed, including the mitochondrial carbamoyl phosphate synthase 1, argininosuccinate synthase, glycine amidino transferase and creatine kinase, possibly also reflecting mitochondrial damage.

When upregulated genes only were considered, phospholipid biosynthesis and remodeling, PI3-Kinase and sphingosine signaling were observed to be impacted. This was driven largely by an upregulation of several isoforms of phospholipase C (which is involved in all 3 pathways). Diacyl glycerol kinase beta was also significantly upregulated.

Comparative Analysis

A direct comparison of the liver gene expression profiles following black cohosh to other liver treatments in the database (DrugMatrix® contains data on the RG230-2 platform for >660 compound-dose-time combinations) revealed no similarities using Pearson's correlation across the top 1000 most variable genes (no similar experiments were found with a correlation coefficient of >0.1).

Figure 24:
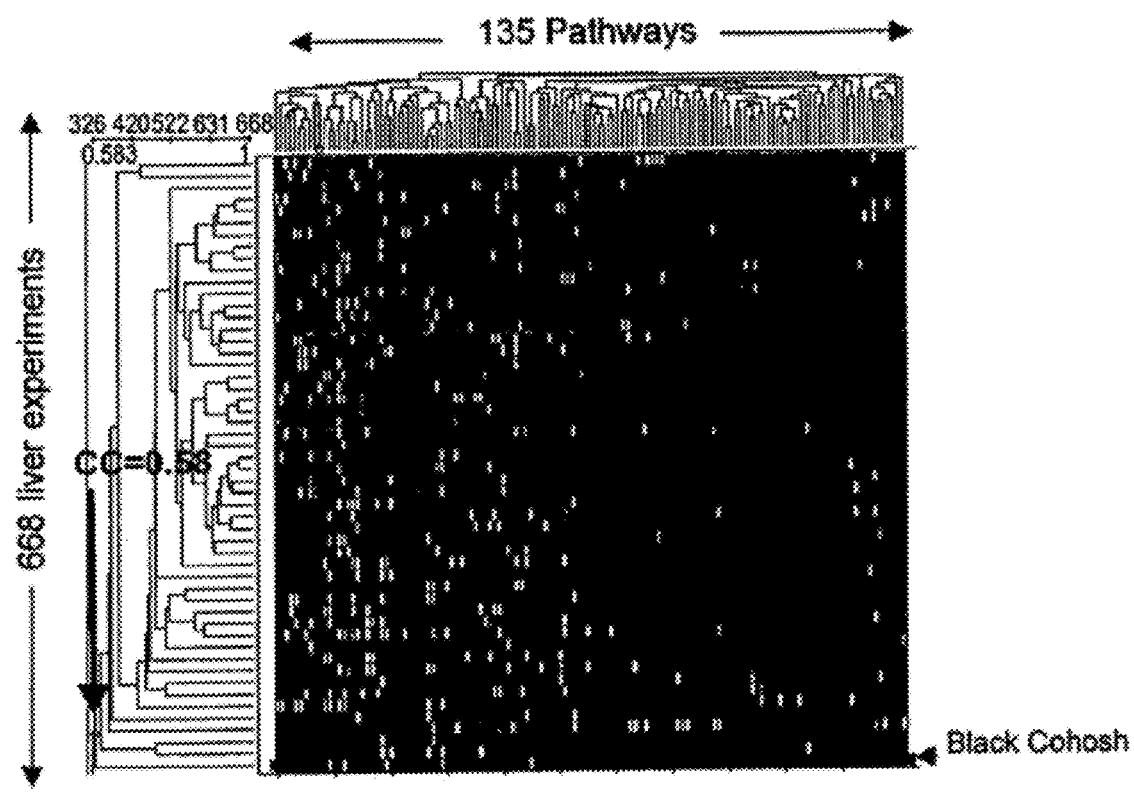
FIG. 24 Zoomed view of hierarchical clustering heat map (UPGMA, Pearson's correlation) of 668 liver experiments across impact against 135 DrugMatrix pathways. Statistical analysis of the treatments in the cluster using the hypergeometric distribution revealed a significant representation of treatments with anti-proliferative compounds, specifically tubulin binding vinca alkaloids (3 experiments, $p=0.0017$) and DNA alkylators (4 experiments, $p=0.029$).

A hierarchical clustering of pathway impact scores of all RG230-2 liver experiments in the database was performed alongside black cohosh (FIG. 24). Black cohosh formed part of a cluster of 51 treatments having a Pearson's correlation coefficient of 0.58. Statistical analysis of the treatments in the cluster using the hypergeometric distribution revealed a significant representation of treatments with anti-proliferative compounds, specifically tubulin binding vinca alkaloids (3 experiments, $p=0.0017$) and DNA alkylators (4 experiments, $p=0.029$). The repression of cyclin D1 previously reported (Le et al., 2004) was also observed in this experiment. There was a mixed effect on the apoptosis pathway, with caspase 9 and IAP5 upregulation (pro-apoptotic) but cytochrome C and BAX downregulation (anti-apoptotic).

Real-Time RT-PCR

Figure 25:
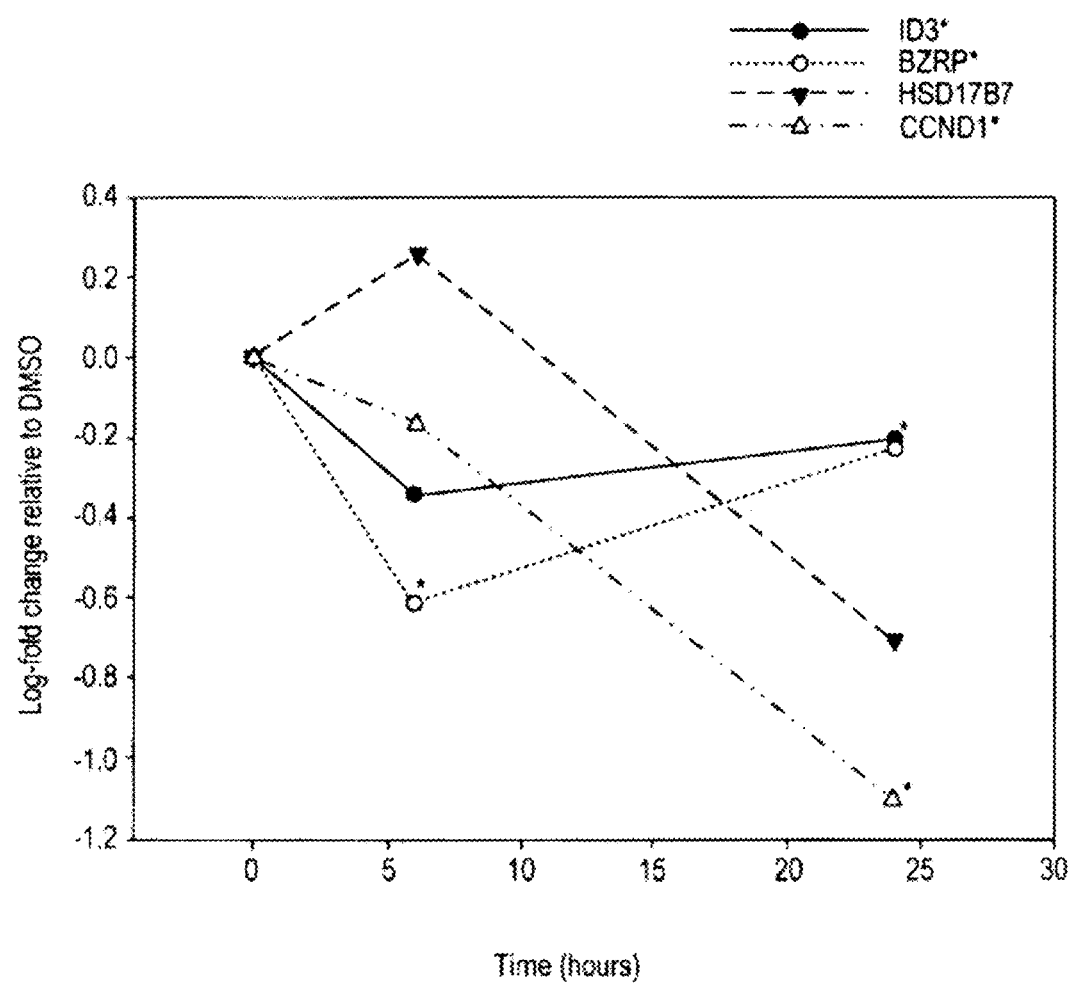
FIG. 25 Real-time RT-PCR of rat liver after treating with black cohosh extract (35.7 mg/kg), which confirmed that black cohosh suppressed the expression of cyclin D1 and ID3.

The more sensitive RT-PCR was used to confirm the microarray results that black cohosh suppressed the expression of cyclin D1 and ID3 (FIG. 25).

Discussion

The effect of an extract of black cohosh enriched for triterpene glycosides on the development of spontaneous mammary tumors in Sprague-Dawley rats was examined. It was found that treatment with an extract of black cohosh enriched for triterpene glycosides (27%) for 40 weeks decreased the incidence of spontaneous mammary tumors and the number of tumor-bearing animals.

Further, fibroadenomas obtained from rats treated with 7.14 mg/kg of the black cohosh extract displayed a decrease in the proportion of glandular and increase in that of connective tissue and, in addition, a decrease in the level of cyclin D1 and Ki67 protein, by IHC. Black cohosh reduced the proliferative rate and thus the malignant potential of the tumors. These findings are in agreement with the results of Seidlova-Wuttke et al. (*Planta Med,* 2006. 72(6): p. 521-26) that the *Cimicifuga racemosa* extract BNO 1055 (aqueous ethanol) reduced the incidence, proliferation, size and malignancy of prostate tumors induced by injection of LNCaP cells in immunodeficient mice. The treated animals developed smaller tumors and less overall tumor tissue, which was mostly confined to connective tissue. The tumors in the treated animals thus appeared to be less malignant than those in the untreated animals, indicating that black cohosh components may inhibit the progression, as well as the development of tumors.

Since the rats appeared healthy and lived for more than 40 weeks during treatment, the extract at 35.7 mg/kg was not toxic. It was, however, found that the extract induced modest liver damage and increased the level of lipids (TTG and FFA) at 24 h after treatment. Although a cause for concern, the dose was, however, 50× the normal human dose.

Gene expression profiling was used to gain an understanding of the alterations of rat liver gene expression induced by actein or an extract of black cohosh. Sprague-Dawley rats were treated with an extract of black cohosh enriched for triterpene glycosides (27%) (at 35.7 mg/kg), and liver samples were obtained for gene expression analysis at 6 and 24 h. The gene expression data was analyzed using an unbiased informatics approach and Iconix Drug Matrix Drug Signature mapping and pathway analysis. To assess the intrasample variation, 3 replicate treated and control samples were analyzed for each treatment. The results were confirmed with real-time RT-PCR for 2 genes.

When the data were analyzed using Iconix Drug Signature® matching, no matches were obtained. Despite the observed lipid accumulation and reported menopausal benefits of black cohosh, no match to any of the 29 signatures was observed. This could be due to the fact that the Iconix database was derived for small molecular weight purified components using juvenile (8-10) week old animals, whereas older female rats (56 weeks old) were treated with an extract of black cohosh that contained many components.

Another tool for analysis is pathway analysis. Considering both up and down-regulated genes in the pathway analysis, the highest impact was observed on the Mitochondrial Oxidative Phosphorylation pathway (Table 11). Actein also altered this pathway (data not shown). This downregulation of mitochondrial genes suggests that black cohosh may cause mitochondrial damage. A disruption of mitochondrial energy generation could explain the observed lipid accumulation in the hepatocytes and also presents a potential mechanism of the hepatitis occasionally observed in human black cohosh users. Several isoforms of phospholipase C (PLC) which catalyse the cleavage of phosphatidylinositol-4,5-bisphosphate to generate the messengers DAG (diacylglycerol) and IP3 (inositol 1,4,5-trisphosphate) were upregulated. IP3, in turn, is required to activate the ER IP3 receptor which releases Ca2+ from the ER. The upregulation of PLC could thus result in a release of calcium from the ER which could account for the induction of stress response genes. Diacyl glycerol kinase beta was also significantly upregulated, suggesting a possible activation of GPCR-signaling cascades.

A hierarchical clustering of pathway impact scores of all RG230-2 liver experiments in the database was performed alongside black cohosh (FIG. 22). The finding that black cohosh clustered with anti-proliferative compounds, specifically tubulin binding vinca alkaloids and DNA alkylators is interesting in relation to its antiproliferative effects on human breast cancer cells in vitro. Einbond, et al. Repression of cyclin D1 was also observed, suggesting the potential for inducing cell cycle arrest at the G1/S boundary. The effects on CCND1 and ID3 were confirmed using the more sensitive technique real-time RT-PCR analysis.

There was a mixed effect on the apoptosis pathway, with caspase 9 and IAP5 upregulation (pro-apoptotic), but cytochrome C and BAX downregulation (anti-apoptotic). This mixed response probably reflects a mixed early mitogenic and apoptotic response among the hepatocytes in the liver.

In support of the findings, a study of the hepatic effects of black cohosh indicated that an ethanolic extract of black cohosh given to female Wistar rats (at doses greater than 500 mg/kg) induced hepatic mitochondrial toxicity; this was evidenced by microvesicular steatosis, inhibition of β-oxidation and the respiratory chain and resulting apoptosis. Modest effects on liver mitochondria were observed after treatment with doses as low as 10 mg/kg. (Lude et al., Hepatic effects of *Cimicifuga racemosa* extract in vivo and in vitro, *Cell Mol Lide Sci*.). Black cohosh reduced mitochondrial β-oxidation starting at 10 μg/ml in freshly isolated rat liver mitochondria; since this effect was pronounced, and was detected at a lower dose than other effects on mitochondria, it could be the primary effect. Blockage of β-oxidation can result in the accumulation of long-chain acyl CoA's, which may induce liver damage and apoptosis. Indeed, the extract induced a dose dependent increase in early apoptotic cells. Blood levels of black cohosh used for treatment of menopausal symptoms, 1.5-3 g/ml, are slightly lower than the dose that inhibits β-oxidation, 10 μg/ml. However, the dose required to cause microvesicular steatosis in rats was significantly higher than human doses, suggesting that black cohosh is safe.

In sum, the chemopreventive potential of an extract of black cohosh on Sprague-Dawley rats was examined based on 3 sets of analyses: 1) the ability of black cohosh to reduce the incidence of mammary tumors; 2) histological examination of fibroadenomas from affected rats, and 3) alterations of rat liver gene expression induced by an extract of black cohosh. Sprague-Dawley rats were treated with an extract of black cohosh enriched in triterpene glycosides (27%) at 0, 0.714 (equivalent to a normal human dose for symptoms of menopause), 7.14 and 35.7 mg/kg, the maximum tolerated dose for 40 weeks, and the incidence of mammary tumors, benign and malignant in the lifetime of the animals was determined. Sprague-Dawley rats were also treated with 0, 7.14 or 35.7 mg/kg black cohosh extract and liver tissue samples for lipid and gene expression analysis at 6 and 24 h and serum samples were obtained for chemistry analysis.

In the chemopreventive study, the intermediate dose, 7.14 mg/kg, reduced the incidence of mammary tumors by 21%. Black cohosh decreased the amount of glandular tissue and increased the connective tissue in fibroadenoma samples from rats treated with black cohosh compared to samples from the control rats. IHC analysis indicated that black cohosh reduced KI67 and cyclin D1 protein expression in fibroadenomas. In the study of rat liver and serum, treatment with the black cohosh extract increased the level of FFA and TTG content in the rat liver at 24 h. Black cohosh extract downregulated mitochondrial phosphorylation genes and upregulated several isoforms of PLC, by microarray analysis. Microarray and RT-PCR analysis indicated that the extract reduced the expression of the cell cycle gene cyclin D1 and the inhibitor of differentiation ID3.

Treatment of Sprague-Dawley rats with an extract of black cohosh enriched for triterpene glycosides resulted in a downregulation of the mitochondrial oxidative phorphorylation pathway, cyclin D1 and ID3 (at 6 and 24 h) and an increase in the liver content of FFA and TTG at 24 h. Black cohosh extract reduced the incidence of spontaneous mammary tumors and the proliferative rate of fibroadenomas.

Example 14

Actein and Digitoxin Combinations: Effect on the Activity of $Na^+$—$K^+$-ATPase and Effect on Growth of Human Breast Cancer Cells Abbreviations Combination Index CI
Dulbecco's Modified Eagle's medium: DMEM
Fetal Bovine Serum: FBS Methods Materials.

All solvents and reagents were reagent grade; $H_2O$ was distilled and deionized. Actein (ChromaDex, Laguna Hills, Calif., lot number 01355-101, purity 89% by HPLC; Planta Analytica, Danbury, Conn., lot number PA-A-037, purity>95% by HPLC), digitoxin and ouabain (Sigma, St. Louis, Mo.) were dissolved in dimethylsulfoxide (DMSO) (Sigma) prior to addition to cell cultures.

Cell Culture.

MDA-MB-453 (ER negative, Her2 overexpressing), MCF7 (ER positive, Her2 low), HCC1569 (ER negative, Her2 overexpressing) cells (ATCC, Manassas, Va.) were grown in Dulbecco's Modified Eagle's medium (DMEM) (Gibco BRL Life Technologies, Inc., Rockville, Md.) containing 10% (v/v) fetal bovine serum (FBS) (Gibco BRL) at 37° C., 5% $CO_2$. BT-474 cells (Incyte Pharmaceuticals, Wilmington, Del.) were grown in DMEM plus 0.01 mg/mL bovine insulin.

Cell Growth Assays

Coulter Counter Assay:

MDA-MB-453 and BT474 cells were seeded at $4\times10^4$ cells per well in 24 well plates (0.875 cm diameter), and attached viable cells were counted 96 hours later using a Coulter Counter model $Z_F$ (Coulter Electronics Inc., Hialeah, Fla.) as previously described. (L. S. Einbond, et al., *Breast Cancer Res* Treat. 83 (2004) 221-31).

MTT Assay:

The MTT assay was used to determine the sensitivity of MDA-MB-453, HCC1569 and MCF7 cells to actein or digitoxin. Following exposure to the various agents for 96 hours, the percent viable cells was assayed using the MTT method, as previously described in L. S. Einbond, et al. (Growth inhibitory activity of extracts and compounds from *Cimicifuga* species on human breast cancer cells, *Phytomedicine* (2007) [Epub ahead of print]).

Enzymatic Assay of Adenosine 5'-triphosphatase.

The enzymatic assay of ATPase (adenosine 5'-triphosphatase, EC 3.6.1.3) followed the Sigma Prod. No. A-7510 protocol (Sigma-Aldrich, St. Louis, Mo., USA). Actein, digitoxin, or ouabain were pipetted with ATPase (0.05 ml, 0.5 unit/ml, Sigma-Aldrich, St. Louis, Mo., USA), mixed and equilibrated for 5 min at 37° C. [P] was determined by the Taussky-Shorr method.

Calculating the Combination Index.

To determine the Combination Index (CI), 1) the $Na^+$—$K^+$-ATPase enzyme or 2) MDA-MB-453 cells were exposed to all combinations of 3, 4 or 5 concentrations of each of the agents tested and a solvent control. (L. S. Einbond, et al., *Planta Med.* 72 (2006) 1200-6). The results of the enzymatic assay of ATPase or MTT assay were analyzed for possible synergistic effects using the median effect principle. Variable ratios of drugs were employed and mutually exclusive equations were assumed. (L. S. Einbond, et al., *Planta Med.* 72 (2006) 1200-6).

RNAi-Mediated Gene Knockdown.

To test the functional relevance of ERK2 (p42/44MAPK pathway), the growth inhibitory effects of actein on MDA-MB-453 cells using the model system RNAi-mediated gene knockdown was examined. Cells were pretreated with siRNA to ERK2 (Hs/Mm MAPK1 siRNA) (Qiagen, Valencia, Calif.) for 24 h, then treated with actein at 20 µg/ml for 48 h, and the percent surviving cells was assayed. Western blot analysis was performed to confirm the ERK2 knockdown.

Western Blot Analysis.

Cells were treated in media containing serum for increasing times with approximately the $IC_{50}$ and twice the $IC_{50}$ concentration, measured at 48 h, of actein. To assay activation of p-Src, cells were allowed to attach for 24 h, incubated in media without serum for 24 h; the medium was replaced with media without serum with DMSO, actein or digtioxin.

Western blot analysis was performed as previously described. (L. S. Einbond, et al., *Breast Cancer Res* Treat. 83 (2004) 221-31). The membrane was incubated with the primary antibodies, cyclin D1 (Santa Cruz Biotechnology; Santa Cruz, Calif.), p-Src, Akt, p-Akt, ERK2 or p-Erk2 (Cell signaling, Beverly, Mass.); β-actin was used as a loading control.

NF-κB Reporter Assay.

The NF-κB promoter luciferase reporter plasmid was from Dr. Jae Won Soh. The method for transient transfection reporter assays was as previously described. (S. M. Masuda M, et al., Effects of epigallocatechin-3-gallate on growth, epidermal growth factor receptor signaling pathways, gene expression, and chemosensitivity in human head and neck squamous cell carcinoma cell lines, *Clin Cancer Res.* 7 (2001) 4220-9).

Statistical Analysis.

The data are expressed as mean+/−SD. Control and treated cells were compared using the student's t-test, $p<0.05$.

Results

Inhibition of ATPase Activity

Figure 27:
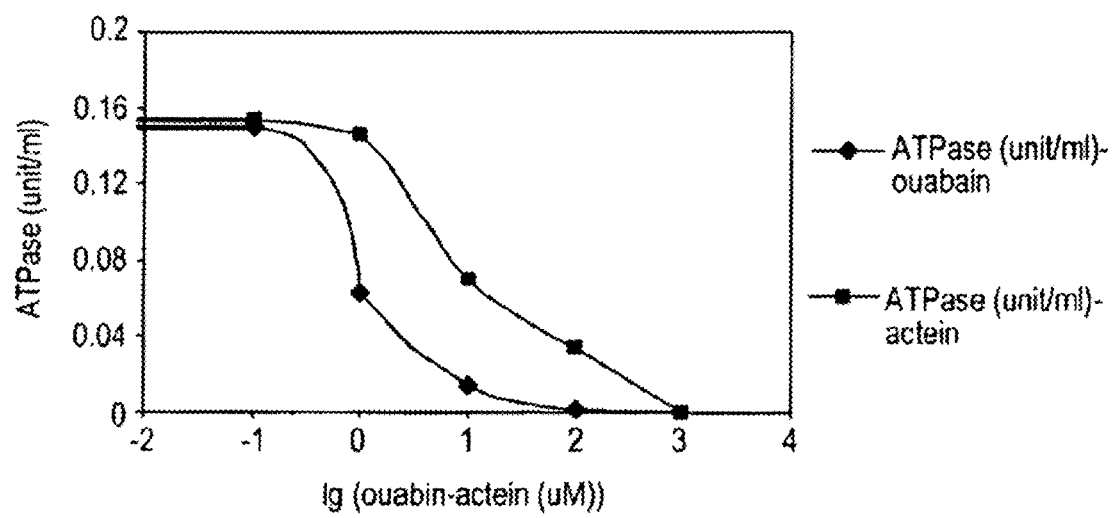
FIG. 27 Inhibition of $Na^+$—$K^+$-ATPase activity in response to increasing concentrations of ouabain or actein. The $Na^+$—$K^+$-ATPase assay was performed as described in Materials and Methods. The DMSO controls contained 3.3% DMSO. Bars: SD of triplicate assays (a).
Figure 28A:
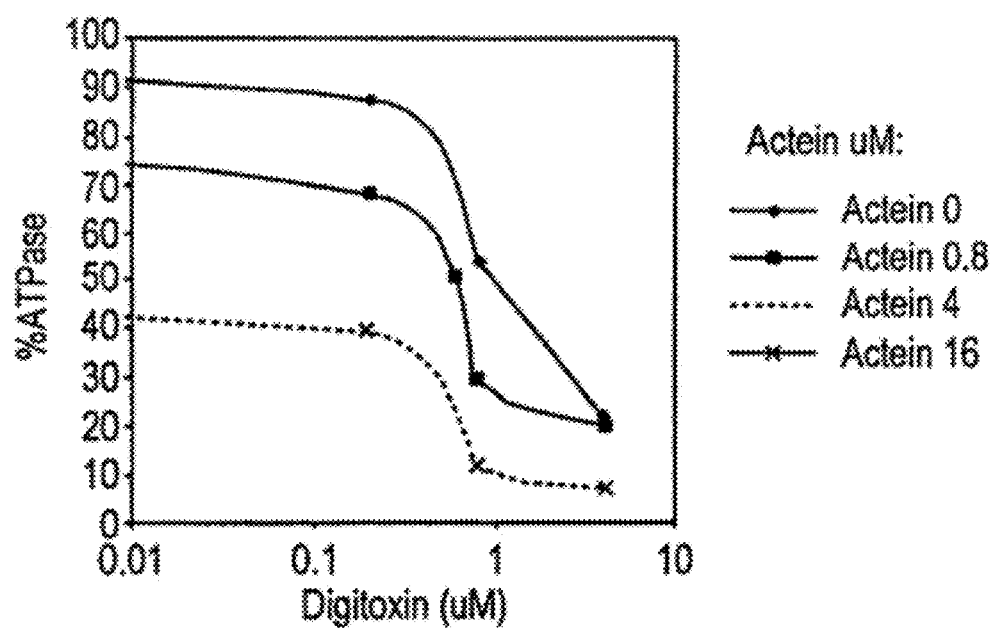
FIG. 28 Effects of increasing concentrations of actein alone or in combination with increasing concentrations of digitoxin on $Na^+$—$K^+$-ATPase activity or cell growth. $Na^+$—$K^+$-ATPase activity: A) x-axis, actein concentration; B) x-axis, digitoxin concentration: Cell proliferation in MDA-MB-453 breast cancer cells: C) x-axis, actein concentration; D) x-axis, digitoxin concentration. The DMSO controls contained 3.3% DMSO (A, B) or 0.33% DMSO(C, D). Similar results (A, B) were obtained in an additional experiment. Bars: SD of triplicate assays (C, D).
Figure 28B:
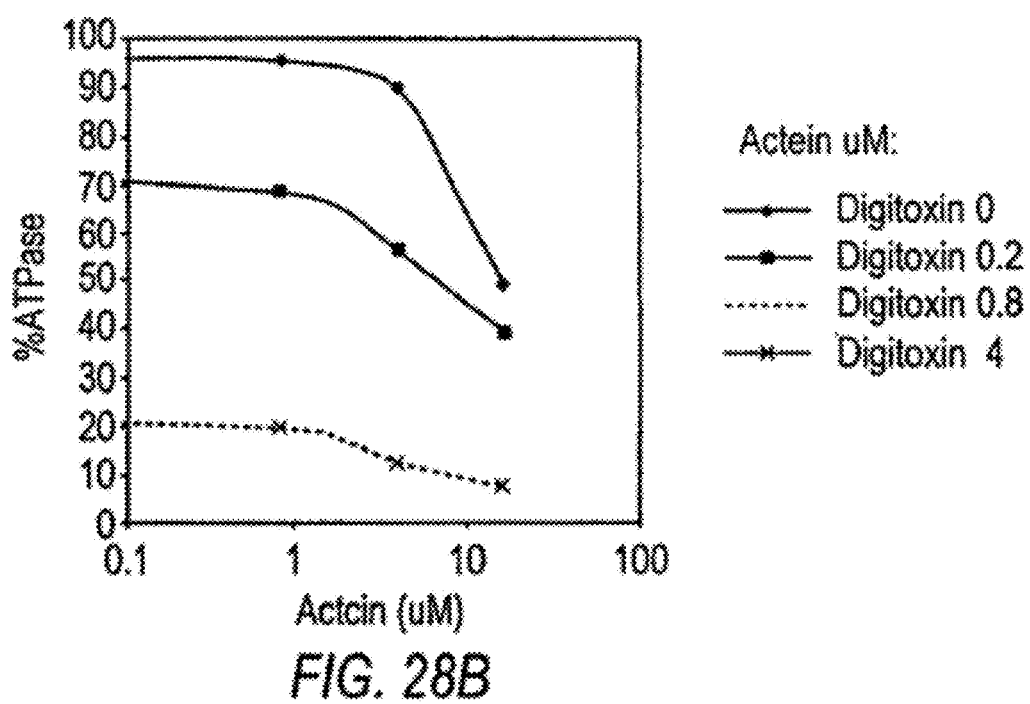

To determine whether the $Na^+$—$K^+$-ATPase is involved in the mechanism of action of actein, the ability of actein to inhibit the in vitro activity of the purified enzyme was assayed, and 50% inhibition was found at a concentration of 11.2 µM (FIG. 27). In the assay this value is about 10× the $IC_{50}$ (concentration that causes 50% inhibition) value of ouabain (0.94 µM) (FIG. 27), and of digitoxin (0.8 µM). When combining increasing concentrations of actein with increasing concentrations of digitoxin (FIGS. 28A and B, and Table 12), moderate synergy (CI 2+) was seen with as little as 0.8 µM actein and 0.2 µM digitoxin, and strong synergy (CI 3+) with 0.8 µM actein and 0.8 µM digitoxin. ATPase activity decreased from 87.8% after treatment with digitoxin alone to 68.2% after treatment with 0.2 µM digitoxin plus 0.8 µM actein, p<0.01 (actein alone: 95.1%). Addition of 0.8 µM actein to 0.8 µM digitoxin decreased ATPase activity from 53.6% to 29.1% (p<0.01).

TABLE 12

Combination indices* of actein and digitoxin on $Na^+$-$K^+$-ATPase inhibition

|  | Digitoxin 0.2 µM | Digitoxin 0.8 µM | Digitoxin 4 µM |
|---|---|---|---|
| Actein 0.8 µM | 0.76 | 0.38 | 0.33 |
| Actein 4 µM | 0.68 | 0.30 | 0.25 |
| Actein 16 µM | 0.43 | 0.05 | 0 |

| *Combination Index | Effect |
|---|---|
| >1.3 | antagonism |
| 1.1–1.3 | moderate antagonixm |
| 0.9–1.1 | additive effect |
| 0.8–0.9 | slight synergism |
| 0.6–0.8 | moderate synergism |
| <0.6 | synergism |

Growth Inhibitory Activity of Actein and Digitoxin on Human Breast Cancer Cells

Figure 28C:
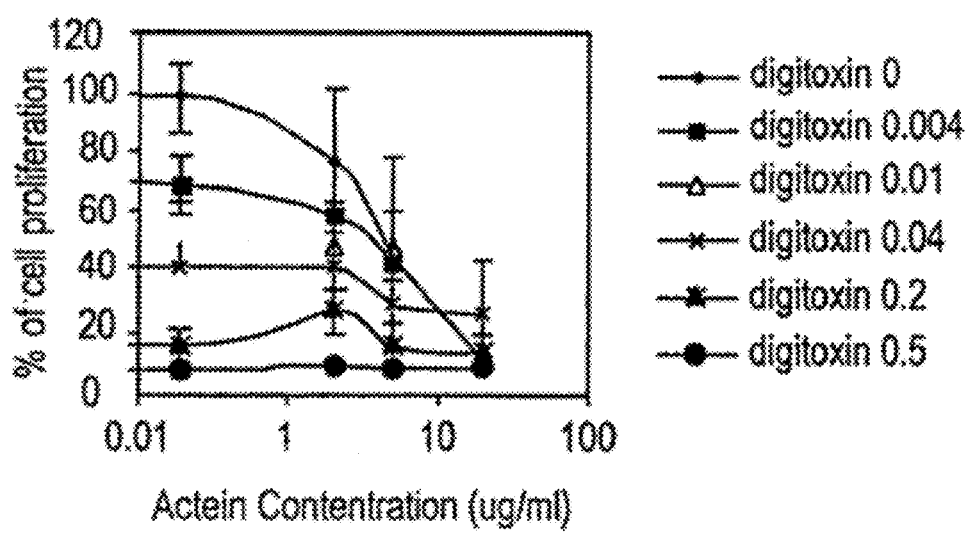
Figure 28D:
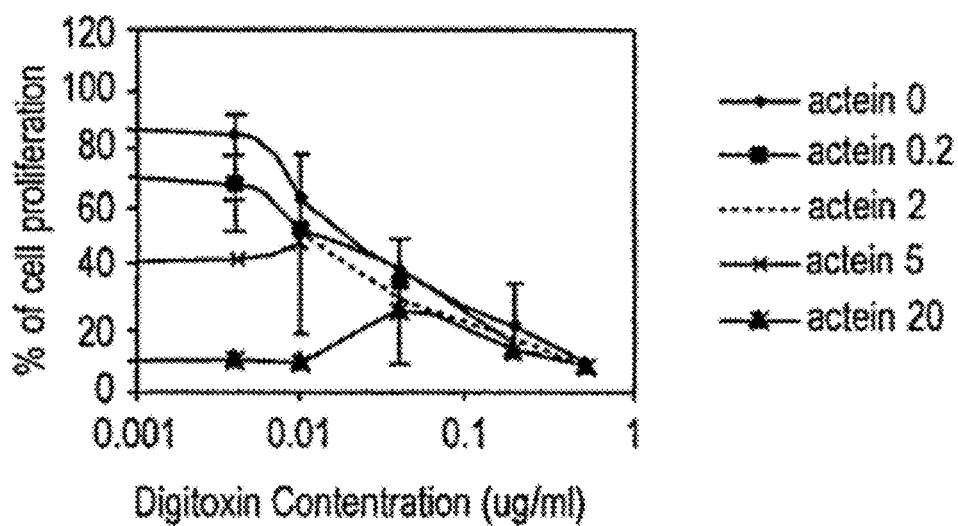

Of the cells that were previously tested, Her2 overexpressing human breast cancer cells appeared to be the most sensitive to growth inhibition by actein and extracts of black cohosh. (L. S. Einbond, et al., *Breast Cancer Res* Treat. 83 (2004) 221-31). Therefore, the effects of actein and digtoxin on the proliferation of MDA-MB-453 Her2 overexpressing human breast cancer cells were compared. The $IC_{50}$'s for actein and digitoxin were about 5 µg/ml (7.4 µM) and 0.025 µg/ml (0.033 µM), respectively (FIGS. 28C, D). Thus, digitoxin is about 200-fold more potent than actein in inhibiting the growth of these cells. The $IC_{50}$ ratio for growth inhibition of HCC1569 (ER-, Her2 overexpressing) by actein and digitoxin was similar (25/0.12=213) to that of the MDA-MB-453 cells, whereas the ratio was significantly lower for MCF7 (ER+Her2 low) human breast cancer cells (20.7/2.61=79) and higher for BT474 (ER+Her2 overexpressing) cells (23.6/0.039=605). The effect on $Na^+$-$K^+$-ATPase may be similar in different cell lines, but the downstream signaling targets appear to differ in cells with different receptors and signaling pathways.

When comparing the compounds' $IC_{50}$'s for ATPase inhibition to the $IC_{50}$'s for growth inhibition of MDA-MB-453 human breast cancer cells, actein's effect on ATPase activity was amplified about 2-fold (16: 7.4) and digitoxin's effect was amplified about 20-fold (0.8: 0.04). The effect of actein was not amplified for the other cells lines, and the amplification of digitoxin was about the same for BT474 (0.8/0.039=20.5-fold) and smaller for MCF7 (0.8/0.26=3.1-fold) and HCC1569 cells (0.8/0.12=6.8-fold) compared to MDA-MB-453 cells.

Synergistic Growth Inhibitory Effects of Actein and Digitoxin on Human Breast Cancer Cells When combining increasing concentrations of actein with increasing concentrations of digitoxin (FIGS. 28C and D, and Table 13), moderate synergy (CI 2+) was seen with as little as 0.2 µg/mL of actein and 0.01 µg/ml digitoxin, and strong synergy (CI 3+) with 2 µg/mL actein and 0.01 µg/ml digitoxin. For the former combination, the percent viable cells decreased from 62.8% after treatment with digitoxin alone to 52.8% after treatment with digitoxin plus actein, p<0.01 (actein alone: 97.8%). Addition of actein (2 µg/ml) to digitoxin (0.01 µg/ml) decreased cell survival from 62.8% to 47.2% (p<0.01) (actein alone: 75.8%).

TABLE 13

Combination indices* of actein and digitoxin on inhibition of MDA-MB-453 cell proliferation

|  | Actein 0.2 µM | Actein 2 µM | Actein 5 µM | Actein 20 µM |
|---|---|---|---|---|
| Digitoxin 0.004 µM | 1.32 | 0.96 | 0.72 | 0.72 |
| Digitoxin 0.01 µM | 0.72 | 0.36 | 0.12 | 0.12 |
| Digitoxin 0.04 µM | 0.6 | 0.24 | 0 | 0 |
| Digitoxin 0.2 µM | 0.6 | 0.24 | 0 | 0 |
| Digitoxin 0.5 µM | 0.6 | 0.24 | 0 | 0 |

| *Combination Index | Effect |
|---|---|
| >1.3 | antagonism |
| 1.1–1.3 | moderate antagonixm |
| 0.9–1.1 | additive effect |
| 0.8–0.9 | slight synergism |
| 0.6–0.8 | moderate synergism |
| <0.6 | synergism |

Actein's Effect on Proteins Downstream of $Na^+$—$K^+$-ATPase

The effects of actein and digitoxin on Src were tested and then the effects of actein on stress response and cell cycle pathways downstream of the ATPase-Src signaling complex were assayed.

Figure 29A:
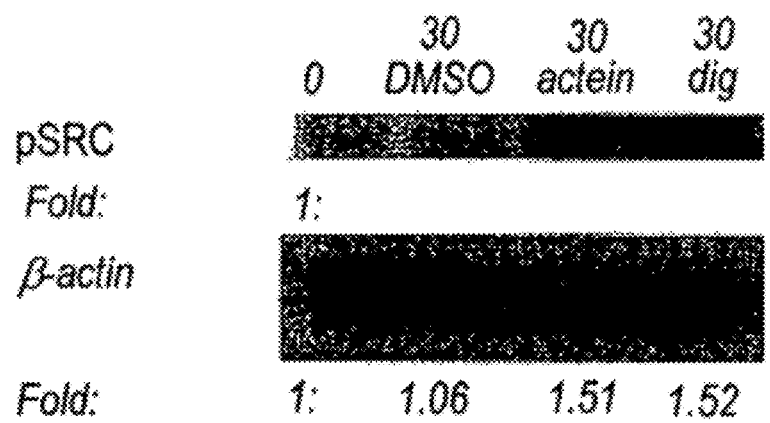
FIG. 29 Effect of actein on targets downstream of Na+—K+-ATPase. All assays were performed on MDA-MB-453 cells as described in Materials and Methods. A) Western blot analysis of p-Src, following cell exposure to actein or digitoxin for 30 minutes (80 ug/ml); fold relative to β-actin; B) Growth inhibitory effects of actein (20 µg/ml for 48 h) on cells pretreated with siRNA to ERK2 for 24 h (p=0.0665); C) Western blot analysis of proteins obtained from cells 3, 8 or 24 hours after treatment with 0, 20 or µg/mL of actein; D) luciferase promoter activity of NF-κB following treatment of cells actein at 20 or 40 µg/ml for 24 h.

Treatment of serum-starved MDA-MB-453 cells with actein at 80 µg/ml (118 µM) or digitoxin at 80 µg/ml (105 µM) for 30 min increased the level of p-Src by 1.5-fold for both treatments (FIG. 29A).

Figure 29B:
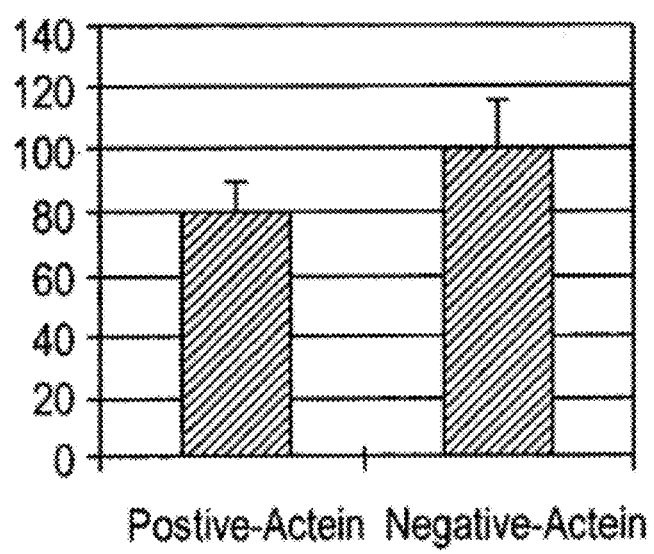
Figure 29C:
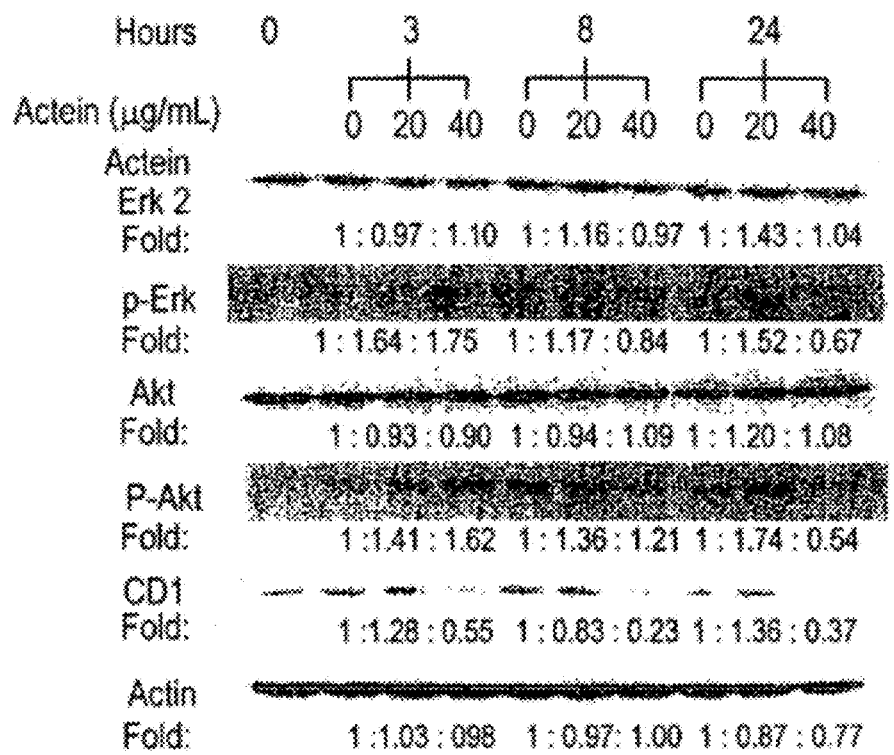

For the survival proteins Akt and Erk, actein appeared to induce a biphasic response; actein upregulated the activated forms at 20 and 40 µg/ml at 3 hours and at 20 µg/ml at 8 and 24 hours, but downregulated these protein levels at 40 µg/ml at 24 hrs (FIG. 29C). Since ERK/MAPKs have been shown to regulate cyclin D1 promoter activity and protein expression (Lavoie J N, et al., Cyclin D1 expression is regulated positively by the p42/p44MAPK and negatively by the p38/HOGMAPK pathway., *J Biol. Chem.* 271 (1996) 20608-16), the effects of actein were tested on cyclin D1. While actein at 20 µg/ml slightly increased the level of cyclin D1 protein at 3 and 24 h, actein at 40 µg/ml decreased the level of cyclin D1 protein at 3, 8 and 24 hours in MDA-MB-453 cells (FIG. 29C).

Figure 29D:
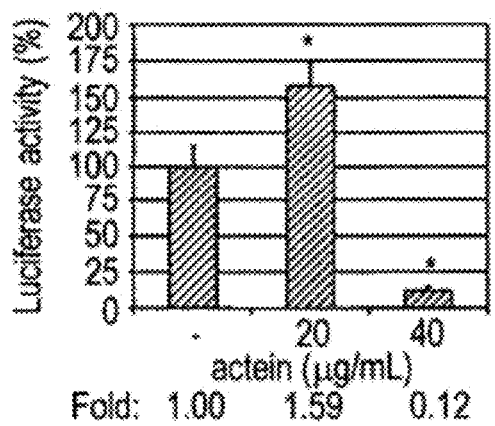

A biphasic response was observed on the promoter activity of NF-κB, which is instrumental in controlling cell proliferation and may be activated by Akt. (Rivas M A, et al., TNF alpha acting on TNFR1 promotes breast cancer growth via p42/P44 MAPK, JNK, Akt and NF-kappa B-dependent pathways, *Exp Cell Res.* 314 (2008) 509-29). Actein induced a 1.59 fold increase in NF-κB promoter activity at 20 µg/ml and a 0.12 fold decrease at 40 µg/ml, at 24 h (FIG. 29D).

RNAi-Mediated Gene Knockdown

Pretreatment with siRNA to ERK2 (MAPK1) reduced the percent growth inhibition from 100% (control siRNA) to 79.6% (ERK2 siRNA) (p=0.0665) in response to actein treatment (20 µg/ml) for 48 h compared to the control. ERK2 may therefore be involved in the survival phase of the digitoxin-induced stress response (FIG. 29B). Western blot analysis indicated that the ERK2 siRNA reduced the quantity of ERK2 protein by about 50%.

Discussion

The primary molecular target of actein has not been identified, but the ubiquitous $Na^+$—$K^+$-ATPase is a good candidate; the enzyme mediates many stress response and proliferation pathways that are affected by actein. The $Na^+$—$K^+$-ATPase enzyme is a known target of cardiac glycosides such as digitoxin and ouabain, which, like actein, are saponins. The enzyme also is important in the action of the chemotherapy agent thapsigargin, an inhibitor of Serca. (J. Tian, et al., Binding of Src to Na+/K+-ATPase forms a functional signaling complex., *Mol Biol Cell.* 17 (2006) 317-26). This study demonstrated that actein inhibits $Na^+$—$K^+$-ATPase activity and subsequently phosphorylates downstream proteins (FIG. 26C), and showed that actein and digitoxin synergize with each other to inhibit the enzyme's activity and proliferation of MDA-MB-453 human breast cancer cells.

Inhibition of the enzyme has been shown to be related to a compound's ability to interact with the enzyme's lipid-rich environment. (Gorshkova I A, et al., Two different modes of inhibition of the rat brain $Na^+$, $K(+)$-ATPase by triterpene glycosides, psolusosides A and B from the holothurian *Psolus fabricii, Comp Biochem Physiol C Pharmacol Toxicol Endocrinol.* 122 (1999) 101-8). An explanation is suggested by a comparison to the triterpene glycosides psolusosides (Ps) A and B from the holothurian *Psolus fabricii*. PsA is highly lipophilic and three-fold more active on rat brain $Na^+$—$K^+$-ATPase than PsB. PsA, but not PsB, binds to cholesterol and generates ion channels. It was suggested that PsA may alter the protomers of the enzyme and the lipid environment, while PsB may primarily affect the protomers. (Gorshkova I A, et al., *Comp Biochem Physiol C Pharmacol Toxicol Endocrinol.* 122 (1999) 101-8). Actein's weaker inhibition of ATPase suggest a protomer-dependent mode of action similar to that of PsB, while digitoxin's 10-fold greater potency for ATPase inhibition is consistent with its highly lipophilic character and suggests that it may have a mode of action similar to that of PsA.

The amplification of ATPase inhibition that was observed for both actein and digitoxin is consistent with reports of cardiotonic steroids exerting growth inhibition in cultured cells and animal models (J. Tian, et al., *Mol Biol Cell.* 17 (2006) 317-26), at low doses without inhibiting cellular $Na^+$—$K^+$-ATPase pumping activity. (Z. Li, et al., The Na/K-ATPase/Src complex and cardiotonic steroid-activated protein kinase cascades., *Pflugers Arch.* February 19; [Epub ahead of print](2008)). The extent of amplification may also be related to lipid affinity, which may in turn account for a compound's ability to activate Src and its downstream signaling cascades. Ouabain has been shown to increase the translocation of cytosolic Src to a triton-insoluble fraction and stimulate Src activity in cultures of cardiac myocytes. (Z. Li, et al., *Pflugers Arch.* February 19; [Epub ahead of print](2008)). The signal amplification that was observed may be due to interaction of the $Na^+$—$K^+$-ATPase protomers in the cell membrane and the induction of clustering of ATPase with neighboring proteins in caveolar microdomains. (M. Haas, et al., Involvement of Src and Epidermal Growth Factor Receptor in the Signal-transducing Function of $Na^+/K^+$-ATPase, *J. Biol. Chem.* 275 (2000) 27832-27837). GRP78, which is expressed on the cell surface and is involved in ouabain-induced endocytosis of the $Na^+$—$K^+$-ATPase in LLC-PK1 cells (R. Kesiry, et al., GRP78/BIP is involved in ouabain-induced endocytosis of the Na/K-ATPase in LLC-PK1 cells., *Front Biosci.* 10 (2005) 2045-55), is also activated by actein (L. S. Einbond, et al., Weinstein, Gene expression analysis of the mechanisms whereby black cohosh inhibits human breast cancer cell growth., *Anticancer Res.* 27 (2007) 697-712), and may therefore be instrumental in actein or digitoxin-mediated ATPase inhibition. It is important to note, however, that although cardiac glycosides have been highly studied, it is not certain that the $Na^+$—$K^+$-ATPase signaling cascade is their primary mechanism of cell growth inhibition. (Arispe N, et al., Heart failure drug digitoxin induces calcium uptake into cells by forming transmembrane calcium channels, *Proc Natl Acad Sci USA.* 105 (2008) 2610-5).

Downstream of $Na^+$—$K^+$-ATPase inhibition, actein's upregulation of ERK2 resembled the effects of paclitaxel (TAX) in human ovarian SKOV3 cells. (Seidman R, et al., The role of ERK 1/2 and p38 MAP-kinase pathways in taxol-induced apoptosis in human ovarian carcinoma cells, *Exp Cell Res.* 268 (2001) 84-92). At low concentrations (1-100 nM), TAX activated ERK1/2 within 0.5-6 h, whereas the activation was reversed at 24 hours or at high concentrations (1-10 μM). High concentrations (1-μM) of TAX activated p38 within 2 h, and this activation continued for over 24 hours. The decrease in ERK activation and the increase in p38 activation coincided with the transition from inhibition of proliferation to apoptosis.

The present study demonstrates a synergistic relationship between actein and digitoxin. Actein potentiated digitoxin's inhibition of ATPase activity, and at lower concentrations potentiated digitoxin's inhibition of cell proliferation. The concentrations required for the latter synergy are within the therapeutic range for digitoxin (13-46 nM) and achievable in vivo for actein, as the bioavailability studies on Sprague-Dawley rats indicated a peak serum level of about 2.4 μg/ml at 6 h after treatment with actein at 35.7 mg/kg (data not shown).

The observed synergy of actein and digitoxin suggests that the two compounds may bind to different active sites on the ATPase, or the binding of one compound may enhance binding of the second agent. Triterpene glycosides from holothurians have been shown to potentiate the inhibitory effect of ouabain on $Na^+$—$K^+$-ATPase activity without altering the specific binding of ouabain to the ATPase. (I. Gorshkova, et al., Inhibition of rat brain Na+—K+-ATPase by triterpene glycosides from holothurians., *Toxicon.* 27 (1989) 927-36). The synergistic effects on growth inhibition may also be due, in part, to the fact that actein and digitoxin inhibit different phases of the cell cycle; actein induces G1 arrest (L. S. Einbond, et al., *Planta Med.* 72 (2006) 1200-6), while digitoxin induces G2 arrest Actein may alter additional targets not altered by digitoxin.

In sum, the $Na^+$—$K^+$-ATPase is a known target of cardiac glycosides such as digitoxin and ouabain. The enzyme is also a target of the structurally-related triterpene glycoside actein, present in the herb black cohosh. Actein's inhibition of $Na^+$—$K^+$-ATPase activity was less potent than that of digitoxin, but actein potentiated digitoxin's inhibitory effect on $Na^+$—$K^+$-ATPase activity and MDA-MB-453 breast cancer cell growth. Different degrees of signal amplification were observed for the two compounds. Actein's inhibitory effect on ATPase activity was amplified two-fold for cell growth inhibition, whereas digitoxin's signal was amplified twenty-fold. Actein induced a biphasic response in proteins downstream of ATPase: low dose and short duration of treatment upregulated NF-κB promoter activity, p-ERK, p-Akt and cyclin D1 protein levels, whereas higher doses and longer exposure inhibited these activities.

The results indicate that actein inhibits the activity of the $Na^+$—$K^+$-ATPase and enhances the growth inhibitory effect of digitoxin on human breast cancer cells. The synergy demonstrated indicates the utility of combinations of digitoxin and actein to prevent and treat breast cancer, but suggests that there may be safety issues for cardiac patients who are prescribed digitalis compounds and simultaneously take black cohosh to alleviate menopausal symptoms. Synergistic combinations of digitoxin and actein or an extract of black cohosh comprising triterpene glycosides of the present invention, preferably digitoxin and actein, have clinically advantageous utility, permitting the use of therapeutic or lower doses of digitoxin and thus reducing the risk of adverse effects.

Example 15

Effects of Digitoxin on Gene Expression and Effects of Digitoxin and Paclitaxel Combinations on Cell Proliferation Materials and Methods
Materials All solvents and reagents were reagent grade; $H_2O$ was distilled and deionized. Digitoxin and paclitaxel were obtained from Sigma (St. Louis, Mo.). These agents were dissolved in dimethylsulfoxide (DMSO) (Sigma; St. Louis, Mo.) prior to addition to the cell cultures.
Cell Culture, Proliferation Assays and Cell Cycle Analysis MDA-MB-453 (ER negative, Her2 overexpressing) and MCF7 (ER positive, Her2 low) cells were obtained and cultured as set forth above in Example 4.

Cell proliferation was determined using: 1) the Coulter Counter assay or 2) the MTT {3-(4,5-dimethyl-2-thiazol)-2,5-diphenyl-2H tetrazolilum bromide}(Dojindo; Tokyo, Japan) cell proliferation assay system, according to the manufacturer's instructions (Roche Diagnostic, Mannheim, Germany). For the Coulter counter assay, cells were seeded at $2 \times 10^4$ cells per well in 24 well plates (0.875 cm diameter) as described previously. (Einbond L S, et al. Growth inhibitory activity of extracts and purified components of black cohosh on human breast cancer cells. *Breast Cancer Res Treat.* 83(3):221-31, 2004.) For the MTT assay, cells were seeded at $1 \times 10^4$ cells/well in 96-well plates and allowed to attach for 24 hours. The medium was replaced with fresh medium containing DMSO or digitoxin. The cells were treated for 96 hours after which the cells were incubated with MTT reagents and the absorbance was read at 575 and 650 nm. Control and treated cells were compared using the student's t-test (p<0.05). For cell cycle analysis the cells were plated ($3 \times 10^5$) onto 6 cm dishes and allowed to attach for 24 hours. Then the medium was replaced with DMEM containing 10% FBS and DMSO or digitoxin. After 24 hours the cells were analyzed by DNA flow cytometry, as described previously. (Einbond L S, et al., *Breast Cancer Res Treat.* 83(3):221-31, 2004.)

Calculating the Combination Index.

To determine the Combination Index (CI), we exposed MDA-MB-453 cells to all combinations of 4 concentrations of each of the agents tested and a solvent control (Einbond L S et al. Actein and a fraction of black cohosh potentiate antiproliferative effects of chemotherapy agents on human breast cancer cells. *Planta Med.* October; 72(13):1200-6, 2006). The results of the MTT assay were analyzed as indicated in the "Calculating the Combination Index" section of Example 14.
RNAi-Mediated Gene Knockdown The procedure in the "RNAi-mediated gene knockdown" section of Example 14 was followed, using digitoxin at 0.4 µg/ml for 24 hours.
RNA Isolation and Oligonucleotide Microarray Analysis RNA was isolated as previously described. (Einbond L S, et al. The growth inhibitory effect of actein on human breast cancer cells is associated with activation of stress response pathways. *Int J Cancer.* November 1; 121(9):2073-83, 2007.) Total cellular RNA was extracted using Trizol (Invitrogen; Carlsbad, Calif.) according to the manufacture's protocol with minor modifications, and then purified twice with Qiagen's RNeasy column as previously described. Total RNA (8 µg) was reverse transcribed with T7-(dT)24 primer and Super Script III reverse transcriptase (Invitrogen). After purification, cDNA was in vitro transcribed into biotin labeled antisense cRNA with the BioArray high yield RNA transcript labeling kit (Enzo Life Sciences; Farmingdale, N.Y.), according to a modified Affymetrix protocol. cRNA (15 µg) was fragmented into the final probe and hybridized to human U133A 2.0 gene chips (Affymetrix, Inc.; Santa Clara, Calif.), comprised of more than 22,000 probe sets. The Institute for Cancer Genetics Core Facility at the Columbia Genome Center performed the hybridization.
Real-time Quantitative RT-PCR and Western Blot Analysis We treated MDA-MB-453 cells with 20 ng/ml, 0.1, 0.2 or 1 µg/mL (26 nM, 0.13, 0.26 and 1.3 µM) of digitoxin for 6 or 24 hours and performed real-time RT-PCR analysis on 2 technical replicates of at least 2 biological sample replicates. (Tsutsumi S et al. Celecoxib upregulates endoplasmic reticulum chaperones that inhibit celecoxib-induced apoptosis in human gastric cells. *Oncogene.* February 16; 25(7):1018-29, 2006.) Primer sequences used in qPCR are listed in Table 14.

For Western blot analysis, cells were treated for increasing times with approximately the $IC_{50}$ and twice the $IC_{50}$ concentration, measured at 48 hours, of digitoxin. Western blot analysis was performed as described previously. (Einbond L S, et al., *Breast Cancer Res* Treat. 83(3):221-31, 2004.) The membrane was incubated with the primary antibodies to ATF3, EGR1 (Santa Cruz Biotechnology, Santa Cruz, Calif.), and ERK2 (Cell signaling, Beverly, Mass.); β-actin was used a loading control.

TABLE 14

Designed primer sequence used in RT-PCR.

| Symbol | Forward sequence | Reverse sequence |
|---|---|---|
| GAPD | ggcctccaaggagtaagacc | aggggtctacatggcaactg |
| ATF3 | tgggaggactccagaagatg | gacagctctccaatggcttc |
| EGR1 | gagaaggtgctggtggagac | tgggttggtcatgctcacta |
| GDF15 | ctccgaagactccagattcc | agagatacgcaggtgcaggt |
| CDKN1A | gcctggactgttttctctcg | attcagcattgtgggaggag |
| HSF2 | atgggaaccctgcttcttct | ttgggttggttctgggtcta |
| DNAJB4 | ccggacaagaacaaatctcc | cctcctttcaacccttcctc |
| HMGCR | gacctttccagagcaagcac | agctgacgtaccccctgacat |
| HMGCS1 | ccccagtgtggtaaaattgg | tggcctggacttaacattcc |

TABLE 14-continued

Designed primer sequence used in RT-PCR.

| Symbol | Forward sequence | Reverse sequence |
|---|---|---|
| INSIG1 | gacagtcacctcggagaacc | caccaaaggcccaaagatag |
| ATF4 | ccaacaacagcaaggaggat | gtgtcatccaacgtggtcag |
| GADD34 | ggaggctgaagacagtggag | cctctagggacactggttgc |
| CDC16- | cgatggctgcttacttcaca | cagagcttggctgaagaacc |

Primers were designed using Primer3 software from the Massachusetts Institute of Technology (frodo.wi.mit.edu/cgi-bin/primer3/primer3_www.cgi).

Gene Expression Analysis

MDA-MB-453 breast cancer cells were treated with digitoxin at 0.1, 0.2 and 1 μg/mL and RNA was collected at 6 and 24 hours for gene expression analysis, and with 20 ng/ml digtoxin for 24 hours. Microarray analysis and an unbiased informatics approach was used to find the genes and signaling pathways whose expression was altered by exposure of the cells to digitoxin. Two or three replicates of each microarray were performed to determine intrasample variation. To bolster the robustness of the analysis, the effects of 4 doses for 2 time periods were examined.

All analyses were performed using the AffyLimmaGUI package in the open-source Bioconductor suite, as previously described. (Einbond L S, et al., *Int J Cancer*. November 1; 121(9):2073-83, 2007.) All samples were normalized to remove chip-dependent regularities using the GCRMA method of Irizarry et al. (Irizarry R A et al. Summaries of Affymetrix GeneChip probe level data. Nucleic Acids Res. 31(4):e15, 2003.) The statistical significance of differential expression was calculated using the empirical Bayesian LIMMA (LI Model for MicroArrays) method of Smyth et al. (Smyth G K et al. Use of within-array replicate spots for assessing differential expression in microarray experiments. *Bioinformatics*. 21(9):2067-75, 2005.) A cut-off B>0 was used for the statistical significance of gene expression. Variability is reported in terms of a p-value representing the probability that differences between treated and untreated could occur by chance. The p-value takes into account both the variability within groups (in this case the groups are treated and control) and the variability between groups.

$$M = \log_2\left(\frac{\text{Intensity.Treatment}}{\text{Intensity.Control}}\right) = \log_2\left(\frac{[\text{Treatment}]}{[\text{Control}]}\right)$$

P-value=The Bayesian P-value (This will not equal the conventional frequentist P-value since the Bayesian method used by LIMMA pools variance across genes to increase statistical power). This P-value was corrected by the Benjamini-Hochberg method to give the number of false discoveries.

$B=\text{Log}_e$ (Odds of differential expression). The Bayesian natural (base e) log of the odds that the genes are differentially expressed. B>0 Odds>1 implies that the genes are differentially expressed for the high-throughput analysis, with especially important genes being validated by PCR.

The genes that displayed significant changes in levels of expression were assigned to Gene Ontology categories and KEGG Pathways. (Khatri P, Draghici S. Ontological analysis of gene expression data. In Encyclopedia of Genetics, Proteomics and Bioinformatics. New York: John Wiley and Sons Inc.; 2005.) Intersections between treatments were calculated using the Gene Traffic program. Clustering was performed with the Program Cluster 3.0. (Einbond L S, et al., *Int J Cancer*. November 1; 121(9):2073-83, 2007; de Hoon M J, et al. Open source clustering software. *Bioinformatics*. 20(9):1453-4, 2004.)

Results

The Effects of Digitoxin on Breast Cancer Cell Growth

After treating Her2 overexpressing, ER low MDA-MB-453 breast cancer cells with increasing concentrations of digitoxin for 96 hours, digitoxin's effects were assessed by the MTT assay and it was found that the concentration of digitoxin that caused 50% inhibition of cell proliferation, the $IC_{50}$ value, was about 0.025 μg/mL (0.04 μM). The Coulter counter assay indicated that digitoxin inhibited growth of the MDA-MB-453 and $ER^+$ BT474 breast cancer cells, with $IC_{50}$ values of 0.04 μg/ml (0.05 μM) and 0.03 μg/ml (0.04 μM), respectively. The $IC_{50}$ values (0.025 to 0.04 μg/mL) are within the therapeutic range, 10-35 ng/mL (13-46 nM). Digitoxin was less potent on ER positive, Her2 low MCF7 breast cancer cells, with an $IC_{50}$ value of 0.2 μg/ml.

Effects of Digitoxin on Cell Cycle Distribution in MDA-MB-453 Human Breast Cancer Cells The effects on cell cycle distribution at 24 hours after exposing MDA-MB-453 cells to 0, 0.2 or 2 μg/mL (0, 0.26 or 2.6 μM) are shown in Table 15 below. After treatment with digitoxin at 0.2 or 2 μg/mL, there was an increase in the subG1 peak, which may indicate apoptosis. Digitoxin induced a dose-dependent increase in the percent of cells in G2 and a decrease in the percent of cells in G1, and, at the higher dose decreases in G1 and S phases.

TABLE 15

Effect of digitoxin on cell cycle distribution in MDA-MB-453 cells treated with 0.2 or 2 mg/ml of digitoxin and analyzed at 24 hours by DNA flow cytometry. The values indicate the percent of cells in the indicated phases of the cell cycle. The control contained 0.01% DMSO. Standard deviations are indicated in parentheses.

| Treatment | SubG1 | G1 | S | G2 |
|---|---|---|---|---|
| 0 μg/mL | 1.93 (1.02) | 57.75 (1.20) | 26.90 (0.99) | 11.45 (4.74) |
| 0.2 μg/mL | 6.77 (1.06) | 46.50 (1.98) | 27.65 (0.64) | 19.05 (0.07) |
| 2.0 μg/mL | 5.78 (1.02) | 41.90 (2.26) | 17.80 (0.42) | 32.10 (1.27) |

Alterations in Gene Expression Induced by a Nontoxic Dose of Digitoxin

When the effect of a therapeutic dose of digitoxin (20 ng/ml) was examined on gene expression patterns at 24 hours, it was found that digitoxin significantly altered the expression of 22 genes. The 11 upregulated genes included corneodesmosin, keratin 23 (histone deacetylase inducible), Desmoplakin, and cysteine-rich secretory protein LCCL domain containing 2; the 11 downregulated genes included calmegin, chromosome 9 open reading frame 127, and ubiquitin specific protease 34 baculoviral IAP repeat-containing 1 (Table 16). Of the 22 genes, 4 were also activated after treatment with a 5-fold higher dose. These included genes involved in response to stress. It is worth noting that several genes were activated by Src mediated pathways: GRB7 is phosphorylated in response to EGF stimulation. RPS6KA5 is activated by ERK. RAB15 is a member of the RAS oncogene family and involved in GTP binding. BIRC1 is anti-apoptotic. Genes involved in regulating the cell cycle are HSF2, which bookmarks DNA during mitosis, and C9orf127. KCNAB2 has a role in mediating potassium voltage-gated channels.

TABLE 16

Differentially expressed genes after treating MDA-MB-453 cells with digitoxin at 20 ng/ml for 24 hours, B > 0.

| Category | ID | Symbol | Name | M | P. Value | B |
|---|---|---|---|---|---|---|
| apoptosis | 206192_at | CDSN | comeodesmosin | 2.255 | 1.34E−05 | 4.96 |
|  | 218963_s_at | KRT23 | keratin 23 (histone deacetylase inducible) | 2.231 | 0.199 | 1.03 |
|  | 204860_s_at | BIRC1 | baculoviral IAP repeat-containing 1 | −0.55 | 0.262 | 0.52 |
| stress | 204635_at | RPS6KA5 | ribosomal protein S6 kinase, 90 kDa, polypeptide 5 | −0.87 | 0.0215 | 2.57 |
| protein | 200606_at | DSP | desmoplakin | 1.176 | 0.24 | 0.71 |
|  | 221541_at | CRISPLD2 | cysteine-rich secretory protein LCCL domain containing 2 | 0.842 | 0.24 | 0.71 |
|  | 215339_at | NKTR | natural killer-tumor recognition sequence | −0.42 | 0.154 | 1.26 |
|  | 212980_at | USP34 | ubiquitin specific protease 34 | −1.1 | 0.271 | 0.39 |
|  | 205830_at | CLGN | calmegin | −1.47 | 0.282 | 0.3 |
| transcription | 207839_s_at | C9orf127 | chromosome 9 open reading frame 127 | −1.12 | 1.34E−05 | 4.91 |
|  | 221810_at | RAB15 | RAB15, member RAS oncogene family | 0.403 | 0.24 | 0.63 |
| ion | 203402_at | KCNAB2 | potassium voltage-gated channel, shaker-related subfamily, beta member 2 | 0.383 | 0.262 | 0.49 |
|  | 210486_at | ANKMY1 | ankyrin repeat and MYND domain containing 1 | 0.199 | 0.121 | 1.57 |
| signal transduction | 210222_s_at | RTN1 | reticulon 1 | 0.172 | 0.24 | 0.66 |
| nucleotide | 201766_at | ELAC2 | elaC homolog 2 (*E. coli*) | −0.16 | 0.282 | 0.29 |
|  | 212913_at | MSH5 | mutS homolog 5 (*E. coli*) | −0.64 | 0.327 | 0.16 |
| Function unknown | 205796_at | FLJ11336 | NA | −0.19 | 0.213 | 0.93 |
|  | 222307_at | LOC282997 | NA | −0.34 | 0.262 | 0.45 |
|  | 215364_s_at | KIAA0467 | NA | −0.42 | 0.0122 | 3.05 |
|  | 219054_at | FLJ14054 | NA | 1.105 | 0.144 | 1.38 |
|  | 221843_s_at | KIAA1609 | NA | 0.916 | 0.015 | 2.84 |

Fold-change (log) is the mean of the ratio of hybridization signals in digitoxin treated versus DMSO control treated cells.
NA designates function not known.

Alterations in Gene Expression Induced by Various Treatments with Digitoxin

Since only a few genes were altered after treatment with the nontoxic dose at 24 hours, MDA-MB-453 breast cancer cells were treated with digitoxin at three higher concentrations, 0.1, 0.2 and 1 μg/mL (0.13, 0.26 and 1.3 μM), RNA was collected at 6 and 24 hours for gene expression analysis in order to maximize the cells' response to digitoxin and delineate its mechanism of action. The number of genes impacted by the individual treatments of digitoxin (|M|>0, p<0.05) increased in a dose- and time-dependent manner. Thus, treatment with 0.1 μg/mL for 6 hours or 24 hours altered 2 and 8 genes respectively; 0.2 μg/mL for 6 and 24 hours altered 6 and 88 genes, respectively; 1 μg/mL for 6 and 24 hours altered 87 and 1491 genes, respectively. Under all treatment conditions at 6 hours (B>0, p<0.05, |M|>0), more genes were induced than repressed by a factor of about 1.0 to 2.5-fold, but the inverse (0.5-0.7-fold) was true at 24 hours.

Using the program Gene Traffic to identify commonly perturbed genes amongst the 3 doses of digitoxin and 2 time periods, no commonly perturbed genes were found at 0.1 μg/mL for 6 or 24 hours, 2 commonly perturbed genes at 0.2 μg/mL, and 61 genes or 61/87 genes (at 6 hours) at 1 μg/mL. Thus, the lower doses of digitoxin altered different sets of genes at 6 and 24 hours, while the highest dose altered similar sets of genes at the two timepoints.

Affymetrix Netaffx analysis showed a significant effect on stress response genes after treatment with digitoxin at 1 μg/ml for 6 hours (see Table 17 below). Among the early effects were upregulation of stress (EGR1, NAB2), apoptotic (1HPK2, ARID5B), lipid biosynthetic (SC5DL), transcription regulation (NR4A1, ZNF297B, RORA), anti-proliferation (BTG1) and RNA processing (DDX26) genes and downregulation of cell cycle (C10orf7), replication (POLR3B) and transcription (EIF2B1) genes. As predicted (Li Z, Xie Z. The Na/K-ATPase/Src complex and cardiotonic steroid-activated protein kinase cascades. *Pflugers Arch.* 2008. [Epub ahead of print]), digitoxin altered the response of genes involved in calcium metabolism (1HPK2, NR4A1).

TABLE 17

Differentially expressed genes after treating MDA-MB-453 cells with digitoxin at 1.0 μg/ml for 6 hours, B > 0, M > 3.

| Category | ID | Symbol | Name | M | P. Value | B |
|---|---|---|---|---|---|---|
| transcription | 36711_at | MAFF | v-maf musculoaponeurotic fibrosarcoma oncogene homolog F (avian) | 8.68 | 0.00805 | 7.23 |
|  | 201693_s_at | EGR1 | early growth response 1 | 6.25 | 0.000282 | 10.08 |
|  | 216017_s_at | NAB2 | NGFI-A binding protein 2 (EGR1 binding protein 2) | 5.75 | 0.000221 | 10.26 |
|  | 205193_at | MAFF | v-maf musculoaponeurotic fibrosarcoma oncogene homolog F (avian) | 5.16 | 0.00103 | 9.03 |
|  | 202340_x_at | NR4A1 | nuclear receptor subfamily 4, group A, member 1 | 3.35 | 0.00269 | 8.22 |
|  | 201725_at | C10orf7 | chromosome 10 open reading frame 7 | −1.24 | 0.00712 | 7.35 |
|  | 214185_at | KHDRBS1 | KH domain containing, RNA binding, signal transduction associated 1 | 2.22 | 0.00366 | 7.95 |
| DNA binding | 210426_x_at | RORA | RAR-related orphan receptor A | 0.679 | 0.000998 | 9.06 |
|  | 212614_at | ARID5B | AT rich interactive domain 5B (MRF1-like) | 1.24 | 0.0033 | 8.04 |
|  | 219459_at | POLR3B | polymerase (RNA) III (DNA directed) polypeptide B | −1.92 | 0.0036 | 7.96 |

TABLE 17-continued

Differentially expressed genes after treating MDA-MB-453
cells with digitoxin at 1.0 µg/ml for 6 hours, B > 0, M > 3.

| Category | ID | Symbol | Name | M | P. Value | B |
|---|---|---|---|---|---|---|
| protein binding | 203002_at | AMOTL2 | angiomotin like 2 | 2.84 | 0.00266 | 8.23 |
| | 204182_s_at | ZNF297B | zinc finger protein 297B | 2.58 | 4.53E−06 | 12.76 |
| | 221890_at | ZNF335 | zinc finger protein 335 | 2.47 | 0.00767 | 7.28 |
| | 78330_at | ZNF335 | zinc finger protein 335 | 0.62 | 0.00393 | 7.88 |
| | 201823_s_at | RNF14 | ring finger protein 14 | −1.13 | 0.00784 | 7.26 |
| | 209630_s_at | FBXW2 | F-box and WD-40 domain protein 2 | −1.93 | 0.00777 | 7.27 |
| | 218819_at | DDX26 | DEAD/H (Asp-Glu-Ala-Asp/His) box polypeptide 26 | 1.39 | 0.00504 | 7.66 |
| cell growth (−), | 218192_at | IHPK2 | inositol hexaphosphate kinase 2 | 2.83 | 0.00379 | 7.91 |
| apoptosis (+), | 200920_s_at | BTG1 | B-cell translocation gene 1, anti-proliferative | 1.72 | 0.00121 | 8.9 |
| oxidative stress | 200797_s_at | MCL1 | myeloid cell leukemia sequence 1 (BCL2-related) | 1.86 | 0.00378 | 7.92 |
| | 214056_at | MCL1 | myeloid cell leukemia sequence 1 (BCL2-related) | 1.76 | 0.00634 | 7.45 |
| phase 2 | 221906_at | TXNRD3 | thioredoxin reductase 3 | −0.755 | 0.00626 | 7.46 |
| protein | 210592_s_at | SAT | spermidine/spermine N1-acetyltransferase | 2.66 | 0.00478 | 7.71 |
| metabolism | 202140_s_at | CLK3 | CDC-like kinase 3 | 1.45 | 0.00155 | 8.69 |
| | 201632_at | EIF2B1 | eukaryotic translation initiation factor 2B, subunit 1 alpha, 26 kDa | −1.21 | 0.00449 | 7.76 |
| lipid metabolism, biosynthesis | 211423_s_at | SC5DL | sterol-C5-desaturase (ERG3 delta-5-desaturase homolog, fungal)-like | 1.98 | 0.00453 | 7.75 |
| Function unknown | 215150_at | DKFZp451J1719 | NA | 2.75 | 0.00592 | 7.51 |
| | 219397_at | FLJ13448 | NA | 1.59 | 0.00557 | 7.57 |
| | 219016_at | FLJ13149 | NA | 1.3 | 0.000151 | 10.54 |

Fold-change (log) is the mean of the ratio of hybridization signals in digitoxin treated versus DMSO control treated cells.

Figure 30:
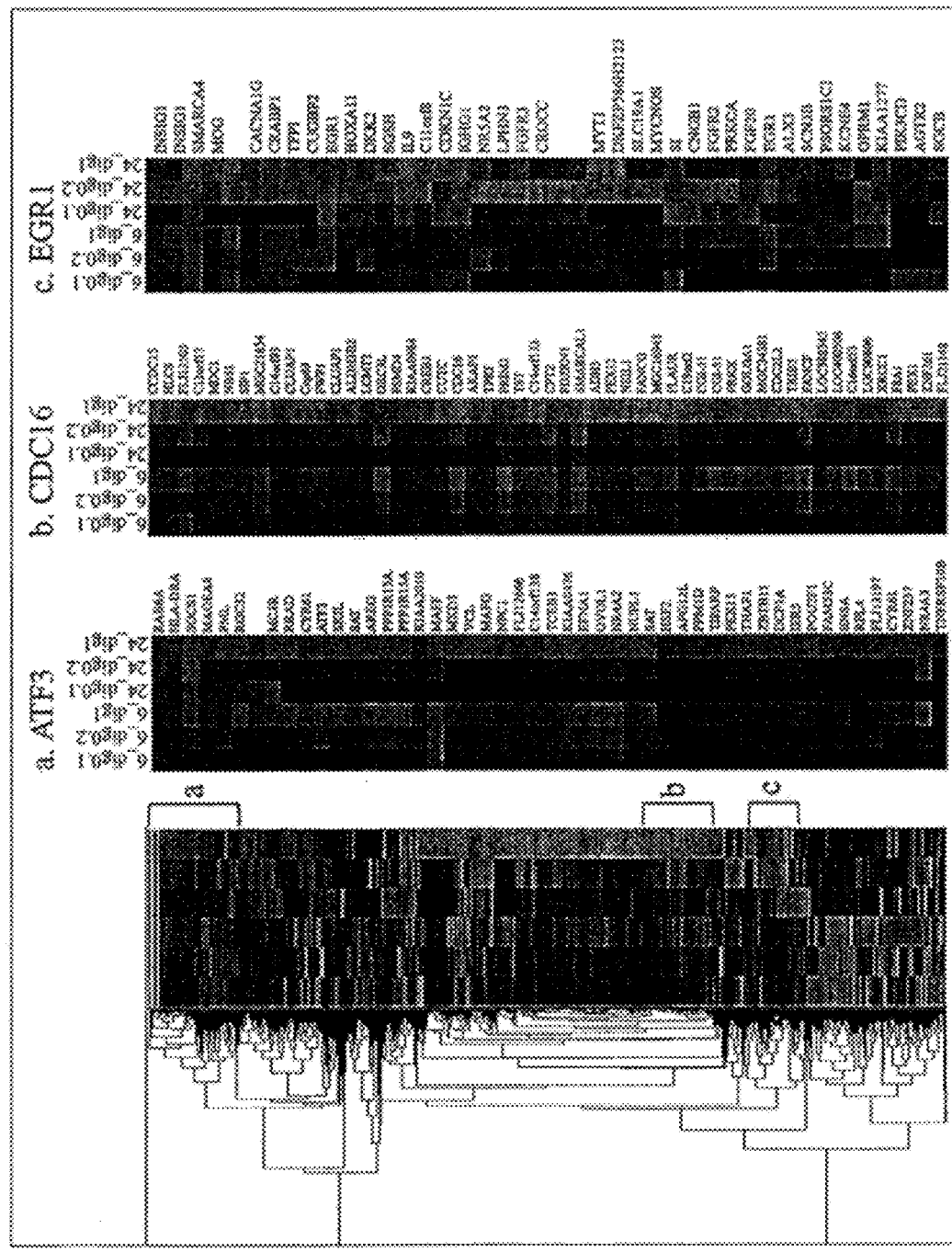
FIG. 30 Hierarchical clustering of differentially expressed genes analyzed on U1332.0A Affymetrix chips after treating MDA-MB-453 wells with digitoxin at 0.1, 0.2 or 1.0 µg/mL for 6 or 24 hours. Clustering was performed with the Program Cluster 3.0 (Khatri et al. 2005). Probesets were restricted to those that corresponded to an absolute value of M (log fold)>2.0 for at least one of the conditions. The threshold for color in the hierarchical clustering map is M>3 log fold. Fold change indicates relative expression in. digitoxin versus DMSO control cells. To pick the blowup region, the area containing a specific gene was expanded to include a well-defined expression pattern. Shown is the full hierarchical clustering map, which contains 4706 probesets A) upregulated gene region amplified for ATF3, B) down regulated gene region amplified for CDC16; C) upregulated gene region amplified for EGR1; red, upregulated; green, downregulated.

Hierarchical Clustering of Alterations in Gene Expression after Treating Cells with Digitoxin Hierarchical clustering was used to reveal genes that are coordinately controlled (FIG. 30B). Probesets were restricted to those that corresponded to an absolute value of M (log fold) greater than 2.0 for at least one of the treatment conditions. The threshold for color in the hierarchical clustering map is M greater than 3 log fold. FIG. 30B shows the full hierarchical clustering map, which contains 4706 probesets. FIGS. 30 A, B and C are expanded displays of specific subcategories of these probesets.

FIG. 30 panel A contains a cluster of genes, which, like ATF3, were mainly activated after treatment with digitoxin at 1 µg/mL, for either 6 or 24 hours, although some of these genes were also activated after treatment with 0.1 or 0.2 µg/mL for 6 or 24 hours. These included additional stress response (GADD34, IER2, HSF2) genes. FIG. 30 panel B displays genes that were downregulated by treatment with digitoxin. They include the cell cycle control gene CDC16 and replication gene ORC3, which were repressed after treatment with digitoxin at 1 µg/mL for 6 hours, further repressed at 24 hours, and slightly repressed after treatment with digitoxin at 0.2 µg/mL for 6 or 24 hours. The cluster of genes displayed in FIG. 30 panel C contains the gene EGR1 which was upregulated after treatment with 0.1, 0.2 or 1 µg/mL of digitoxin for 6 hours, but this did not persist at 24 hours. This cluster also contained lipid biosynthetic genes (INSIG1). A fourth region, expanded for CDKN1A, showed a progressive increase in expression after treatment with digitoxin at 0.1, 0.2 and 1 µg/ml for 6 or 24 hours, with a more pronounced increase at 24 hours. This cluster also contained the stress gene DNAJB4 and the apoptotic gene GDF15.

The Effects of Digitoxin on Expression of Specific mRNAs Determined by Real-Time RT-PCR To verify some of the digitoxin-induced changes observed in gene expression detected by microarray analysis, MDA-MB-453 cells were also treated with 0.1, 0.2 or 1 µg/mL of digitoxin for 6 or 24 hours, and real-time RT-PCR analysis was performed on 12 genes related to the stress response or cell cycle control. The RT-PCR results (FIG. 31 and Tables 18 and 19 as set forth below) were consistent with those obtained in the microarray analysis. To show how the data varied, p-values are indicated for all microarray and PCR genes in the tables.

TABLE 18

Comparison of the effects of digitoxin on selected genes by real-time PCR and microarray
analysis after treating MDA-MB-453 cells with digitoxin at 0.1, 0.2 or 1.0 µg/mL for 6 or 24 hours.

| | | | Fold-change relative to DMSO fold change (p value) | | | | | | | | | |
|---|---|---|---|---|---|---|---|---|---|---|---|---|
| | | Affymetrix | Digitoxin treatment (6 h, 0.1 µg/mL) | | | | Digitoxin treatment (6 h, 0.2 µg/mL) | | | | Digitoxin treatment (6 h, 1.0 µg/mL) | |
| Categories | Gene | Number | RT-PCR | | Microarray | | RT-PCR | | Microarray | | RT-PCR | | Microarray | |
| Stress response | hsf2 | 211220_s_at | 0.41 | (0.06) | 1.266 | (1.0) | 0.905 | * | 1.93 | (0.35) | 1.34 | * | 2.45 | 0.049 |
| | ATP1A1 | 220948_s_at | 0.188 | (0.17) | 0.158 | (1.0) | 0.62 | (0.088) | 0.223 | (1.0) | 0.415 | 0.032 | 0.241 | (1.0) |
| | ATF3 | 202672_s_at | −0.25 | (0.38) | 0.16 | (1.0) | 1.15 | * | 1.66 | (1.0) | 3.99 | * | 6.91 | (0.10) |
| | DNAJB4 | 202887_s_at | 0.09 | (0.48) | 0.80 | (1.0) | 0.30 | * | 0.88 | (1.0) | 1.43 | * | 2.52 | (.1.0) |
| | EGR-1 | 211936_at | 1.18 | (0.13) | 1.68 | (1.0) | 3.26 | * | 3.43 | (1.0) | 5.15 | * | 5.05 | (1.0) |
| | INSIG1 | 201625_s_at | 1.53 | * | 1.71 | (1.0) | 2.29 | * | 2.33 | (1.0) | 2.77 | * | 2.85 | (0.88) |
| | ATF4 | 200779_at | −0.49 | (−0.003) | −0.38 | (1.0) | −0.12 | (0.26) | −0.19 | (1.0) | 0.97 | * | 0.56 | (1.0) |
| | GADD34 | 37028_at | 1.32 | (0.07) | 1.78 | (1.0) | 2.48 | * | 3.42 | (1.0) | 4.05 | * | 5.49 | (0.02) |

TABLE 18-continued

Comparison of the effects of digitoxin on selected genes by real-time PCR and microarray
analysis after treating MDA-MB-453 cells with digitoxin at 0.1, 0.2 or 1.0 μg/mL for 6 or 24 hours.

| | | | Fold-change relative to DMSO fold change (p value) | | | | | | | | | |
|---|---|---|---|---|---|---|---|---|---|---|---|---|
| | | Affymetrix | Digitoxin treatment (6 h, 0.1 μg/mL) | | | | Digitoxin treatment (6 h, 0.2 μg/mL) | | | | Digitoxin treatment (6 h, 1.0 μg/mL) | | | |
| Categories | Gene | Number | RT-PCR | | Microarray | | RT-PCR | | Microarray | | RT-PCR | | Microarray | |
| Promote apoptosis | CDKN1A | 209383_at | 0.73 | (0.09) | 1.22 | (1.0) | 1.62 | * | 2.06 | (1.0) | 2.61 | * | 3.41 | (0.34) |
| | GDF15 | 221577_x_at | 0.14 | (0.68) | 0.19 | (1.0) | 0.60 | (0.12) | 0.73 | (1.0) | 1.34 | * | 1.75 | (1.0) |
| Cell Cycle | CDC16 | 209658_at | −0.51 | * | −0.83 | (1.0) | −0.67 | * | −1.55 | (1.0) | −1.31 | * | −2.82 | (0.05) |
| Cholesterol/ fatty acid biosynthesis | HMGCS1 | 205822_s_at | 1.20 | 0.01 | 1.09 | (1.0) | 2.04 | * | 1.69 | (1.0) | 2.75 | * | 2.53 | (1.0) |

TABLE 19

24 hours.

| | | | Fold-change relative to DMSO fold change (p value) | | | | | | | | | |
|---|---|---|---|---|---|---|---|---|---|---|---|---|
| | | Affymetrix | Digitoxin treatment (24 h, 0.1 μg/mL) | | | | Digitoxin treatment (24 h, 0.2 μg/mL) | | | | Digitoxin treatment (24 h, 1.0 μg/mL) | | | |
| Categories | Gene | Number | RT-PCR | | Microarray | | RT-PCR | | Microarray | | RT-PCR | | Microarray | |
| Stress response | hsf2 | 211220_s_at | 0.4 | (0.062) | 1.17 | (0.54) | 0.63 | 0.013 | 1.64 | (1.0) | 2.32 | * | 3.23 | * |
| | ATP1A1 | 220948_s_at | −0.099 | (0.38) | 0.35 | (1.0) | 0.0025 | (0.98) | 0.5 | (1.0) | −0.028 | (0.78) | 0.67 | (1.0) |
| | ATF3 | 202672_s_at | −1.04 | * | −0.10 | (1.0) | 0.62 | 0.13 | 0.85 | (1.0) | 5.32 | * | 8.42 | (0.02) |
| | DNAJB4 | 202887_s_at | −0.49 | 0.15 | 0.20 | (1.0) | 0.35 | 0.18 | 2.15 | (1.0) | 3.51 | * | 6.00 | * |
| | EGR-1 | 211936_at | −2.00 | * | −2.40 | (1.0) | −3.38 | * | −4.07 | (1.0) | −2.30 | * | −2.49 | (1.0) |
| | INSIG1 | 201625_s_at | −0.58 | 0.15 | −0.50 | (1.0) | −1.51 | * | −1.31 | (1.0) | −1.08 | 0.02 | −0.61 | (1.0) |
| | ATF4 | 200779_at | −1.54 | * | −1.08 | (1.0) | −0.66 | * | −0.49 | (1.0) | 2.71 | * | 1.65 | (1.0) |
| | GADD34 | 37028_at | 0.96 | (0.04) | 0.69 | (1.0) | 1.64 | * | 1.80 | (1.0) | 4.36 | * | 5.50 | (0.02) |
| Promote apoptosis | CDKN1A | 209383_at | 0.73 | (0.09) | 1.52 | (1.0) | 1.62 | * | 2.76 | (1.0) | 2.61 | * | 5.22 | (0.01) |
| | GDF15 | 221577_x_at | 0.97 | 0.01 | 1.41 | (1.0) | 2.35 | 0.01 | 2.94 | (1.0) | 3.20 | * | 4.25 | (1.0) |
| Cell cycle | CDC16 | 209658_at | −0.33 | (0.12) | −0.87 | (1.0) | −0.44 | (0.19) | −1.71 | (1.0) | −1.58 | * | −4.93 | * |
| Cholesterol/ fatty acid biosynthesis | HMGCS1 | 205822_s_at | −1.06 | (0.07) | −0.54 | (1.0) | −1.89 | * | −1.88 | (1.0) | −2.01 | * | −1.01 | (1.0) |

Figure 31A:
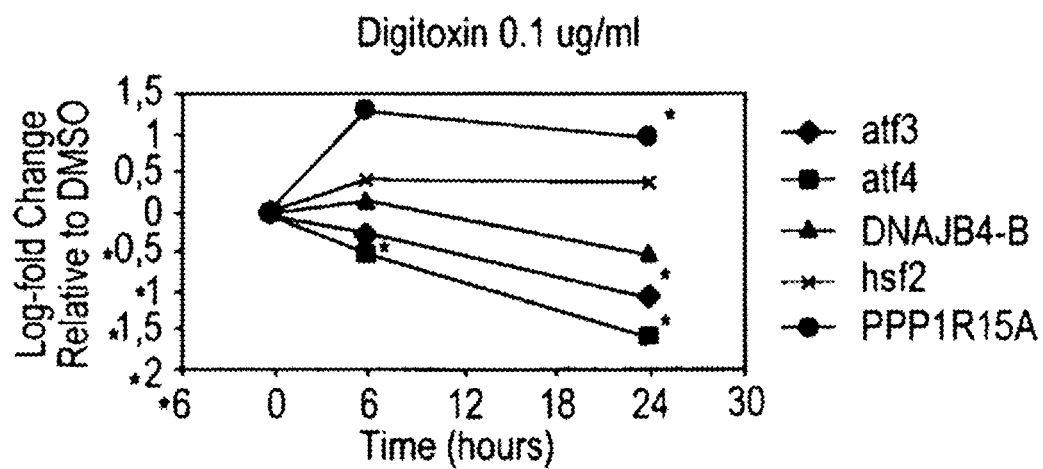
FIG. 31 A, B, C) Real-time RT-PCR analysis after treating MDA-MB-453 cells with digitoxin at 0.1 µg/mL for 6 or 24 hours. The cells were treated with 0.1 µg/mL of digitoxin and, after 6 or 24 hours, extracts were prepared and analyzed by Real-time RT-PCR, as described in Materials and Methods. Fold change indicates relative expression in digitoxin versus DMSO control cells. * indicates p<0.05. A, B and C display different patterns of gene expression. D, E, F) Real-time RT-PCR analysis after treating MCF7 cells with digitoxin at 1 µg/mL for 6 or 24 hours, as described in Materials and Methods. Fold change indicates relative expression in digitoxin versus DMSO control cells. All p values were <0.05.
Figure 31B:
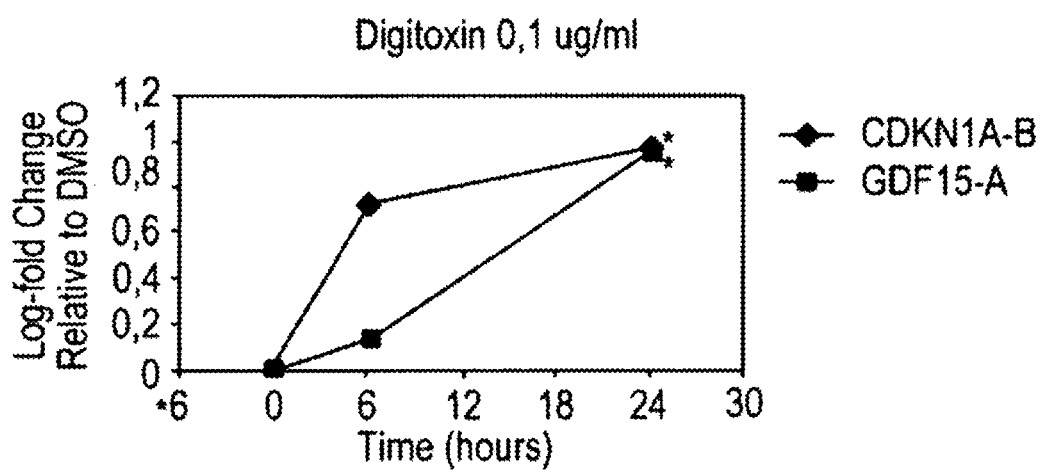
Figure 31C:
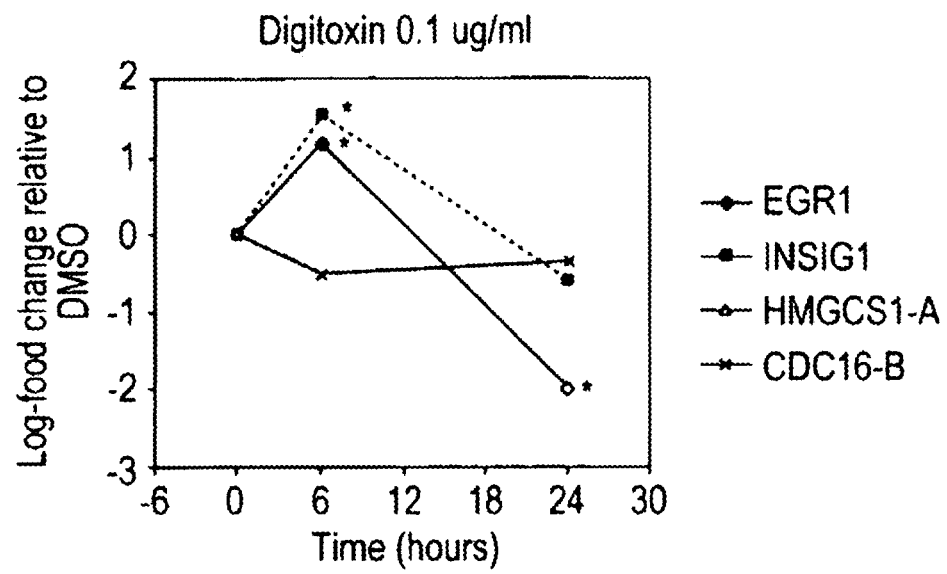

Exponentially dividing cultures of MDA-MB-453 cells were treated with digitoxin at 0.1, 0.2 and 1.0 μg/ml, and then collected for RNA extraction at 6 or 24 hours.
Microarray analysis was performed as described in Materials and Methods.
Fold-change (log) is the mean of the ratio of hybridization signals in digitoxin treated versus DMSO control treated cells.
Real-time RT-PCR was performed as previously described (Einbond et al. 2007a, b);
p values are <0.01, unless indicated in parentheses Consistent with the hierarchical clustering results, there were four main patterns of expression: (1) mRNAs for the ER stress gene EGR1 and the lipid genes INSIG1 and HMGCS1 increased at 6 hours and decreased at 24 hours, (FIG. 31C); (2) the integrated stress response (ISR) genes ATF4, ATF3, PPP1R15A and DNAJB4-B and HSF2 displayed complex expression patterns after treatment with the 3 doses; at 0.1 μg/ml the expression of ATF3, ATF4 and DNAJB4 decreased from 6 to 24 hours and the expression of HSF2 and PPP1R15A increased and then leveled off (FIG. 31A) (after treatment with 1 μg/ml, they showed a progressive increase in mRNA expression; (3) expression of the apoptotic genes GDF15-A, CDKN1A and the Na$^+$—K$^+$-ATPase ATP1A1 progressively increased after treatment with digitoxin at all doses for 6 or 24 hours (FIG. 31B, Tables 18 and 19); and 4) the expression of CDC16 decreased at 6 hours and then leveled off (FIG. 31C). Thus, digitoxin activated early response, cholesterol biosynthetic and integrated stress response genes, depending on the dose and the duration of treatment, and progressively induced the expression of apoptotic genes.

Figure 32A:
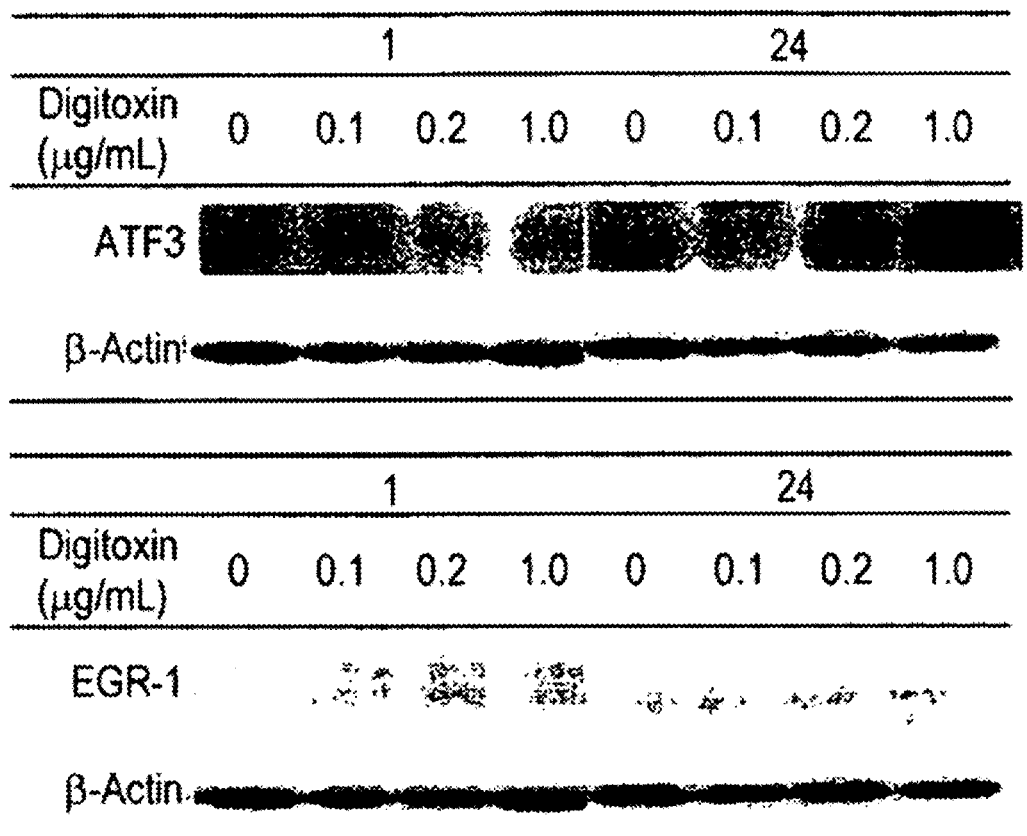
FIG. 32. A) Effects of digitoxin on the level of ATF3, EGR1 protein. Western blot analysis of extracts obtained from MDA-MB-453 cells treated with digitoxin. Cells were treated with 0, 0.1, 0.2 or 1 µg/mL of digitoxin and after 1, 6 or 24 hours extracts were prepared and analyzed by Western blotting; an antibody to β-actin was used as a loading control. B) siRNA to Erk2. Cell were pretreated with control and MAPK1 (Erk2) siRNA for 24 hours, exposed to digitoxin (0.4 µg/ml) for 24 h and percent inhibition of cell growth determined by the MTT assay. Positive=Mapk1; Erk2; Negative=Control siRNA. Percentages are normalized to DMSO.

The Effects of Digitoxin on Expression of ATF3 and EGR1 Protein in MDA-MB-453 Cells Digitoxin significantly upregulated the expression of the transcription factor ATF3 and the early response genes EGR1, both in the microarray analysis studies and in the RT-PCR analysis. Western blot analysis confirmed that when MDA-MB-453 cells were treated with digitoxin, EGR1 protein was induced after treating with digitoxin at 0.1, 0.2 or 1.0 μg/mL for 1 hour, whereas the ATF3 protein was induced after treating with digitoxin at 1.0 μg/mL for 24 hours (FIG. 32A). Treatment of serum-starved MDA-MB-453 cells with digitoxin at 80 μg/ml (105 μM) for 30 min yielded a 1.5-fold increase in the level of pSrc.

RNAi-Mediated Gene Knockdown

Figure 32B:
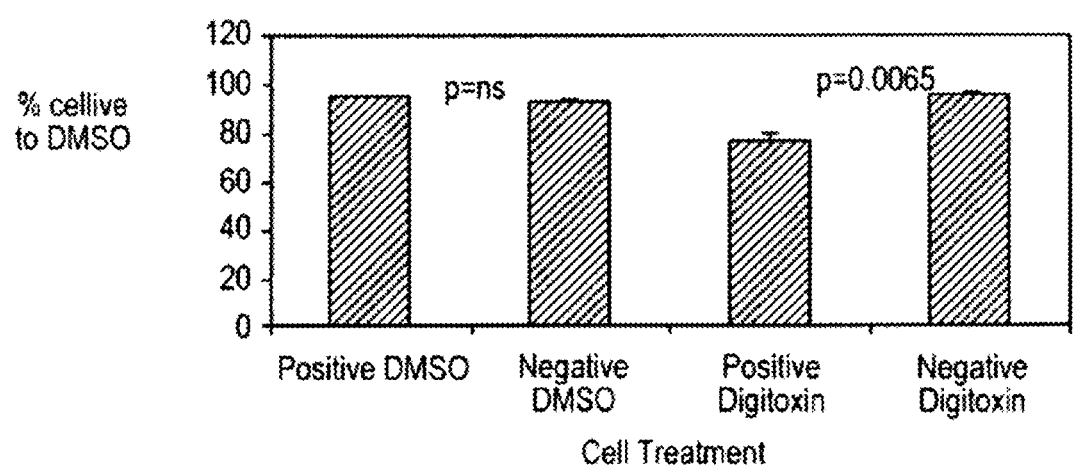

To clarify the effects of digitoxin on the ISR survival and apoptotic responses, the growth inhibitory effects of digitoxin were examined using the model system RNAi-mediated gene knockdown. Pretreating cells with siRNA to MAPK1 before treating with digitoxin (0.4 μg/ml) for 24 hours resulted in a decrease in cell proliferation from 96.0% to 76.9%, indicating that MAPK1 is involved in the survival phase of the digitoxin-induced stress response (FIG. 32B). Western blot analysis confirmed that ERK2 siRNA did, in fact, reduce the quantity of ERK2 protein by about 50%.

Gene Expression Analysis of the Effects of Digitoxin on MCF7 Cells

Figure 31D:
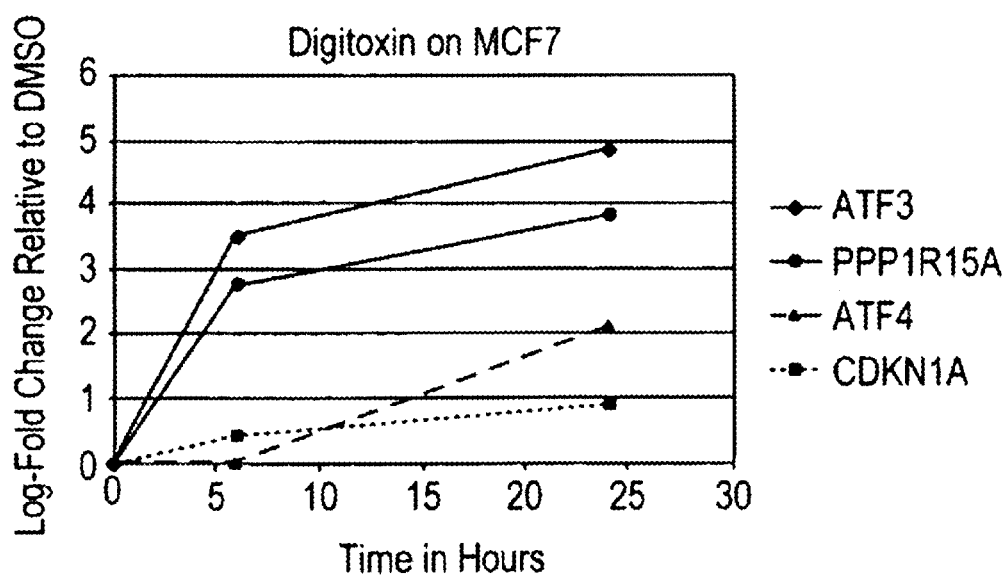
Figure 31E:
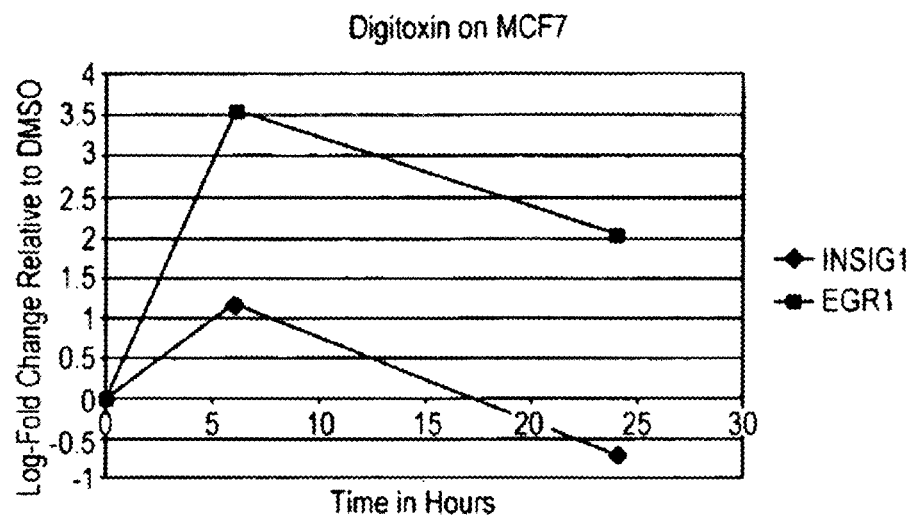
Figure 31F:
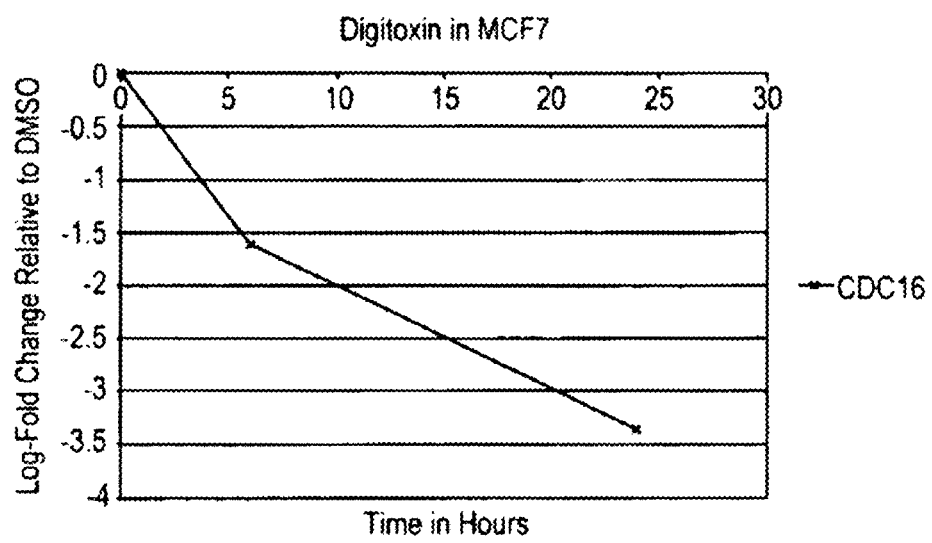

To determine whether other cell lines would react similarly to digitoxin, the effect of digitoxin was tested at 1 µg/mL for 6 or 24 hours on ER positive MCF7 cells, using real-time RT-PCR analysis. Patterns of expression were observed similar to those found with MDA-MB-453 cells. Thus, 1) mRNAs for the ER stress gene EGR1 and the lipid gene INSIG1 increased at 6 hours and decreased at 24 hours; 2) the stress genes ATF4, ATF3 and GADD34 showed a progressive increase in expression of the related mRNAs after treatment with digitoxin at 1 µg/mL for 6 or 24 hours; and 3) the cell cycle gene CDC 16 showed a progressive decrease in expression (FIGS. 31D, E, F). All p values were <0.05.

Digitoxin in Combination Therapy

Figure 33A:
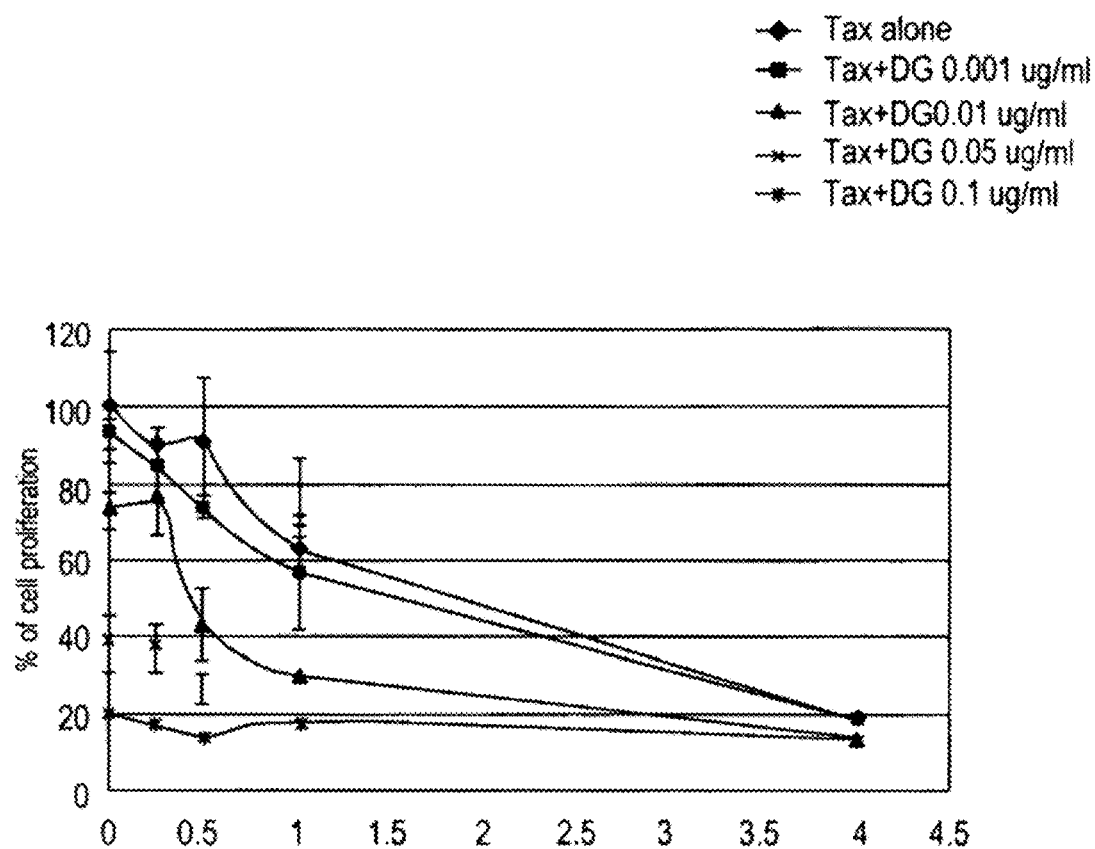
FIG. 33 Effects of digitoxin alone or in combination with TAX on cell proliferation in MDA-MB-453 breast cancer cells: A) x-axis, TAX concentration, B) Table of Combination Index (CI) Values, C) x-axis, digitoxin concentration. The DMSO control contained <0.1% DMSO; Bars: SD.
Figure 33C:
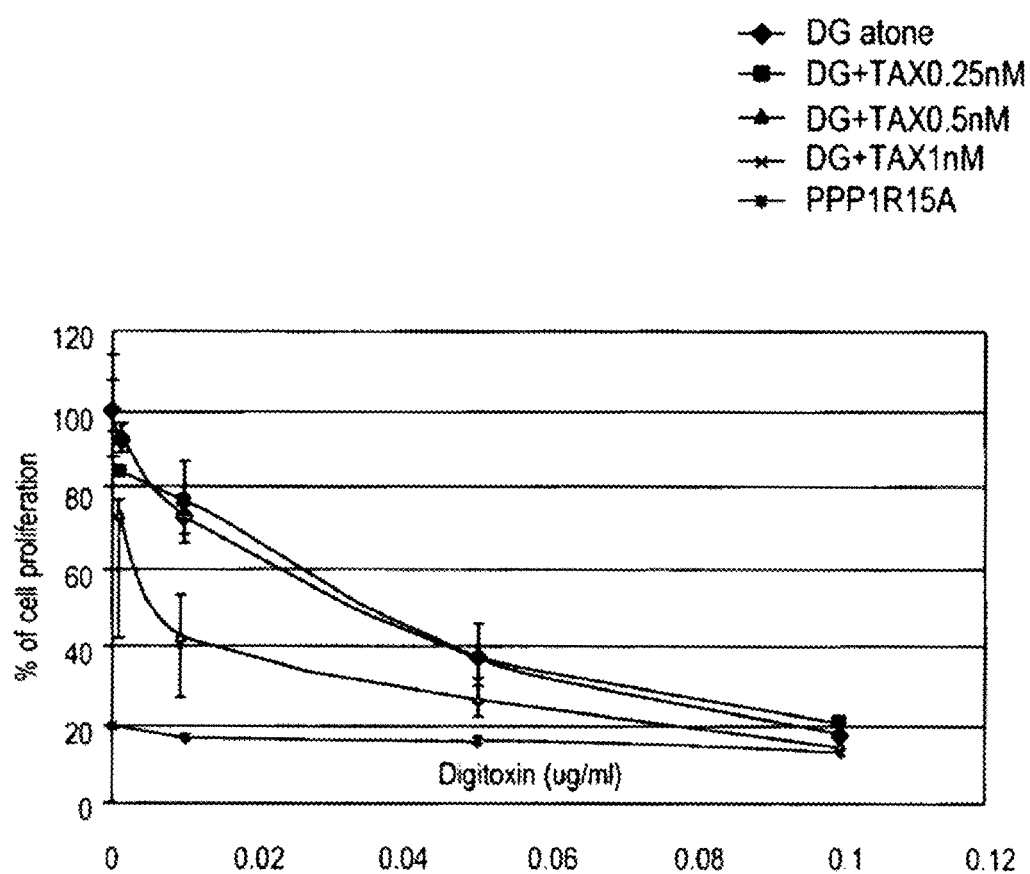

The effects of digitoxin on cell proliferation in combination with the chemotherapy agent paclitaxel on the MDA-MB-453 cell line were explored. The data obtained when increasing concentrations of paclitaxel were combined with increasing concentrations of digitoxin are shown in FIGS. 33 A and C. In these studies the two test agents were added simultaneously to the cells. These data were analyzed for the respective Combination indices (CI) (FIG. 33B). Additive effect was seen with as little as 0.01 µg/ml digitoxin and 0.5 nM of taxol, and moderate synergy with 0.01 µg/ml digitoxin and 1 nM of paclitaxel. With the former combination, the percent viable cells decreased from 90.6% after treatment with paclitaxel alone to 42.9% after treatment with paclitaxel plus digitoxin, p<0.01 (digitoxin alone: 73.0%). Addition of digitoxin (0.01 µg/ml) to paclitaxel (1 nM) decreased cell survival from 63.2% to 30.3% (p<0.01).

Gene expression profiles were used to identify the genes and signaling pathways whose expression was altered by exposure of the cells to digitoxin in order to obtain insights into mechanisms by which the cardiac glycoside digitoxin inhibited the growth of breast cancer cells. The studies indicated that digitoxin at low dose activated the expression of Src-mediated signaling pathways and enhanced the effect of the chemotherapy agent paclitaxel; higher doses of digitoxin activated the expression of stress response and apoptotic genes.

A significant impact on stress response genes was consistently found following exposure to low and high doses for 6 and 24 hours. Digitoxin at a nontoxic dose activated the expression of Src pathway genes, induced the expression of apoptotic genes and repressed the expression of replication genes at 24 hours. At higher doses, digitoxin induced expression of the ISR transcription factors ATF4, ATF3, ISR genes PPP1R15A and DNAJB4, apoptotic genes EGR1, CDKN1A and GDF15 and lipid related genes (Table 17). Real-time RT-PCR validated these findings (Tables 18 and 19).

Digitoxin altered the expression of several genes involved in calcium homeostasis, including EGR1, 1HPK2 and NR4A1 (Table 17). Microarrays, hierarchical clustering, and PCR analysis showed several potential intermediaries of the growth inhibitory effects of digitoxin, including increased expression of EGR-1, ATF3 and p21, and decreased expression of the cell cycle related gene CDC16 and replication gene POLR3B.

The results are consistent with the finding that the induction of ATF3 occurs via EGR1 downstream of pSrc and ERK1/2. (Bottone F G, Jr. et al. Transcriptional regulation of activating transcription factor 3 involves the early growth response-1 gene. *J Pharmacol Exp Ther.* 315(2):668-77, 2005.) To test the functional relevance of ERK, we employed MDA-MB-453 cells and RNAi-mediated gene knockdown; ERK upstream of EGR-1 appears to mediate the survival response. These results are consistent with the finding that digitoxin inhibits $Na^+$—$K^+$-ATPase in cardiac myocytes, thereby activating Src and downstream ERK signaling cascades that eventually inhibit cell proliferation.

Digitoxin's upregulation of lipid biosynthetic genes 6 hours after treatment with 0.1, 0.2 or 1.0 µg/mL of digitoxin may be due to the ability of ERK to activate gene transcription mediated by sterols in HepG2 liver cancer cells [Kotzka J et al. Sterol regulatory element binding proteins (SREBP)-1a and SREBP-2 are linked to the MAP-kinase cascade. *Journal of Lipid Research* 41:99-108, 2000.]. This finding may be a cause for concern and requires additional research. Since digitoxin altered very different sets of genes after treatment with various dose and time combinations, doses must be carefully monitored for optimal clinical outcomes.

The effects of digitoxin on the expression of genes related to the ISR are not limited to the MDA-MB-453 cell line; though the MCF7 cell line was less sensitive to the growth inhibitory effect of digitoxon, it exhibited increased expression of ATF4, DDIT3, GDF15, SLC7A11 and CYP1A1 in response to digitoxin treatment. The results of real-time RT-PCR analysis were remarkably similar between the two lines (FIG. 31 and Tables 18 and 19): digitoxin activated early response, cholesterol biosynthetic and integrated stress response genes, depending on the duration of treatment, and progressively induced the expression of apoptotic genes.

To further explore the anticancer potential of nontoxic concentrations of digitoxin, the effect of nontoxic doses of digitoxin combined with the chemotherapy agent paclitaxel was tested and a strong synergy was found. Paclitaxel and digitoxin inhibit the in vitro activity of purified $Na^+$—$K^+$-ATPtpase. The percent inhibition for paclitaxel and digitoxin at 20 µM were 21.7 and 35.2%, respectively. Results indicate that paclitaxel is a potent inhibitor of the $Na^+$—$K^+$-ATPase (data not shown). Consistent with these findings, paclitaxel has been shown to competitively inhibit ATP binding activity of the NTPase/helicase of hepatitis C virus with an $IC_{50}$ of about 16 µM (Borowski P. et al., Biochemical properties of a minimal functional domain with ATP-binding activity of the NTPase/helicase of hepatitis C virus. *Eur. J. Biochem.* 266(3):715-23, 1999.). It is possible that digitoxin and paclitaxel alter different sites on the $Na^+$—$K^+$-ATPase or have different molecular targets. The ability of low concentrations of digitoxin to potentiate the effects of paclitaxel permits the use of lower doses of this toxic chemotherapy agent in cancer treatment.

It is also noted that actein inhibited the in vitro activity of purified $Na^+$—$K^+$-ATPtpase, although not to the extent of the inhibition seen with either of digitoxin or paclitaxel. The activities of digitoxin and actein for ATPase inhibition appeared to be correlated with their activities for cell growth inhibition.

The risks, pharmacokinetics and pharmacodynamics of digitoxin administration are well known in humans, (López-Lázaro M et al. Digitoxin inhibits the growth of cancer cell lines at concentrations commonly found in cardiac patients. *J Nat. Prod.* 68(11):1642-5, 2005). Digitoxin activated transcription of apoptotic factors and repressed cell cycle related genes and at low concentrations enhanced the growth inhibitory effect of paclitaxel on human breast cancer cells.

In sum, an unbiased informatics approach was used to characterize the genes and pathways perturbed by digitoxin in breast cancer cells. Her2 overexpressing, ER low MDA-MB-453 human breast cancer cells were treated with digitoxin at 4 doses (20 ng/ml to 1 µg/ml; 26 nM to 1.3 µM)

RNA was collected at 6 hours and 24 hours. At doses that inhibited cell proliferation, digitoxin activated the expression of Src-mediated genes. To reveal primary effects, digitoxin's effect was examined 6 hours after treatment with the highest dose, 1 µg/ml. Upregulation of the stress response genes EGR-1 and NAB2, lipid biosynthetic genes and the tumor suppressor gene p21 was found, and downregulation of the mitotic cell cycle gene CDC16 and the replication gene PolR3B was found. Hierarchical clustering and real-time RT-PCR assays confirmed four expression patterns: 1) the induction of the early genes and lipid genes did not increase with time or concentration; 2) ISR genes displayed a complex response depending on the dose and duration of exposure; 3) the induction of the apoptotic genes increased with time and dose; and 4) the expression of the cell cycle gene CDC16 decreased at 6 hours. Thus, digitoxin appears to inhibit cell growth by activating the transcription of apoptotic factors (p21, EGR-1, DNAJB4) and repressing cell-cycle-related genes (CDC16), depending on the dose and the duration of treatment. Low concentrations of digitoxin enhanced the growth inhibitory effects of the chemotherapy agent paclitaxel.

Example 16

This example examines the chemopreventive potential and action of the herb black cohosh on Sprague-Dawley rats. Among female rats treated at 35.7 and 7.14 mg/kg b.w. there was a dose-related reduction (p<0.05) of the incidence of mammary adenocarcinomas when compared to the treatment of 0.714 mg/kg b.w., with a protection index (calculated relative to the group III; PI=[total tumours×100 animals of group III]−[total tumours×100 animals of the group I (or group II)]/[total tumours of group III]×100) for mammary adenocarcinomas of 87.5 and 48.8%, respectively. In sum, treatment of Sprague-Dawley rats with an extract of black cohosh enriched for triterpene glycosides resulted in a marked dose-related reduction of mammary adenocarcinomas.

Materials and Methods.
Materials.
All solvents and reagents were reagent grade; water was distilled and deionized. Naturex, Inc. (South Hackensack, N.J., USA) generously provided the black cohosh n-butanol dry extract containing 27% triterpene glycosides, as previously described in Einbond et al., *Phytomedicine* 15:504-511 (2008). In the periodic feed and water analysis for constituents and potential undesired contaminants, no presence of chemical endocrine disruptors was found.

Treatment for Chemoprevention Study:
In order to test the chemopreventive effect of the black cohosh extract on mammary tumors, four groups of 97, 96, 97 and 97 females were treated by oral intubation with 35.7 (the maximum tolerated dose (MTD) based on the results of preliminary toxicity studies), 7.14, 0.714 or 0 mg/kg body weight (b.w.) of extract, suspended in water, for 40 weeks, from 56 to 96 weeks of age (the window of age for higher risk of mammary cancer in this strain of rats). After stopping treatment, the animals were kept under observation until the end of the experiment (over 130 weeks of age). At 138 weeks of age, almost 12% of the experimental animals were still alive, homogeneously distributed among the groups. At this time, sacrifice of the animals still alive following a specific calendar was planned in order to distribute the sacrifices homogeneously among the groups. The sacrifices were completed in two weeks.

Necropsy.
All animals of the four groups were submitted to complete necropsy encompassing all organs and tissues and every macroscopic lesion (with a part of normal tissue). A small sample of each tumor from necropsy was frozen in liquid nitrogen and then stored at −70° C. for further molecular biology studies. Samples of normal mammary gland tissue from five rats randomly selected from each group were also provided for immunohistochemical analysis.

Analyses. Histopathology:
In the chemoprevention studies, all mammary tumors and mammary glands (4 levels) were trimmed following the CRCCM/RI laboratory Standard Operating Procedure. Trimmed specimens were processed as paraffin blocks, and 3-50 ☐m sections of every specimen were obtained. Sections were routinely stained with hematoxylin and eosin.

Immunohistochemical (IHC) Staining for Tumors and Mammary Glands:
Tissue was labeled with a primary antibody for 90 minutes at room temperature. For tumor, the primary antibodies used were anti-cyclin D1 (cat. #2978; 1:600) and anti-KI67 (cat. #2586; 1:200) (Cell Signaling, Beverly, Mass., USA); for normal mammary glands: the primary reagents were mouse anti-ER antibody (cat.#MS-354-PO; 1:150) and Her-2Neu antibody (cat. #RM-9103-S0; 1:200) (Lab Vision, Fremont, Calif., USA). For the secondary reagent, the EnVision® detection system (DAKO Cytomation, Glostrup, Denmark A/S) was used according to the manufacturer's instructions. Appropriate positive and negative controls were included.

Lipid Analysis:
Hepatic lipids were measured as previously described in Einbond et al., *Funda Clin Pharmacol* 23: 311-321, 2009.

Blood Samples:
From the last five animals alive from each group, blood samples were collected through contusion of the retrobulbar plexus with a siliconated glass Pasteur pipette, after anesthetization with ethyl ether. Blood collection was performed three days before the start of the treatment and then at 10, 20, 30, 40 weeks after the start of the experiment.

Statistical Evaluation in the Chemoprevention Study.
Using the time of the first occurrence of the particular type of mammary lesion being analyzed, a Cox proportional hazard analysis was used. Individual experimental group comparisons were carried out. For dose-response analyses, a Cox proportional hazard regression was used in which the logarithm of the hazard ratio was assumed to depend linearly on the logarithm of the administered dose rates. For the analysis of the combined endpoints of dysplasia and adenocarcinoma, for any animal with both lesions, the time to the appearance of the first lesion was used in the analysis.

Cell Cultures.
MDA-MB-453 (Her2 overexpressing, low ER expression) human breast cancer cells were obtained from the American Type Culture Collection (ATCC; Manassas, Va., USA). Cells were grown in Dulbecco's modified Eagle's medium (DMEM; Gibco BRL Life Technologies, Inc., Rockville, Md., USA) containing 10% (v/v) fetal bovine serum (FBS) (Gibco BRL) at 37° C. with 5% $CO_2$.

Proliferation Assay.
The 3-[4,5-dimethylthiazol-2-yl]-2,5-diphenyl tetrazolium bromid (MTT) assay was used to determine the sensitivity of MDA-MB-453 human breast cancer cells to increasing concentrations of black cohosh/actein, as previously described Einbond et al., *Int J Cancer* 121: 2073-83, 2007.

Statistical Analysis.

For cell growth assays, the data are expressed as mean+/−standard deviation. Control and treated cells were compared using the student's t-test, p<0.05. The control and black cohosh treated rat samples for lipid analysis were also compared using the student's t-test, p<0.05.

Results

Chemoprevention.

Black cohosh did not have any adverse effects on the health of the Sprague-Dawley rats when considering water and feed consumption, body weight and survival.

Incidence of palpable mammary lesions clinically observed during the biophase was assessed. The data show that at 96 weeks of age (end of the treatment), the incidence of palpable mammary lesions and total number of palpable mammary lesions per 100 animals were higher among the females treated at 0.714 mg/kg b.w. compared to the other groups (including the negative control group). The differences were slightly altered with aging. This trend is also represented by the cumulative prevalence of palpable mammary lesions.

Data on mammary gland tissues and palpable lesions histopatologically evaluated were assessed. The data show: i) no difference of the incidence of fibroadenomas among the groups; ii) an increased incidence of animals bearing cellular atypia in mammary tissue and in fibroadenomas at the dose level of 0.714 mg/kg b.w. compared to the other groups; iii) an increased incidence of animals bearing mammary adenocarcinomas and of the total number of adenocarcinomas among the females treated at 7.14 and 0.714 mg/kg b.w. compared to the animals treated at 35.7 mg/kg b.w. and to the negative controls; and iv) the same trend was observed when adenocarcinomas were aggregated according to their atypical precursors.

On the basis of these results, the potential chemopreventive effect of black cohosh on mammary adenocarcinomas may be hidden in this study by the exceptionably low incidence of mammary adenocarcinomas (1%) in the negative control group when compared to the incidence of the negative historical controls of the colony (overall 8.9%; range 2.9-14%). If (using the observed time of occurrence) the incidence of mammary adenocarcinomas among the females treated at 35.7 or 7.14 mg/kg b.w. was compared with the females treated at 0.714 mg/kg b.w. (as positive control group which has an incidence of mammary adenocarcinomas equivalent to that of the overall negative historical controls, the data show: i) a significant dose-related decrease (p<0.05) of carcinomas, particularly in the females treated at the dose of 35.7 mg/kg b.w. (p<0.05); and ii) a significant dose-related decrease (p<0.01) of the number of aggregated adenocarcinomas plus their precursors, and specifically among the females treated at 35.7 mg/kg b.w. (p<0.05) or at 7.14 mg/kg b.w. (p<0.05).

Histopathological Examination of Mammary Tissues and Tumors.

Histopathological examination of IHC stained sections of mammary tissues and H and E and IHC stained of sections of fibroadenomas was performed.

IHC Staining of Mammary Tissue.

The normal mammary tissue was positive for ER in the nucleus and negative for Her2 expression. These findings helped guide the choice of signaling pathways to explore in separate gene expression studies.

H and E and IHC Staining of Fibroadenomas

The fibroadenomas from rats treated with 7.14 or 35.7 mg/kg black cohosh displayed a decrease in the proportion of glandular tissue and an increase in the proportion of connective tissue in treated versus control samples (3 each), whereas one fibroadenoma from rats treated with the lowest dose (0.714 mg/kg) exhibited an increase in the proportion of glandular tissue.

IHC were used to examine the level of Ki-67 and cyclin D1 in fibroadenomas from Sprague-Dawley rats treated with 7.14 or 35.7 mg/kg black cohosh. A significant difference in Ki-67 and cyclin D1 staining was found for rats treated with black cohosh versus water (control). Positive cells were counted in 10 separate fields on each slide and averaged the results. For Ki-67 positivity, the control rate was 5-15%, while that for treated (7.14 mg/kg) animals was <5%. For cyclin D1, the control rate was ~40%, while that for treated (7.14 mg/kg) animals was 5-15%.

Lipid Analysis of Rat Serum.

Analysis of the lipid content of rat serum indicated that treatment for prolonged times (2 or 20 weeks) with an extract of black cohosh at 35.7 or 0.714 mg/kg did not alter the level of lipids in the serum, except that black cohosh at 0.714 mg/kg did reduce the level of triglycerides at 20 weeks (0.69-fold, p=0.024). Treatment with black cohosh extract at 7.14 mg/kg resulted in a modest increase in the level of free fatty acids at 2 weeks (1.39-fold, p=0.026) and weeks (1.46-fold, p=0.010) and triglycerides at 20 weeks (1.77-fold, p=0.04).

Effect of Black Cohosh on the Growth of Breast Cancer Cells.

Black cohosh inhibited the growth of MDA-MB-453 Her2-overexpressing breast cancer cells with an $IC_{50}$ value, the concentration that caused 50% inhibition of cell proliferation of approximately 8 µg/ml compared to that for the triterpene glycoside actein of approximately 9 µg/ml (13 µM). These agents were more active than the chemopreventive compounds resveratrol ($IC_{50}$=8 µg/ml; 35 µM) and EGCG ($IC_{50}$>25 µg/ml; >55 µM).

Treatment with an extract of black cohosh enriched for triterpene glycosides (27%) at 35.7 and 7.14 mg/kg b.w. for 40 weeks (starting from 56 weeks of age) resulted in a significant dose-related reduction (p<0.05) of the incidence of mammary adenocarcinomas when compared to the incidence among the females treated at 0.714 mg/kg b.w. (considered as the positive control) and a significant dose-related decrease (p<0.01) of the number of aggregated adenocarcinomas plus their precursors. Furthermore, fibroadenomas obtained from rats treated with 35.7 and 7.14 mg/kg black cohosh displayed a decrease in the proportion of glandular tissue and an increase in the proportion of connective tissue, as well as a decrease in the level of cyclin D1 and Ki-67 protein by IHC. These findings suggest that black cohosh reduced the proliferative rate and thus the malignant potential of the tumors. It is important to note that the chemoprevention of mammary adenocarcinomas is persistent after the end of the treatment (96 weeks of age). Black cohosh inhibits the growth of MDA-MB-453 Her2-overexpressing human breast cancer cells. Black cohosh prevents and treats mammary cancer in females.

Example 17

This example examines the pharmacological and toxicological effects of an extract of black cohosh on female Sprague-Dawley rats in the short term. The rats were treated with an extract of black cohosh enriched in triterpene glycosides (27%) at 0 or 35.7 mg/kg. Four animals for each group were sacrificed at 1, 6 and 24 hours after receiving the treatment and liver tissue samples for lipid and gene expression analysis were obtained. Microarray analysis of rat liver tissue indicated that black cohosh downregulated mitochondrial oxidative phosphorylation genes and upregulated several isoforms of PLC at 24 h; by microarray and RT-PCR analysis, black cohosh reduced the expression of the cell cycle gene cyclin D1 and the inhibitor of differentiation gene ID3. In addition, black cohosh downregulated the expression of the antiapoptotic gene Birc6_predicted and clustered with antiproliferative compounds, specifically tubulin binding vinca alkaloids and DNA alkylators. In support of these findings, the extract inhibited the proliferation of HepG2, p53 positive, liver cancer cells. As such, the results show that black cohosh has chemopreventive activities.

Gene expression profiling was used to gain an understanding of the alterations of rat liver gene expression induced by an extract of black cohosh. The data in DrugMatrix® and the signatures derived from that data were generated for purified compounds using juvenile (8-10 week-old) male rats. Notably, this experiment was performed using 56 week-old female rats. It is likely that differences in biological and transcriptional responses of the rats used in this study compared to the reference dataset animals overwhelm the subtle expression signals captured by signatures. No match to any of the 29 liver signatures was observed. Using Entelos pathway analysis, the highest impact was observed on the Mitochondrial Oxidative Phosphorylation pathway. The downregulation of mitochondrial genes suggests that black cohosh may cause mitochondrial damage. A disruption of mitochondrial energy generation could explain the observed lipid accumulation in the hepatocytes and also presents a potential mechanism of the hepatitis occasionally observed in human black cohosh users. Mitochondrial damage following extended use of nucleoside analogs in antiretroviral therapy has been associated with steatohepatitis and occasional liver failure.

A study of the hepatic effects of black cohosh indicated that an ethanolic extract of black cohosh given to female Wistar rats (at doses greater than 500 mg/kg) induced hepatic mitochondrial toxicity, as evidenced by microvesicular steatosis, inhibition of beta-oxidation and the respiratory chain and resulting apoptosis. Modest effects on liver mitochondria were observed after treatment with doses as low as 10 mg/kg.

In addition, an upregulation of several isoforms of phospholipase C, which catalyses the cleavage of phosphatidylinositol-4,5-bisphosphate to generate the messengers DAG (diacylglycerol) and IP3 (inositol 1,4,5-trisphosphate), was observed. IP3, in turn, is required to activate the ER IP3 receptor, which releases $Ca^{2+}$ from the ER. The upregulation of PLC could thus result in a release of calcium from the ER which could account for the induction of stress response genes that was observed in vitro in response to treatment with an extract of black cohosh (*Anticancer Res* 27 (2007) 697-712).

Diacyl glycerol kinase beta was also significantly upregulated, suggesting a possible activation of GPCR-signaling cascades, though the involvement of any specific receptor(s) was not identified in this experiment.

In regard to apoptosis, black cohosh activated the expression of caspase 9 and IAP5 (pro-apoptotic), but repressed the expression of cytochrome C and BAX (anti-apoptotic). This mixed response probably reflects a mixed early mitogenic and apoptotic response among the hepatocytes in the liver. Expression data from longer exposures to compounds would likely resolve the overriding effect and help further elucidate the mechanism behind it.

The finding that black cohosh clustered with antiproliferative compounds, specifically tubulin binding vinca alkaloids and DNA alkylators, is significant. Repression of cyclin D was also observed in this experiment, suggesting the potential for inducing cell cycle arrest at the G1/S boundary. The effects on cyclin D1 and ID3 were validated using the more sensitive technique real-time RT-PCR analysis. It is noteworthy that black cohosh downregulated the expression of the antiapoptotic gene Birc6_predicted, by microarray analysis. Recent studies indicate that inhibition of inhibitor of apoptosis proteins (IAP) results in selective killing of tumor cells; IAP genes function in stem cells turning cancerous (Garcia-Frenandez et al., *Genes and Development* 24 (2010) 2282-2293).

In support of the anticancer finding of black cohosh, the extract inhibited the proliferation of HepG2, p53 positive, liver cancer cells. The results do not agree with the studies of Huang et al. (*Curr Drug Saf* 5 (2010) 118-24) indicating that black cohosh (up to 50 μg/ml) does not inhibit the growth of HepG2 liver cancer cells. One explanation to account for this discrepancy is that Huang et al. used crude extracts (40% isopropanol or 75 or 80% ethanol), whereas an extract enriched for triterpene glycosides was used in the instant invention, of which the triterpene glycoside actein, in particular, has been shown to inhibit the growth of liver cancer cells (Einbond et al., *Fundamental and Clinical Pharmacology* 23 (2009) 311-321).

To ascertain the nature of the components responsible for the observed effects of the black cohosh extract, the effects of the extract and the triterpene glycoside actein was compared. Specific to actein, AffyLimma and DrugMatrix analysis indicated that actein upregulated the expression of the cholesterol biosynthesis pathway and exhibited a weak match to the Cholesterol biosynthesis inhibitor (statin) signature. In support of this finding, when the effect of actein (35.7 mg/kg) was examined on lipid levels in the rat livers, a 0.6-fold decrease was found in the free fatty acid and cholesterol levels of the treated livers compared to the controls at 24 h; whereas treatment with an extract of black cohosh at 35.7 mg/kg resulted in a 3.9 and 4.6-fold increase in the free fatty acid and triglyceride content, respectively, of the treated livers compared to the controls at 24 h. These results suggest that components other than actein and related triterpene glycosdies in black cohosh are responsible for increasing the level of lipids in the rat liver. Common to both black cohosh and actein, Drug Matrix analysis indicated that both markedly downregulated mitochondrial oxidative phosphorylation genes suggesting both may induce mitochondrial damage. AffyLimma and Drug Matrix microarray and RT-PCR analysis indicated that both repressed the expression of cell cycle (cyclin D1) and cell growth regulator (ID3) genes at 24 h. In support of this, both the extract and actein inhibited the proliferation of HepG2, p53 positive, liver cancer cells. Thus the anticancer effects of black cohosh may be due at least in part to the triterpene glycoside content. The anticancer effects of black cohosh are further supported by the observation that black cohosh clustered with antiproliferative compounds, specifically tubulin binding vinca alkaloids and DNA alkylators.

Microarray analysis of rat liver tissue indicated that black cohosh markedly downregulated mitochondrial oxidative phosphorylation genes. Phospholipid biosynthesis and remodeling, PI3-Kinase and sphingosine signaling were upregulated, driven largely by an upregulation of several isoforms of phospholipase C. Hierarchical clustering indicated that black cohosh clustered with antiproliferative compounds, specifically tubulin binding vinca alkaloids and DNA alkylators. In support of this, black cohosh repressed the expression of cyclin D1 and ID3, and inhibited the proliferation of HepG2, p53 positive, liver cancer cells. Black cohosh reduced the level of free fatty acids at 6 and 24 hours and triglycerides at 6 hours in the serum, but increased the free fatty acid and triglyceride content of the treated livers at 24 h.

Materials and Methods

Materials

All solvents and reagents were reagent grade; $H_2O$ was distilled and deionized. Naturex, Inc. (South Hackensack, N.J.) generously provided the black cohosh extract containing 27% triterpene glycosides, as previously described [3]. The extract of black cohosh enriched for triterpene glycosides (27%) contained 3.4% actein and 1.8% isoferulic acid; the most abundant components were cimicifugoside (5.0%) and cimigenol arabinoside (3.7%).

Cell Cultures

HepG2 (p53 positive) human liver cancer cells were obtained from the ATCC (Manassas, Va.). Cells were grown in Dulbecco's Modified Eagle's medium (DMEM) (Gibco BRL Life Technologies, Inc., Rockville, Md.) containing 10% (v/v) fetal bovine serum (FBS) (Gibco BRL) at 37° C., 5% $CO_2$.

Proliferation Assay

The MTT assay was used to determine the sensitivity of HepG2 p53 positive human liver cancer cells to black cohosh/actein, as described in Einbond et al., *Int J Cancer* 121 (2007) 2073-83.

Analyses

Gene Expression Analysis.

Labeled cDNA was generated from liver tissue from each study animal and hybridized to Affymetrix RG230-2 rat whole genome arrays at Columbia University, following standard Affymetrix protocols. Analyses were performed using 2 approaches: 1) AffyLimmaGUI: Analysis was performed using the AffyLimmaGUI package in the open-source Bioconductor suite, as previously described in Sakurai et al., *Bioorg Med Chem* 13 (2005)1403-1408; 2) DrugMatrix®: Array data were transmitted to Iconix Pharmaceuticals as CEL files and uploaded into the Iconix database (DrugMatrix®) for Drug Signature and pathway analysis, as previously described *Fundamental and Clinical Pharmacology* 23 (2009) 311-321.

Real-Time RT-PCR Analysis.

Real-time quantitative RT-PCR methods were used to determine the nature of the RNA induced by treatment with black cohosh extract, using the Real Time PCR machine Stratagene MX3005P QPCR System.

Statistical Analysis.

For cell growth and real-time PCR assay, the data are expressed as mean+/−standard deviation. Control and treated cells were compared using the student's t-test, p<0.05. The control and black cohosh treated rat samples for lipid analysis were also compared using the student's t-test, p<0.05.

For gene expression analysis: the samples were analyzed as previously described for AffyLima analysis Einbond et al., *Int J Cancer* 121 (2007) 2073-83 and for Iconix Drug Matrix analysis Einbond et al., Einbond et al., *Fundamental and Clinical Pharmacology* 23 (2009) 311-321.

AffyLimma Analysis:

The statistical significance of differential expression was calculated using the empirical Bayesian LIMMA (LI Model for MicroArrays) method of Smyth et al. [11]: B=$\log_e$ (Odds of differential expression); the Bayesian natural (base e) log of the odds that the genes are differentially expressed (Einbond et al., *Int J Cancer* 121 (2007) 2073-83).

Iconix Drug Matrix Analysis:

For Iconix Pathway analysis, Fisher's Exact Test calculated the statistical likelihood that the same number of expression changes observed in pathway genes would be observed against the same number of randomly-chosen array probe sets. For Iconix hierarchical clustering, statistical analysis of the treatments in the cluster was performed using the hypergeometric distribution.

Results

Pharmacology

Histopathological and Lipid Examination of Liver and Kidney Tissues

Liver tissues from rats treated with black cohosh (35.7 mg/kg dosage) were stained with H and E or with Oil Red O for lipids and counterstained with H&E. Lipid accumulation was not as obvious in control liver tissue as it was in the treated sample. The localization in the treated tissue occurred between the central veins (Periportal—closer to the portal triad area). The samples displayed mild toxicity, as shown by microvesicular lipid droplets; the droplets were small, diffuse, lobular, subendothelial, and perivenule.

Analysis of the lipid content of the livers revealed a 3.9 (p=1.14×E−5) and 4.6-fold (p=0.00131) increase in the free fatty acid and triglyceride content, respectively, of the treated livers compared to the controls at 24 h.

Lipid Content Analysis of Rat Serum

Analysis of the lipid content of the serum revealed that treatment with an extract of black cohosh at 35.7 mg/kg reduced the level of free fatty acids at 6 hours (0.71-fold, p=0.003) and 24 hours (0.68-fold, p=0.038) and triglycerides at 6 hours (0.71-fold, p=0.038), but nonsignificantly increased the level of triglycerides at 24 hours (1.2-fold, p=0.058).

Gene Expression Analysis of Rat Liver Tissue

A dataset derived from the livers of female rats treated with an extract of black cohosh (35.7 mg/kg) was analyzed and observed for 24 h.

Affy Limma Analysis

After exposure for 24 h, Affy-Limma analysis indicated that the extract altered the expression of two genes (B>0) {B=log e (Odds of differential expression); the Bayesian natural (base e) log of the odds that the genes are differentially expressed}: the mitochondrial gene benzodiazepin receptor BZRP (log fold: 0.56) and the transcription factor F-box only protein 30 (log fold: −0.57). The 12 genes with the highest B values include genes involved in: (upregulated) inflammatory response (S100a8), protein transport (Lin7a); (downregulated) cell growth and replication (Igfbp3, Id3), antiapoptotic activity (Birc6_predicted) and cell cycle (ppp3cb). Among the most highly altered genes were those involved in: (upregulated >2-logfold) immune (Igh-1a_predicted) and inflammatory response (Lcn2, A2m), lipid binding (Rbp2), oxidoreductase (Cyp2b15) and phosphatase (Dusp1) activity; (downregulated <−1.36-fold) xenobiotic metabolic response (Hamp), cell growth (Id, Igfbp3), fatty acid synthesis (SCD1), transport (Syt12), metabolic process (Aldhla4) and cell cycle (Ccnd1).

Drug Matrix Analysis

No match to any of the 29 Drug Signatures® derived on the RG230-2 array platform for liver was observed. A lack of compatibility with Drug Signatures® does not preclude the use of other comparative analysis tools. One such tool is pathway analysis. Considering both up and down-regulated genes in the analysis, the highest impact was observed on the Mitochondrial Oxidative Phosphorylation pathway. When the expression data for the genes in this pathway were overlaid on a map of the pathway, it is clear that there is a profound downregulation of genes in this pathway in response to black cohosh exposure.

A general decrease in genes involved in urea and aspartate metabolism was also observed, including the mitochondrial carbamoyl phosphate synthase 1, argininosuccinate synthase, glycine amidino transferase and creatine kinase, possibly also reflecting mitochondrial damage.

When upregulated genes alone were considered, phospholipid biosynthesis and remodeling, PI3-Kinase and sphingosine signaling were observed to be impacted. This was driven largely by an upregulation of several isoforms of phospholipase C, which is involved in all 3 pathways. Diacyl glycerol kinase beta was also significantly upregulated.

Comparative Analysis

A hierarchical clustering of pathway impact scores of all RG230-2 liver experiments in the database was performed alongside black cohosh. Black cohosh formed part of a cluster of 51 treatments having a Pearson's correlation coefficient of 0.58. Statistical analysis of the treatments in the cluster using the hypergeometric distribution revealed a significant representation of treatments with anti proliferative compounds, specifically tubulin binding vinca alkaloids (3 experiments, p=0.0017) and DNA alkylators (4 experiments, p=0.029). The repression of cyclin D1 that was previously reported (Einbond et al., *Anticancer Res* 27 (2007) 697-712) was corroborated in this experiment (AffyLimma: −1.37-logfold). There was a mixed effect on the apoptosis pathway, with upregulation of pro-apoptotic caspase 9 and IAP5, but downregulation of anti-apoptotic cytochrome C and BAX.

Real-Time RT-PCR

The more sensitive tool Reverse Transcription-Polymerase Chain Reaction (RT-PCR) confirmed the microarray results indicating that black cohosh suppressed the expression of cyclin D1 and ID3 at 24 h (p<0.05).

Growth Inhibitory Effect of Black Cohosh on Liver Cancer Cells

Black cohosh inhibited the growth of p53 positive HepG2 liver cancer cells with an $IC_{50}$ value, the concentration that caused 50% inhibition of cell proliferation, of 37 μg/ml compared to that for the triterpene glycoside actein, 26 μg/ml (38 μM). Actein was more active than the chemopreventive compounds resveratrol: 21 μg/mL (51 μM); curcumin: 25 μg/mL (68 μM); or EGCG: >100 μM.

TABLE 20

Combination index (CI) values for MDA-MB-453 cells treated with (A) actein plus paclitaxel (TAX) or (B) the ethyl acetate (EtOAc) fraction plus doxorubicin (DOX)

(A)

| | | Actein (μg/mL) | | | | | |
|---|---|---|---|---|---|---|---|
| | | 0.1 | | 1 | | 10 | |
| TAX | 0.25 | 2.10 | -- | 1.70 | -- | 1.00 | +/− |
| (nM) | 1 | 1.15 | − | 0.75 | ++ | 0.05 | +++ |
| | 4 | 1.10 | +/− | 0.70 | ++ | 0.00 | +++ (A) |

(B)

| | | EtOAc fraction (μg/mL) | | | | | |
|---|---|---|---|---|---|---|---|
| | | 0.2 | | 2 | | 5 | | 20 |
| DOX | 3.4 | 2.17 | -- | 2.06 | -- | 2.03 | -- | 1.41 | -- |
| (nM) | 7 | 1.61 | -- | 1.50 | -- | 1.48 | -- | 0.85 | + |
| | 17 | 0.78 | ++ | 0.67 | ++ | 0.65 | ++ | 0.02 | +++ |
| | 34 | 0.76 | ++ | 0.65 | ++ | 0.62 | ++ | 0 | +++ |

$IC_{50}$ values determined from the graphs in FIG. 2 were used to obtain combination index values, for actein or the EtOAc fraction plus the indicated chemotherapy agent.
CI = [$IC_{50}$ (actein/extract + agent)/$IC_{50}$ (actein/extract alone)] + [$IC_{50}$ (agent + actein/extract)/$IC_{50}$ (agent alone)].
Symbols:
CI (--) >1.3 antagonism, (−) 1.1-1.3 moderate antagonism, (+/−) 0.9-1.1 additive effect. (+) 0.8-0.9 slight synergism. (++) 0.6-0.8 moderate synergism, (+++) <0.6 synergism.

TABLE 21

Synergistic combinations (CI) of actein or the ethyl acetate (EtOAc) fraction with chemotherapy agents

| Agent 1 | (μg/mL) | Agent 2 | (nM) | CI | |
|---|---|---|---|---|---|
| Actein * | 0.2 | DOX | 17 | 0.61 | 2+ |
| Actein | 1 | TAX | 1 | 0.75 | 2+ |
| Actein | 2 | 5-FU | 15 | 0.53 | 3+ |
| EtOAc | 0.2 | DOX | 17 | 0.78 | 2+ |

$IC_{50}$ values were determined from the combination of 3 concentrations of actein and 3 concentrations of the specific chemotherapy agent for actein plus paclitaxel or 5-fluorouracil (5-FU) and from the combination of 4 concentrations of actein and 4 concentrations of chemotherapy agent for actein plus doxorubicin or the EtOAc fraction plus doxorubicin and the solvent control on MDA-MB-453 cells.
* Actein: 1 μg/mL = 1.48 μM.

While the foregoing invention has been described in some detail for purposes of clarity and understanding, it will be appreciated by one skilled in the art, from a reading of the disclosure, that various changes in form and detail can be made without departing from the true scope of the invention in the appended claims

What is claimed is:

1. A method for treating a neoplasia in a human, comprising administering to the human an amount of actein effective to treat the neoplasia and an effective anti-neoplastic amount of at least one additional chemotherapeutic agent, wherein the at least one additional chemotherapeutic agent is selected from the group consisting of cisplatin, doxorubicin, 5-fluorouracil, herceptin, paclitaxel, and tamoxifen,
   wherein the amount of actein is about 0.2 µg/ml to 20.0 µg/ml; and
   wherein the amount of cisplatin is about 2 µg/ml to 20 µg/ml,
   the amount of doxorubicin is about 0.02 µg/ml to 0.2 µg/ml,
   the amount of 5-fluorouracil is about 0.002 µg/ml to 0.2 µg/ml,
   the amount of herceptin is about 0.8 µg/ml to 32 µg/ml,
   the amount of tamoxifen is about 2 µg/ml to 50 µg/ml, and
   the amount of paclitaxel is about 0.5 nM to 5 nM.

2. The method of claim 1, wherein the neoplasia is a carcinoma, a lymphocytic leukemia, a myeloid leukemia, a malignant lymphoma, a malignant melanoma, a myeloproliferative disease, a sarcoma, a brain tumor, a childhood tumor, or a mixed type of neoplasia.

3. The method of claim 2, wherein the carcinoma is a breast carcinoma or a colon carcinoma.

4. The method of claim 1, wherein the chemotherapeutic agent is paclitaxel, wherein the amount of actein is between about 0.5 µg/ml to about 5 µg/ml, and the amount of paclitaxel is between about 0.5 nM to about 5 nM.

5. The method of claim 1, wherein the chemotherapeutic agent is herceptin, wherein the amount of actein is between about 0.2 µg/ml to about 2 µg/ml, and the amount of herceptin is about 8 µg/ml to 32 µg/ml.

* * * * *

UNITED STATES PATENT AND TRADEMARK OFFICE
CERTIFICATE OF CORRECTION

PATENT NO.       : 9,561,244 B2
APPLICATION NO.  : 13/374496
DATED            : February 7, 2017
INVENTOR(S)      : Linda Saxe Einbond It is certified that error appears in the above-identified patent and that said Letters Patent is hereby corrected as shown below:

In the Specification

Column 22, Line 29:
Now reads: "1.5 gm"
Should read: -- 1.5 mg --

Column 25, Line 59:
Now reads: "14 µ/ml"
Should read: -- 14 µg/ml --

Column 28, Line 15:
Now reads: "h e structure of which"
Should read: -- the structure of which --

Column 43, Line 27:
Now reads: "an amount of an a cardiac"
Should read: -- an amount of a cardiac --

Column 61, Line 19:
Now reads: "digtoxin for 24 hours."
Should read: -- digitoxin for 24 hours --

Column 73, Line 23:
Now reads: "histopatologically"
Should read: -- histopathologically --

Signed and Sealed this
Twentieth Day of February, 2018

Andrei Iancu
*Director of the United States Patent and Trademark Office*

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: synthetic construct; gapd forward

<400> SEQUENCE: 1
ggcctccaag gagtaagacc                                              20

<210> SEQ ID NO 2
<211> LENGTH: 20
<212> TYPE: DNA

```
<213> ORGANISM: Artificial Sequence
<220> FEATURE:
<223> OTHER INFORMATION: synthetic construct; gapd reverse

<400> SEQUENCE: 2
aggggtctac atggcaactg                                                 20

<210> SEQ ID NO 3
<211> LENGTH: 20
<212> TYPE: DNA
<213> ORGANISM: Artificial Sequence
<220> FEATURE:
<223> OTHER INFORMATION: synthetic construct; atf3-forward

<400> SEQUENCE: 3
tgggaggact ccagaagatg                                                 20

<210> SEQ ID NO 4
<211> LENGTH: 20
<212> TYPE: DNA
<213> ORGANISM: Artificial Sequence
<220> FEATURE:
<223> OTHER INFORMATION: synthetic construct; atf3-reverse

<400> SEQUENCE: 4
gacagctctc caatggcttc                                                 20

<210> SEQ ID NO 5
<211> LENGTH: 20
<212> TYPE: DNA
<213> ORGANISM: Artificial Sequence
<220> FEATURE:
<223> OTHER INFORMATION: synthetic construct; egr1-forward

<400> SEQUENCE: 5
gagaaggtgc tggtggagac                                                 20

<210> SEQ ID NO 6
<211> LENGTH: 20
<212> TYPE: DNA
<213> ORGANISM: Artificial Sequence
<220> FEATURE:
<223> OTHER INFORMATION: synthetic construct; egr1-reverse

<400> SEQUENCE: 6
tgggttggtc atgctcacta                                                 20

<210> SEQ ID NO 7
<211> LENGTH: 20
<212> TYPE: DNA
<213> ORGANISM: Artificial Sequence
<220> FEATURE:
<223> OTHER INFORMATION: synthetic construct; gdf15-forward

<400> SEQUENCE: 7
ctccgaagac tccagattcc                                                 20

<210> SEQ ID NO 8
<211> LENGTH: 20
<212> TYPE: DNA
<213> ORGANISM: Artificial Sequence
<220> FEATURE:
<223> OTHER INFORMATION: synthetic construct; gdf15-reverse

<400> SEQUENCE: 8
agagatacgc aggtgcaggt                                                 20
```

```
<210> SEQ ID NO 9
<211> LENGTH: 20
<212> TYPE: DNA
<213> ORGANISM: Artificial Sequence
<220> FEATURE:
<223> OTHER INFORMATION: synthetic construct; cdkn1a-forward

<400> SEQUENCE: 9
gcctggactg ttttctctcg                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic construct; cdkn1a-reverse

<400> SEQUENCE: 10
attcagcatt gtgggaggag                                               20

<210> SEQ ID NO 11
<211> LENGTH: 20
<212> TYPE: DNA
<213> ORGANISM: Artificial Sequence
<220> FEATURE:
<223> OTHER INFORMATION: synthetic construct; hsf2 forward

<400> SEQUENCE: 11
atgggaaccc tgcttcttct                                               20

<210> SEQ ID NO 12
<211> LENGTH: 20
<212> TYPE: DNA
<213> ORGANISM: Artificial Sequence
<220> FEATURE:
<223> OTHER INFORMATION: synthetic construct; hsf2-reverse

<400> SEQUENCE: 12
ttgggttggt tctgggtcta                                               20

<210> SEQ ID NO 13
<211> LENGTH: 20
<212> TYPE: DNA
<213> ORGANISM: Artificial Sequence
<220> FEATURE:
<223> OTHER INFORMATION: synthetic construct; dnajb4-forward

<400> SEQUENCE: 13
ccggacaaga acaaatctcc                                               20

<210> SEQ ID NO 14
<211> LENGTH: 20
<212> TYPE: DNA
<213> ORGANISM: Artificial Sequence
<220> FEATURE:
<223> OTHER INFORMATION: synthetic construct; dnajb4-reverse

<400> SEQUENCE: 14
cctcctttca acccttcctc                                               20

<210> SEQ ID NO 15
<211> LENGTH: 20
<212> TYPE: DNA
<213> ORGANISM: Artificial Sequence
<220> FEATURE:
<223> OTHER INFORMATION: synthetic construct; hmgcr-forward

<400> SEQUENCE: 15
```
gacctttcca gagcaagcac                                                   20

<210> SEQ ID NO 16
<211> LENGTH: 20
<212> TYPE: DNA
<213> ORGANISM: Artificial Sequence
<220> FEATURE:
<223> OTHER INFORMATION: synthetic construct; hmgcr-reverse

<400> SEQUENCE: 16
agctgacgta cccctgacat                                                   20

<210> SEQ ID NO 17
<211> LENGTH: 20
<212> TYPE: DNA
<213> ORGANISM: Artificial Sequence
<220> FEATURE:
<223> OTHER INFORMATION: synthetic construct; hmgcs1

<400> SEQUENCE: 17
ccccagtgtg gtaaaattgg                                                   20

<210> SEQ ID NO 18
<211> LENGTH: 20
<212> TYPE: DNA
<213> ORGANISM: Artificial Sequence
<220> FEATURE:
<223> OTHER INFORMATION: synthetic construct; hmgcs1-reverse

<400> SEQUENCE: 18
tggcctggac ttaacattcc                                                   20

<210> SEQ ID NO 19
<211> LENGTH: 20
<212> TYPE: DNA
<213> ORGANISM: Artificial Sequence
<220> FEATURE:
<223> OTHER INFORMATION: synthetic construct; insig1 forward

<400> SEQUENCE: 19
gacagtcacc tcggagaacc                                                   20

<210> SEQ ID NO 20
<211> LENGTH: 20
<212> TYPE: DNA
<213> ORGANISM: Artificial Sequence
<220> FEATURE:
<223> OTHER INFORMATION: synthetic construct; insig1 reverse

<400> SEQUENCE: 20
caccaaaggc ccaaagatag                                                   20

<210> SEQ ID NO 21
<211> LENGTH: 20
<212> TYPE: DNA
<213> ORGANISM: Artificial Sequence
<220> FEATURE:
<223> OTHER INFORMATION: synthetic construct; atf4 forward

<400> SEQUENCE: 21
ccaacaacag caaggaggat                                                   20

<210> SEQ ID NO 22
<211> LENGTH: 20
<212> TYPE: DNA

```
<213> ORGANISM: Artificial Sequence
<220> FEATURE:
<223> OTHER INFORMATION: synthetic construct; atf4-reverse

<400> SEQUENCE: 22
gtgtcatcca acgtggtcag                                           20

<210> SEQ ID NO 23
<211> LENGTH: 20
<212> TYPE: DNA
<213> ORGANISM: Artificial Sequence
<220> FEATURE:
<223> OTHER INFORMATION: synthetic construct; gadd34 forward

<400> SEQUENCE: 23
ggaggctgaa gacagtggag                                           20

<210> SEQ ID NO 24
<211> LENGTH: 20
<212> TYPE: DNA
<213> ORGANISM: Artificial Sequence
<220> FEATURE:
<223> OTHER INFORMATION: synthetic construct; gadd34 reverse

<400> SEQUENCE: 24
cctctaggga cactggttgc                                           20

<210> SEQ ID NO 25
<211> LENGTH: 20
<212> TYPE: DNA
<213> ORGANISM: Artificial Sequence
<220> FEATURE:
<223> OTHER INFORMATION: synthetic construct; cdc16-forward

<400> SEQUENCE: 25
cgatggctgc ttacttcaca                                           20

<210> SEQ ID NO 26
<211> LENGTH: 20
<212> TYPE: DNA
<213> ORGANISM: Artificial Sequence
<220> FEATURE:
<223> OTHER INFORMATION: synthetic construct; cdc16-reverse

<400> SEQUENCE: 26
cagagcttgg ctgaagaacc                                           20
```